(12) United States Patent
Fan et al.

(10) Patent No.: US 11,584,744 B2
(45) Date of Patent: Feb. 21, 2023

(54) INHIBITORS OF TYPE 1 METHIONYL-TRNA SYNTHETASE AND METHODS OF USING THEM

(71) Applicant: UNIVERSITY OF WASHINGTON, Seattle, WA (US)

(72) Inventors: Erkang Fan, Seattle, WA (US); Zhongsheng Zhang, Seattle, WA (US); Wenlin Huang, Seattle, WA (US); Frederick S. Buckner, Seattle, WA (US)

(73) Assignee: University of Washington, Seattle, WA (US)

( * ) Notice: Subject to any disclaimer, the term of this patent is extended or adjusted under 35 U.S.C. 154(b) by 65 days.

(21) Appl. No.: 16/625,460

(22) PCT Filed: Jun. 22, 2018

(86) PCT No.: PCT/US2018/039145
§ 371 (c)(1),
(2) Date: Dec. 20, 2019

(87) PCT Pub. No.: WO2018/237349
PCT Pub. Date: Dec. 27, 2018

(65) Prior Publication Data
US 2021/0155617 A1  May 27, 2021

Related U.S. Application Data

(60) Provisional application No. 62/639,916, filed on Mar. 7, 2018, provisional application No. 62/523,999, filed on Jun. 23, 2017.

(51) Int. Cl.
| | | |
|---|---|---|
| C07D 471/04 | (2006.01) | |
| C07D 401/14 | (2006.01) | |
| C07D 403/06 | (2006.01) | |
| C07D 487/04 | (2006.01) | |
| C07D 519/00 | (2006.01) | |

(52) U.S. Cl.
CPC ......... *C07D 471/04* (2013.01); *C07D 401/14* (2013.01); *C07D 403/06* (2013.01); *C07D 487/04* (2013.01); *C07D 519/00* (2013.01)

(58) Field of Classification Search
CPC .............. C07D 471/04; C07D 401/14; C07D 403/06; C07D 487/04; C07D 519/00
See application file for complete search history.

(56) References Cited

U.S. PATENT DOCUMENTS

| | | | |
|---|---|---|---|
| 6,995,279 B2 | 2/2006 | Ushioda et al. | |
| 9,331,296 B2 | 5/2016 | Okajima et al. | |
| 2005/0143381 A1* | 6/2005 | Yu | A61P 3/04 514/248 |
| 2008/0146609 A1 | 6/2008 | Guiles et al. | |
| 2009/0175852 A1* | 7/2009 | Ciavarri | C07D 487/04 424/130.1 |
| 2009/0264406 A1* | 10/2009 | Furet | A61P 43/00 514/233.2 |
| 2010/0041891 A1* | 2/2010 | Setoh | C07D 263/56 546/281.1 |
| 2012/0101093 A1* | 4/2012 | Mjalli | A61P 25/28 514/233.2 |
| 2013/0059882 A1* | 3/2013 | Su | A61P 31/00 514/307 |
| 2015/0291598 A1* | 10/2015 | Chatterjee | A61K 31/5377 514/224.2 |
| 2016/0237090 A1* | 8/2016 | Hu | A61P 31/20 |

FOREIGN PATENT DOCUMENTS

| | | | | |
|---|---|---|---|---|
| WO | WO-2013000994 A1 * | 1/2013 | ............. | A61P 25/00 |
| WO | WO-2015038503 A1 * | 3/2015 | ........... | C07D 409/14 |

OTHER PUBLICATIONS

Katritzky; Journal of the Chemical Society, Perkin Transactions 1, 1982, 143-151. (Year: 1982).*
Zhang; RSC Med. Chem., 2020, 11, 885-895. (Year: 2020).*
Chemical Abstracts STN Registry database record for RN 1070440-80-0, "3-(3-Fluorophenyl)-4,5,6,7-tetrahydro-5-(phenylmethyl)isoxazolo[4,5-c]pyridine", Entered on Nov. 4, 2008. (Year: 2008).*
Chemical Abstracts STN Registry database record for RN 1070228-57-7, "5-(1H-Benzimidazol-2-ylmethyl)-3-(2-fluorophenyl)-4,5,6,7-tetrahydro-1H-pyrazolo[4,3-c]pyridine", Entered on Nov. 3, 2008. (Year: 2008).*
Chemical Abstracts STN Registry database record for RN 1332205-09-0, "3-(4-Chlorophenyl)-4,5,6,7-tetrahydro-5-[(6-methyl-1H-benzimidazol-2-yl)methyl]isoxazolo[4,5-c]pyridine", Entered on Sep. 14, 2011. (Year: 2011).*
Chemical Abstracts STN Registry Database record for RN 1417186-54-9, Entered into STN Jan. 22, 2013. (Year: 2013).*
Chemical Abstracts STN Registry Database record for RN 535972-18-0, Entered into STN Jun. 23, 2003. (Year: 2003).*
Chemical Abstracts STN Registry Database record for RN 1639954-90-7, Entered into STN Dec. 31, 2014. (Year: 2014).*
Khajondetchairit; Chemical Biology & Drug Design (2017), 90, 987-994. (Year: 2017).*
Slatter et al, "Pharmacokinetics, toxicokinetics, distribution, metabolism and excretion of linezolid in mouse, rat and dog", Xenobiotica 32:907-924 (2002).
Wang et al, "Pharmacodynamics of cefquinome in a neutropenic mouse thigh model of *Staphylococcus aureus* infection", Antimicrob. Agents Chemother. 58:3008-3012 (2014).
"Wikler et al., Clinical and Laboratory Standards Institute, ""Methods for dilution antimicrobial susceptibility tests for bacteria that grow aerobically"", 7th edition. Approved standard M7-A7., In:vol. 26 No. 2. Clinical and Laboratory Standards Institute, Wayne, PA (2006)".

(Continued)

*Primary Examiner* — Daniel R Carcanague
(74) *Attorney, Agent, or Firm* — McDonnell Boehnen Hulbert & Berghoff LLP

(57) ABSTRACT

The present disclosure is generally directed to compositions useful in the inhibition of MetRS and methods for treating diseases that are ameliorated by the inhibition of MetRS.

20 Claims, 5 Drawing Sheets

Specification includes a Sequence Listing.

(56) References Cited

OTHER PUBLICATIONS

Wikler et al., Clinical and Laboratory Standards Institute, Performance standards for Antimicrobial susceptibility testing, Approved standard M100-S17, In: vol. 27 No. 1. Clinical and Laboratory Standards Institute, Wayne, PA. (2007).
Williams et al, "Promising antituberculosis activity of the oxazolidinone PNU-100480 relative to that of linezolid in a murine model", Antimicrob.Agents Chemother. 53:1314-1319 (2009).
Young et al, "Leakage of periplasmic enzymes from envA1 strains of *Escherichia coli*", J.Bacteriol. 173:3609-3614 (1991).
Young, "In vitro antibacterial resistance selection and quantitation", Curr. Protoc. Pharmacol. Chapter 13:Unit13A (2006).
Zhang et al, "5-Fluoroimidazo[4,5-b]pyridine Is a privileged fragment that conveys bioavailability to potent trypanosomal methionyl-tRNA synthetase inhibitors", ACS Infect.Dis. 2:399-404 (2016).
The International Search Report (ISR) with Written Opinion PCT/US2018/039145 dated Oct. 15, 2018, pp. 1-17.
"Pubchem CID 69035391" Create Date: Nov. 30, 2012 (Nov. 30, 2012) Date Accessed: Oct. 15, 2018 (Oct. 15, 2018); p. 3, compound listed.
Amsterdam et al, "Susceptibility testing of antimicrobials in liquid media", p. 51-148. In: Amsterdam D (ed.), Antibiotics in Laboratory Medicine. 6th ed. Wolters Kluwer, Philadelphia (2015).
Barry et al.—Clinical and Laboratory Standards Institute— "Methods for determining bactericidal activity of antimicrobial agents: approved guideline", M26-A. Clinical and Laboratory Standards Institute, Wayne, PA (1999).
Brown et al, "Horizontal transfer of drug-resistant aminoacyl-transfer-RNA synthetases of anthrax and Gram-positive pathogens", EMBO Rep. 4:692-698 (2003).
Cherian et al, "Chemical modulation of the biological activity of reutericyclin: a membrane-active antibiotic from Lactobacillus reuteri", Sci.Rep. 4:4721 (2014).
Cohen et al, "Mitochondrial translational inhibitors in the pharmacopeia", Biochim.Biophys.Acta 1819:1067-1074 (2012).
Critchley et al, "Antibacterial activity of REP8839, a new antibiotic for topical use", Antimicrob.Agents Chemother. 49:4247-4252 (2005).
Critchley et al, "Recent advances in the preclinical evaluation of the topical antibacterial agent REP8839", Curr. Opin.Chem.Biol. 12:409-417 (2008).
Critchley et al, "Spectrum of activity and mode of action of REP3123, a new antibiotic to treat Clostridium difficile infections", J.Antimicrob.Chemother. 63:954-963 (2008).
Cunningham et al, "Distinguishing on-target versus off-target activity in early antibacterial drug discovery using a macromolecular synthesis assay", J.Biomol.Screen. 18:1018-1026 (2013).
Dirheimer et al, "Primary, secondary, and tertiary structures of tRNAs", p. 93-126. In: tRNA: Structure, biosynthesis and function. ASM Press,Washington, DC, (1995).
Donowitz et al, "Chapter 33: Linezolid and Other Oxazolidinones" in Mandell, G. L., J. E. Bennett, and R. Dolin. Principles and Practice of Infectious Diseases. Churchill Livingston Elsevier (2010).
Faghih et al, "Development of Methionyl-tRNA Synthetase Inhibitors as Antibiotics for Gram-Positive Bacterial Infections" Antimicrob Agents Chemother. Oct. 24;61(11) (2017).
Garrabou et al, "Reversible inhibition of mitochondrial protein synthesis during linezolid-related hyperlactatemia", Antimicrob. Agents Chemother. 51:962-967 (2007).
Gentry et al, "Variable sensitivity to bacterial methionyl-tRNA synthetase inhibitors reveals subpopulations of *Streptococcus pneumoniae* with two distinct methionyl-tRNA synthetase genes", Antimicrob.Agents Chemother. 47:1784-1789. 21 (2003).
Green et al, "Inhibition of methionyl-tRNA synthetase by REP8839 and effects of resistance mutations on enzyme activity", Antimicrob. Agents Chemother. 53:86-94 (2009).
Griffith et al, "In vivo antibacterial activity of RWJ-54428, a new cephalosporin with activity against gram-positive bacteria", Antimicrob. Agents Chemother. 47:43-47 (2003).
Guiles et al, "New agents for Clostridium difficile-associated disease", Expert.Opin.Investig.Drugs 17:1671-1683 (2008).
Hegde et al, "Pharmacodynamics of TD-1792, a novel glycopeptide-cephalosporin heterodimer antibiotic used against Gram-positive bacteria, in a neutropenic murine thigh model", Antimicrob.Agents Chemother. 56:1578-1583 (2012).
Hooper et al, Chapter 35 "Quinolones" in Mandell, G. L., J. E. Bennett, and R. Dolin. Principles and Practice of Infectious Diseases. Churchill Livingston Elsevier pp. 487-510 (2010).
Huang et al, ". Structure-guided design of novel Trypanosoma brucei Methionyl-tRNA synthetase inhibitors", Eur.J.Med.Chem. 124:1081-1092 (2016).
Ibba et al, "Aminoacyl-tRNA synthesis", Annu.Rev.Biochem. 69:617-650 (2000).
Infectious Diseases Society of America, "The 10 X '20 Initiative: pursuing a global commitment to develop 10 new antibacterial drugs by 2020", Clin Infect Dis 50:1081-1083 (2010).
Jarvest et al, "Conformational restriction of methionyl tRNA synthetase inhibitors leading 20 to analogues with potent inhibition and excellent-gram-positive antibacterial activity", Bioorg. Med.Chem.Lett. 13:1265-1268 (2003).
Jarvest et al, "Definition of the heterocyclic pharmacophore of bacterial methionyl tRNA synthetase inhibitors: potent antibacterially active non-quinolone analogues", Bioorg.Med.Chem.Lett. 14:3937-3941 (2004).
Jarvest et al, "Nanomolar inhibitors of *Staphylococcus aureus* methionyl tRNA synthetase with potent antibacterial activity against gram-positive pathogens", J.Med.Chem. 45:1959-1962 (2002).
Jarvest et al, "Optimisation of aryl substitution leading to potent methionyl tRNA synthetase inhibitors with excellent gram-positive antibacterial activity", Bioorg. Med.Chem.Lett. 13:665-668 (2003).
Keel et al, "Comparative efficacies of human simulated exposures of tedizolid and linezolid against *Staphylococcus aureus* in the murine thigh infection model", Antimicrob.Agents Chemother. 56:4403-4407 (2012).
Kerns et al, "Chapter 14: Plasma Protein Binding In: Drug-like properties: concepts, structure design and methods", Academic Press, Burlington, MA. p. 187-196 (2008).
Knudsen et al, ". Activities of vancomycin and teicoplanin against penicillin-resistant pneumococci in vitro and in vivo and correlation to pharmacokinetic parameters in the mouse peritonitis model", Antimicrob.Agents Chemother. 41:1910-1915 (1997).
Kodali et al, "Determination of selectivity and efficacy of fatty acid synthesis inhibitors", J.Biol.Chem. 280:1669-1677 (2005).
Koh et al, "Distinct states of methionyl-tRNA synthetase indicate inhibitor binding by conformational selection", Structure. Oct. 10;20(10):1681-91 (2012).
Koh et al, "Structures of Trypanosoma brucei methionyl-tRNA synthetase with urea-based inhibitors provide guidance for drug design against sleeping sickness", PLoS.Negl.Trop.Dis. 8:e2775 (2014).
Kraus et al, "Rational modification of a candidate cancer drug for use against Chagas disease", J Med Chem 52:1639-1647 (2009).
Laue et al, Effect of human plasma on the antimicrobial activity of iclaprim in vitro. J.Antimicrob.Chemother. 60:1388-1390 (2007).
Mani et al, "In vitro characterization of the antibacterial spectrum of novel bacterial type II topoisomerase inhibitors of the aminobenzimidazole class" Antimicrob.Agents Chemother. 50:1228-1237 (2006).
Mehlin et al, "Heterologous expression of proteins from Plasmodium falciparum: results from 1000 genes", Mol. Biochem. Parasitol. 148:144-160 (2006).
Moren et al, "The Role of Therapeutic Drugs on Acquired Mitochondrial Toxicity", Curr.Drug Metab 17:648-662 (2016).
Murray et al, Chapter 31 "Glycopeptides (Vancomycin and Teicoplanin), Streptogramins (Quinupristin-Dalfopristin), and Lipopeptides (Daptomycin)" in Mandell, G. L., J. E. Bennett, and R. Dolin. Principles and Practice of Infectious Diseases. Churchill Livingston Elsevier p. 449-467 (2010).
Nakama et al, "Structural basis for the recognition of isoleucyladenylate and an antibiotic, mupirocin, by isoleucyl-tRNA synthetase", J.Biol. Chem. 276:47387-47393 (2001).

(56) References Cited

OTHER PUBLICATIONS

Ochsner et al, "Mode of action and biochemical characterization of REP8839, a novel inhibitor of methionyl-tRNA synthetase", Antimicrob. Agents Chemother. 49:4253-4262 (2005).
O'Dwyer et al, "Bacterial resistance to leucyl-tRNA synthetase inhibitor GSK2251052 develops during treatment of complicated urinary tract infections", Antimicrob.Agents Chemother. 59:289-298 (2015).
Ojo et al, "*Brucellamelitensis* Methionyl-tRNA-Synthetase (MetRS), a Potential Drug Target for Brucellosis", PLoS. One. 11:e0160350 (2016).
O'Neill et al, "Preclinical evaluation of novel antibacterial agents by microbiological and molecular techniques", Expert.Opin.Investig. Drugs 13:1045-1063 (2004).
Papadopoulos et al, "Cobalt: constraint-based alignment tool for multiple protein sequences", Bioinformatics. 23:1073-1079 (2007).
Pedro-Rosa et al, "Identification of Potent Inhibitors of the Trypanosoma brucei Methionyl-tRNA Synthetase via High-Throughput Orthogonal Screening", J.Biomol.Screen (2014).
Ranade et al, "Inhibitors of Methionyl-tRNA Synthetase Have Potent Activity against Giardia intestinalis Trophozoites", Antimicrob Agents Chemother. 59:7128-7131 (2015).
Shibata et al, "Selective Inhibitors of Methionyl-tRNA Synthetase Have Potent Activity against Trypanosoma brucei Infection in Mice", Antimicrob. Agents Chemother. 55:1982-1989 (2011).
Shibata et al, "Urea-based inhibitors of Trypanosoma brucei methionyl-tRNA synthetase: selectivity and in vivo characterization", J.Med. Chem. 55:6342-6351 (2012).
Shinabarger, "Mechanism of action of the oxazolidinone antibacterial agents", Expert. Opin. Investig. Drugs 8:1195-1202 (1999).
Sievers et al, "Fast, scalable generation of high-quality protein multiple sequence alignments using Clustal Omega", Mol.Syst. Biol. 7:539 (2011).

\* cited by examiner

Treated days 6-10 with 2093 at 50 mg/kg PO BID

INHIBITORS OF TYPE 1 METHIONYL-TRNA SYNTHETASE AND METHODS OF USING THEM

CROSS-REFERENCE TO RELATED APPLICATIONS

This application is a U.S. national phase of International Application No. PCT/US2018/039145, filed on Jun. 22, 2018, which claims priority to U.S. Provisional Application No. 62/523,999, filed Jun. 23, 2017; and U.S. Provisional Application No. 62/639,916, filed Mar. 7, 2018, all of which are incorporated by reference herein in their entirety.

STATEMENT OF GOVERNMENT SUPPORT

This invention was made with government support under Grant No. RO1 AI097177, awarded by the National Institutes of Health. The government has certain rights in the invention.

BACKGROUND OF DISCLOSURE

Field of Disclosure

The present disclosure is generally directed to compositions and methods for treating diseases that are ameliorated by the inhibition of methionyl-tRNA synthetase (MetRS).

Technical Background

Gram-positive bacteria such as *Staphylococcus, Streptococcus*, and *Enterococcus* are major human pathogens responsible for a myriad of clinical syndromes. Antibiotic resistant strains such as methicillin resistant *Staphylococcus aureus* (MRSA) and vancomycin resistant *Enterococcus* (VRE) are widespread and limit the effectiveness of available antibiotics. CDC statistics show that there are 80,461 severe infections and 11,285 deaths due to MRSA per year in the USA. Similarly, there are 20,000 infections and 1,300 deaths per year due to VRE. Concern about the diminishing availability of effective antibiotics has led to urgent calls for the development of new antibiotics, such as the "10x'20 Initiative" by the Infectious Diseases Society of America. Launched in 2010, this is a plea to the global community to produce 10 new systemic antibiotics by 2020. As of 2016, six new systemic antibiotics have been approved (ceftaroline, dalbavancin, tedizolid, oritavancin, ceftolozane/tazobactam, and ceftazidime/avibactam) representing progress. However, none of these new antibiotics works by a novel mechanism of action (with the exception of the new beta-lactamase inhibitor avibactam) and thus may be at risk for rapid evolution of resistant bacterial strains. Moreover, many patients with existing drug allergies (e.g. to beta lactam drugs) or other contraindications to these drug classes may not benefit from these antibiotics. As a result, antibiotics acting by novel mechanisms of action are urgently needed to strengthen the treatment options.

Targeting the prokaryotic protein synthesis machinery has been a highly successful strategy for developing antibiotics. Aminoglycosides, tetracyclines, macrolides, ketolides, and oxazolidinones are major classes of antibiotics that all interfere with bacterial protein translation.

With respect to the target, bacteria and all living organisms contain a complement of tRNA synthetases that are responsible for charging tRNAs with their corresponding amino acids for subsequent delivery to the ribosome. tRNA synthetases, including methionyl-tRNA synthetase (MetRS), catalyze a two-step reaction as follows:

$$E + aa + ATP \rightleftharpoons E \cdot aa \sim AMP + PP_i \quad (1)$$

$$E \cdot aa \sim AMP + tRNA \rightleftharpoons E + aa - tRNA + AMP \quad (2)$$

In the first step, a highly reactive aminoacyl adenylate (aa~AMP) is formed through condensing ATP with the carboxylate of the amino acid. The second step uses this activated species to transfer the amino acid to the 3'-end of the tRNA (aa–tRNA). The bacterial MetRS enzymes are categorized in two forms (MetRS1 and MetRS2) based on sequence similarity and sensitivity to inhibitors. Bacteria generally have a single MetRS enzyme with most Gram positive genera containing the MetRS1 form (*Staphylococcus, Streptococcus, Enterococcus, Bacillus, Clostridium*, and others) and most Gram negative bacteria containing the MetRS2 form (*Escherichia, Klebsiella, Pseudomonas, Haemophilus, Bacteroides*, and others). Exceptions include *Bacillus anthracis* and a subset of *Streptococcus pneumoniae* which contain both MetRS1 and MetRS2 isoforms. In mammals, distinct tRNA synthetases typically operate in the cytoplasm and the mitochondria. The human mitochondrial MetRS encoded in the mitochondrial genome has close sequence homology to bacterial enzymes of the MetRS1 variety, whereas the human cytoplasmic MetRS is nuclear encoded with close homology to the MetRS2 variety.

Inhibition of tRNA synthetases represents another possible approach to target prokaryotic protein translation. The widely used antibiotic, mupirocin, works by inhibiting the bacterial isoleucyl-tRNA synthetase. Mupirocin is used as an ointment to treat or decolonize patients with cutaneous infections due to *Staphylococcus* or *Streptococcus*, however, its use is limited to the topical route of administration. Another bacterial tRNA synthetase inhibitor, a boron-containing compound targeting the bacterial leucyl-tRNA synthetase (GSK2251052) made it to phase 2 trials for Gram negative infections. Unfortunately, its development was discontinued due to high rates of resistance occurring during treatment, which may be related to the targeting of the editing domain of the enzyme rather than the catalytic domain. Investigators at GlaxoSmithKline reported on inhibitors to the *S. aureus* MetRS as having excellent antibiotic potency, but poor oral bioavailability that restricted its development (pre—New Drug Application) to topical use for skin infections and to oral use for *Clostridium difficile* infections where oral absorption is not needed.

Therefore, there remains a need for broad spectrum antibiotics that act by inhibiting MetRS but also have good bioavailability and pharmacokinetic properties.

SUMMARY OF DISCLOSURE

The disclosure provides novel MetRS inhibitor compounds that show promising antibiotic and antiprotozoal activity.

Thus, one aspect of the disclosure provides compounds of formula (I):

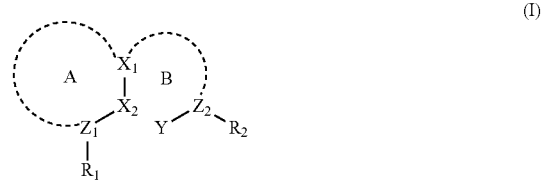

(I)

or a pharmaceutically acceptable salt thereof, wherein
A and B together form a fused ring system AB in which at least one of A or B is an aryl or a heteroaryl ring, wherein one of A or B is a 6-membered ring, and the other is a 5- or 6-membered ring, and wherein the fused ring AB is optionally substituted with one, two or three $R_3$;

each $R_3$ is independently selected from halogen, —$NO_2$, —CN, $C_1$-$C_6$ alkyl, $C_1$-$C_6$ haloalkyl, —$NH_2$, —NH($C_1$-$C_6$ alkyl), —NH(aryl), —N($C_1$-$C_6$ alkyl)$_2$, —N(aryl)$_2$, —N($C_1$-$C_6$ alkyl)(aryl), —OH, $C_1$-$C_6$ alkoxy, $C_1$-$C_6$ haloalkoxy, aryloxy, —SH, —S($C_1$-$C_6$ alkyl), —S(aryl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—NH(aryl), —$CH_2$—N($C_1$-$C_6$ alkyl)$_2$, —$CH_2$N(aryl)$_2$, —$CH_2$—N($C_1$-$C_6$ alkyl)(aryl), —$CONH_2$, —CONH($C_1$-$C_6$ alkyl), —CONH(aryl), —CON($C_1$-$C_6$ alkyl)$_2$, —CON(aryl)$_2$, —CON($C_1$-$C_6$ alkyl)(aryl), —CONH—OH, —CONH—$NH_2$, —C(O)H, —$CO_2$H, —$CO_2$($C_1$-$C_6$ alkyl), —OCO($C_1$-$C_6$ alkyl), —NHCO($C_1$-$C_6$ alkoxy), —NHCO($C_1$-$C_6$ alkyl), —NHCO(aryl), —$NHCONH_2$, —NHCONH($C_1$-$C_6$ alkyl), —NHCONH(aryl), —S(O)$_{1-2}$—($C_1$-$C_6$ alkyl), —NH—S(O)$_{0-2}$—($C_1$-$C_6$ alkyl), —NH—S(O)$_{0-2}$-aryl, —NH—S(O)$_{0-2}$-heteroaryl, aryl($C_0$-$C_6$ alkyl), heteroaryl($C_0$-$C_6$ alkyl), heterocyclyl($C_0$-$C_6$ alkyl), —$CH_2$—$NHCONH_2$, —$CH_2$—NHCONH($C_1$-$C_6$ alkyl), —$CH_2$—NHCONH(aryl), and —$CH_2$—OCO($C_1$-$C_6$ alkyl), or two $R_3$ substituents when attached to the same atom form an oxo or a thioxo group, and wherein each alkyl, aryl, heteroaryl, or heterocyclyl moiety is optionally substituted with one or more $R_5$;

each $R_5$ is independently selected from halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—N($C_1$-$C_6$ alkyl)$_2$, —$CONH_2$, —CONH($C_1$-$C_6$ alkyl), —CON($C_1$-$C_6$ alkyl)$_2$, —CONH—OH, —CONH—$NH_2$, —COH, —$CO_2$H, —$CO_2$($C_1$-$C_6$ alkyl), —CO($C_1$-$C_6$ alkyl), —OCO($C_1$-$C_6$ alkyl), —NHCO($C_1$-$C_6$ alkoxy), —NHCO($C_1$-$C_6$ alkyl), —$NHCONH_2$, —NHCONH($C_1$-$C_6$ alkyl), —NH—S(O)$_{0-2}$—($C_1$-$C_6$ alkyl), —NH—S(O)$_{0-2}$-aryl, —NH—S(O)$_{0-2}$-heteroaryl, —$CH_2$—$NHCONH_2$, —$CH_2$—NHCONH($C_1$-$C_6$ alkyl), and —$CH_2$—OCO($C_1$-$C_6$ alkyl);

$X_1$ and $X_2$, the fusion positions, are independently C or N;
Y is CH, $CH_2$, N, NH, O, or S;
$Z_1$ and $Z_2$ are independently C or N; and
$R_1$ and $R_2$ are independently -L-$R_6$,
wherein each L is independently absent or a linker selected from $C_1$-$C_6$ alkanes, $C_1$-$C_6$ alkenes, $C_1$-$C_6$ alkynes, ethers, thio ethers, amines, amides, carbamates, ureas and combinations thereof, each optionally substituted at any available position with $R_4$;
wherein $R_4$ is selected from ($C_1$-$C_6$)alkyl, ($C_1$-$C_6$) haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, and —S($C_1$-$C_6$ alkyl);

wherein each $R_6$ independently represents aryl optionally substituted with one or more $R_7$, heteroaryl optionally substituted with one or more $R_7$, or heterocyclyl optionally substituted with one or more $R_8$;

each $R_7$ is independently selected from halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —N(aryl)$_2$, —N($C_1$-$C_6$ alkyl)(aryl), —OH, $C_1$-$C_6$ alkoxy, $C_1$-$C_6$ haloalkoxy, —SH, —S($C_1$-$C_6$ alkyl), —S(aryl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—NH(aryl), —$CH_2$—N($C_1$-$C_6$ alkyl)$_2$, —$CH_2$N(aryl)$_2$, —$CH_2$—N($C_1$-$C_6$ alkyl)(aryl), —$CONH_2$, —CONH($C_1$-$C_6$ alkyl), —CONH(aryl), —CON($C_1$-$C_6$ alkyl)$_2$, —CON(aryl)$_2$, —CON($C_1$-$C_6$ alkyl)(aryl), —CONH—OH, —CONH—$NH_2$, —COH, —$CO_2$H, —$CO_2$($C_1$-$C_6$ alkyl), —OCO($C_1$-$C_6$ alkyl), —NHCO($C_1$-$C_6$ alkoxy), —NHCO($C_1$-$C_6$ alkyl), —NHCO(aryl), —$NHCONH_2$, —NHCONH($C_1$-$C_6$ alkyl), —NHCONH(aryl), —NH—S(O)$_{0-2}$—($C_1$-$C_6$ alkyl), —NH—S(O)$_{0-2}$-aryl, —NH—S(O)$_{0-2}$-heteroaryl, —$CH_2$—$NHCONH_2$, —$CH_2$—NHCONH($C_1$-$C_6$ alkyl), —$CH_2$—NHCONH(aryl), and —$CH_2$—OCO($C_1$-$C_6$ alkyl);

each $R_8$ is independently selected from halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$—N(aryl)$_2$, —N($C_1$-$C_6$ alkyl)(aryl), —OH, $C_1$-$C_6$ alkoxy, $C_1$-$C_6$ haloalkoxy, —SH, —S($C_1$-$C_6$ alkyl), —S(aryl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—NH(aryl), —$CH_2$—N($C_1$-$C_6$ alkyl)$_2$, —$CH_2$N(aryl)$_2$, —$CH_2$—N($C_1$-$C_6$ alkyl)(aryl), —$CONH_2$, —CONH($C_1$-$C_6$ alkyl), —CONH(aryl), —CON($C_1$-$C_6$ alkyl)$_2$, —CON(aryl)$_2$, —CON($C_1$-$C_6$ alkyl)(aryl), —CONH—OH, —CONH—$NH_2$, —COH, —$CO_2$H, —$CO_2$($C_1$-$C_6$ alkyl), —OCO($C_1$-$C_6$ alkyl), —NHCO($C_1$-$C_6$ alkoxy), —NHCO($C_1$-$C_6$ alkyl), —NHCO(aryl), —$NHCONH_2$, —NHCONH($C_1$-$C_6$ alkyl), —NHCONH(aryl), —NH—S(O)$_{0-2}$—($C_1$-$C_6$ alkyl), —NH—S(O)$_{0-2}$-aryl, —NH—S(O)$_{0-2}$-heteroaryl, —$CH_2$—$NHCONH_2$, —$CH_2$—NHCONH($C_1$-$C_6$ alkyl), —$CH_2$—NHCONH(aryl), and —$CH_2$—OCO($C_1$-$C_6$ alkyl); or two $R_8$ substituents when attached to the same atom form an oxo group or a thioxo group.

Another aspect of the disclosure provides compounds of formula (II)

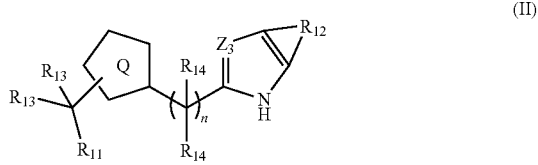

(II)

or a pharmaceutically acceptable salt thereof, wherein
n is an integer 1 or 2;
$R_{11}$ is an aryl or heteroaryl ring, each optionally substituted with one or more $R_{16}$;
each $R_{16}$ is independently selected from halogen, —$NO_2$, —CN, $C_1$-$C_6$ alkyl, $C_1$-$C_6$ haloalkyl, —$NH_2$, —NH ($C_1$-$C_6$ alkyl), —NH(aryl), —N($C_1$-$C_6$ alkyl)$_2$, —N(aryl)$_2$, —N($C_1$-$C_6$ alkyl)(aryl), —OH, $C_1$-$C_6$ alkoxy, $C_1$-$C_6$ haloalkoxy, aryloxy, —SH, —S($C_1$-$C_6$ alkyl), —S(aryl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—NH(aryl), —$CH_2$—N($C_1$-$C_6$ alkyl)$_2$, —$CH_2$N(aryl)$_2$, —$CH_2$—N($C_1$-$C_6$ alkyl)(aryl), —$CONH_2$, —CONH($C_1$-$C_6$ alkyl), —CONH(aryl), —CON($C_1$-$C_6$ alkyl)$_2$, —CON(aryl)$_2$, —CON($C_1$-$C_6$ alkyl)(aryl), —CONH—OH, —CONH—$NH_2$, —C(O)H, —$CO_2$H, —$CO_2(C_1$-$C_6$ alkyl), —$OCO(C_1$-$C_6$ alkyl), —NHCO($C_1$-$C_6$ alkoxy), —NHCO($C_1$-$C_6$ alkyl), —NHCO(aryl), —$NHCONH_2$, —NHCONH($C_1$-$C_6$ alkyl), —NHCONH(aryl), —$S(O)_{1\text{-}2}$—($C_1$-$C_6$ alkyl), —NH—$S(O)_{0\text{-}2}$—($C_1$-$C_6$ alkyl), —NH—$S(O)_{0\text{-}2}$-aryl, —NH—$S(O)_{0\text{-}2}$-heteroaryl, aryl($C_0$-$C_6$ alkyl), heteroaryl($C_0$-$C_6$ alkyl), heterocyclyl($C_0$-$C_6$ alkyl), —$CH_2$—$NHCONH_2$, —$CH_2$—NHCONH($C_1$-$C_6$ alkyl), —$CH_2$—NHCONH(aryl), and —$CH_2$—OCO($C_1$-$C_6$ alkyl);

$R_{12}$ is an aryl or heteroaryl ring, each optionally substituted with one or more $R_{17}$;

each $R_{17}$ is independently selected from halogen, —$NO_2$, —CN, $C_1$-$C_6$ alkyl, $C_1$-$C_6$ haloalkyl, —$NH_2$, —NH($C_1$-$C_6$ alkyl), —NH(aryl), —N($C_1$-$C_6$ alkyl)$_2$, —N(aryl)$_2$, —N($C_1$-$C_6$ alkyl)(aryl), —OH, $C_1$-$C_6$ alkoxy, $C_1$-$C_6$ haloalkoxy, aryloxy, —SH, —S($C_1$-$C_6$ alkyl), —S(aryl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—NH(aryl), —$CH_2$—N($C_1$-$C_6$ alkyl)$_2$, —$CH_2$N(aryl)$_2$, —$CH_2$—N($C_1$-$C_6$ alkyl)(aryl), —$CONH_2$, —CONH($C_1$-$C_6$ alkyl), —CONH(aryl), —CON($C_1$-$C_6$ alkyl)$_2$, —CON(aryl)$_2$, —CON($C_1$-$C_6$ alkyl)(aryl), —CONH—OH, —CONH—$NH_2$, —C(O)H, —$CO_2$H, —$CO_2(C_1$-$C_6$ alkyl), —$OCO(C_1$-$C_6$ alkyl), —NHCO($C_1$-$C_6$ alkoxy), —NHCO($C_1$-$C_6$ alkyl), —NHCO(aryl), —$NHCONH_2$, —NHCONH($C_1$-$C_6$ alkyl), —NHCONH(aryl), —$S(O)_{1\text{-}2}$—($C_1$-$C_6$ alkyl), —NH—$S(O)_{0\text{-}2}$—($C_1$-$C_6$ alkyl), —NH—$S(O)_{0\text{-}2}$-aryl, —NH—$S(O)_{0\text{-}2}$-heteroaryl, aryl($C_0$-$C_6$ alkyl), heteroaryl($C_0$-$C_6$ alkyl), heterocyclyl($C_0$-$C_6$ alkyl), —$CH_2$—$NHCONH_2$, —$CH_2$—NHCONH($C_1$-$C_6$ alkyl), —$CH_2$—NHCONH(aryl), and —$CH_2$—OCO($C_1$-$C_6$ alkyl);

each $R_{13}$ is independently hydrogen, $C_1$-$C_6$ alkyl, $C_1$-$C_6$ haloalkyl, OH, or $NH_2$, or two $R_{13}$ substituents when attached to the same atom form an oxo or thioxo group;

each $R_{14}$ is independently hydrogen, $C_1$-$C_6$ alkyl, $C_1$-$C_6$ haloalkyl, OH, or $NH_2$, or two $R_{14}$ substituents when attached to the same atom form an oxo or thioxo group;

$Z_3$ is N, CH, or C($C_1$-$C_6$ alkyl); and ring Q is a 5-member heteroaryl or heterocycyl ring substituted with one or more $R_{15}$, each $R_{15}$ is independently selected from halogen, —$NO_2$, —CN, $C_1$-$C_6$ alkyl, $C_1$-$C_6$ haloalkyl, —$NH_2$, —NH($C_1$-$C_6$ alkyl), —NH(aryl), —N($C_1$-$C_6$ alkyl)$_2$, —N(aryl)$_2$, —N($C_1$-$C_6$ alkyl)(aryl), —OH, $C_1$-$C_6$ alkoxy, $C_1$-$C_6$ haloalkoxy, —SH, —S($C_1$-$C_6$ alkyl), —S(aryl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—NH(aryl), —$CH_2$—N($C_1$-$C_6$ alkyl)$_2$, —$CH_2$N(aryl)$_2$, —$CH_2$—N($C_1$-$C_6$ alkyl)(aryl), —$CONH_2$, —CONH($C_1$-$C_6$ alkyl), —CONH(aryl), —CON($C_1$-$C_6$ alkyl)$_2$, —CON(aryl)$_2$, —CON($C_1$-$C_6$ alkyl)(aryl), —CONH—OH, —CONH—$NH_2$, —COH, —$CO_2$H, —$CO_2(C_1$-$C_6$ alkyl), —$OCO(C_1$-$C_6$ alkyl), —NHCO($C_1$-$C_6$ alkoxy), —NHCO($C_1$-$C_6$ alkyl), —NHCO(aryl), —$NHCONH_2$, —NHCONH($C_1$-$C_6$ alkyl), —NHCONH(aryl), —$S(O)_{1\text{-}2}$—($C_1$-$C_6$ alkyl), —NH—$S(O)_{0\text{-}2}$—($C_1$-$C_6$ alkyl), —NH—$S(O)_{0\text{-}2}$-aryl, —NH—$S(O)_{0\text{-}2}$-heteroaryl, aryl($C_0$-$C_6$ alkyl), heteroaryl($C_0$-$C_6$ alkyl), heterocyclyl($C_0$-$C_6$ alkyl), cycloalkyl($C_0$-$C_6$ alkyl), —$CH_2$—$CO_2$H, —$CH_2$—$CO_2(C_1$-$C_6$ alkyl), —$CH_2$—$CONH_2$, —$CH_2$—CONH($C_1$-$C_6$ alkyl), —$CH_2$—CON($C_1$-$C_6$ alkyl)$_2$, —$CH_2$—$NHCONH_2$, —$CH_2$—NHCONH($C_1$-$C_6$ alkyl), —$CH_2$—NHCON($C_1$-$C_6$ alkyl)$_2$, —$CH_2$—NHCONH(aryl), and —$CH_2$—OCO($C_1$-$C_6$ alkyl), or two $R_{15}$ substituents when attached to the same atom form an oxo or thioxo group, and wherein each alkyl, aryl, heteroaryl, or heterocyclyl moiety is optionally substituted with one or more $R_{18}$;

wherein each $R_{18}$ is independently selected from halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —CO($C_1$-$C_6$ alkyl), —NHCO($C_1$-$C_6$ alkyl), and pyridinyl.

Another aspect of the disclosure provides pharmaceutical compositions comprising one or more of compounds of the disclosure and a pharmaceutically acceptable carrier, diluent, or excipient.

Another aspect of the disclosure provides methods for treating diseases that are ameliorated by the inhibition of MetRS, the methods include administering to a patient in need thereof a therapeutically effective amount of a compound or a pharmaceutical composition of the disclosure. In certain embodiments, the disease is a protozoan infection selected from the group consisting of *Cryptosporidia, Cyclospora, Giardia, Leishmania, Trichomonas,* and *Trypanosoma*. In certain embodiments, the disease is a bacterial infection caused by Gram positive bacteria, such as *Staphylococcus, Streptococcus, Enterococcus, Clostridia, Bacillus, Listeria, Corynebacteria, Arcanobacteria, Rothia,* and *Rhodococcus*, Gram negative bacteria, such as *Brucella, Campylobacter,* and *Helicobacter, Mycobacteria,* such as *M. tuberculosis, M. avium, M. abscessus, M. kansasii, M. chelonae, M. marinum, M. ulcerans,* and *M. haemophilum,* or Mycoplasma. In certain embodiments, the disease is caused by *Staphylococcus aureus*, including methicillin resistant *Staphylococcus aureus* (MRSA), *Enterococcus faecalis* and *Enterococcus faecium*, including vancomycin resistant *Enterococcus* (VRE).

BRIEF DESCRIPTION OF THE DRAWINGS

The accompanying drawings are included to provide a further understanding of the methods and compositions of the disclosure, and are incorporated in and constitute a part of this specification. The drawings illustrate one or more embodiment(s) of the disclosure and, together with the description, serve to explain the principles and operation of the disclosure.

DETAILED DESCRIPTION

Figure 1:
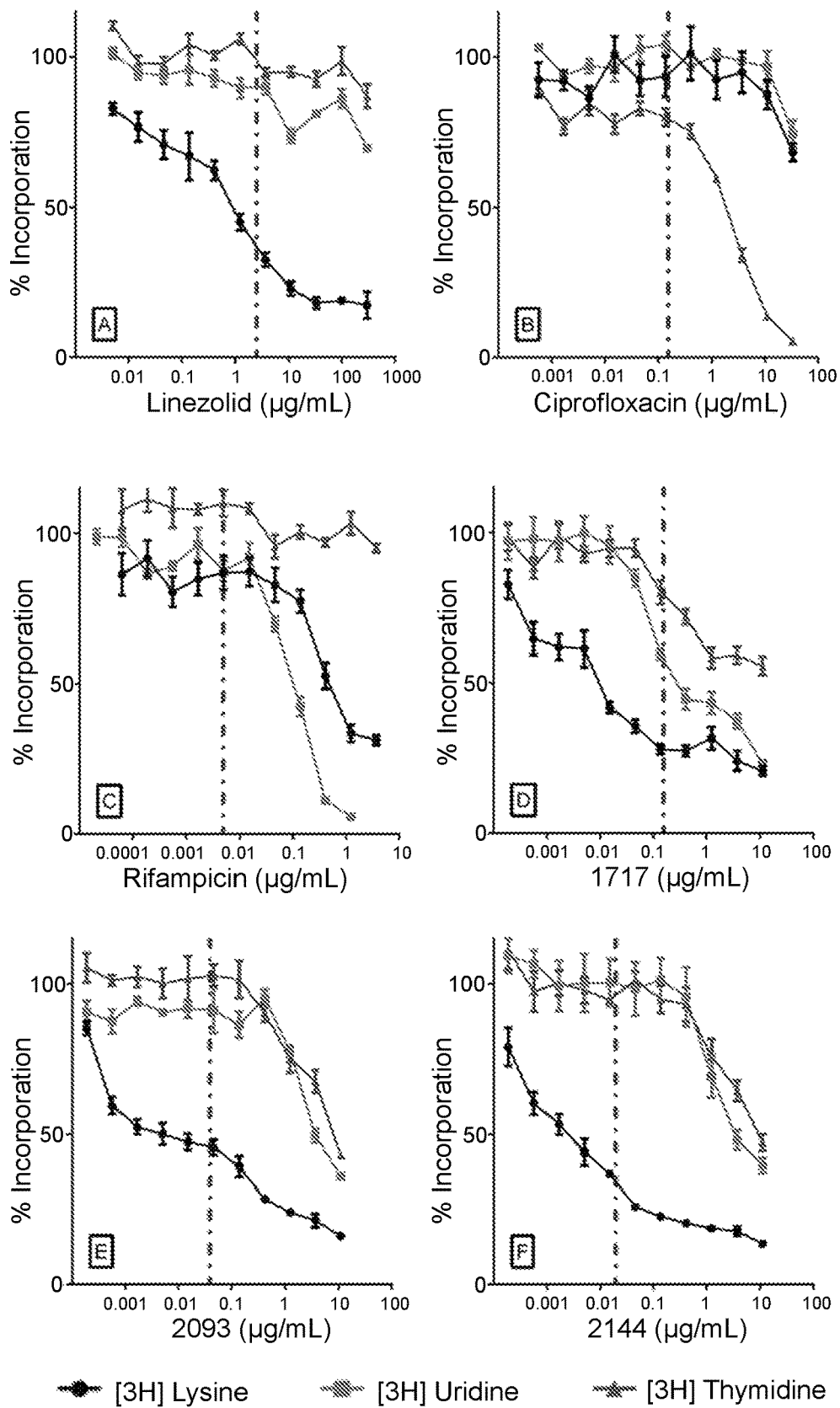
FIG. 1 illustrates macromolecular synthesis experiments. Incorporation of radiolabeled precursors into *S. aureus* (ATCC 29213) in 30 minute incubations in the presence of established antibiotics or MetRS inhibitors. The dashed vertical line indicates the MIC.
Figure 2:
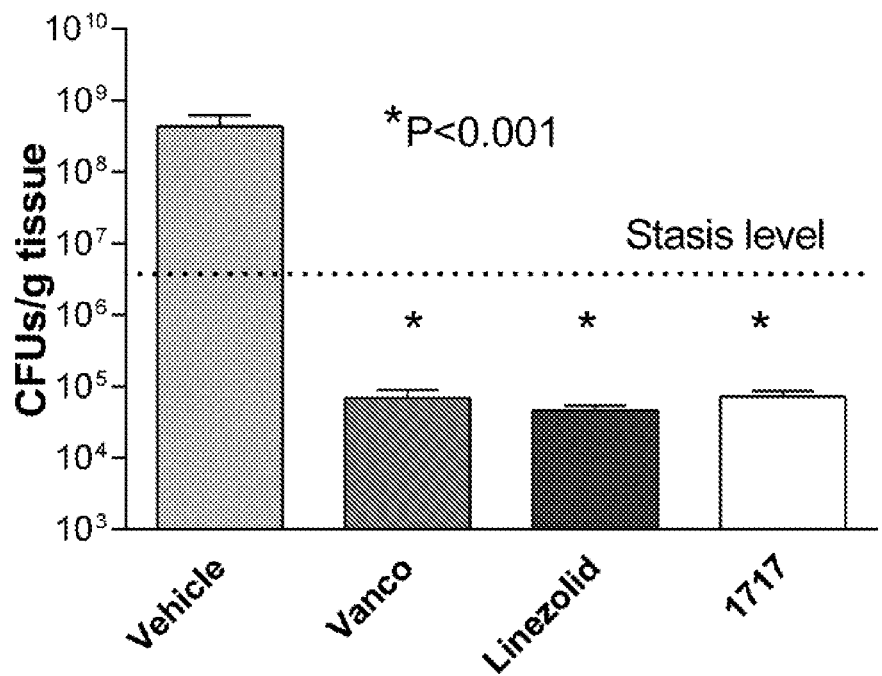
FIG. 2 illustrates efficacy of MetRS inhibitors in neutropenic mouse *S. aureus* thigh infection model. Error bars are SEMs. Test compounds were given as described in the examples. Stasis level was determined from untreated mice sacrificed 1 h post-infection (p.i.).
Figure 2:
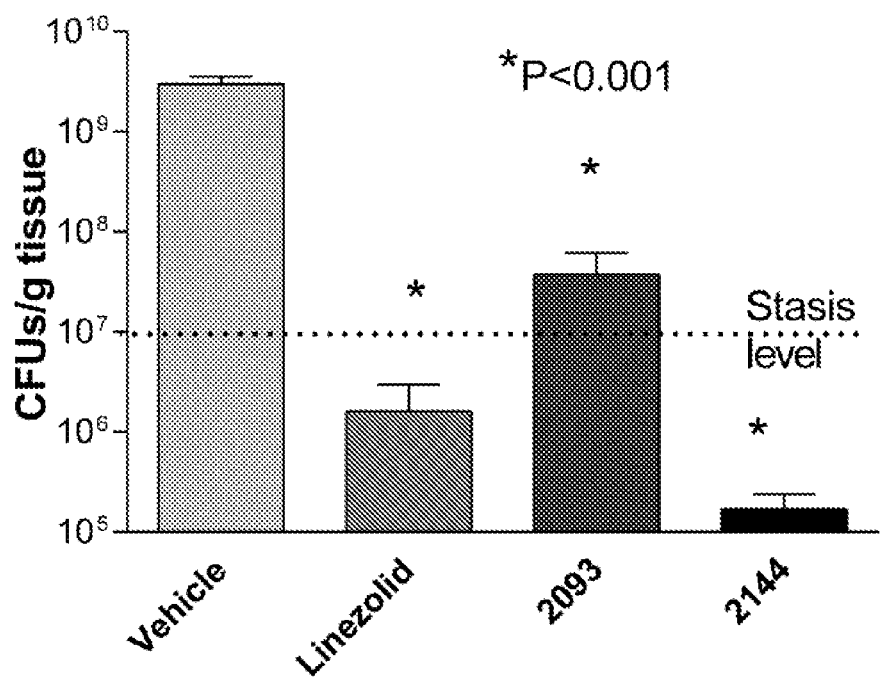

Before the disclosed processes and materials are described, it is to be understood that the aspects described herein are not limited to specific embodiments, apparatus, or configurations, and as such can, of course, vary. It is also to be understood that the terminology used herein is for the purpose of describing particular aspects only and, unless specifically defined herein, is not intended to be limiting.

In view of the present disclosure, the methods and compositions described herein can be configured by the person of ordinary skill in the art to meet the desired need. In general, the disclosed materials, methods, and apparatus provide improvements in treatment of bacterial and/or protozoan infections. The disclosure provides novel MetRS inhibitor compounds that show promising antibiotic and antiprotozoal activity. At the same time, in certain embodiments, the compounds of the disclosure show good oral bioavailability and pharmacokinetic properties.

Thus, one aspect of the disclosure provides compounds of formula (I).

In one embodiment, the disclosure provides compounds of formula (I) wherein the fused ring system AB, one of A or B is a 6-membered ring, and the other is a 5-membered ring. In one embodiment, the fused ring system AB, one of A or B is a 6-membered ring, and the other is a 6-membered ring.

Another embodiment of the disclosure provides compounds of formula (I), wherein the fused ring AB is selected from the group consisting of:

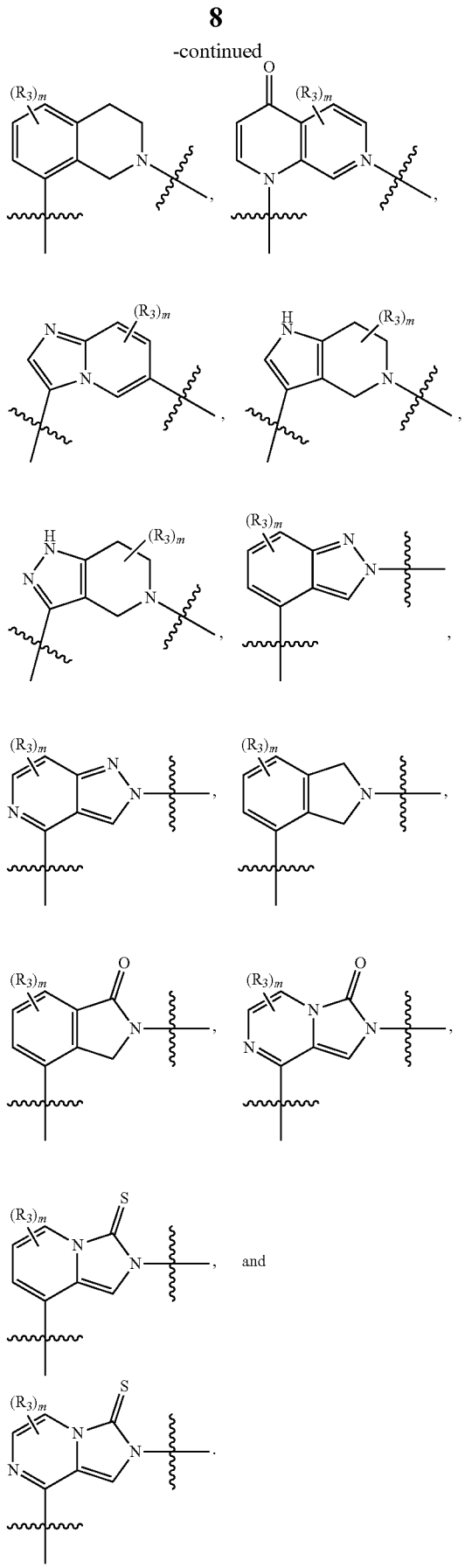

In one embodiment, the fused ring AB is selected from:

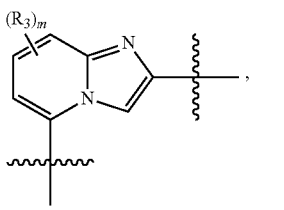,

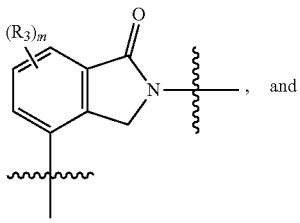, and

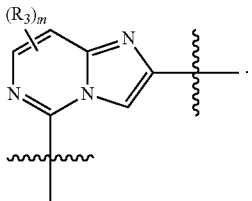.

In one embodiment, the fused ring AB is selected from:

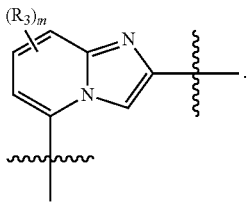.

Another embodiment of the disclosure provides compounds of formula (I), wherein the fused ring AB is unsubstituted.

Another embodiment of the disclosure provides compounds of formula (I), wherein the fused ring AB is optionally substituted with one or two $R_3$; or wherein the fused ring AB is optionally substituted with one $R_3$.

In certain embodiments, each $R_3$ is independently selected from halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —S($C_1$-$C_6$ alkyl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—N($C_1$-$C_6$ alkyl)$_2$, —$CONH_2$, —CONH($C_1$-$C_6$ alkyl), —CON($C_1$-$C_6$ alkyl)$_2$, —CONH—OH, —CONH—$NH_2$, —COH, —$CO_2$H, —$CO_2$($C_1$-$C_6$ alkyl), —NHCO($C_1$-$C_6$ alkyl), —NHCO($C_1$-$C_6$ alkoxy), —NH—S(O)$_{0-2}$—($C_1$-$C_6$ alkyl), —S(O)$_{1-2}$—($C_1$-$C_6$ alkyl), —NHCONH($C_1$-$C_6$ alkyl), 4-acetyl-piperazin-1-yl, and benzyl, or two $R_3$ substituents when attached to the same atom form an oxo or a thioxo group, and wherein each alkyl, aryl, heteroaryl, or heterocyclyl moiety is optionally substituted with one or more $R_5$. In some embodiments, each $R_3$ is independently selected from halogen, $C_1$-$C_6$ alkyl, —$NH_2$, —NH($C_1$-$C_6$ alkyl), —N($C_1$-$C_6$ alkyl)$_2$, —S($C_1$-$C_6$ alkyl), —NHCO($C_1$-$C_6$ alkyl), —NHCO($C_1$-$C_6$ alkoxy), —NH—S(O)$_2$—($C_1$-$C_6$ alkyl), —S(O)$_{1-2}$—($C_1$-$C_6$ alkyl), —NHCONH($C_1$-$C_6$ alkyl), 4-acetyl-piperazin-1-yl, and benzyl, or two $R_3$ substituents when attached to the same atom form an oxo or a thioxo group, and wherein each alkyl, aryl, heteroaryl, or heterocyclyl moiety is optionally substituted with one or more $R_5$. In some embodiments, each $R_3$ is independently selected from halogen, $C_1$-$C_6$ alkyl, —$NH_2$, —$SCH_3$, —$NHCOCH_3$, —$NHCO_2CH_3$, —NH—$SO_2$—$CH_3$, —$SO_2CH_3$, —NHCO—$NHCH_3$, 4-acetyl-piperazin-1-yl, and benzyl, or two $R_3$ substituents when attached to the same atom form an oxo or a thioxo group, and wherein each alkyl, aryl, heteroaryl, or heterocyclyl moiety is optionally substituted with one or more $R_5$. In some embodiments, each $R_3$ is independently selected from halogen, $C_1$-$C_6$ alkyl, —$NH_2$, —$SCH_3$, —$NHCOCH_3$, —$NHCO_2CH_3$, —NH—$SO_2$—$CH_3$, —$SO_2CH_3$, —NHCO—$NHCH_3$, 4-acetyl-piperazin-1-yl, and benzyl, or two $R_3$ substituents when attached to the same atom form an oxo or a thioxo group.

Another embodiment of the disclosure provides compounds of formula (I), wherein at least one L is absent; or one L is absent and another L is a linker; or each L is a linker. For example, in certain embodiments, L in $R_1$ is absent, and L in $R_1$ is a linker. In certain other embodiments, L in $R_1$ is a linker, and L in $R_2$ is absent.

In certain embodiments, the linker is a $C_1$-$C_6$ alkane, ether, or amine group, each optionally substituted at any available position with $R_4$. In certain embodiments, the linker is a $C_1$-$C_6$ alkane or amine group, each optionally substituted at any available position with $R_4$. In certain embodiments, the linker is methylene or ethylene. In certain embodiments, the linker is methylene. In certain embodiments, the linker is a methylene or —NH—methyl-. In certain embodiments, one L (e.g., in $R_1$) is absent and the other L (e.g., in $R_2$) is methylene.

Some particular embodiments include those wherein $R_6$ represents aryl optionally substituted with one or more $R_7$ or a heteroaryl optionally substituted with one or more $R_7$.

Other particular embodiments include those wherein $R_1$ is —$R_6$.

Particular embodiments of the disclosure provides compounds of formula (I) wherein $R_6$ (e.g., in $R_1$) represents aryl optionally substituted with one or more $R_7$. In certain embodiments, $R_6$ represents phenyl optionally substituted with one or more $R_7$. In certain embodiments, $R_6$ represents phenyl optionally substituted with one or two $R_7$. In certain embodiments, $R_6$ represents phenyl substituted with one or two $R_7$. In certain embodiments, $R_6$ is phenyl substituted with two $R_7$.

Some particular embodiments include those wherein each $R_7$ (e.g., on $R_6$ in $R_1$) is independently selected from halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl). Other particular embodiments include those wherein each $R_7$ is independently selected from halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy.

Another embodiment of the disclosure provides compounds of formula (I), wherein $R_6$ (e.g., in $R_1$) is phenyl optionally substituted with one or two substituents selected from halogen and $C_1$-$C_6$ alkoxy.

Some particular embodiments of compounds of formula (I) include the compounds having the following formula:

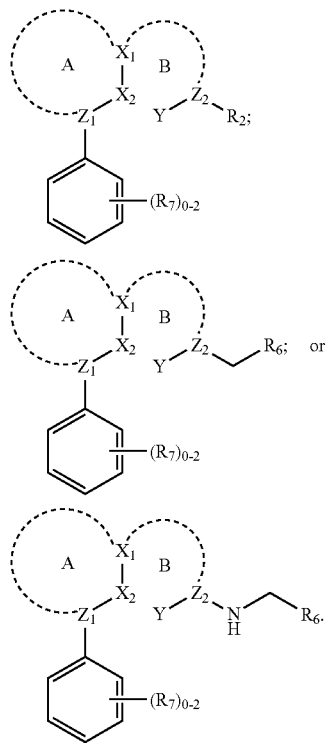

In certain embodiments, compounds of formula (I) include the compounds having the following formula:

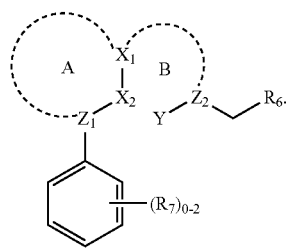

Another embodiment of the disclosure provides compounds of formula (I), wherein $R_2$ is -L-$R_6$, wherein L is the linker. In some embodiments, $R_2$ is —$CH_2$—$R_6$. For example, in some embodiments, $R_6$ (e.g., in $R_2$) is heteroaryl optionally substituted with one or more $R_7$. In some embodiments, $R_6$ (e.g., in $R_2$) is imidazo[4,5-b]pyridine or benzo[d]imidazole, each optionally substituted with one or more $R_7$.

For example, in some embodiments, each $R_7$ (e.g., on $R_6$ in $R_2$) is independently selected from halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl). In some embodiments, each $R_7$ is independently selected from halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy.

Some particular embodiments of compounds of formula (I) include the compounds having the following formula:

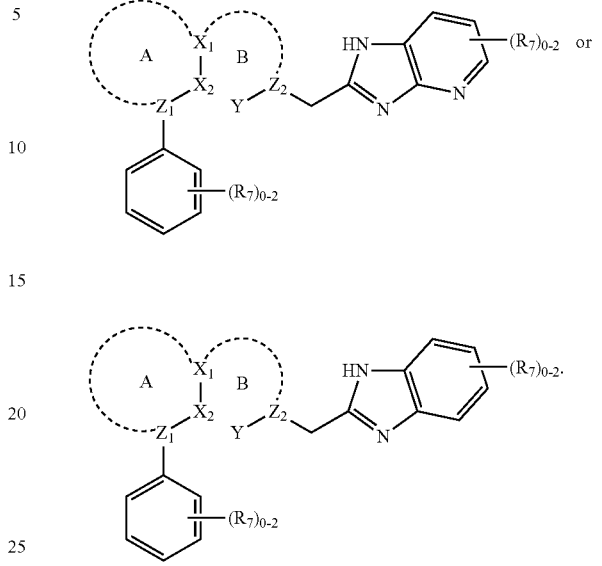

Some particular embodiments of compounds of formula (I) include the compounds having the following formula:

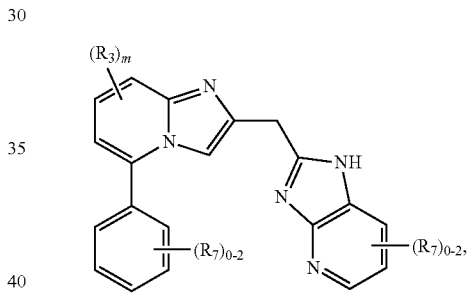

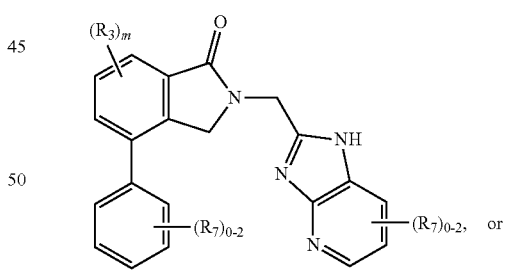

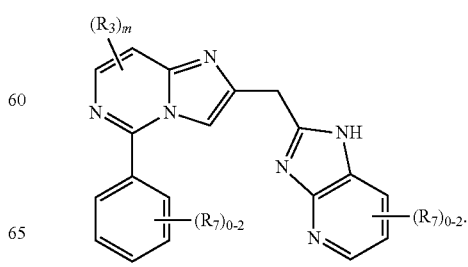

Some particular embodiments of compounds of formula (I) include the compounds having the following formula:

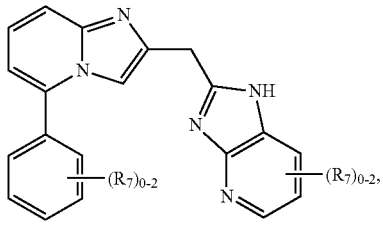

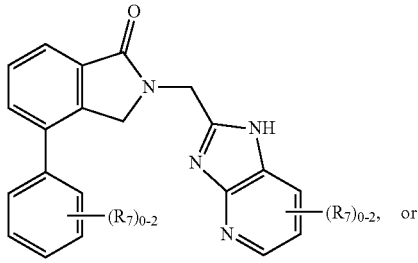

or

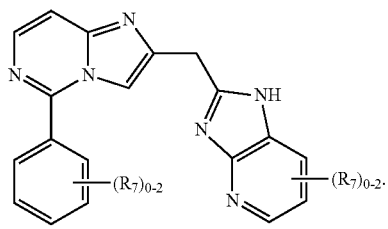

Another aspect of the disclosure provides compounds of formula (II).

In one embodiment, the compound of formula (II) is not: 1-(1H-1,3-benzodiazol-2-ylmethyl)-4-[(2,4-dichlorophenyl)methyl]-2,3-dihydro-1H-imidazol-2-one; 1-(1H-1,3-benzodiazol-2-ylmethyl)-4-[(2,4-dichlorophenyl)methyl]-2,3-dihydro-1H-imidazol-2-ol; or 4-[(2,4-dichlorophenyl)methyl]-1-({5-fluoro-3H-imidazo[4,5-b]pyridin-2-yl}methyl)-2,3-dihydro-1H-imidazol-2-one.

In one embodiment, the compound of formula (II) is not: 4-[(2,4-dichlorophenyl)methyl]-3-ethyl-1-({5-fluoro-1H-imidazo[4,5-b]pyridin-2-yl}methyl)-2,3-dihydro-1H-imidazol-2-one; or 1-({5-chloro-1H-imidazo[4,5-b]pyridin-2-yl}methyl)-4-[(2-chloro-4-methoxyphenyl)methyl]-3-ethyl-2,3-dihydro-1H-imidazol-2-one.

Another embodiment of the disclosure provides compounds of formula (II), wherein Q ring is imidazole or dihydroimidazole. In some embodiments, Q is imidazole or dihydroimidazole substituted with one, two, or three $R_{15}$.

Some particular embodiments of compounds of formula (II) include the compounds having the following formula:

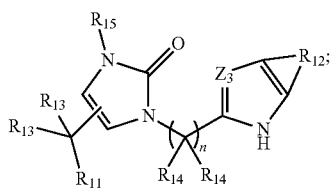

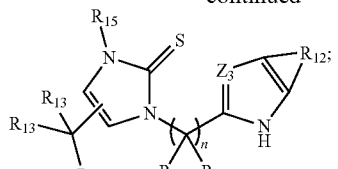

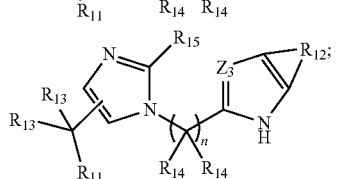

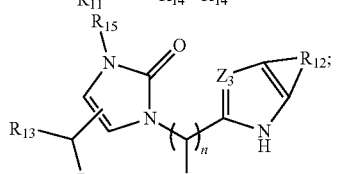

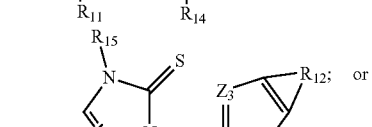

or

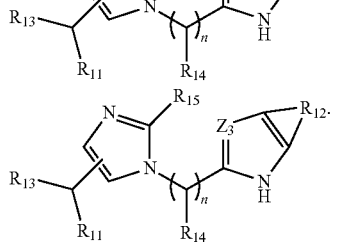

Some particular embodiments of compounds of formula (II) include the compounds having the following formula:

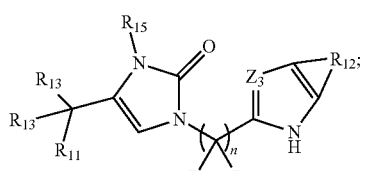

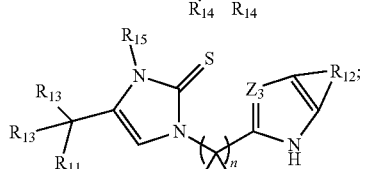

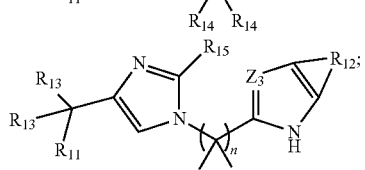

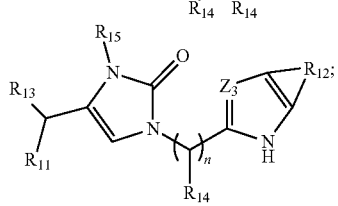

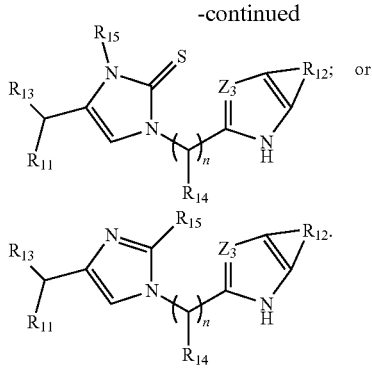

Another embodiment of the disclosure provides compounds of formula (II), wherein each $R_{13}$ is independently hydrogen or methyl. In certain embodiments, one $R_{13}$ is hydrogen and other $R_{13}$ is methyl. In certain embodiments, each $R_{13}$ is independently hydrogen.

Another embodiment of the disclosure provides compounds of formula (II), wherein each $R_{14}$ is independently hydrogen or methyl; or one $R_{14}$ is hydrogen and other $R_{14}$ is methyl. In certain embodiments, each $R_{14}$ is independently hydrogen.

Some particular embodiments of compounds of formula (II) include those wherein n is 1.

Some particular embodiments of compounds of formula (II) include the compounds having the following formula:

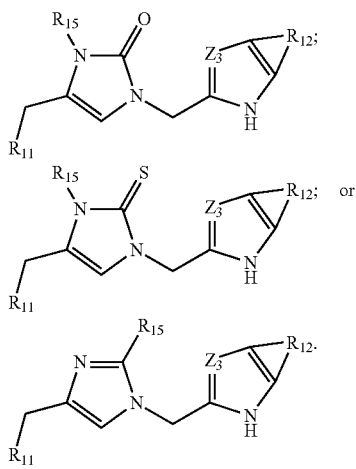

Some particular embodiments of compounds of formula (II) include those wherein $R_{11}$ represents aryl optionally substituted with one or more $R_{16}$. In some embodiments, $R_{11}$ represents phenyl optionally substituted with one or more $R_{16}$. In some embodiments, $R_{11}$ represents phenyl optionally substituted with one or two $R_{16}$. In some embodiments, $R_{11}$ represents phenyl substituted with one or two $R_{16}$. In some embodiments, $R_{11}$ is phenyl substituted with two $R_{16}$.

Another embodiment of the disclosure provides compounds of formula (II), wherein each $R_{16}$ is independently selected from halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl). In certain embodiments, each $R_{16}$ is independently selected from halogen, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy. In certain embodiments, $R_{16}$ phenyl optionally substituted with one or two substituents selected from halogen and $C_1$-$C_6$ alkoxy.

Some embodiments of compounds of formula (II) include those wherein $Z_3$ is N.

Other particular embodiments of compounds of formula (II) include those wherein $R_{12}$ is unsubstituted phenyl or pyridyl ring. In certain embodiments, $R_{12}$ is phenyl or pyridyl ring, each optionally substituted with one or more $R_{17}$. In certain embodiments, each $R_{17}$ is independently selected from halogen, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl). In certain embodiments, each $R_{17}$ is independently selected from halogen, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy. In certain embodiments, each $R_{17}$ is independently selected from halogen, $C_1$-$C_6$ alkyl, $C_1$-$C_6$ haloalkyl, $C_1$-$C_6$ alkoxy, and $C_1$-$C_6$ haloalkoxy.

Another embodiment of the disclosure provides compounds of formula (II), wherein $R_{12}$ is phenyl or pyridyl ring, each optionally substituted with halogen or $C_1$-$C_6$ alkyl.

Some particular embodiments of compounds of formula (II) include those wherein $R_{15}$ is independently selected from $C_1$-$C_6$ alkyl, $C_1$-$C_6$ haloalkyl, —NH$_2$, —NH($C_1$-$C_6$ alkyl), —N($C_1$-$C_6$ alkyl)$_2$, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —CH$_2$—NH($C_1$-$C_6$ alkyl), —CH$_2$—N($C_1$-$C_6$ alkyl)$_2$, —CONH$_2$, —CONH($C_1$-$C_6$ alkyl), —S(O)$_{1-2}$—($C_1$-$C_6$ alkyl), —NH—S(O)$_{0-2}$—($C_1$-$C_6$ alkyl), —NH—S(O)$_{0-2}$-aryl, —NH—S(O)$_{0-2}$-heteroaryl, aryl($C_0$-$C_6$ alkyl), heteroaryl($C_0$-$C_6$ alkyl), heterocyclyl($C_0$-$C_6$ alkyl), cycloalkyl($C_0$-$C_6$ alkyl), —CH$_2$—CO$_2$H, —CH$_2$—CO$_2$($C_1$-$C_6$ alkyl), —CH$_2$—CONH$_2$, —CH$_2$—CONH($C_1$-$C_6$ alkyl), —CH$_2$—CON($C_1$-$C_6$ alkyl)$_2$, —CH$_2$—NHCON($C_1$-$C_6$ alkyl)$_2$, and —CH$_2$—OCO($C_1$-$C_6$ alkyl), or two $R_{15}$ substituents when attached to the same atom form an oxo or thioxo group, and wherein each alkyl, aryl, heteroaryl, or heterocyclyl moiety is optionally substituted with one or more $R_{18}$. Some other embodiments of compounds of formula (II) include those wherein $R_{15}$ is independently selected from $C_1$-$C_6$ alkyl, $C_1$-$C_6$ haloalkyl, —S($C_1$-$C_6$ alkyl), hydroxy($C_1$-$C_6$ alkyl), alkoxy($C_1$-$C_6$ alkyl), amino($C_1$-$C_6$ alkyl), —CH$_2$—NH($C_1$-$C_6$ alkyl), —CONH$_2$, —CONH($C_1$-$C_6$ alkyl), —S(O)$_{1-2}$—($C_1$-$C_6$ alkyl), —NH—S(O)$_{0-2}$—($C_1$-$C_6$ alkyl), heterocyclyl($C_0$-$C_6$ alkyl), cycloalkyl($C_0$-$C_6$ alkyl), —CH$_2$—CO$_2$H, —CH$_2$—CO$_2$($C_1$-$C_6$ alkyl), —CH$_2$—CONH$_2$, —CH$_2$—CONH($C_1$-$C_6$ alkyl), and —CH$_2$—OCO($C_1$-$C_6$ alkyl), or two $R_{15}$ substituents when attached to the same atom form an oxo or thioxo group, and wherein each alkyl, aryl, heteroaryl, or heterocyclyl moiety is optionally substituted with one or more $R_{18}$.

Therapeutics Applications

The compounds of the disclosure are capable of inhibiting the activity of MetRS. Inhibition of MetRS may be either in vivo and/or in vitro. Accordingly, the disclosure provides methods for treating diseases that are ameliorated by the inhibition of MetRS providing to a patient in need of such treatment a therapeutically effective amount of either a compound of the disclosure (e.g., compounds formulae (I)-(II) or any preceding embodiment), or a pharmaceutical composition comprising one or more of compounds of the disclosure.

In certain embodiments, the diseases that are ameliorated by the inhibition of MetRS by the compounds of the present disclosure include bacterial and protozoan infections.

Examples of protozoan infection include those caused by, but not limited to, *Cryptosporidia, Cyclospora, Giardia, Leishmania, Trichomonas,* and *Trypanosoma*. In certain embodiments, protozoan infection is caused by one of *Trypanosoma brucei, Trypanosoma cruzi,* or *Leishmania* species.

Examples of bacterial diseases include those caused by, but not limited to, Gram positive bacteria, such as *Staphylococcus, Streptococcus, Enterococcus, Clostridia, Bacillus, Listeria, Corynebacteria, Arcanobacteria, Rothia,* and *Rhodococcus,* Gram negative bacteria, such as *Brucella, Campylobacter,* and *Helicobacter, Mycobacteria,* such as *M. tuberculosis, M. avium, M. abscessus, M. kansasii, M. chelonae, M. marinum, M. ulcerans,* and *M. haemophilum,* and Mycoplasma. Some particular embodiments include infections caused by *Staphylococcus aureus,* including methicillin resistant *Staphylococcus aureus* (MRSA), *Enterococcus faecalis* or *Enterococcus faecium,* including vancomycin resistant *Enterococcus* (VRE).

In certain embodiment, the method also includes administering a second antibacterial compound. Such second antibacterial compounds may be, but are not limited to, a quinolone, an acridine, a phenothiazine, an aminoglycoside, a macrolide, an amphenicol, a steroid, an ansamycin, an antifolate, a polymyxin, a glycopeptide, a cephalosporin, a lactam, and any combination thereof In certain embodiments, the second antibacterial compound may be administered in an amount below its minimum inhibitory concentration (MIC) established in the absence of the one or more compounds. For example, the second antibacterial compound may be administered in an amount less than 1% of, e.g., less than 10%, or less than 25%, or less than 50%, or less than 75%, or even less than 90% of the minimum inhibitory concentration (MIC).

The development of the compositions of the present application is highly significant as it solves the problem of poor oral bioavailability of MetRS inhibitors. Thus, in certain embodiments, the compounds of the disclosure are orally administered.

Pharmaceutical Compositions

In another aspect, the present disclosure provides compositions comprising one or more of compounds as described above with respect to formula (I) or (II) and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds. In certain embodiments, the composition may include one or more antibiotic compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any technique, such as lyophilization, and reconstituted prior to use.

For transmucosal administration, penetrants appropriate to the barrier to be permeated are used in the formulation.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by several methods, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound. For buccal administration, the compositions may take the form of tablets or lozenges formulated in conventional manner. For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles are suitable for administering compounds to the eye.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are examples of delivery vehicles that may be used to deliver compound(s). Certain organic solvents such as dimethyl sulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models may be used for testing the efficacy of the active metabolites to treat or prevent the various diseases described above. Animal models suitable for testing the bioavailability and/or metabolism of compounds into active metabolites can be used. Such information can be adapted to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective dosages without undue experimentation.

Definitions

The following terms and expressions used herein have the indicated meanings.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Terms used herein may be preceded and/or followed by a single dash, "—", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, and —CH$_2$CH(CH$_2$CH$_3$)CH$_2$—.

The term "alkylene" refers to a bivalent alkyl group. An "alkylene chain" is a polymethylene group, i.e., —(CH$_2$)$_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thioxo groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl.

The term "halo" or "halogen" as used herein, means —Cl, —Br, —I or —F.

The terms "haloalkyl" and "haloalkoxy" refer to an alkyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl.

The terms "heterocyclyl" and "heterocycloalkyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thioxo" as used herein means a =S group.

The term "unsaturated" as used herein means the referenced chemical structure contains at least one carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated.

"Treating" or "treatment" as used herein covers the treatment of a disease or disorder described herein, in a subject, preferably a human, and includes:
 i. inhibiting a disease or disorder, i.e., arresting its development;
 ii. relieving a disease or disorder, i.e., causing regression of the disorder;
 iii. slowing progression of the disorder; and/or
 iv. inhibiting, relieving, ameliorating, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

Methods of Preparation

Many general references providing chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, N.Y. 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/l, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage.

The compounds disclosed herein can be made using procedures familiar to the person of ordinary skill in the art and as described herein. For example, compounds of structural formula (I) and/or (I) can be prepared according to Schemes 1-53 (below), or analogous synthetic schemes. One of skill in the art can adapt the reaction sequences of Schemes 1-53 to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether.

EXAMPLES

The preparation of the compounds of the disclosure is illustrated further by the following examples, which are not to be construed as limiting the disclosure in scope or spirit to the specific procedures and compounds described in them. Unless otherwise stated, all chemicals were purchased from commercial suppliers and used without further purification. The microwave irradiation was performed in a CEM Discover System. The final purity of all compounds was determined by analytical LCMS with Phenomenex Onyx Monolithic C18 column (4.6 mm×100 mm). The products were detected by UV at the detection frequency of 220 nm. All compounds were determined to be >95% pure by this method. The purification by preparative HPLC was performed on Waters Xterra Prep RP18 OBD 5 µM (19 mm×50 mm) with $CH_3CN/H_2O$ and 0.1% TFA as eluent. The mass spectra were recorded with the Agilent Liquid Chromatograph—Ion Trap Mass Spectrometer. Unless otherwise noted, NMR spectra were recorded with Bruker 500 MHz spectrometer at ambient temperature.

Example 1

Scheme 1

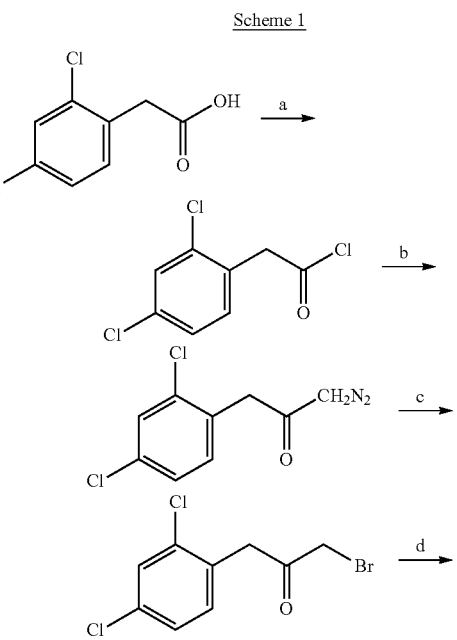

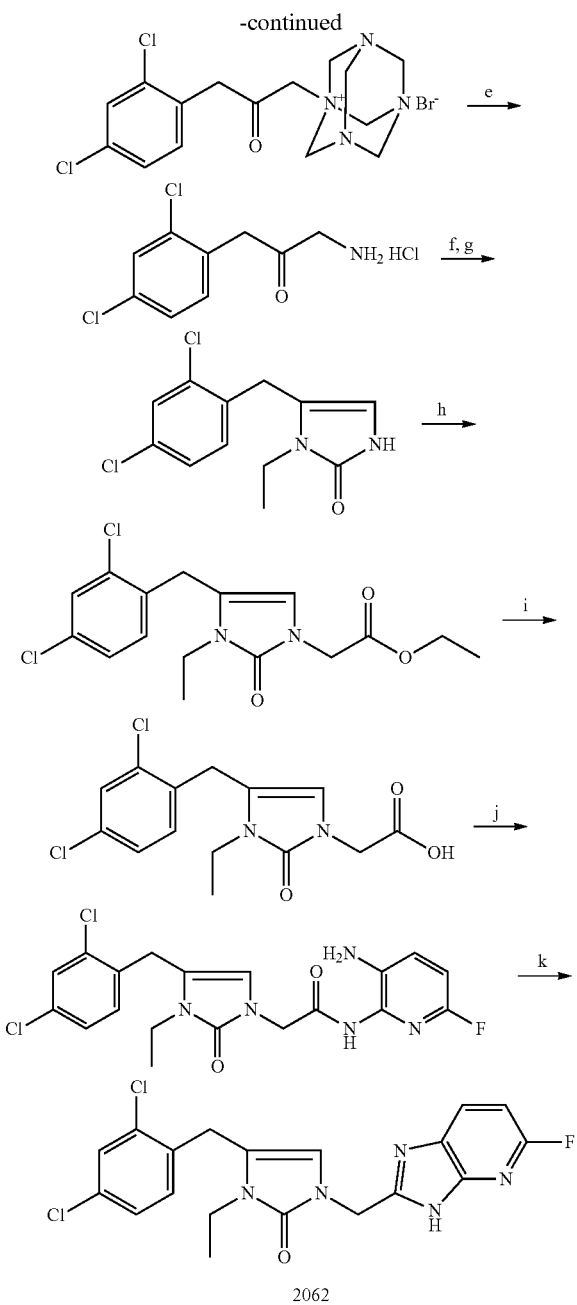

Reagents and conditions (a) oxalyl chloride, DMF, DCM; (b) trimethylsilyldiazomethane, THF/MeCN; (c) HBr; (d) hexamethylenetetramine, DCM; (e) ethanol/HCl; (f) ethyl isocyanate, DCM; (g) TFA; (h) ethyl bromoacetate, K$_2$CO$_3$,; (i) LiOH, ethanol/water; (j) EDC, 6-fluoropyridine-2,3-diamine, pyridine; (k) HOAc, microwave irradation.

General Procedure 1 (2062, 2067-2070, 2079-2081, 2084, 2087-2088, 2091-2093, 2103, 2262, 2210, 2275, 2295, 2286):

Oxalyl chloride (0.21 mL, 2.3 mmol) was added dropwise to a solution of 2,4-dichlorophenylacetic acid (308 mg, 1.5 mmol) and one drop of dry DMF in dry THF (6 mL) at room temperature. The reaction mixture was stirred at room temperature overnight and the solvent was completely removed in vacuo to obtain 2,4-dichlorophenylacetyl chloride.

The residue was dissolved in anhydrous MeCN (8 ml) and THF (8 ml) and added 5.25 mL (3.15 mmol) of a 0.6 M solution of trimethylsilyldiazomethane in hexane at 0° C. for 1 h. Then the mixture was stirred overnight at room temperature. The mixture was cooled to 0° C. and 0.5 ml of 48% HBr was added dropwise (gas evolution). After stirring 15 min at 0° C. and room temperature for 2 h, the mixture was concentrated in vacuo. The residues was dissolved with EtOAc and washed successively with water and brine. The organic layer was dried over Na$_2$SO$_4$ and concentrated in vacuo. The residue was purified by flash column chromatography (hexane/EtOAc), giving bromo-3-(2,4-dichlorophenyl)acetone in 71% yield (299 mg).

A mixture of bromo-3-(2,4-dichlorophenyl)acetone (241 mg, 0.859 mmol) and HMTA (hexamethylenetetramine, 140 mg, 0.945 mmol) in DCM (5 mL) was stirred at room temperature overnight. After cooled down at 4° C., the white solid is collected and washed with cold DCM to obtain 307 mg quaternary ammonium HBr salt. The salt was dissolved in 10 ml of EtOH and combined with 2 ml of concentrated HCl. After refluxing for 10 h, the mixture was concentrated in vacuo. The residues was rinsed with ether to give 1-amino-3-(2,4-dichlorophenyl)propan-2-one as a white salt, which was used in the next reaction without purification.

To an ice-cold suspension of half of above salt in 20 ml of anhydrous methylene chloride, 200 μl of DIPEA and 25 μl of ethyl isocyanate (0.51 mmol) was added. The mixture was added more DIPEA to keep basic if necessary and stirred at room temperature for 4 h. Then 1 ml of TFA was added and the mixture was stirred at room temperature for 50 min. After most solvent was removed, the mixture was diluted with EtOAc and washed successively with saturated NaHCO$_3$, and then brine. The organic layer was dried over Na$_2$SO$_4$ and concentrated in vacuo. The residue was purified by flash column chromatography (DCM/MeOH), yielding 5-(2,4-dichlorobenzyl)-1-ethyl-1H-imidazol-2(3H)-one (67 mg). 5-(2,4-dichlorobenzyl)-1-ethyl-1H-imidazol-2(3H)-one (67 mg, 0.246 mmol) was dissolved in 10 ml anhydrous acetonitrile and treated with 82 μl (0.738 mmol) of ethyl bromoacetate and 102 mg of potassium carbonate (0.738 mmol). The mixture was refluxed overnight. After the reaction solvent was evaporated, the residues was dissolved with EtOAc and washed successively with water and brine. The organic layer was dried over Na$_2$SO$_4$ and concentrated in vacuo. The residue was purified by flash chromatography on silica gel (dichloromethane/methanol) to obtain ethyl 2-(5-(2,4-dichlorobenzyl)-1-ethyl-1,2-dihydr$_{0-2}$-oxoimidazol-3-yl)acetate in 92% yield (81 mg, 0.226 mmol).

Ethyl 2-(5-(2,4-dichlorobenzyl)-1-ethyl-1,2-dihydr$_{0-2}$-oxoimidazol-3-yl)acetate (81 mg, 0.226 mmol) was added in 2 ml of ethanol and 4 ml of water, mixed with LiOH (22 mg, 0.9 mml) and stirred for 50 min at room temperature. The solution was acidified with 0.2N hydrochloric acid and the solvent was completely removed in vacuo. The residue was dissolved in 3 ml of pyridine, then 6-fluoropyridine-2,3-diamine (0.25 mmol) and EDC hydrochloride (52 mg, 0.27 mmol) were added. The mixture was stirred at room temperature overnight. The solvent was removed on the rotary evaporator. The residue was dissolved in EtOAc (30 ml) and washed with water and brine. The organic layer was dried over Na$_2$SO$_4$ and concentrated in vacuo. The residue was purified by flash chromatography on silica gel to give 2-(5-(2,4-dichlorobenzyl)-1-ethyl-1,2-dihydr$_{0-2}$-oxoimidazol-3-yl)—N-(3-amino-6-fluoropyridin-2-yl)acetamide. 2-(5-(2,4-dichlorobenzyl)-1-ethyl-1,2-dihydr$_{0-2}$-oxoimidazol-3-yl)—N-(3-amino-6-fluoropyridin-2-yl)acetamide was dissolved in 2 ml of acetic acid and the solution was microwave irradiated at 125° C. for 1 h. After the solvent was removed on the rotary evaporator, the residue was purified by flash column chromatography (DCM/MeOH), giving 95 mg of 2062 (4-[(2,4-dichlorophenyl)methyl]-3-ethyl-1-({5-fluoro-1H-imidazo[4,5-b]pyridin-2-yl}methyl)-2,3-dihydro-1H-imidazol-2-one) in 45% yield. LC/MS: (ESI) (M+H)$^+$=421.5.

Example 2

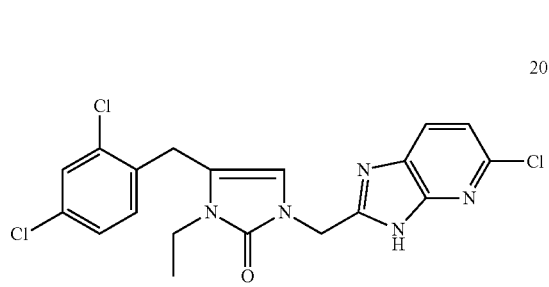

2067 (1-({5-chloro-1H-imidazo[4,5-b]pyridin-2-yl}methyl)-4-[(2,4-dichlorophenyl)methyl]-3-ethyl-2,3-dihydro-1H-imidazol-2-one) was synthesized using 6-chloropyridine-2,3-diamine following General Procedure 1. $^1$H NMR (MeOD) δ 7.86 (d, J=12.2 Hz, 1H), 7.44 (s, 1H), 7.32-7.16 (m, 3H), 6.11 (s, 1H), 5.00 (s, 2H), 3.87 (s, 2H), 3.59 (q, J=7.2 Hz, 2H), 1.08 (t, J=8.6 Hz, 3H). LC/MS: (ESI) (M+H)$^+$=437.6.

Example 3

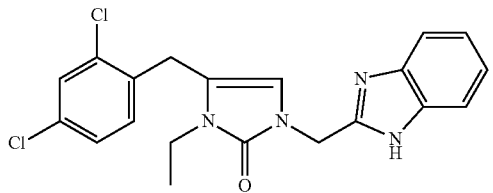

2068 (1-[(1H-1,3-benzodiazol-2-yl)methyl]-4-[(2,4-dichlorophenyl)methyl]-3-ethyl-2,3-dihydro-1H-imidazol-2-one) was synthesized using benzene-1,2-diamine following General Procedure 1. LC/MS: (ESI) (M+H)$^+$=402.5.

Example 4

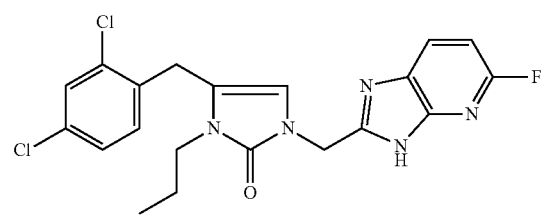

2069 (4-[(2,4-dichlorophenyl)methyl]-1-({5-fluoro-1H-imidazo[4,5-b]pyridin-2-yl}methyl)-3-propyl-2,3-dihydro-1H-imidazol-2-one) was synthesized using propyl isocyanate following General Procedure 1. $^1$H NMR (MeOD) δ 8.12-7.77 (m, 1H), 7.43 (s, 1H), 7.24 (s, 2H), 6.87 (d, J=8.5 Hz, 1H), 6.10 (s, 1H), 6.05 (s, 1H), 4.98(s, 2H), 3.77 (s, 2H), 3.85 (s, 3H), 3.61-3.39 (m, 2H), 1.53-1.48 (m, 2H), 0.83 (t, J=7.4 Hz, 3H). LC/MS: (ESI) (M+H)$^+$=435.3.

Example 5

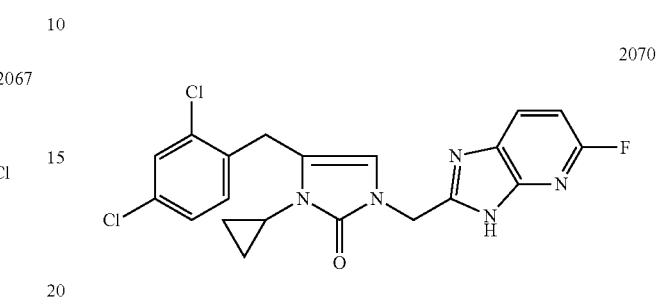

2070 (3-cyclopropyl-4-[(2,4-dichlorophenyl)methyl]-1-({5-fluoro-1H-imidazo[4,5-b]pyridin-2-yl}methyl)-2,3-dihydro-1H-imidazol-2-one) was synthesized using cyclopropyl isocyanate following General Procedure 1. LC/MS: (ESI) (M+H)$^+$=433.2.

Example 6

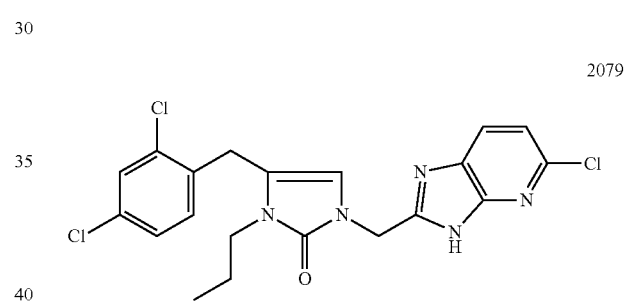

2079 (1-({5-chloro-1H-imidazo[4,5-b]pyridin-2-yl}methyl)-4-[(2,4-dichlorophenyl)-methyl]-3-propyl-2,3-dihydro-1H-imidazol-2-one) was synthesized using propyl isocyanate and 6-chloropyridine-2,3-diamine following General Procedure 1. $^1$H NMR (MeOD) δ 7.90-7.80 (m, 1H), 7.42 (s, 1H), 7.21 (m, 3H), 6.10 (s, 1H), 5.00 (s, 2H), 3.77 (s, 2H), 3.84 (s, 3H), 3.53-3.43 (m, 2H), 1.53-1.49 (m, 2H), 0.83 (t, J=7.4 Hz, 3H)LC/MS: (ESI) (M+H)$^+$=452.0.

Example 7

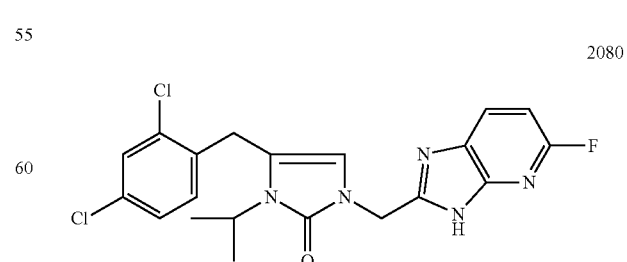

2080 (4-[(2,4-dichlorophenyl)methyl]-1-({5-fluoro-1H-imidazo[4,5-b]pyridin-2-yl}methyl)-3-(propan-2-yl)-2,3-dihydro-1H-imidazol-2-one) was synthesized using isopropyl isocyanate following General Procedure 1. LC/MS: (ESI) (M+H)⁺=435.4.

Example 8

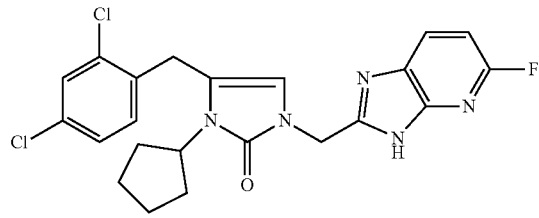

2081

2081 (3-cyclopentyl-4-[(2,4-dichlorophenyl)methyl]-1-({5-fluoro-1H-imidazo[4,5-b]pyridin-2-yl}methyl)-2,3-dihydro-1H-imidazol-2-one) was synthesized using cyclopentyl isocyanate following General Procedure 1. LC/MS: (ESI) (M+H)⁺=461.3.

Example 9

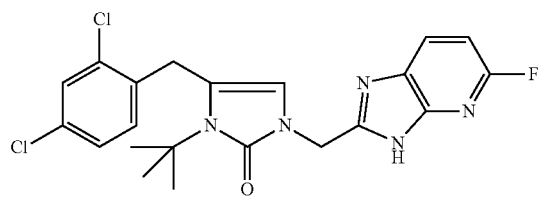

2084

2084 (3-tert-butyl-4-[(2,4-dichlorophenyl)methyl]-1-({5-fluoro-1H-imidazo[4,5-b]pyridin-2-yl}methyl)-2,3-dihydro-1H-imidazol-2-one) was synthesized using tert-butyl isocyanate following General Procedure 1. LC/MS: (ESI) (M+H)⁺=449.8.

Example 10

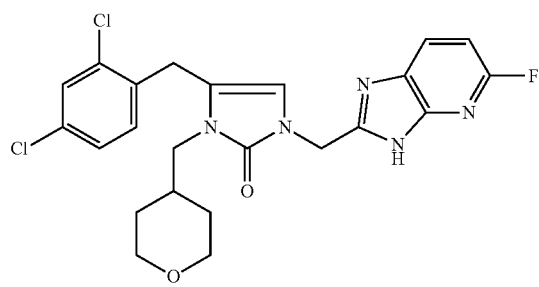

2087

2087 (4-[(2,4-dichlorophenyl)methyl]-1-({5-fluoro-1H-imidazo[4,5-b]pyridin-2-yl}methyl)-3-[(oxan-4-yl)methyl]-2,3-dihydro-1H-imidazol-2-one) was made using tetrahydro-4-(isocyanatomethyl)-2H-pyran of General Procedure 1. LC/MS: (ESI) (M+H)⁺=491.5.

Example 11

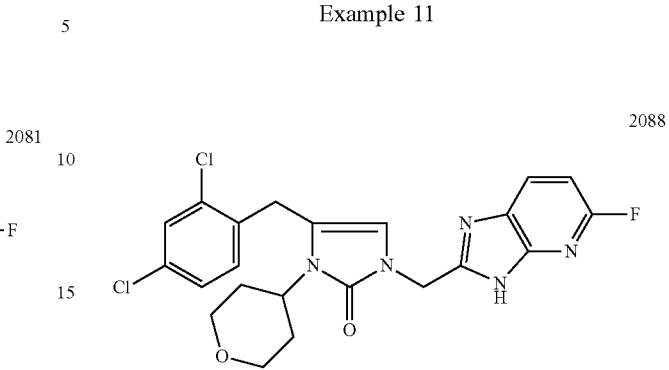

2088

2088 (4-[(2,4-dichlorophenyl)methyl]-1-({5-fluoro-1H-imidazo[4,5-b]pyridin-2-yl}methyl)-3-(oxan-4-yl)-2,3-dihydro-1H-imidazol-2-one) was synthesized using tetrahydro-4-isocyanato-2H-pyran following General Procedure 1. LC/MS: (ESI) (M+H)⁺=477.2.

Example 12

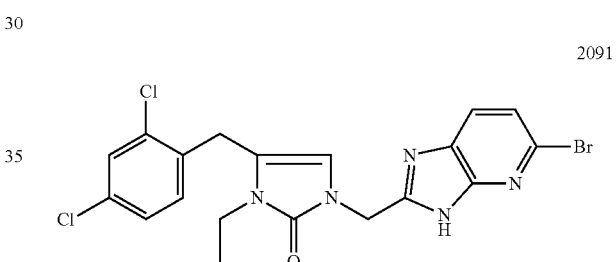

2091

2091 (1-({5-bromo-1H-imidazo[4,5-b]pyridin-2-yl}methyl)-4-[(2,4-dichlorophenyl)-methyl]-3-ethyl-2,3-dihydro-1H-imidazol-2-one) was synthesized using 6-bromopyridine-2,3-diamine following General Procedure 1. LC/MS: (ESI) (M+H)⁺=482.4.

Example 13

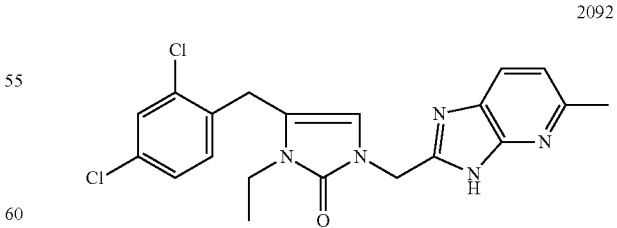

2092

2092 (4-[(2,4-dichlorophenyl)methyl]-3-ethyl-1-({5-methyl-1H-imidazo[4,5-b]pyridin-2-yl}methyl)-2,3-dihydro-1H-imidazol-2-one) was synthesized using 6-methylpyridine-2,3-diamine following General Procedure 1. LC/MS: (ESI) (M+H)⁺=416.3.

Example 14

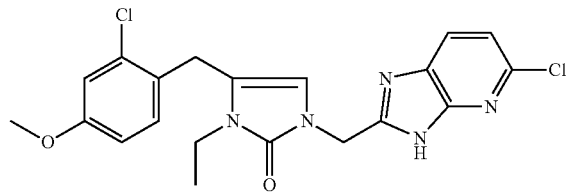

2093

2093 (1-({5-chloro-1H-imidazo[4,5-b]pyridin-2-yl}methyl)-4-[(2-chloro-4-methoxyphenyl)methyl]-3-ethyl-2,3-dihydro-1H-imidazol-2-one) was synthesized using 2-(2-chloro-4-methoxyphenyl)acetic acid and 6-chloropyridine-2,3-diamine following General Procedure 1. $^1$H NMR (MeOD) δ 7.83 (d, J=8.4 Hz, 1H), 7.20 (d, J=8.4 Hz, 1H), 7.12 (d, J=8.6 Hz, 1H), 6.90 (d, J=2.6 Hz, 1H), 6.76 (dd, J=8.6, 2.6 Hz, 1H), 6.05 (s, 1H), 4.99(s, 2H), 3.77 (s, 2H), 3.69 (s, 3H), 3.57-3.55 (m, 2H), 1.06 (s, 3H). LC/MS: (ESI) (M+H)$^+$=433.4.

Example 15

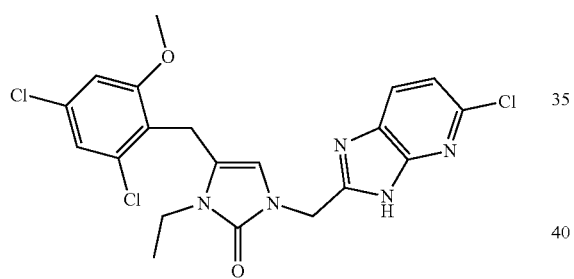

2295

2295 (1-({5-chloro-1H-imidazo[4,5-b]pyridin-2-yl}methyl)-4-(2-chloro-4-methoxybenzoyl)-3-ethyl-2,3-dihydro-1H-imidazol-2-one) was synthesized using 2-(2,4-dichloro-6-methoxyphenyl)acetic acid and 6-chloropyridine-2,3-diamine following General Procedure 1. LC/MS: (ESI) (M+H)$^+$=467.6.

Example 16

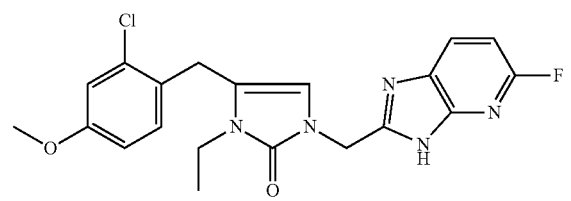

2114

2114 (4-[(2-chloro-4-methoxyphenyl)methyl]-3-ethyl-1-({5-fluoro-1H-imidazo[4,5-b]pyridin-2-yl}methyl)-2,3-dihydro-1H-imidazol-2-one) was synthesized using 2-(2-chloro-4-methoxyphenyl)acetic acid following General Procedure 1. $^1$H NMR (MeOD) δ 8.01-7.90 (m, 1H), 7.13 (d, J=5.6 Hz, 1H), 6.91 (s, 1H), 6.86 (d, J=8.5 Hz, 1H), 6.77 (m, 1H), 6.05 (s, 1H), 4.98 (s, 2H), 3.78 (s, 2H), 3.70 (s, 3H), 3.64-3.53 (m, 2H), 1.07 (t, J=7.1 Hz, 3H). LC/MS: (ESI) (M+H)$^+$=416.9.

Example 17

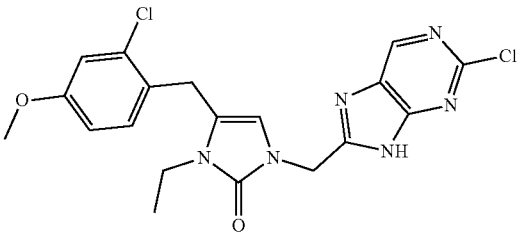

2286

2286 (4-[(2-chloro-4-methoxyphenyl)methyl]-1-[(2-chloro-7H-purin-8-yl)methyl]-3-ethyl-2,3-dihydro-1H-imidazol-2-one) was synthesized using 2-(2-chloro-4-methoxyphenyl)acetic acid and 2-chloropyrimidine-4,5-diamine following General Procedure 1. LC/MS: (ESI) (M+H)$^+$=434.5.

Example 18

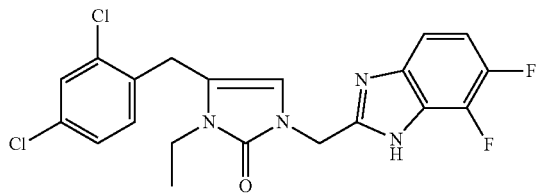

2262

2262 (4-[(2,4-dichlorophenyl)methyl]-1-[(6,7-difluoro-1H-1,3-benzodiazol-2-yl)methyl]-3-ethyl-2,3-dihydro-1H-imidazol-2-one) was synthesized using 3,4-difluorobenzene-1,2-diamine following General Procedure 1. LC/MS: (ESI) (M+H)$^+$=438.4.

Example 19

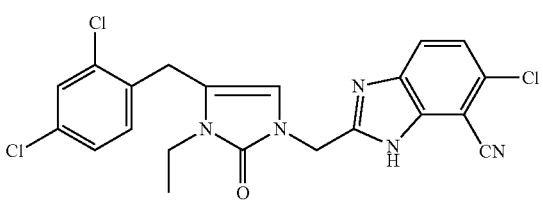

2210

2210 (6-chloro-2-({4-[(2,4-dichlorophenyl)methyl]-3-ethyl-2-oxo-2,3-dihydro-1H-imidazol-1-yl}methyl)-1H-1,3-benzodiazole-7-carbonitrile) was synthesized using 2,3- diamino-6-chlorobenzonitrile following General Procedure 1. LC/MS: (ESI) (M+H)⁺=461.6.

Example 20

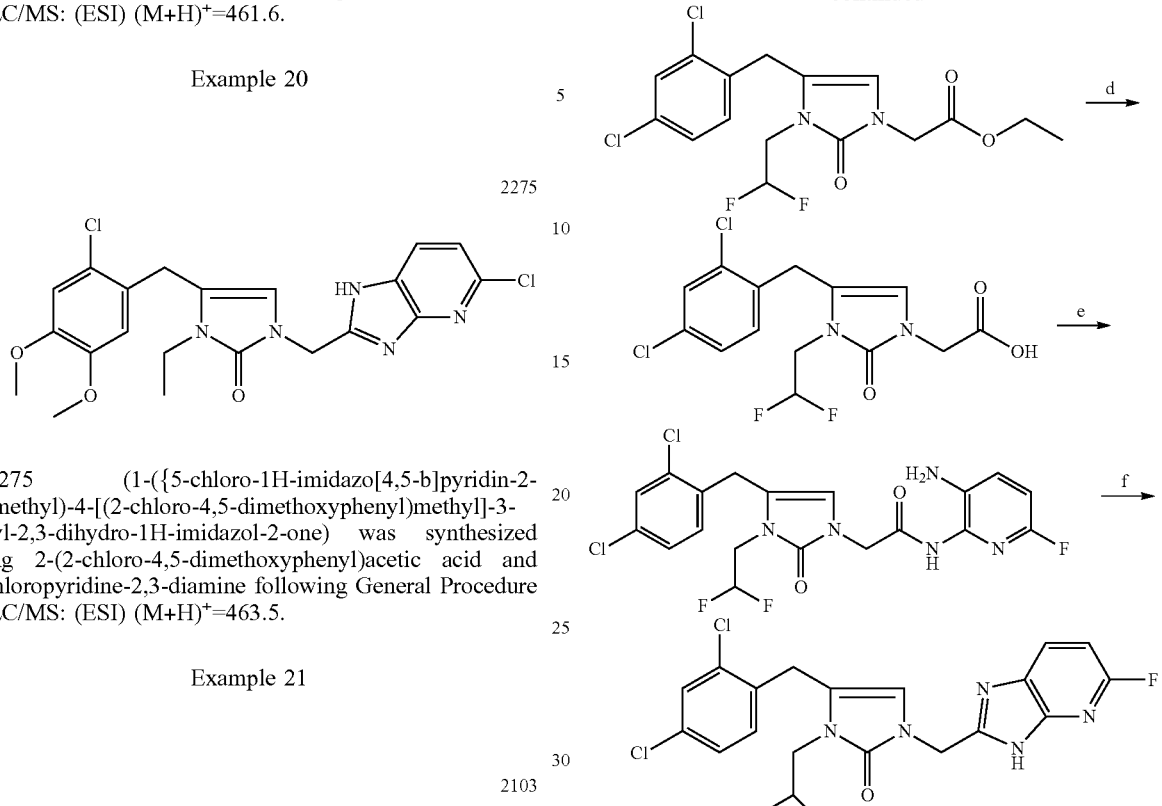

2275  (1-({5-chloro-1H-imidazo[4,5-b]pyridin-2-yl}methyl)-4-[(2-chloro-4,5-dimethoxyphenyl)methyl]-3-ethyl-2,3-dihydro-1H-imidazol-2-one) was synthesized using 2-(2-chloro-4,5-dimethoxyphenyl)acetic acid and 6-chloropyridine-2,3-diamine following General Procedure 1. LC/MS: (ESI) (M+H)⁺=463.5.

Example 21

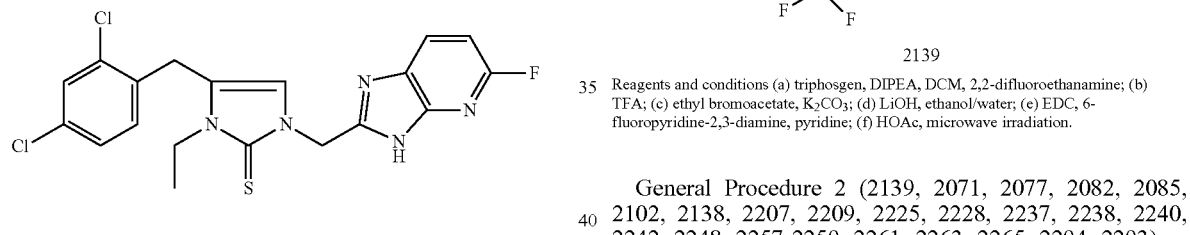

2103  (4-[(2,4-dichlorophenyl)methyl]-3-ethyl-1-({5-fluoro-1H-imidazo[4,5-b]pyridin-2-yl}methyl)-2,3-dihydro-1H-imidazole-2-thione) was synthesized using ethyl isothiocyanate following General Procedure 1. LC/MS: (ESI) (M+H)⁺=437.4.

Example 22

Scheme 2

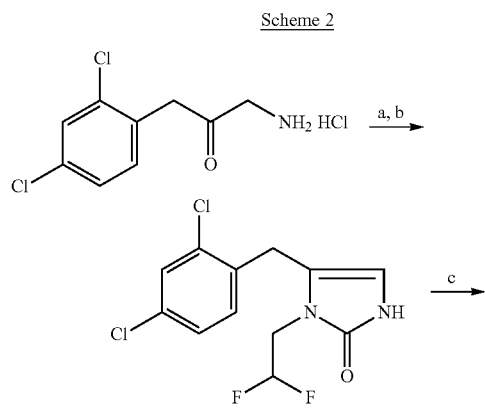

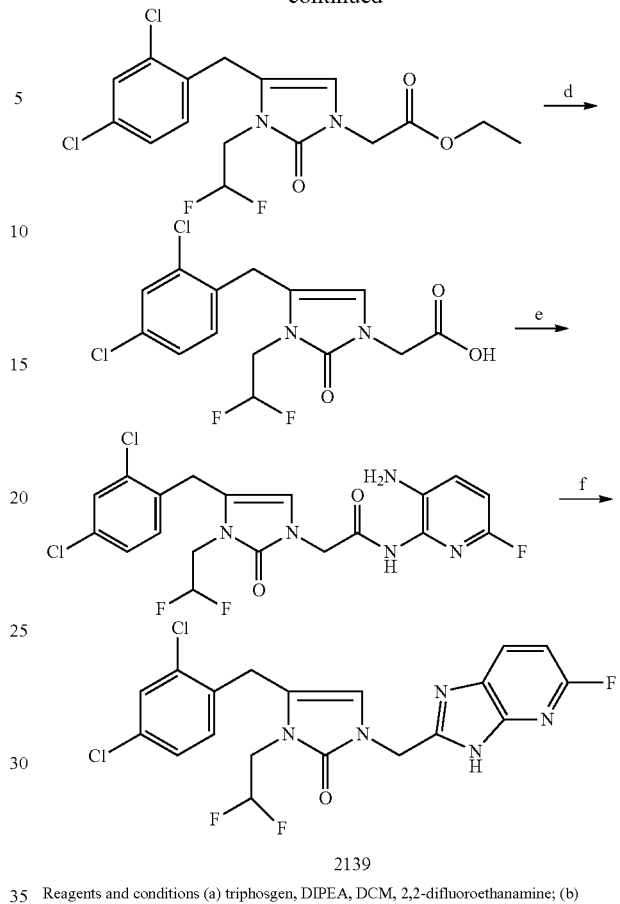

Reagents and conditions (a) triphosgen, DIPEA, DCM, 2,2-difluoroethanamine; (b) TFA; (c) ethyl bromoacetate, K₂CO₃; (d) LiOH, ethanol/water; (e) EDC, 6-fluoropyridine-2,3-diamine, pyridine; (f) HOAc, microwave irradiation.

General Procedure 2 (2139, 2071, 2077, 2082, 2085, 2102, 2138, 2207, 2209, 2225, 2228, 2237, 2238, 2240, 2242, 2248, 2257-2259, 2261, 2263, 2265, 2294, 2293):

To an ice-cooled suspension of 1-amino-3-(2,4-dichlorophenyl)propan-2-one HCl salt (25.4 mg 0.1 mmol) in anhydrous methylene chloride (10 mL), DIPEA (50 μL) and triphosgene (5.9 μl, 0.035 mmol) were added. After the mixture was stirred at 0° C. for 1 h, 2,2-difluoroethanamine (0.11 mmol) was added. The mixture was stirred at 0° C. for 30 min and room temperature for 1 h. Then 1 ml of TFA was added and the mixture was stirred at room temperature for 50 min. After most solvent was removed, the mixture was diluted with EtOAc and washed successively with saturated NaHCO₃ and brine. The organic layer was dried over Na₂SO₄ and concentrated in vacuo. The residue was purified by flash column chromatography (DCM/MeOH), yielding 5-(2,4-dichlorobenzyl)-1-(2,2-difluoroethyl)-1H-imidazol-2 (3H)-one (15 mg). 5-(2,4-dichlorobenzyl)-1-ethyl-1H-imidazol-2(3H)-one (15 mg, 0.049 mmol) was dissolved in 10 ml anhydrous acetonitrile and treated with 16.3 μl (0.147 mmol) of ethyl bromoacetate and potassium carbonate (20.3 mg, 0.147 mmol). The mixture was refluxed overnight. After the reaction solvent was evaporated, the residues was dissolved with EtOAc and washed successively with water and brine. The organic layer was dried over Na₂SO₄ and concentrated in vacuo. The residue was purified by flash chromatography on silica gel (dichloromethane/methanol) to obtain ethyl 2-(5-(2,4-dichlorobenzyl)-1-(2,2-difluoroethyl)-1,2-dihydro-2-oxoimidazol-3-yl)acetate in 90% yield (17.3 mg, 0.044 mmol).

Ethyl 2-(5-(2,4-dichlorobenzyl)-1-(2,2-difluoroethyl)-1,2-dihydr₀₋₂-oxoimidazol-3-yl)acetate (17.3 mg, 0.044 mmol) was added in 1 ml of ethanol and 3 ml of water, mixed with LiOH (1.1 mg, 0.176 mml) and stirred for 50 min at room temperature. The solution was acidified with 0.2 N hydrochloric acid and the solvent completely removed in vacuo. The residue was dissolved in 3 ml of pyridine, then 6-fluoropyridine-2,3-diamine (0.25 mmol) and EDC hydrochloride (52 mg, 0.27 mmol) were added. The mixture was stirred at room temperature overnight. The solvent was removed on a rotary evaporator. The residue was dissolved in EtOAc (30 ml) and washed with water and brine. The organic layer was dried over Na₂SO₄ and concentrated in vacuo. The residue was purified by flash chromatography on silica gel to give 2-(5-(2,4-dichlorobenzyl)-1-(2,2-difluoroethyl)-1,2-dihydr₀₋₂-oxoimidazol-3-yl)—N-(3-amino-6-fluoropyridin-2-yl)acetamide. 2-(5-(2,4-dichlorobenzyl)-1-(2,2-difluoroethyl)-1,2-dihydr₀₋₂-oxoimidazol-3-yl)—N-(3-amino-6-fluoropyridin-2-yl)acetamide was dissolved in 2 ml of acetic acid and the solution was microwave irradiated at 125° C. for 1 h. After the solvent was removed on a rotary evaporator, the residue was purified by flash column chromatography (DCM/MeOH), producing 2139 (4-[(2,4-dichlorophenyl)methyl]-3-(2,2-difluoroethyl)-1-({5-fluoro-1H-imidazo[4,5-b]pyridin-2-yl}methyl)-2,3-dihydro-1H-imidazol-2-one) in 41% yield (8.2 mg). LC/MS: (ESI) (M+H)⁺=457.3.

Example 23 roethyl)-2,3-dihydro-1H-imidazol-2-one) was synthesized using 6-chloropyridine-2,3-diamine following General Procedure 2. LC/MS: (ESI) (M+H)⁺=473.6.

Example 25

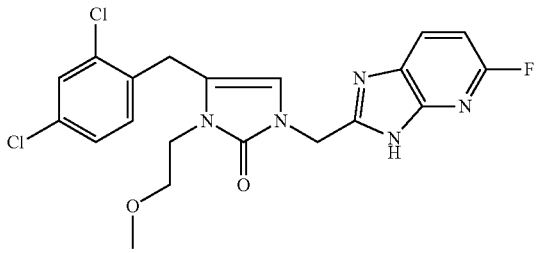

2077 (4-[(2,4-dichlorophenyl)methyl]-1-({5-fluoro-1H-imidazo[4,5-b]pyridin-2-yl}methyl)-3-(2-methoxyethyl)-2,3-dihydro-1H-imidazol-2-one) was synthesized using 2-methoxyethanamine following General Procedure 2. LC/MS: (ESI) (M+H)⁺=451.3.

Example 26

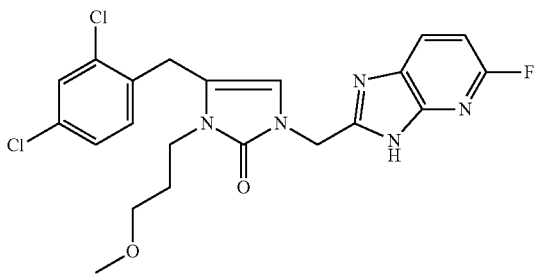

2071 (3-cyclohexyl-4-[(2,4-dichlorophenyl)methyl]-1-({5-fluoro-1H-imidazo[4,5-b]pyridin-2-yl}methyl)-2,3-dihydro-1H-imidazol-2-one) was synthesized using cyclohexanamine following General Procedure 2. LC/MS: (ESI) (M+H)⁺=475.4.

Example 24

2082 (4-[(2,4-dichlorophenyl)methyl]-1-({5-fluoro-1H-imidazo[4,5-b]pyridin-2-yl}methyl)-3-(3-methoxypropyl)-2,3-dihydro-1H-imidazol-2-one) was synthesized using 3-methoxypropan-1-amine following General Procedure 2. LC/MS: (ESI) (M+H)⁺=465.4.

Example 27

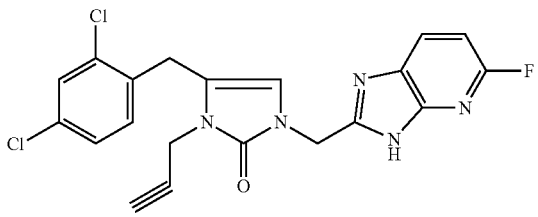

2138 (1-({5-chloro-1H-imidazo[4,5-b]pyridin-2-yl}methyl)-4-[(2,4-dichlorophenyl)-methyl]-3-(2,2-difluo- 2085 (4-[(2,4-dichlorophenyl)methyl]-1-({5-fluoro-1H-imidazo[4,5-b]pyridin-2-yl}methyl)-3-(prop-2-yn-1-yl)-2, 3-dihydro-1H-imidazol-2-one) was synthesized using prop-2-yn-1-amine following General Procedure 2. LC/MS: (ESI) (M+H)⁺=431.6.

Example 28

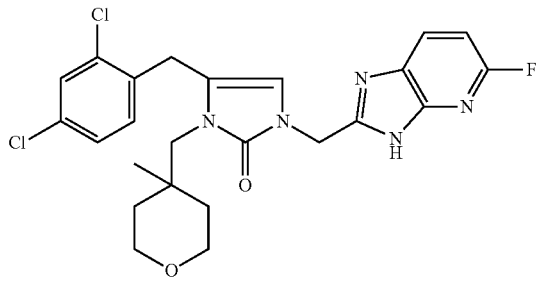

2102 (4-[(2,4-dichlorophenyl)methyl]-1-({5-fluoro-1H-imidazo[4,5-b]pyridin-2-yl}methyl)-3-[(4-hydroxyoxan-4-yl)methyl]-2,3-dihydro-1H-imidazol-2-one) was synthesized using (tetrahydro-4-methyl-2H-pyran-4-yl)methanamine following General Procedure 2. LC/MS: (ESI) (M+H)⁺=505.5.

Example 29

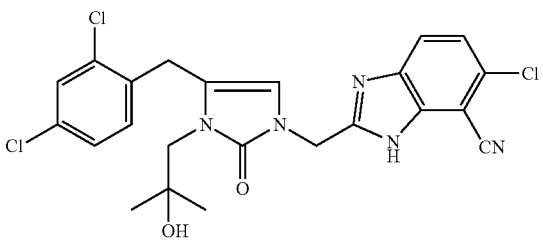

2228 (6-chlor$_{0-2}$-({4-[(2-chloro-4-methoxyphenyl)methyl]-3-(2-hydroxy-2-methylpropyl)-2-oxo-2,3-dihydro-1H-imidazol-1-yl}methyl)-1H-1,3-benzodiazole-7-carbonitrile) was synthesized using 2-(2-chloro-4-methoxyphenyl)acetic acid, 1-amin$_{0-2}$-methylpropan-2-ol and 2,3-diamino-6-chlorobenzonitrile General Procedure 1 and 2. LC/MS: (ESI) (M+H)⁺=501.5.

Example 30

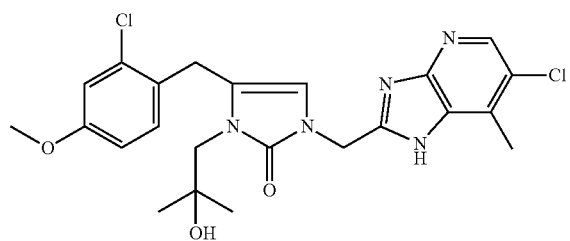

2238 (4-[(2-chloro-4-methoxyphenyl)methyl]-1-({6-chloro-7-methyl-1H-imidazo[4,5-b]pyridin-2-yl}methyl)-3-(2-hydroxy-2-methylpropyl)-2,3-dihydro-1H-imidazol-2-one) was synthesized using 2-(2-chloro-4-methoxyphenyl)acetic acid, 1-amin$_{0-2}$-methylpropan-2-ol and 5-chloro-4-methylpyridine-2,3-diamine following General Procedure 1 and 2. LC/MS: (ESI) (M+H)⁺=491.5.

Example 31

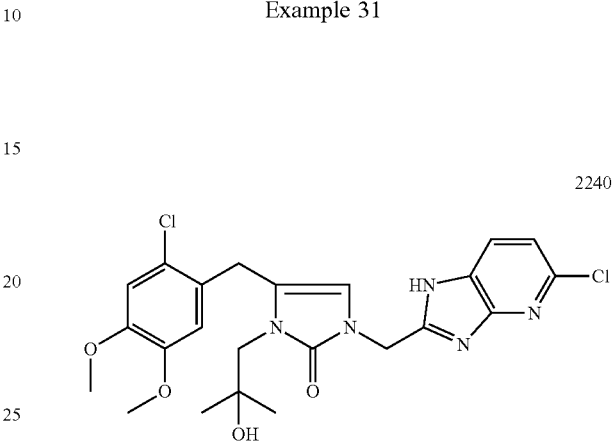

2240 (1-({5-chloro-1H-imidazo[4,5-b]pyridin-2-yl}methyl)-4-[(2-chloro-4,5-dimethoxyphenyl)methyl]-3-(2-hydroxy-2-methylpropyl)-2,3-dihydro-1H-imidazol-2-one) was synthesized using 2-(2-chloro-4,5-dimethoxyphenyl)acetic acid, 1-amin$_{0-2}$-methylpropan-2-ol and 6-chloropyridine-2,3-diamine following General Procedure 1 and 2. LC/MS: (ESI) (M+H)⁺=507.3.

Example 32

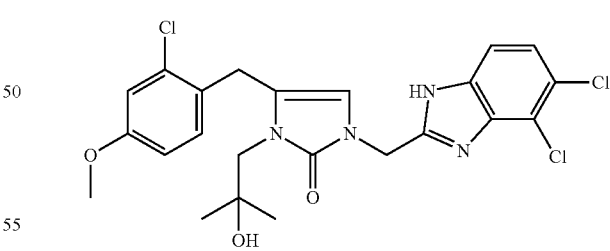

2242 (4-[(2-chloro-4-methoxyphenyl)methyl]-1-[(6,7-dichloro-1H-1,3-benzodiazol-2-yl)methyl]-3-(2-hydroxy-2-methylpropyl)-2,3-dihydro-1H-imidazol-2-one) was synthesized using 2-(2-chloro-4-methoxyphenyl)acetic acid, 1-amin$_{0-2}$-methylpropan-2-ol and 3,4-dichlorobenzene-1,2-diamine following General Procedure 1 and 2. LC/MS: (ESI) (M+H)⁺=510.7.

Example 33

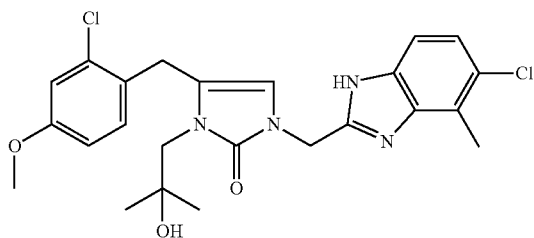

2248 (4-[(2-chloro-4-methoxyphenyl)methyl]-1-[(5-chloro-4-methyl-1H-1,3-benzodiazol-2-yl)methyl]-3-(2-hydroxy-2-methylpropyl)-2,3-dihydro-1H-imidazol-2-one) was synthesized using 2-(2-chloro-4-methoxyphenyl)acetic acid, 1-amin₀-₂-methylpropan-2-ol and 4-chloro-3-methylbenzene-1,2-diamine following General Procedure 1 and 2. LC/MS: (ESI) (M+H)⁺=490.4.

Example 34

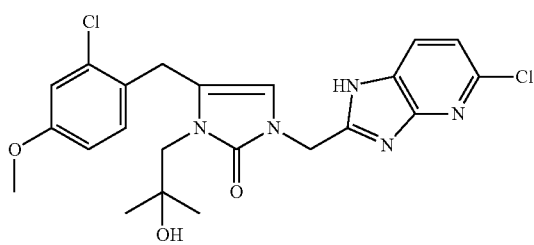

2207 (1-({5-chloro-1H-imidazo[4,5-b]pyridin-2-yl}methyl)-4-[(2-chloro-4-methoxyphenyl)methyl]-3-(2-hydroxy-2-methylpropyl)-2,3-dihydro-1H-imidazol-2-one) was synthesized using 2-(2-chloro-4-methoxyphenyl)acetic acid and 1-amin₀-₂-methylpropan-2-ol following General Procedure 1 and 2. LC/MS: (ESI) (M+H)⁺=477.5.

Example 35

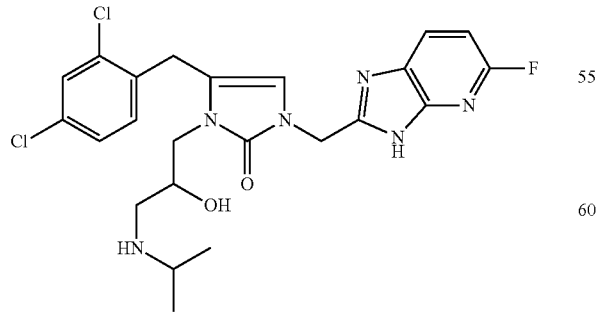

2294 (4-[(2,4-dichlorophenyl)methyl]-1-({5-fluoro-1H-imidazo[4,5-b]pyridin-2-yl}methyl)-3-{2-hydroxy-3-[(propan-2-yl)amino]propyl}-2,3-dihydro-1H-imidazol-2-one) was synthesized using 1-amino-3-(isopropylamino)propan-2-ol following General Procedure 1 and 2. LC/MS: (ESI) (M+H)⁺=508.6.

Example 36

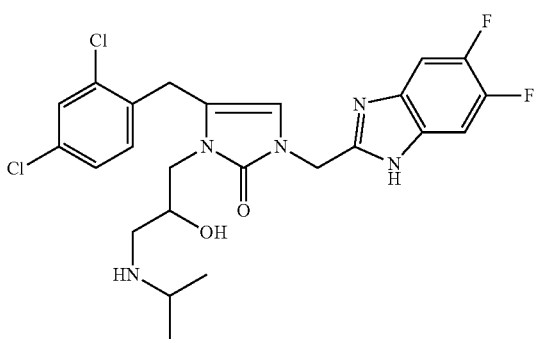

2293 (4-[(2,4-dichlorophenyl)methyl]-1-[(5,6-difluoro-1H-1,3-benzodiazol-2-yl)methyl]-3-{2-hydroxy-3-[(propan-2-yl)amino]propyl}-2,3-dihydro-1H-imidazol-2-one) was synthesized using 1-amino-3-(isopropylamino)propan-2-ol and following General Procedure 1 and 2. LC/MS: (ESI) (M+H)⁺=525.4

Example 37

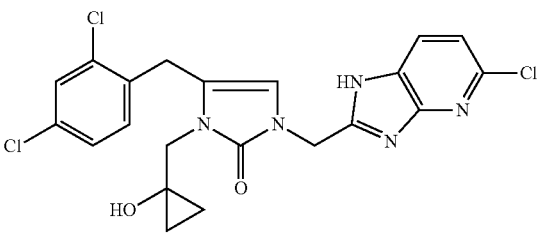

2225 (1-({5-chloro-1H-imidazo[4,5-b]pyridin-2-yl}methyl)-4-[(2,4-dichlorophenyl)-methyl]-3-[(1-hydroxycyclopropyl)methyl]-2,3-dihydro-1H-imidazol-2-one) was synthesized using 1-(aminomethyl)cyclopropanol following General Procedure 2. LC/MS: (ESI) (M+H)⁺=479.8.

Example 38

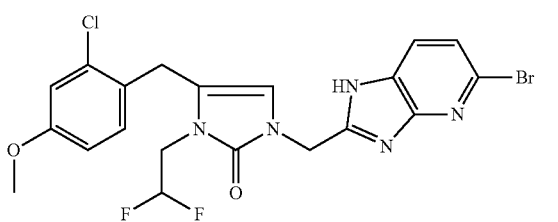

2257 (1-({5-bromo-1H-imidazo[4,5-b]pyridin-2-yl}methyl)-4-[(2-chloro-4-methoxyphenyl)methyl]-3-(2,2-difluoroethyl)-2,3-dihydro-1H-imidazol-2-one) was synthesized using 2-(2-chloro-4-methoxyphenyl)acetic acid and 6-bromopyridine-2,3-diamine following General Procedure 1 and 2. LC/MS: (ESI) (M+H)$^+$=514.1.

Example 39

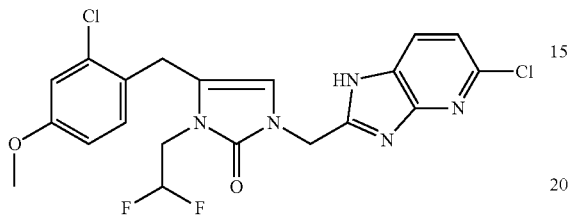

2258

2258 (1-({5-chloro-1H-imidazo[4,5-b]pyridin-2-yl}methyl)-4-[(2-chloro-4-methoxyphenyl)methyl]-3-(2,2-difluoroethyl)-2,3-dihydro-1H-imidazol-2-one) was synthesized using 2-(2-chloro-4-methoxyphenyl)acetic acid and 6-chloropyridine-2,3-diamine following General Procedure 1 and 2. LC/MS: (ESI) (M+H)$^+$=469.4.

Example 40

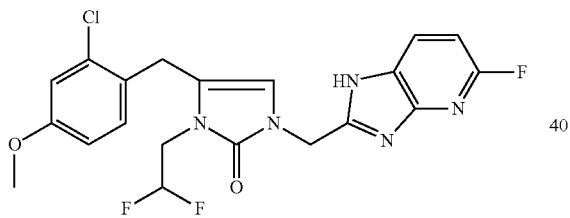

2259

2259 (4-[(2-chloro-4-methoxyphenyl)methyl]-3-(2,2-difluoroethyl)-1-({5-fluoro-1H-imidazo[4,5-b]pyridin-2-yl}methyl)-2,3-dihydro-1H-imidazol-2-one) was synthesized using 2-(2-chloro-4-methoxyphenyl)acetic acid following General Procedure 1 and 2. LC/MS: (ESI) (M+H)$^+$=452.7.

Example 41

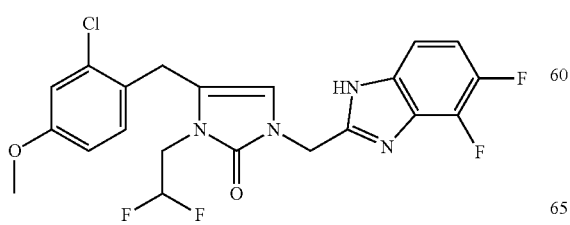

2261

2261 (4-[(2-chloro-4-methoxyphenyl)methyl]-1-[(6,7-difluoro-1H-1,3-benzodiazol-2-yl)methyl]-3-(2,2-difluoroethyl)-2,3-dihydro-1H-imidazol-2-one) was synthesized using 2-(2-chloro-4-methoxyphenyl)acetic acid and 3,4-difluorobenzene-1,2-diamine following General Procedure 1 and 2. LC/MS: (ESI) (M+H)$^+$=469.9.

Example 42

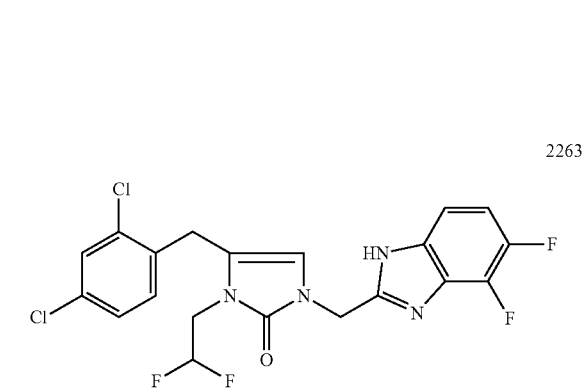 [SMILES: O=c1n(Cc2nc3c(F)c(F)ccc3[nH]2)cc(Cc2ccc(Cl)cc2Cl)n1CC(F)F]

2263

2263 (4-[(2,4-dichlorophenyl)methyl]-1-[(6,7-difluoro-1H-1,3-benzodiazol-2-yl)methyl]-3-(2,2-difluoroethyl)-2,3-dihydro-1H-imidazol-2-one) was synthesized using 3,4-difluorobenzene-1,2-diamine following General Procedure 2. LC/MS: (ESI) (M+H)$^+$=474.4.

Example 43

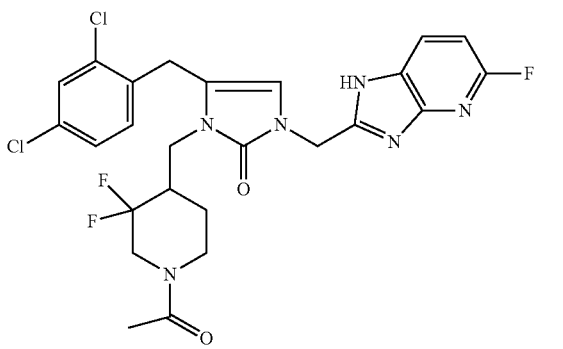

2265

2265 (3-[(1-acetyl-3,3-difluoropiperidin-4-yl)methyl]-4-[(2,4-dichlorophenyl)methyl]-1-({5-fluoro-1H-imidazo[4,5-b]pyridin-2-yl}methyl)-2,3-dihydro-1H-imidazol-2-one) was synthesized using (3,3-difluoro-1-Boc-piperidin-4-yl)methanamine following General Procedure 2. LC/MS: (ESI) (M+H)$^+$=568.5.

Example 44

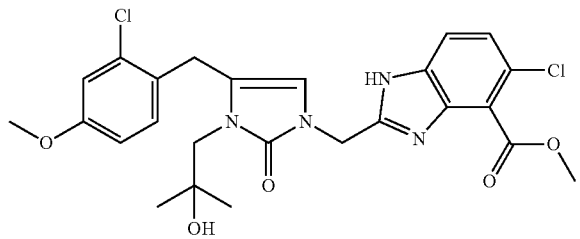

2237

2237 (methyl 5-chlor₀₋₂-({4-[(2-chloro-4-methoxyphenyl)methyl]-3-(2-hydroxy-2-methylpropyl)-2-oxo-2,3-dihydro-1H-imidazol-1-yl}methyl)-1H-1,3-benzodiazole-4-carboxylate) was synthesized using 2-(2-chloro-4-methoxyphenyl)acetic acid, 1-amin₀₋₂-methylpropan-2-ol and methyl 2,3-diamino-6-chlorobenzoate following General Procedure 1 and 2. LC/MS: (ESI) (M+H)⁺=534.4.

Example 45

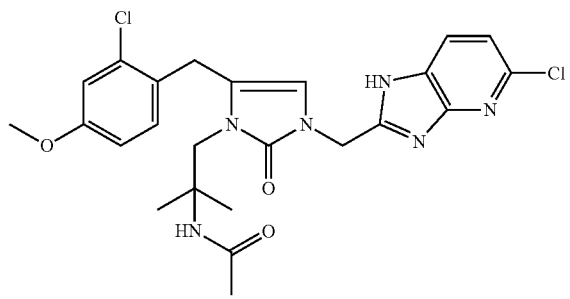

2209

2209 (N-{1-[3-({5-chloro-1H-imidazo[4,5-b]pyridin-2-yl}methyl)-5-[(2-chloro-4-methoxyphenyl)methyl]-2-oxo-2,3-dihydro-1H-imidazol-1-yl]-2-methylpropan-2-yl}acetamide) was synthesized using 2-(2-chloro-4-methoxyphenyl)acetic acid, N2-Boc-2-methylpropane-1,2-diamine following General Procedure 1 and 2. LC/MS: (ESI) (M+H)⁺=518.5.

Example 46

Scheme 3

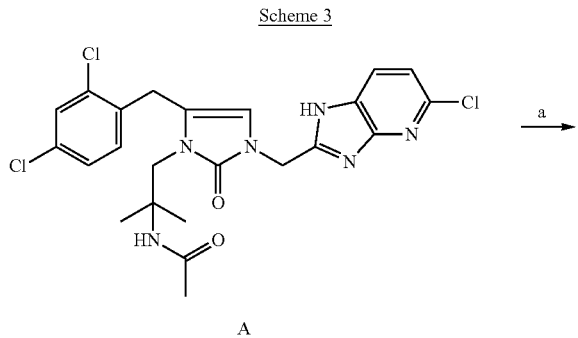

A

Example 46 -continued

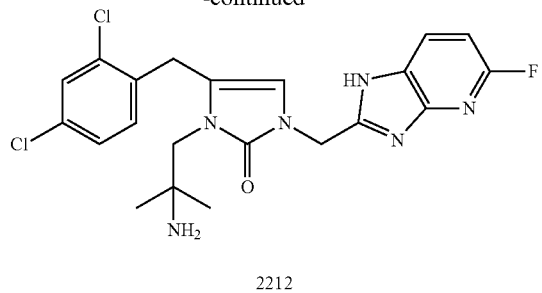

2212

Reagents and conditions (a) 6N HCl, microwave irradiation

N-(1-(5-(2,4-dichlorobenzyl)-3-((5-chloro-1H-imidazo[4,5-b]pyridin-2-yl)methyl)-2,3-dihydro-2-oxoimidazol-1-yl)-2-methylpropan-2-yl)acetamide (A) (10.4 mg, 0.02 mmol) was synthesized using N2-Boc-2-methylpropane-1,2-diamine following General Procedure 2 and added 1 ml of 6 N HCl. The solution was microwave irradiated at 100° C. for 15 min. After the solvent was removed, the residue was purified using silica gel chromatography, eluted with MeOH/DCM/1% NH₄OH to give 5-(2,4-dichlorobenzyl)-1-(2-amin₀₋₂-methylpropyl)-3-((5-chloro-1H-imidazo[4,5-b]pyridin-2-yl)methyl)-1H-imidazol-2(3H)-one (2212) (7.5 mg). LC/MS: (ESI) (M+H)⁺=480.6.

Example 47

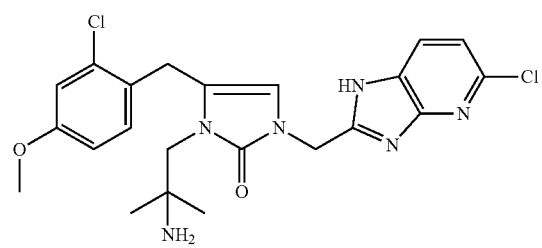

2208

2208 (3-(2-amin₀₋₂-methylpropyl)-1-({5-chloro-1H-imidazo[4,5-b]pyridin-2-yl}methyl)-4-[(2-chloro-4-methoxyphenyl)methyl]-2,3-dihydro-1H-imidazol-2-one) was synthesized via the same procedure as 2212 from 2209. LC/MS: (ESI) (M+H)⁺=476.3.

Example 48

Scheme 4

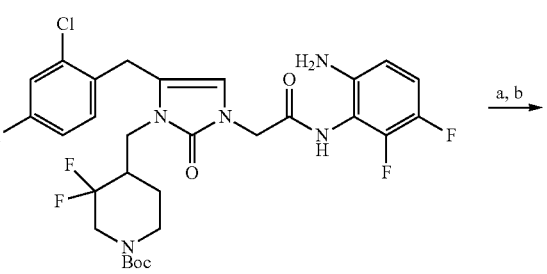

B

-continued

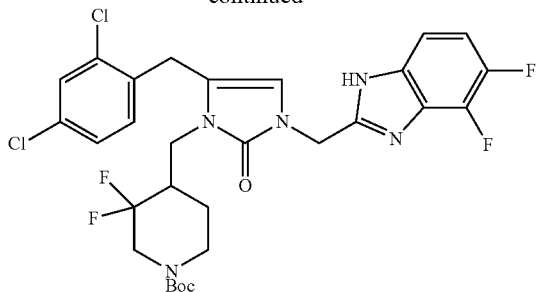

2264

Reagents and conditions (a) HOAc, 50° C., microwave irradiation; (b) TFA/DCM 2-(5-(2,4-dichlorobenzyl)-1-((3,3-difluoro-1-Boc-piperidin-4-yl)methyl)-1,2-dihydr$o_{-2}$-oxoimidazol-3-yl)—N-(6-amino-2,3-difluorophenyl)acetamide (B) (15 mg, 0.023 mmol) was synthesized using 3,4-difluorobenzene-1,2-diamine and (3,3-difluoro-1-Boc-piperidin-4-yl)methanamine following General Procedure 2 and cyclized via microwave irradiated at 50° C. for 20 min. After the solvent was removed, the residue was purified using silica gel chromatography and the product was treated with DCM/TFA (2 ml/2 ml) for 1 hour at room temperature. The solvents were removed and treated with 1.25M HCl in methanol to convert to HCl salt. After the solvents were removed, a white solid of 5-(2,4-dichlorobenzyl)-3-((4,5-difluoro-1H-benzo[d]imidazol-2-yl)methyl)-1-((3,3-difluoropiperidin-4-yl)methyl)-1H-imidazol-2(3H)-one HCl salt (2264) (12 mg) was obtained. LC/MS: (ESI) (M+H)$^+$=543.4.

Example 49 added to the solution dropwise at −78° C. After 10 min, the reaction mixture was allowed to warm to room temperature and was stirred at room temperature for 1 h. The reaction mixture was concentrated under vacuum and basified with 1 N NaOH solution. The compound was extracted with EtOAc (3×20 mL). The combined organic solution was concentrated in vacuo and the residue was purified via HPLC preparation to give 2086 (4-[(2,4-dichlorophenyl)-methyl]-1-({5-fluoro-1H-imidazo[4,5-b]pyridin-2-yl}methyl)-3-(2-hydroxyethyl)-2,3-dihydro-1H-imidazol-2-one) as TFA salt (3.3 mg). LC/MS: (ESI) (M+H)$^+$=437.3.

Example 50

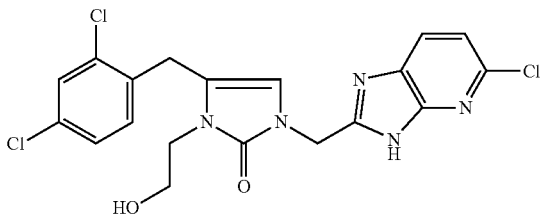

2213

2213 (1-({5-chloro-1H-imidazo[4,5-b]pyridin-2-yl}methyl)-4-[(2,4-dichlorophenyl)-methyl]-3-(2-hydroxyethyl)-2,3-dihydro-1H-imidazol-2-one) was synthesized via the same procedure as 2086 by using 6-chloropyridine-2,3-diamine. LC/MS: (ESI) (M+H)$^+$=453.6.

Example 51

Scheme 5

2077

2086

Reagents and conditions (a) BBr$_3$, DCM 5-(2,4-dichlorobenzyl)-3-((5-fluoro-3H-imidazo[4,5-b]pyridin-2-yl)methyl)-1-(2-methoxyethyl)-1H-imidazol-2(3H)-one (2077) (4.5 mg, 0.01 mmol) was dissolved in DCM and the reaction mixture was cooled in acetone/dry ice (−78° C.). Boron tribromide (1.6 µl) in 1 ml of DCM was Scheme 6

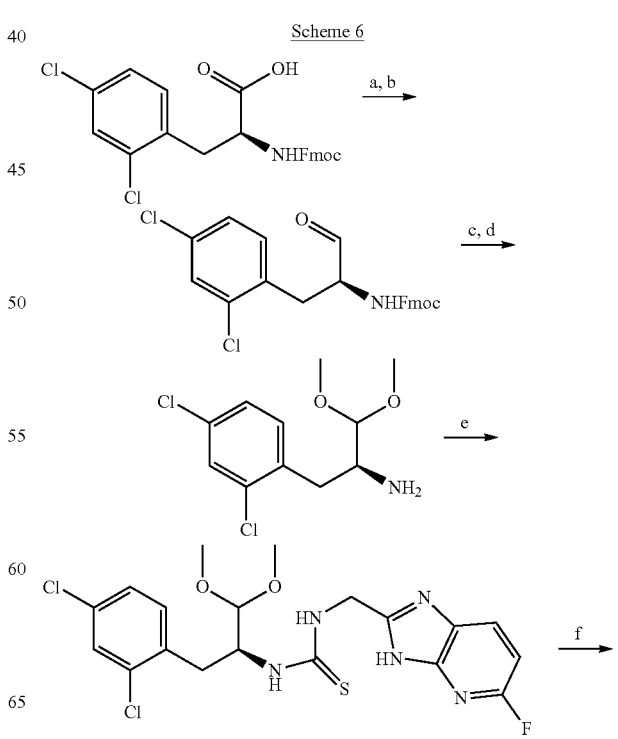

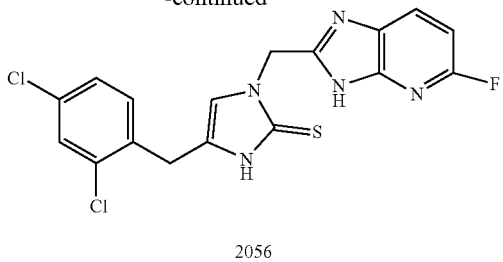

2056

Reagents and conditions (a) HATU, methoxymethanamine, DMF (b) LiAlH₄, THF, 0° C.; (c) MeOH, HCl, microwave irradiation, 80° C., 10 min; (d) DBU, ethyl acetate; (e) thiophosgene, DIPEA, DCM, (5-fluoro-3H-imidazo[4,5-b]pyridin-2-yl)methanamine; (f) 2N HCl, acetone, 90° C., 30 min, microwave irradiation.

A solution of (S)-2-Fmoc-amino-3-(2,4-dichlorophenyl) propanoic acid (228 mg, 0.5 mmol), N-methoxymethanamine HCl (58 mg, 0.6 mmol), HATU (0.6 mmol) and DIPEA (1.2 mmol) in 5 ml of DMF was stirred at room temperature overnight. The solvent was then removed under vacuum. The residue was dissolved in EtOAc (25 mL). The organic layer was washed with brine (25 mL), dried and concentrated under vacuum. Purification by chromatography afforded (S)-2-Fmoc-amino-3-(2,4-dichlorophenyl)—N-methoxy—N-methylpropanamide (200 mg, 0.4 mmol). (S)-2-Fmoc-amino-3-(2,4-dichlorophenyl)—N-methoxy—N-methylpropanamide (200 mg, 0.4 mmol) in anhydrous THF was slowly added LiAlH₄ (0.5 mmol) at 0° C. The mixture was stirred for 1 h and water was added slowly. The mixture was extracted into ether (3×20 mL), and the combined organic layer was washed with brine, dried over Na₂SO₄. After solvent was removed, the residue was purified using silica gel chromatography, eluted with MeOH/DCM to give (S)-2-Fmoc-amino-3-(2,4-dichlorophenyl) propanal (150 mg, 0.34 mmol). (S)-2-Fmoc-amino-3-(2,4-dichlorophenyl)propanal (15 mg, 0.034 mmol) was dissolved in 1 mL of methanol and concentrated HCl (4 μL) was added. The solution was microwave irradiated at 80° C. for 10 min. After the solvent was removed, the residue was dissolved in ethyl acetate and washed with saturated NaHCO₃. The organic layer was treated with DBU (0.035 mmol) for 10 min with stirring. The organic layer was washed with water, brine, dried over Na₂SO₄. After solvent was removed, the residue was dissolved in anhydrous DCM. To the solution was added DIPEA (0.04 mmol) and thiophosgene (0.036 mmol) at 0° C. The solution was stirred at 0° C. for 1 h and room temperature for 2 h, then (5-fluoro-3H-imidazo[4,5-b]pyridin-2-yl)methanamine (0.035 mmol) was added. The reaction was performed at room temperature for 1 h. The solution was diluted with DCM and washed with water, brine, dried over Na₂SO₄. After solvent was removed, the residue was purified using silica gel chromatography, eluted with MeOH/DCM to give 1-((S)-3-(2,4-dichlorophenyl)-1,1-dimethoxypropan-2-yl)-3-((5-fluoro-3H-imidazo[4,5-b]pyridin-2-yl)methyl)thiourea. 1-((S)-3-(2,4-dichlorophenyl)-1,1-dimethoxypropan-2-yl)-3-((5-fluoro-3H-imidazo[4,5-b]pyridin-2-yl)methyl)thiourea (9.4 mg, 0.02 mmol) was dissolved in 1 mL of acetone and 2.5 mL of 2N HCl. The solution was microwave irradiated at 90° C. for 30 min. After the solvent was removed, the residue was dissolved in ethyl acetate and washed with saturated NaHCO₃, brine, dried over Na₂SO₄. After solvent was removed, the residue was purified using silica gel chromatography, eluted with MeOH/DCM to 5-(2,4-dichlorobenzyl)-3-((5-fluoro-3H-imidazo[4,5-b]pyridin-2-yl)methyl)-1H-imidazole-2 (3H)-thione (2056) (6.5 mg). LC/MS: (ESI) (M+H)⁺=409.6.

Examples 52 and 53

Scheme 7

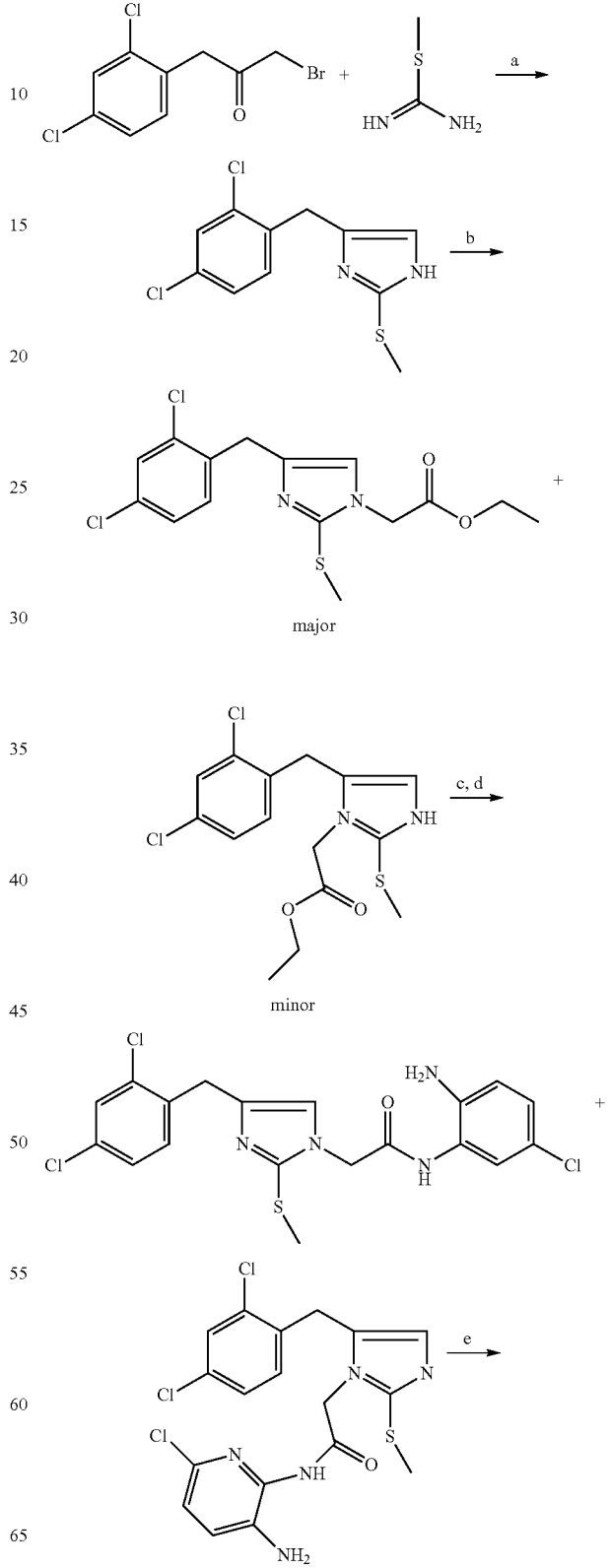

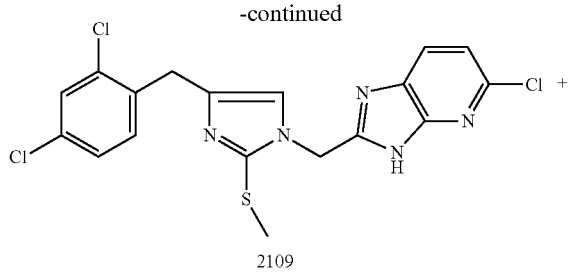

2109

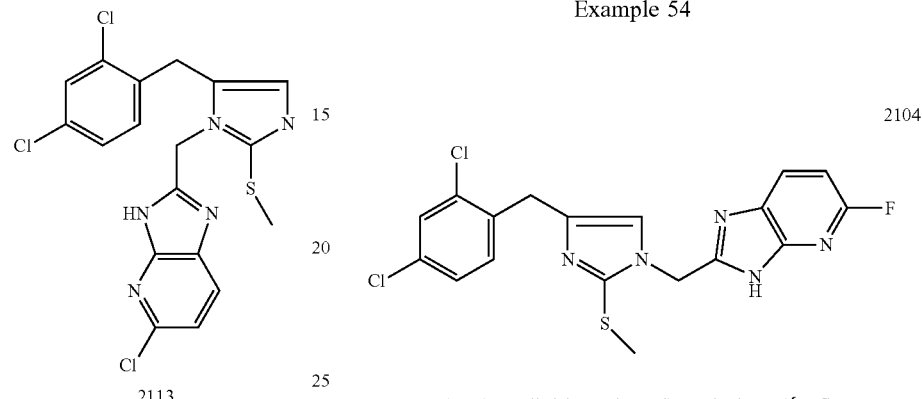

2113

Reagents and conditions (a) MeCN, DIPEA, microwave irradiation, 100° C., 15 min; (b) ethyl bromoacetate, K₂CO₃; (i) LiOH, ethanol/water; (j) EDC, 6-chloropyridine-2,3-diamine, pyridine; (k) HOAc, microwave irratiation.

General Procedure 3 (2109, 2113, 2104):

The mixture of 1-amino-3-(2,4-dichlorophenyl)propan-2-one (59 mg, 0.21 mmol), DIPEA (1.4 mmol) and methyl carbamimidothioate hydroiodide (92 mg, 0.42 mmol) in ethanol was microwave irradiation at 100° C. for 15 min. The mixture was diluted with EtOAc and washed successively with saturated NaHCO₃ and brine. The organic layer was dried over Na₂SO₄ and concentrated in vacuo. The residue was purified by flash column chromatography (DCM/MeOH), yielding 4-(2,4-dichlorobenzyl)-2-(methylthio)-1H-imidazole (43.7 mg, 0.16 mmol). 4-(2,4-dichlorobenzyl)-2-(methylthio)-1H-imidazole (41 mg, 0.15 mmol) was dissolved in 10 ml anhydrous acetonitrile and treated with 26 μl (0.24 mmol) of ethyl bromoacetate and Cs₂CO₃ (98 mg, 0.3 mmol). The mixture is stirred at 50° C. overnight. After the reaction mixture is evaporated. The residues was dissolved with EtOAc and washed successively with water and brine. The organic layer was dried over Na₂SO₄ and concentrated in vacuo. The residue was purified by flash chromatography on silica gel (dichloromethane/methanol) to obtain ethyl 2-(4-(2,4-dichlorobenzyl)-2-(methylthio)-1H-imidazol-1-yl)acetate (41 mg, 0.09 mmol) and ethyl 2-(5-(2,4-dichlorobenzyl)-2-(methylthio)-1H-imidazol-1-yl)acetate (8.2 mg, 0.018 mmol).

Ethyl 2-(4-(2,4-dichlorobenzyl)-2-(methylthio)-1H-imidazol-1-yl)acetate (0.09 mmol) and ethyl 2-(5-(2,4-dichlorobenzyl)-2-(methylthio)-1H-imidazol-1-yl)acetate (0.018 mmol) were added in 1 ml of ethanol and 3 ml of water, mixed with LiOH (4 equiv) respectively and stirred for 50 min at room temperature. The solution was acidified with 0.2 N hydrochloric acid and the solvent completely removed in vacuo. The residue was dissolved in 3 ml of pyridine, then 6-chloropyridine-2,3-diamine (1.2 equiv) and EDC hydrochloride (1.5 equiv) were added. The mixture was stirred at room temperature overnight. The solvent was removed on the rotary evaporator. The residue was dissolved in 2 ml of acetic acid and the solution was microwave irradiated at 125° C. for 1 h. After the solvent was removed on the rotary evaporator, the residue was purified by flash column chromatography (DCM/MeOH), yielding 2109 (1-({5-chloro-1H-imidazo[4,5-b]pyridin-2-yl}methyl)-4-[(2,4-dichlorophenyl)methyl]-2-(methylsulfanyl)-1H-imidazole) (31 mg, 0.07 mmol) and 2113 (1-({5-chloro-1H-imidazo[4,5-b]pyridin-2-yl}methyl)-5-[(2,4-dichlorophenyl)methyl]-2-(methylsulfanyl)-1H-imidazole) (4.4 mg, 0.01 mmol). LC/MS: (ESI) (M+H)⁺=439.9.

Example 54

2104

2104 (4-[(2,4-dichlorophenyl)methyl]-1-({5-fluoro-1H-imidazo[4,5-b]pyridin-2-yl}methyl)-2-(methylsulfanyl)-1H-imidazole) was synthesized using 6-floropyridine-2,3-diamine following General Procedure 3. LC/MS: (ESI) (M+H)⁺=423.6.

Example 55

Scheme 8

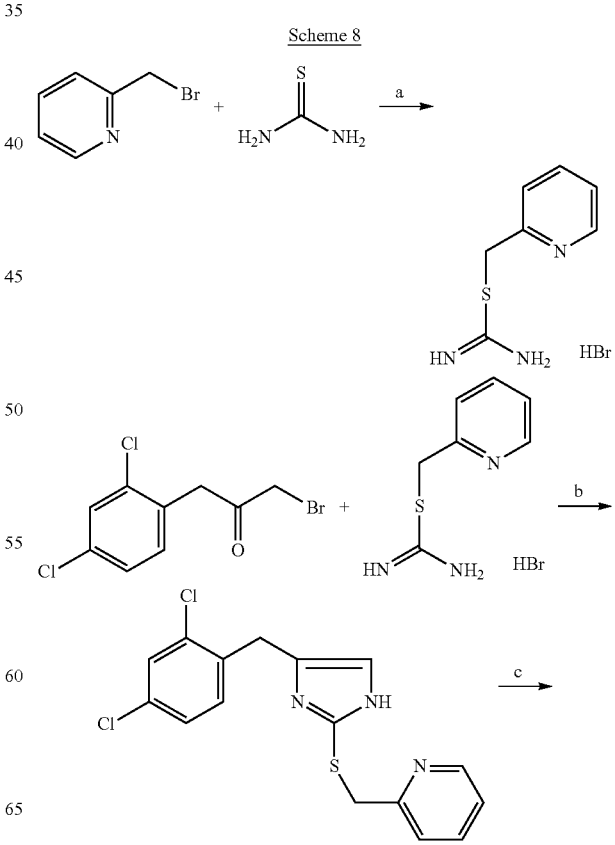

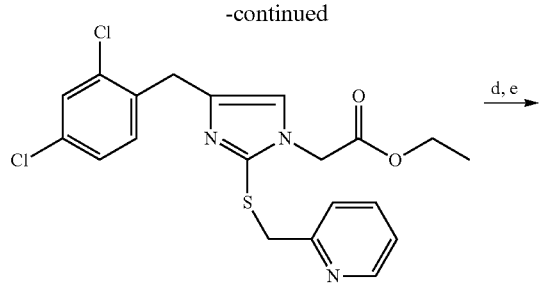

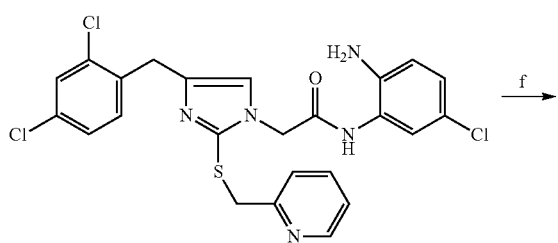

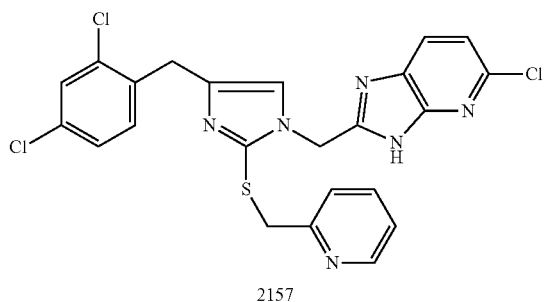

2157

Reagents and conditions (a) ethanol, refluxing, 2 h; (b) MeCN, DIPEA, microwave irradiation, 100° C., 20 min; (c) ethyl bromoacetate, Cs₂CO₃; (d) LiOH, ethanol/water; (e) EDC, 6-chloropyridine-2,3-diamine, pyridine; (f) HOAc, microwave irratiation The mixture of 2-(bromomethyl)pyridine (172 mg, 1.0 mmol) and urea (77.5 mg, 1.05 mmol) in ethanol was refluxed for 2 h. The precipitate of 2-((pyridin-2-yl)methyl)isothiourea HBr salt was collected and directly used.

The mixture of 1-amino-3-(2,4-dichlorophenyl)propan-2-one (56.4 mg, 0.2 mmol), DIPEA (1.2 mmol) and 2-((pyridin-2-yl)methyl)isothiourea hydrobromide (99.2 mg, 0.4 mmol) in ethanol was microwave irradiation at 100° C. for 20 min. The mixture was diluted with EtOAc and washed successively with saturated NaHCO₃ and brine. The organic layer was dried over Na₂SO₄ and concentrated in vacuo. The residue was purified by flash column chromatography (DCM/MeOH), yielding 2-((4-(2,4-dichlorobenzyl)-1H-imidazol-2-ylthio)methyl)pyridine (38.5 mg, 0.11 mmol). 2-((4-(2,4-dichlorobenzyl)-1H-imidazol-2-ylthio)methyl)pyridine (38.5 mg, 0.11 mmol) was dissolved in 10 ml anhydrous acetonitrile and treated with 20 µl (0.18 mmol) of ethyl bromoacetate and Cs₂CO₃ (65 mg, 0.20 mmol). The mixture was stirred at 50° C. overnight. After the reaction solvent was evaporated, the residues was dissolved with EtOAc and washed successively with water and brine. The organic layer was dried over Na₂SO₄ and concentrated in vacuo. The residue was purified by flash chromatography on silica gel (DCM/methanol) to obtain ethyl 2-(2-((pyridin-2-yl)methylthio)-4-(2,4-dichlorobenzyl)-1H-imidazol-1-yl) acetate (35 mg, 0.08 mmol).

Ethyl 2-(2-((pyridin-2-yl)methylthio)-4-(2,4-dichlorobenzyl)-1H-imidazol-1-yl)acetate (35 mg, 0.08 mmol) was added in 1 ml of ethanol and 3 ml of water, mixed with LiOH (1.9 mg, 0.32 mmol) and stirred for 50 min at room temperature. The solution was acidified with 0.2 N hydrochloric acid and the solvent was completely removed in vacuo. The residue was dissolved in 3 ml of pyridine, then 6-chloropyridine-2,3-diamine (13.8 mg, 0.096 mmol) and EDC hydrochloride (23 mg, 0.12 mmol) were added. The mixture was stirred at room temperature overnight. The solvent was removed on the rotary evaporator. The residue was dissolved in 2 ml of acetic acid and the solution was microwave irradiated at 125° C. for 1 h. After the solvent was removed on the rotary evaporator, the residue was purified by flash column chromatography (DCM/MeOH), yielding 2157 (2-({[1-({5-chloro-1H-imidazo[4,5-b]pyridin-2-yl}methyl)-4-[(2,4-dichlorophenyl)methyl]-1H-imidazol-2-yl]sulfanyl}methyl)pyridine) (21 mg). LC/MS: (ESI) (M+H)⁺=517.1.

Example 56

Scheme 9

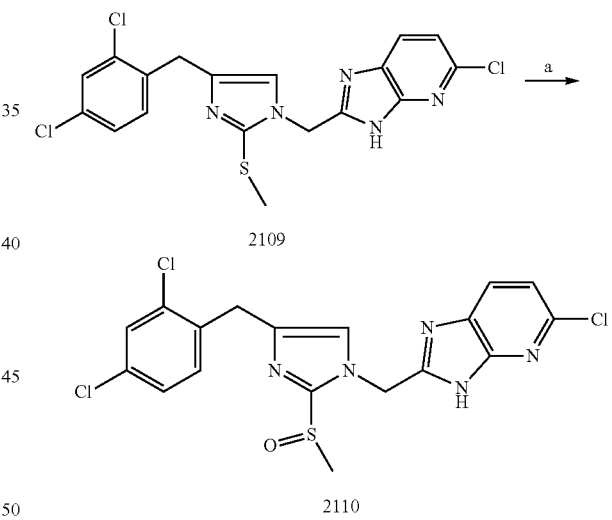

Reagents and conditions (a) mCPBA, DCM, 2.5 h

General Procedure 4 (2110, 2120):

To a solution of 2-((4-(2,4-dichlorobenzyl)-2-(methylthio)-1H-imidazol-1-yl)methyl)-5-chloro-3H-imidazo[4,5-b]pyridine (2109) (17.5 mg, 0.04 mmol) in DCM (10 mL) was added mCPBA (8.3 mg, 0.048 mmol) at 0° C. The mixture was stirred at room temperature for 2.5 h, and then washed with 10 mL of saturated NaHCO₃ twice. Methylene chloride layer was separated, washed with brine, and dried over anhydrous Na₂SO₄. The solvent was evaporated under reduced pressure. The residue was purified by silica gel column chromatography to give 2110 (1-({5-chloro-1H-imidazo[4,5-b]pyridin-2-yl}methyl)-4-[(2,4-dichlorophenyl)methyl]-2-methanesulfinyl-1H-imidazole) (15.4 mg, 0.034 mmol). LC/MS: (ESI) (M+H)⁺=455.6.

Example 57

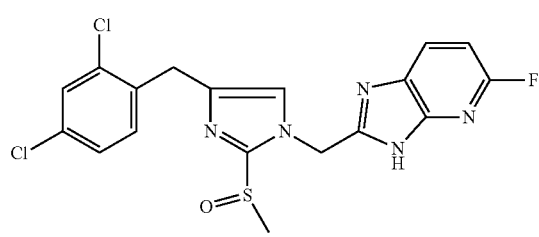

2120

2120 (4-[(2,4-dichlorophenyl)methyl]-1-({5-fluoro-1H-imidazo[4,5-b]pyridin-2-yl}methyl)-2-methanesulfinyl-1H-imidazole) was synthesized from 2104 following General Procedure 4. $^1$H NMR (MeOD) δ 8.02-7.94 (m, 1H), 7.37 (s, 1H), 7.37 (s, 1H), 7.26 (d, J=8.3 Hz, 1H), 7.19 (m, 1H), 7.12 (s, 1H), 6.88 (d, J=8.6 Hz, 1H), 5.72 (s, 2H), 3.98 (s, 2H), 3.06 (s, 3H). LC/MS: (ESI) (M+H)$^+$=439.5.

Example 58

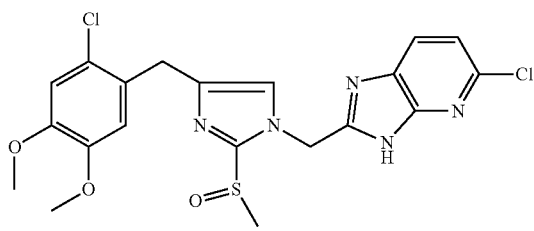

2241

2241 (1-({5-chloro-1H-imidazo[4,5-b]pyridin-2-yl}methyl)-4-[(2-chloro-4,5-dimethoxyphenyl)methyl]-2-methanesulfinyl-1H-imidazole) was synthesized using 2-(2-chloro-4,5-dimethoxyphenyl)acetic acid following General Procedure 3 with subsequent oxidation using General Procedure 4. LC/MS: (ESI) (M+H)$^+$=481.1.

Example 59

Scheme 10

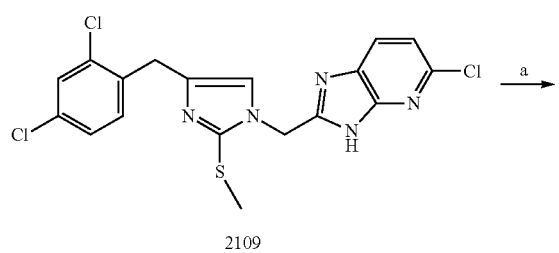

2109

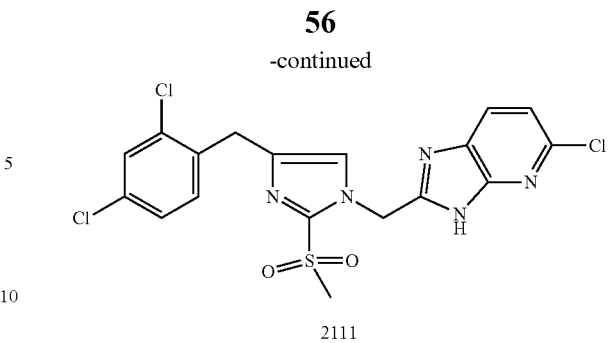

2111

Reagents and conditions (a) mCPBA, DCM, 1 h

General Procedure 5 (2111, 2105):

To a solution of 2-((4-(2,4-dichlorobenzyl)-2-(methylthio)-1H-imidazol-1-yl)methyl)-5-chloro-3H-imidazo[4,5-b]pyridine (2109) (17.5 mg, 0.04 mmol) in DCM (10 mL) was added mCPBA (21 mg, 0.12 mmol) at 0° C. The mixture was stirred at room temperature for 1 h, and then washed with 10 mL of saturated NaHCO$_3$ twice. Methylene chloride layer was separated, washed with brine, and dried over anhydrous Na$_2$SO$_4$. The solvent was evaporated under reduced pressure. The residue was purified by silica gel column chromatography to give 2111 (1-({5-chloro-1H-imidazo[4,5-b]pyridin-2-yl}methyl)-4-[(2,4-dichlorophenyl)methyl]-2-methanesulfonyl-1H-imidazole) (16.5 mg, 0.035 mmol). LC/MS: (ESI) (M+H)$^+$=472.1.

Example 60

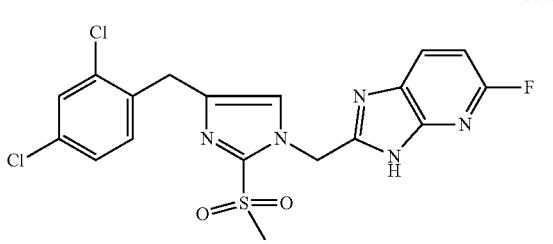

2105

2105 (4-[(2,4-dichlorophenyl)methyl]-1-({5-fluoro-1H-imidazo[4,5-b]pyridin-2-yl}methyl)-2-methanesulfonyl-1H-imidazole) was synthesized from 2104 following General Procedure 5. LC/MS: (ESI) (M+H)$^+$=455.6.

Example 61

Scheme 11

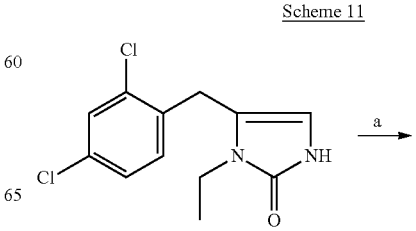

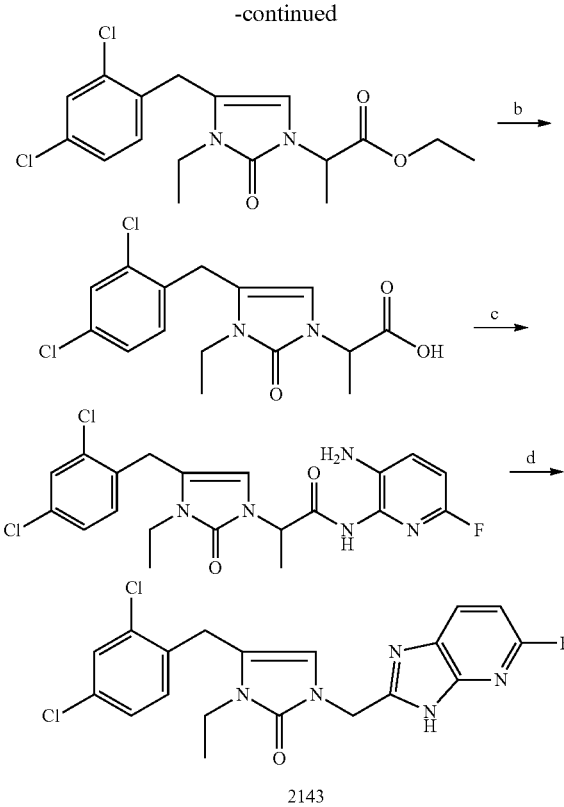

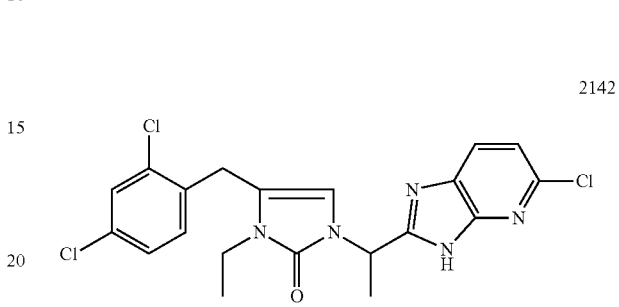

Reagents and conditions (a) ethyl 2-bromopropanoate, K$_2$CO$_3$,; (b) LiOH, ethanol/water; (c) EDC, 6-floropyridine-2,3-diamine, pyridine; (d) HOAc, microwave irradiation General Procedure 6 (2143, 2142, 2121):

5-(2,4-dichlorobenzyl)-1-ethyl-1H-imidazol-2(3H)-one (10.8 mg, 0.04 mmol, from Scheme 1) was dissolved in 10 ml anhydrous acetonitrile and treated with 22 mg (0.12 mmol) of ethyl 2-bromopropanoate and 16.6 mg (0.12 mmol) of potassium carbonate. The mixture was heated at 60° C. for 24 hours. After the reaction mixture was evaporated. The residues was dissolved with EtOAc and washed successively with water and brine. The organic layer was dried over Na$_2$SO$_4$ and concentrated in vacuo. The residue was purified by flash chromatography on silica gel (DCM/methanol) to obtain ethyl 2-(5-(2,4-dichlorobenzyl)-1-ethyl-1,2-dihydr$_{0-2}$-oxoimidazol-3-yl)propanoate (7.8 mg, 0.021 mmol).

Ethyl 2-(5-(2,4-dichlorobenzyl)-1-ethyl-1,2-dihydr$_{0-2}$-oxoimidazol-3-yl)propanoate (7.8 mg, 0.021 mmol) was added in 2 ml of ethanol and 4 ml of water, mixed with LiOH (2 mg, 0.084 mmol) and stirred for 50 min at room temperature. The solution was acidified with 0.2 N hydrochloric acid and the solvent was completely removed in vacuo. The residue was dissolved in 3 ml of pyridine, then 6-fluoro-pyridine-2,3-diamine (4 mg, 0.03 mmol) and EDC hydrochloride (8.1 mg, 0.042 mmol) were added. The mixture was stirred at room temperature overnight. The solvent was removed on the rotary evaporator. The residue was dissolved in EtOAc (30 ml) and washed with water and brine. The organic layer was dried over Na$_2$SO$_4$ and concentrated in vacuo. The residue was purified by flash chromatography on silica gel to give 2-(5-(2,4-dichlorobenzyl)-1-ethyl-1,2-dihydr$_{0-2}$-oxoimidazol-3-yl)—N-(3-amino-6-fluoropyridin-2-yl)propanamide. 2-(5-(2,4-dichlorobenzyl)-1-ethyl-1,2-dihydr$_{0-2}$-oxoimidazol-3-yl)—N-(3-amino-6-fluoropyridin-2-yl)propanamide was dissolved in 2 ml of acetic acid and the solution was microwave irradiated at 125° C. for 1 h. After the solvent was removed on a rotary evaporator, the residue was purified by flash column chromatography (DCM/MeOH), yielding 2143 (4-[(2,4-dichlorophenyl)methyl]-3-ethyl-1-(1-{5-fluoro-1H-imidazo[4,5-b]pyridin-2-yl}ethyl)-2,3-dihydro-1H-imidazol-2-one) (4.6 mg, 0.011 mmol). LC/MS: (ESI) (M+H)$^+$=435.4.

Example 62

2142 (1-(1-{5-chloro-1H-imidazo[4,5-b]pyridin-2-yl}ethyl)-4-[(2,4-dichlorophenyl)-methyl]-3-ethyl-2,3-dihydro-1H-imidazol-2-one) was synthesized using 6-chloro-pyridine-2,3-diamine following General Procedure 6. LC/MS: (ESI) (M+H)$^+$=451.7.

Example 63

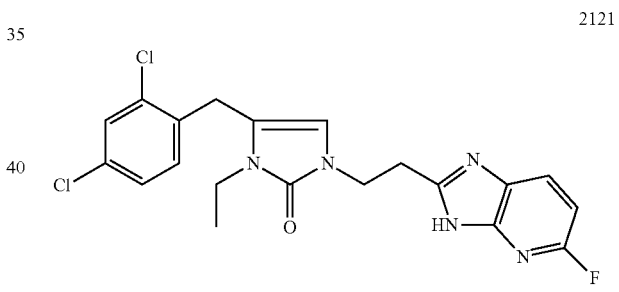

2121 (4-[(2,4-dichlorophenyl)methyl]-3-ethyl-1-(2-{5-fluoro-1H-imidazo[4,5-b]pyridin-2-yl}ethyl)-2,3-dihydro-1H-imidazol-2-one) was synthesized using ethyl 3-bromopropanoate following General Procedure 6. LC/MS: (ESI) (M+H)$^+$=435.4.

Example 64

Scheme 12

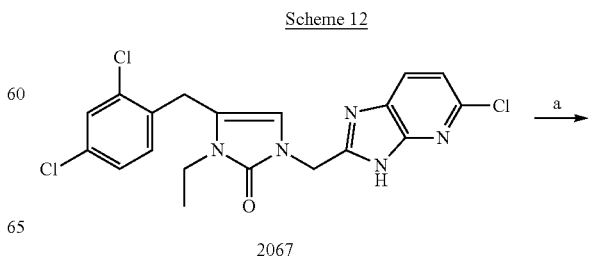

-continued

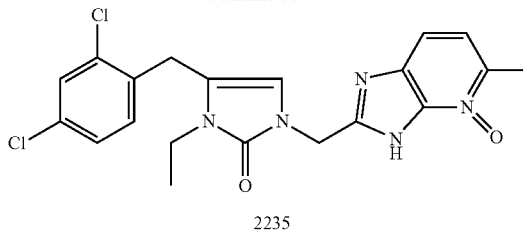

2235

Reagents and conditions (a) mCPBA, acetic acid

To compound 2067 (10 mg, 0.023 mmol) in 2 ml of acetic acid was added meta-chloroperoxybenzoic acid (mCPBA) (6 mg, 0.0345 mmol). The mixture was stirred at room temperature for 2 hours. After the solvent was removed, the residue was purified using silica gel chromatography to obtain 2235 (1-({5-chloro-4-oxo-1H-4λ$^5$-imidazo[4,5-b]pyridin-2-yl}methyl)-4-[(2,4-dichlorophenyl)methyl]-3-ethyl-2,3-dihydro-1H-imidazol-2-one) (7.3 mg). LC/MS: (ESI) (M+H)$^+$=453.8.

Example 65

Scheme 13

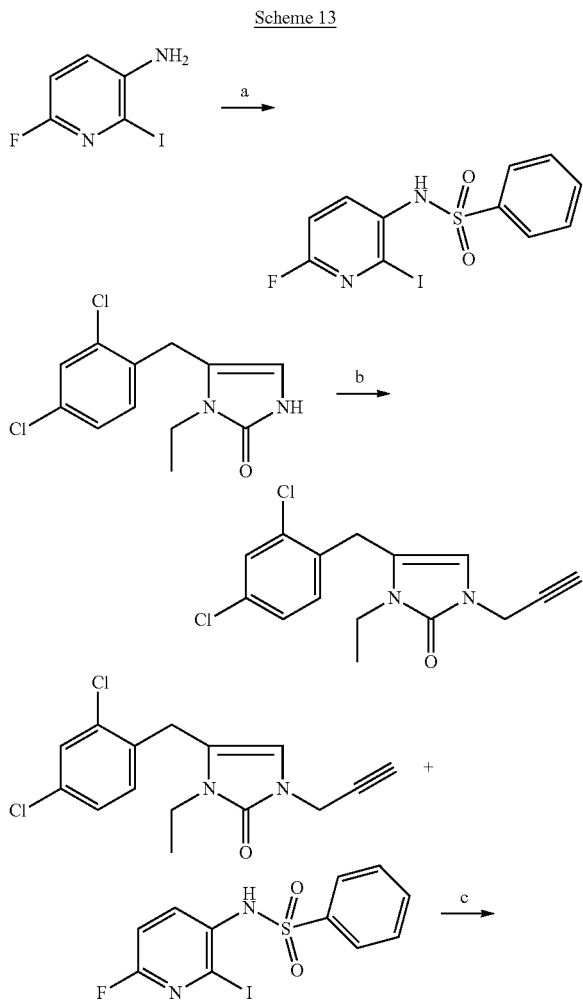

-continued

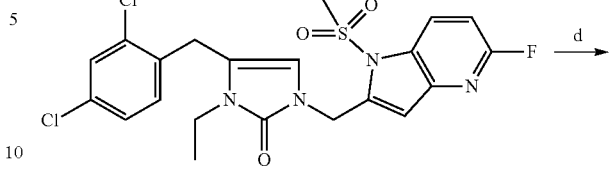

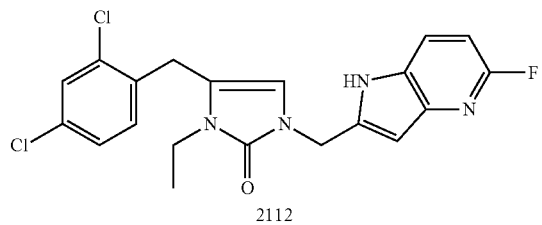

2112

Reagents and conditions (a) benzenesulfonyl chloride, pyridine, microwave irradiation; (b) 3-bromoprop-1-yne, K$_2$CO$_3$, microwave irradiation; (c) DMF, CuI, PdCl$_2$(PPh$_3$)$_2$, TEA, microwave irradiation; (d) MeOH, 1N NaOH, microwave irradiation The mixture of 6-fluor$_{0-2}$-iodopyridin-3-amine (50 mg, 0.21 mmol) and benzenesulfonyl chloride (60 µl, 0.47 mmol) in pyridine was microwave irradiated at 100° C. for 15 min. After the solvent was removed, the residue was purified by flash column chromatography (DCM/MeOH) to obtain N-(6-fluor$_{0-2}$-iodopyridin-3-yl)benzenesulfonamide (60 mg, 0.16 mmol)

The mixture of 5-(2,4-dichlorobenzyl)-1-ethyl-1H-imidazol-2(3H)-one (15.8 mg, 0.054 mmol), 40 µl of 9.2M 3-bromoprop-1-yne in toluene, and potassium carbonate (25 mg, 1.63 mmol) in acetonitrile was microwave irradiated at 120° C. for 30 min. After the solvent was removed, the residue was purified by flash column chromatography (DCM/MeOH) to obtain 5-(2,4-dichlorobenzyl)-1-ethyl-3-(prop-2-ynyl)-1H-imidazol-2(3H)-one (12.3 mg, 0.04 mmol).

The mixture of 5-(2,4-dichlorobenzyl)-1-ethyl-3-(prop-2-ynyl)-1H-imidazol-2(3H)-one (6.8 mg, 0.022 mmol), N-(6-fluor$_{0-2}$-iodopyridin-3-yl)benzenesulfulonamide (8.3 mg, 0.022 mmol), CuI (1 mg), PdCl$_2$(PPh$_3$)$_2$ (1 mg) and Et$_3$N (3.5 µl) in DMF was microwave irradiated at 120° C. for 15 min. After the solvent was removed, the residue was purified by flash column chromatography (DCM/MeOH) to obtain 5-(2,4-dichlorobenzyl)-1-ethyl-3-((5-fluoro-1H-pyrrolo[3,2-b]pyridin-2-yl) (benzenesulfonyl)methyl)-1H-imidazol-2(3H)-one (8.6 mg, 0.015 mmol).

5-(2,4-dichlorobenzyl)-1-ethyl-3-((5-fluoro-1H-pyrrolo[3,2-b]pyridin-2-yl) (benzenesulfonyl)methyl)-1H-imidazol-2(3H)-one (8.6 mg, 0.015 mmol) in 1 ml of MeOH and 20 µl of 1 N NaOH was microwave irradiated at 100° C. for 20 min. After the solvent was removed, the residue was purified by flash column chromatography (DCM/MeOH) to obtain 5-(2,4-dichlorobenzyl)-1-ethyl-3-((5-fluoro-1H-pyrrolo[3,2-b]pyridin-2-yl)methyl)-1H-imidazol-2(3H)-one (2112) (5.0 mg, 0.012 mmol). LC/MS: (ESI) (M+H)$^+$=420.3.

Example 66

Scheme 14

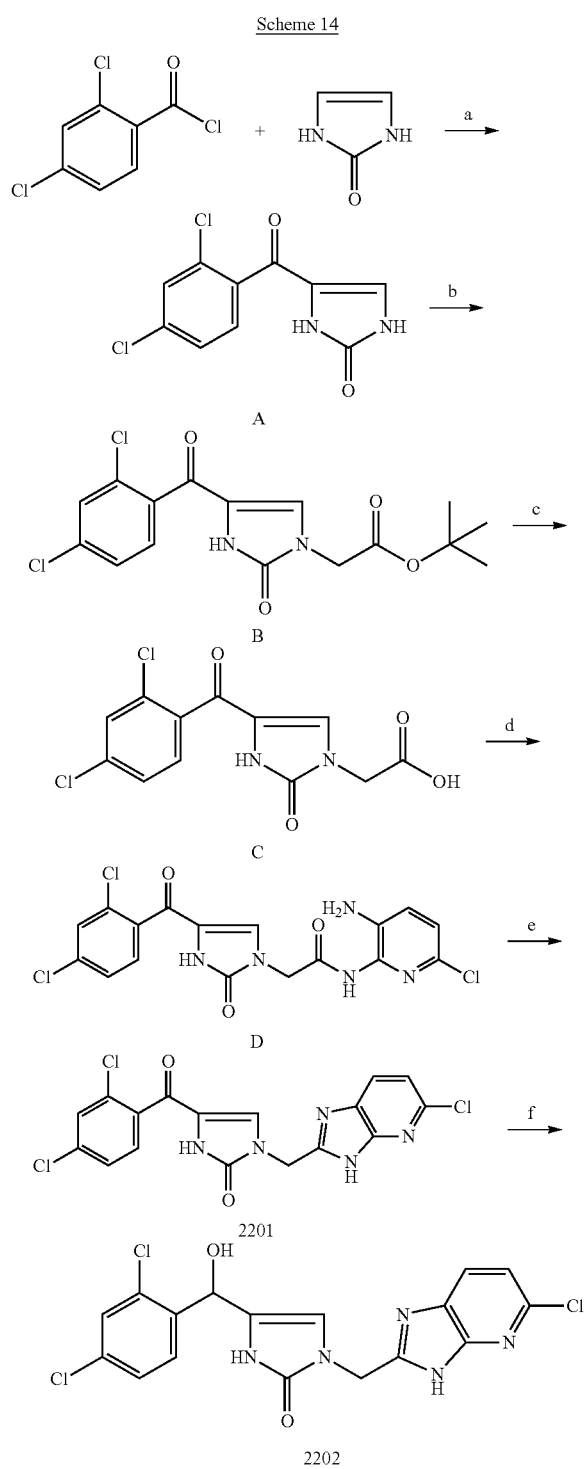

Reagents and conditions (a) AlCl₃, PhNO₂; (b) t-butyl bromoacetate, Cs₂CO₃; (c) DCM/TFA; (d) EDC, 6-chloropyridine-2,3-diamine, pyridine; (e) HOAc, microwave irradiation; (f) NaBH₄, MeOH To a solution of 1H-imidazol-2(3H)-one (56 mg, 0.67 mmol) in nitrobenzene (0.5 ml) was added AlCl₃ (178 mg, 1.34 mmol) and 2,4-dichlorobenzoyl chloride (140.4 mg, 0.67 mmol). The mixture was heated to dissolve AlCl₃. The mixture was microwave irradiated at 80° C. for 40 min. To the mixture was added 50 ml of ether and 60 ml of 0.2 N NaOH. The aqueous layer was collected and neutralized with HCl. The cloudy solution was extracted with 50 ml of EtOAc. The organic layer was dried over Na₂SO₄ and concentrated in vacuo. The residue was purified by flash chromatography on silica gel (EtOAc/hexane) to give 62 mg (40% yield) of A. Compound A (62 mg, 0.24 mmol) was dissolved in 10 ml anhydrous DMF and treated with 28 µl (0.192 mmol) of t-butyl bromoacetate and 180 mg of K₂CO₃ (0.36 mmol). The mixture was stirred at 50° C. overnight. After the reaction solvent was evaporated, the residues was dissolved with EtOAc and washed successively with water and brine. The organic layer was dried over Na₂SO₄ and concentrated in vacuo. The residue was purified by flash chromatography on silica gel (EtOAc/hexane) to obtain B in 60% yield (53 mg, 0.144 mmol).

Compound B (53 mg, 0.144 mmol) was added in 2 ml of DCM and 2 ml of TFA. The mixture was stirred for 1 hour at room temperature. The solvent was completely removed in vacuo. The residue was dissolved in 3 ml of pyridine, then 6-chloropyridine-2,3-diamine (0.22 mmol) and EDC hydrochloride (52 mg, 0.27 mmol) were added. The mixture was stirred at room temperature overnight. The solvent was removed on the rotary evaporator. The residue was dissolved in EtOAc (30 ml) and washed with water and brine. The organic layer was dried over Na₂SO₄ and concentrated in vacuo. The residue was purified by flash chromatography on silica gel to give D. Compound D was dissolved in 2 ml of acetic acid and the solution was microwave irradiated at 125° C. for 1 h. After the solvent was removed on the rotary evaporator, the residue was purified by flash column chromatography (DCM/MeOH), giving 27 mg of 2201 (1-({5-chloro-1H-imidazo[4,5-b]pyridin-2-yl}methyl)-4-(2,4-dichlorobenzoyl)-2,3-dihydro-1H-imidazol-2-one) in 45% yield. LC/MS: (ESI) (M+H)⁺=423.5.

Example 67

Compound 2201 (15 mg, 0.036 mmol) was dissolved in 4 ml of MeOH and NaBH₄ (4.9 mg, 0.13 mmol). The mixture was stirred at room temperature overnight. After the solvent was removed on the rotary evaporator, the residue was purified by flash column chromatography (DCM/MeOH), giving 13.7 mg of 2202 (1-({5-chloro-1H-imidazo[4,5-b]pyridin-2-yl}methyl)-4-[(2,4-dichlorophenyl)(hydroxy)methyl]-2,3-dihydro-1H-imidazol-2-one) in 90% yield. LC/MS: (ESI) (M+H)⁺=425.5.

Example 68

Scheme 15

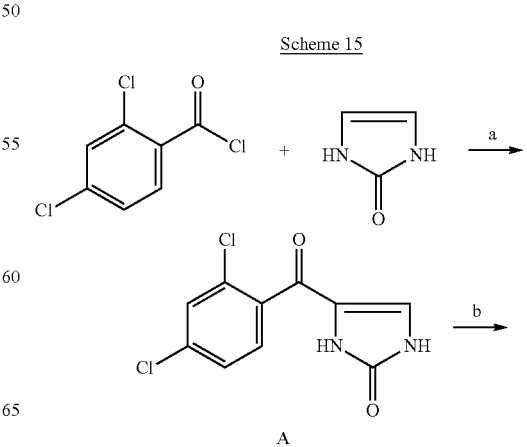

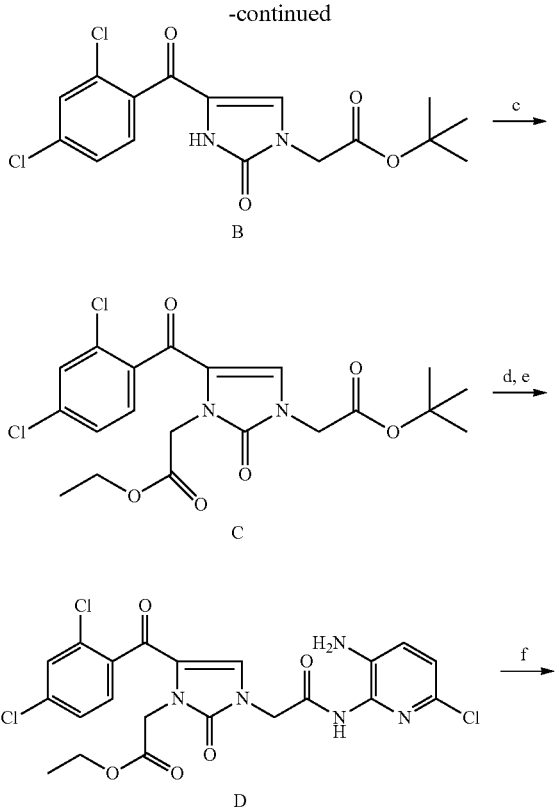

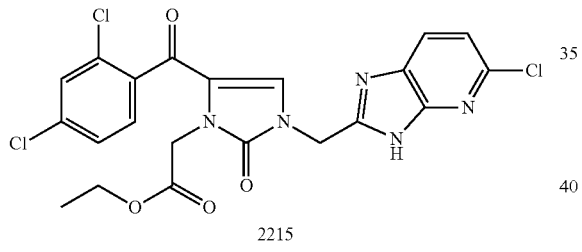

Reagents and conditions (a) AlCl₃, PhNO₂; (b) t-butyl bromoacetate, Cs₂CO₃; (c) NaH, ethyl bromoacetate, DMF; (d) DCM/TFA; (e) EDC, 6-chloropyridine-2,3-diamine, pyridine; (f) HOAc, microwave irradiation To a solution of 1H-imidazol-2(3H)-one (56 mg, 0.67 mmol) in nitrobenzene (0.5 ml) was added AlCl₃ (178 mg, 1.34 mmol) and 2,4-dichlorobenzoyl chloride (140.4 mg, 0.67 mmol). The mixture was heated to dissolve AlCl₃. The mixture was microwave irradiated at 80° C. for 40 min. The mixture was added 50 ml of ether and 60 ml of 0.2 N NaOH. The aqueous layer was collected and neutralized with HCl. The cloudy solution was extracted with 50 ml of EtOAc. The organic layer was dried over Na₂SO₄ and concentrated in vacuo. The residue was purified by flash chromatography on silica gel (EtOAc/hexane) to give 62 mg (40% yield) of A. Compound A (62 mg, 0.24 mmol) was dissolved in 10 ml anhydrous DMF and treated with 28 µl (0.192 mmol) of t-butyl bromoacetate and 180 mg of K₂CO₃ (0.36 mmol). The mixture was stirred at 50° C. overnight. After the reaction solvent was evaporated, the residues was dissolved with EtOAc and washed successively with water and brine. The organic layer was dried over Na₂SO₄ and concentrated in vacuo. The residue was purified by flash chromatography on silica gel (EtOAc/hexane) to obtain B in 60% yield (53 mg, 0.144 mmol).

To compound B (40 mg, 0.11 mmol) in 2 ml of anhydrous DMF was added Cs₂CO₃ (54 mg, 0.165 mmol) and ethyl bromoacetate (11 µl, 0.10 mmol). The mixture was stirred at room temperature for 50 min. After the solvent was removed on the rotary evaporator, the residue was purified by flash column chromatography (DCM/MeOH), giving 22.6 mg of C in 45% yield.

Compound C (22.6 mg, 0.05 mmol) was added in 2 ml of DCM and 2 ml of TFA. The mixture was stirred for 1 hour at room temperature. The solvent was completely removed in vacuo. The residue was dissolved in 3 ml of pyridine, then 6-chloropyridine-2,3-diamine (0.075 mmol) and EDC hydrochloride (19 mg, 0.10 mmol) were added. The mixture was stirred at room temperature overnight. The solvent was removed on the rotary evaporator. The residue was dissolved in EtOAc (30 ml) and washed with water and brine. The organic layer was dried over Na₂SO₄ and concentrated in vacuo. The residue was purified by flash chromatography on silica gel to give D. Compound D was dissolved in 2 ml of acetic acid and the solution was microwave irradiated at 125° C. for 1 h. After the solvent was removed on the rotary evaporator, the residue was purified by flash column chromatography (DCM/MeOH), giving 8.9 mg of 2215 (ethyl 2-[3-({5-chloro-1H-imidazo[4,5-b]pyridin-2-yl}methyl)-5-(2,4-dichlorobenzoyl)-2-oxo-2,3-dihydro-1H-imidazol-1-yl]acetate) in 35% yield. LC/MS: (ESI) (M+H)⁺=509.8.

Example 69

Scheme 16

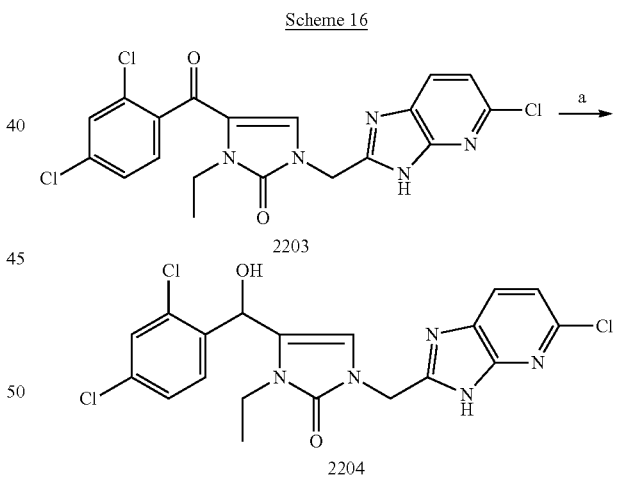

Reagents and conditions (a) NaBH₄, MeOH

The synthetic procedure of compound 2203 was the same as 2215 via using bromoethane. Compound 2203 (15 mg, 0.033 mmol) was dissolved in 4 ml of MeOH and NaBH₄ (4.5 mg, 0.12 mmol). The mixture was stirred at room temperature overnight. After the solvent was removed on the rotary evaporator, the residue was purified by flash column chromatography (DCM/MeOH), giving 12.8 mg of 2204 (1-({5-chloro-1H-imidazo[4,5-b]pyridin-2-yl}methyl)-4-[(2,4-dichlorophenyl)(hydroxy)methyl]-3-ethyl-2,3-dihydro-1H-imidazol-2-one) in 85% yield. LC/MS: (ESI) (M+H)⁺=453.5.

Example 70

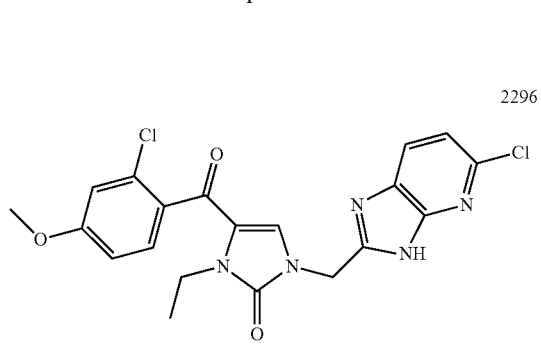

2296 (1-({5-chloro-1H-imidazo[4,5-b]pyridin-2-yl}methyl)-4-(2-chloro-4-methoxybenzoyl)-3-ethyl-2,3-dihydro-1H-imidazol-2-one) was synthesized as compound 2215 starting with 2-chloro-4-methoxybenzoyl chloride and using bromoethane following Scheme 15. $^1$H NMR (300 MHz, CDCl$_3$) δ 7.86 (d, J=8.4 Hz, 1H), 7.29 (d, J=8.5 Hz, 1H), 7.21 (d, J=8.4 Hz, 1H), 6.93 (s, 2H), 6.79 (m, 1H), 5.16 (s, 2H), 4.22 (q, J=7.0 Hz, 2H), 3.84 (s, 3H), 1.28 (t, J=7.0 Hz, 3H). LC/MS: (ESI) (M+H)$^+$=447.2.

Example 71

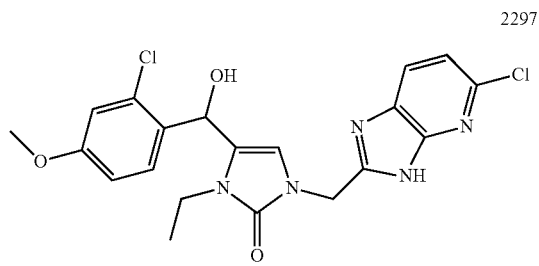 [SMILES: CCn1c(C(O)c2ccc(OC)cc2Cl)cn(Cc2nc3ccc(Cl)nc3[nH]2)c1=O]

2297 (1-({5-chloro-1H-imidazo[4,5-b]pyridin-2-yl}methyl)-4-[(2-chloro-4-methoxyphenyl)(hydroxy)methyl]-3-ethyl-2,3-dihydro-1H-imidazol-2-one) was synthesized from 2296 following Scheme 16. $^1$H NMR (300 MHz, MeOD) δ 7.90 (d, J=8.4 Hz, 1H), 7.58 (d, J=9.4 Hz, 1H), 7.27 (d, J=8.4 Hz, 1H), 6.95 (m, 2H), 5.95 (d, J=5.7 Hz, 2H), 5.01 (m, 2H), 3.86 (m, 5H), 1.29 (t, J=7.1 Hz, 3H). LC/MS: (ESI) (M+H)$^+$=449.4.

Example 72

Scheme 17

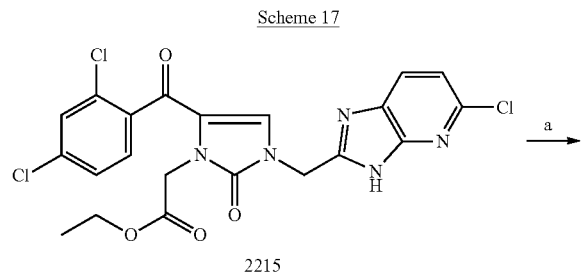

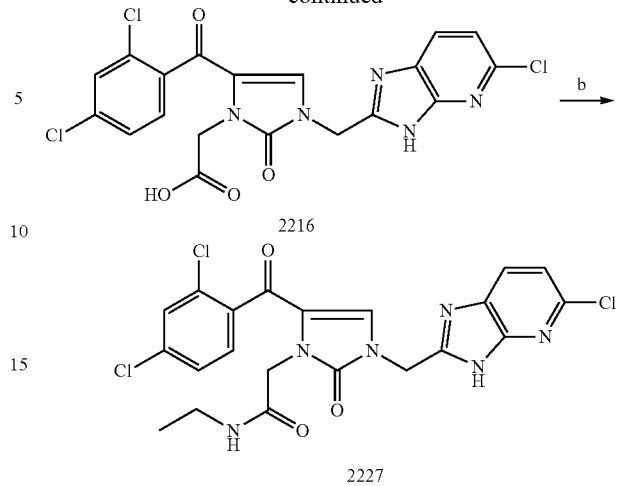

Reagents and conditions (a) LiOH, EtOH/H$_2$O; (b) EDC, ethylamine, pyridine

Compound 2215 (20 mg, 0.039 mmol) was added in 2 ml of ethanol and 4 ml of water, mixed with LiOH (3.8 mg, 0.156 mmol) and stirred for 50 min at room temperature. The solution was acidified with 0.2 N hydrochloric acid and the solvent was removed in vacuo. The residue was dissolved in EtOAc and washed with water and brine. The organic layer was dried over Na$_2$SO$_4$ and concentrated in vacuo to give 2216 (2-[3-({5-chloro-1H-imidazo[4,5-b]pyridin-2-yl}methyl)-5-(2,4-dichlorobenzoyl)-2-oxo-2,3-dihydro-1H-imidazol-1-yl]acetic acid) (18.7 mg, 0.039 mmol). LC/MS: (ESI) (M+H)$^+$=481.8.

Example 73

Compound 2216 (6.2 mg, 0.013 mmol) was dissolved in 3 ml of pyridine, then ethylamine (0.03 mmol) and EDC hydrochloride (4 mg, 0.021 mmol) were added. The mixture was stirred at room temperature overnight. The solvent was removed on the rotary evaporator. The residue was dissolved in EtOAc (30 ml) and washed with water and brine. The organic layer was dried over Na$_2$SO$_4$ and concentrated in vacuo. The residue was purified by flash chromatography on silica gel to yield 2227 (2-[3-({5-chloro-1H-imidazo[4,5-b]pyridin-2-yl}methyl)-5-(2,4-dichlorobenzoyl)-2-oxo-2,3-dihydro-1H-imidazol-1-yl]—N-ethylacetamide) (5.9 mg, 0.012 mmol). LC/MS: (ESI) (M+H)$^+$=508.7.

Example 74

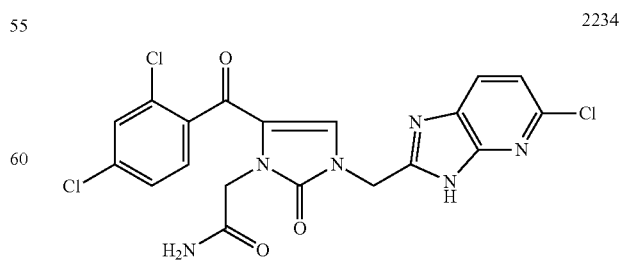

The synthetic procedure of 2234 (2-[3-({5-chloro-1H-imidazo[4,5-b]pyridin-2-yl}methyl)-5-(2,4-dichlorobenzoyl)-2-oxo-2,3-dihydro-1H-imidazol-1-yl]acetamide) was the same as 2227 via using NH₄OH. LC/MS: (ESI) (M+H)⁺=480.6.

Example 75

Scheme 18

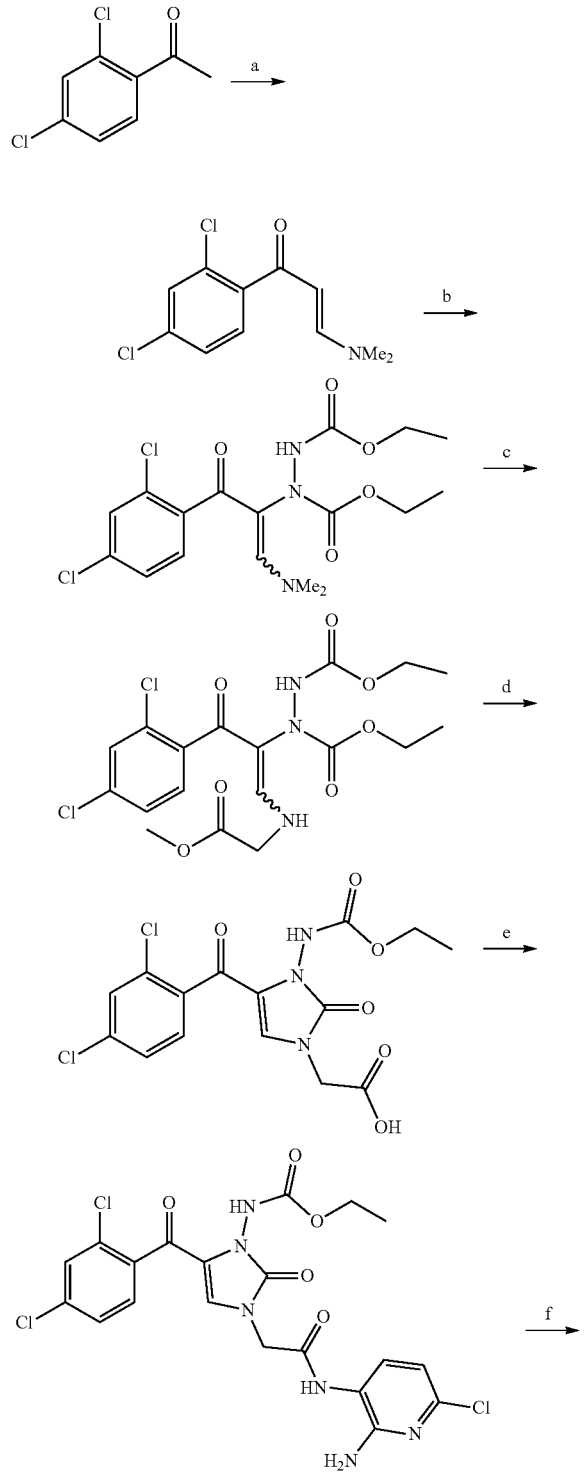

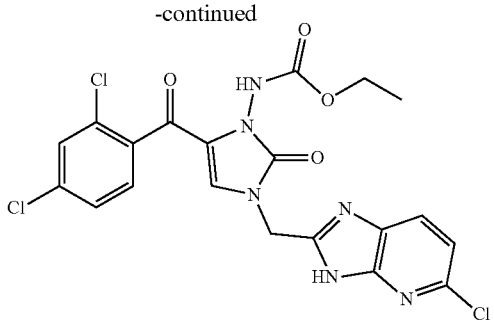

2244

Reagents and conditions: (a) dimethylformamide dimethylacetale; (b) diethyl azodicarboxylate; (c) acetic acid, glycine methyl ester; (d) NaOH, EtOH; (e) EDC, 6-chloropyridine-2,3-diamine, pyridine; (f) HOAc, microwave irradiation The mixture of 1-(2,4-dichloro-phenyl)-ethanone (296 mg, 1.57 mmol) and 0.3 ml of dimethylformamide dimethylacetale was microwave irradiated at 100° C. for 30 min. After the solvent was removed on the rotary evaporator, the residue was purified by flash column chromatography (DCM/MeOH), giving 345 mg of 1-(2,4-dichloro-phenyl)-3-dimethylamino-propenone in 90% yield. To the solution of 1-(2,4-dichloro-phenyl)-3-dimethylamino-propenone (74 mg, 0.303 mmol) in 1 ml of MeCN was added a solution of DEAD in toluene (0.33 mmol). The mixture was stirred at room temperature overnight. After the solvent was removed on the rotary evaporator, the residue was purified by flash column chromatography (DCM/MeOH), giving 127 mg of diethyl 1-(1-(dimethylamino)-3-oxo-3-(2,4-dichlorophenyl) prop-1-en-2-yl)hydrazine-1,2-dicarboxylate in 100% yield.

To the solution of diethyl 1-(1-(dimethylamino)-3-oxo-3-(2,4-dichlorophenyl)prop-1-en-2-yl)hydrazine-1,2-dicarboxylate (77 mg, 0.185 mmol) in 2 ml of HOAc was added glycine methyl ester HCl (23.2 mg, 0.185 mmol). The mixture was microwave irradiated at 110° C. for 30 min. After the solvent was removed on the rotary evaporator, the residue was purified by flash column chromatography (EtOAc/hexane), giving 77 mg of diethyl 1-(1-(glycine methyl)-3-oxo-3-(2,4-dichlorophenyl)prop-1-en-2-yl)hydrazine-1,2-dicarboxylate in 90% yield.

To the solution of diethyl 1-(1-(glycine methyl)-3-oxo-3-(2,4-dichlorophenyl)prop-1-en-2-yl)hydrazine-1,2-dicarboxylate (32.6 mg, 0.071 mmol) in 1 ml of EtOH was added solid NaOH (5.6 mg, 0.14 mmol). The mixture was microwave irradiated at 100° C. for 20 min. After the solvent was removed on the rotary evaporator, the residue was purified by flash column chromatography (MeOH/DCM), giving 20 mg (0.05 mmol) of ethyl (5-(2,4-dichloro-phenyl)-3-glycine-2-oxo-2,3-dihydro-1H-imidazol-1-yl)carbamate.

To a solution of 20 mg (0.05 mmol) of ethyl (5-(2,4-dichloro-phenyl)-3-glycine-2-oxo-2,3-dihydro-1H-imidazol-1-yl)carbamate in 1 ml of pyridine was added 6-chloropyridine-2,3-diamine (0.075 mmol) and EDC hydrochloride (19.2 mg, 0.10 mmol) were added. The mixture was stirred at room temperature overnight. The solvent was removed on a rotary evaporator. The residue was dissolved in EtOAc (30 ml) and washed with water and brine. The organic layer was dried over Na₂SO₄ and concentrated in vacuo. The residue was dissolved in 1 ml of acetic acid and the solution was microwave irradiated at 125° C. for 1 h. After the solvent was removed on a rotary evaporator, the residue was purified by flash column chromatography (DCM/MeOH), producing 2244 (N-[3-({5-chloro-1H-imidazo[4,5-b]pyridin-2-yl}methyl)-5-(2,4-dichlorobenzoyl)-2-oxo-2,3-dihydro-1H-imidazol-1-yl] ethoxyformamide) in 38% yield (9.7 mg). LC/MS: (ESI) (M+H)$^+$=457.3.

Example 76

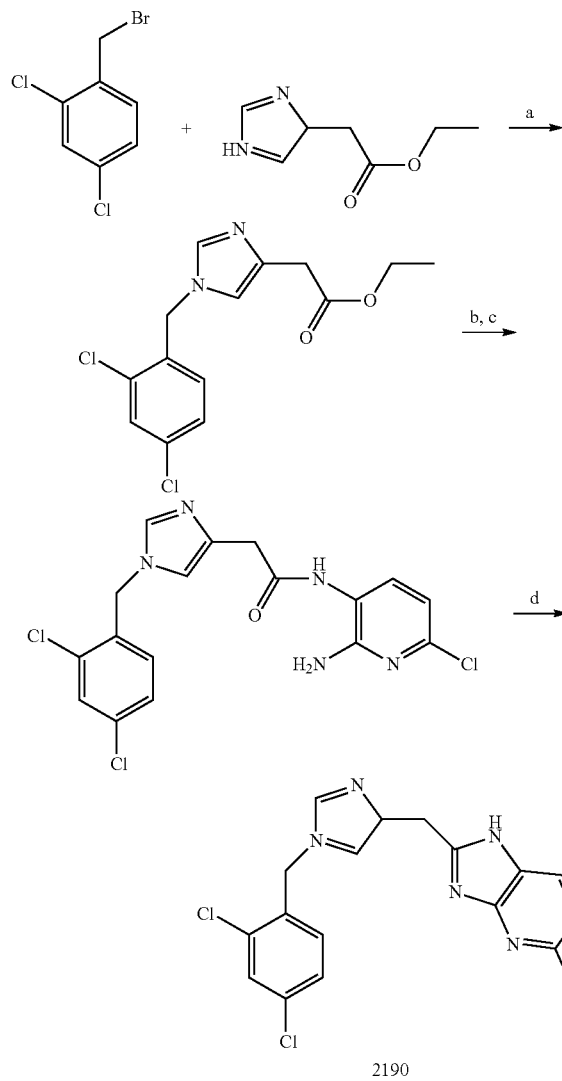

2190

Reagents and conditions: (a) NaH, DMF; (b) LiOH, EtOH/H$_2$O; (c) EDC, 6-fluoropyridine-2,3-diamine, pyridine; (d) HOAc, microwave irradiation To a solution of (1H-Imidazol-4-yl)-acetic acid ethyl ester (61 mg, 0.4 mmol) in 2 ml of anhydrous was added sodium hydride (0.44 mmol, 60% dispersion in mineral oil) at 0° C. The mixture was stirred at room temperature for 30 min and 1-bromomethyl-2,4-dichloro-benzene (95 mg, 0.4 mmol) was added. The mixture was stirred at room temperature for 2 hours. After most solvent was removed, the residues was dissolved with EtOAc and washed successively with water and brine. The organic layer was dried over Na$_2$SO$_4$ and concentrated in vacuo. The residue was purified by flash chromatography to give 92 mg of [1-(2,4-dichloro-benzyl)-1H-imidazol-4-yl]-acetic acid ethyl ester.

[1-(2,4-dichloro-benzyl)-1H-imidazol-4-yl]-acetic acid ethyl ester (20 mg, 0.064 mmol) was added in 1 ml of ethanol and 2 ml of water, mixed with LiOH (6.1 mg, 0.26 mml) and stirred for 50 min at room temperature. The solution was acidified with 0.2 N hydrochloric acid and the solvent was completely removed in vacuo. The residue was dissolved in 1 ml of pyridine, then 6-chloropyridine-2,3-diamine (0.1 mmol) and EDC hydrochloride (24.6 mg, 0.13 mmol) were added. The mixture was stirred at room temperature overnight. The solvent was removed on the rotary evaporator. The residue was dissolved in EtOAc (30 ml) and washed with water and brine. The organic layer was dried over Na$_2$SO$_4$ and concentrated in vacuo. The residue was dissolved in 1 ml of acetic acid and the solution was microwave irradiated at 125° C. for 1 h. After the solvent was removed on the rotary evaporator, the residue was purified by flash column chromatography (DCM/MeOH), giving 15.5 mg of 2190 (4-({5-chloro-1H-imidazo[4,5-b] pyridin-2-yl}methyl)-1-[(2,4-dichlorophenyl)methyl]-1H-imidazole) in 62% yield. LC/MS: (ESI) (M+H)$^+$=393.7.

Example 77

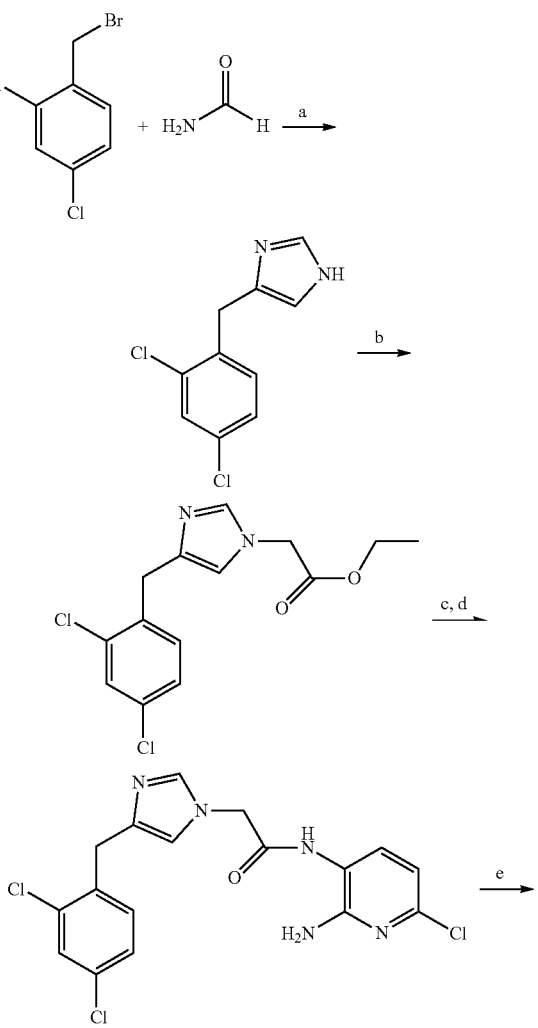

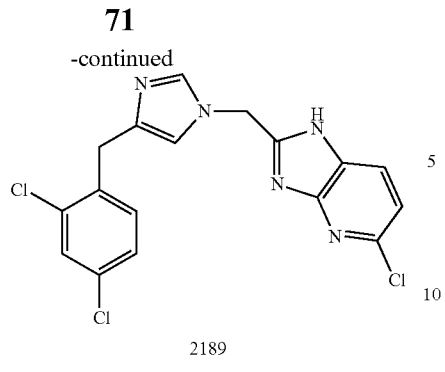

2189

Reagents and conditions: (a) 190° C.; (b) ethyl bromoacetate, NaH; (c) LiOH, EtOH/H₂O; (d) EDC, 6-chloropyridine-2, 3-diamine, pyridine; (e) HOAc, microwave irradiation A solution of 1-bromomethyl-2,4-dichloro-benzene (77 mg, 0.274 mmol) was heated (190° C.) in formamide (2 mL) for 1 h. The solution was allowed to cool to room temperature and the mixture was diluted with saturated NaHCO₃ (20 mL) and the aqueous phase was extracted with EtOAc (100 mL). The organic layers were washed with water, brine, dried (Na₂SO₄) and concentrated in vacuo to afford the crude residue which was purified by flash column chromatography on silica gel to yield 62 mg of 4-(2,4-dichloro-benzyl)-1H-imidazole.

To a solution of 4-(2,4-dichloro-benzyl)-1H-imidazole (62 mg, 0.273 mmol) in 2 ml of anhydrous was added sodium hydride (0.30 mmol, 60% dispersion in mineral oil) at 0° C. The mixture was stirred at room temperature for 30 min and ethyl bromoacetate (0.273 mmol) was added. The mixture was stirred at room temperature for 20 min. After most solvent was removed, the residues was dissolved with EtOAc and washed successively with water and brine. The organic layer was dried over Na₂SO₄ and concentrated in vacuo. The residue was purified by flash chromatography to give 46 mg of [4-(2,4-Dichloro-benzyl)-imidazol-1-yl]-acetic acid ethyl ester.

[4-(2,4-Dichloro-benzyl)-imidazol-1-yl]-acetic acid ethyl ester (20 mg, 0.064 mmol) was added in 1 ml of ethanol and 2 ml of water, mixed with LiOH (6.1 mg, 0.26 mml) and stirred for 50 min at room temperature. The solution was acidified with 0.2 N hydrochloric acid and the solvent was completely removed in vacuo. The residue was dissolved in 1 ml of pyridine, then 6-chloropyridine-2,3-diamine (0.1 mmol) and EDC hydrochloride (24.6 mg, 0.13 mmol) were added. The mixture was stirred at room temperature overnight. The solvent was removed on the rotary evaporator. The residue was dissolved in EtOAc (30 ml) and washed with water and brine. The organic layer was dried over Na₂SO₄ and concentrated in vacuo. The residue was dissolved in 1 ml of acetic acid and the solution was microwave irradiated at 125° C. for 1 h. After the solvent was removed on the rotary evaporator, the residue was purified by flash column chromatography (DCM/MeOH), giving 16.3 mg of 2189 (1-({5-chloro-1H-imidazo[4,5-b]pyridin-2-yl}methyl)-4-[(2,4-dichlorophenyl)methyl]-1H-imidazole) in 65% yield. LC/MS: (ESI) (M+H)⁺=393.7.

Example 78

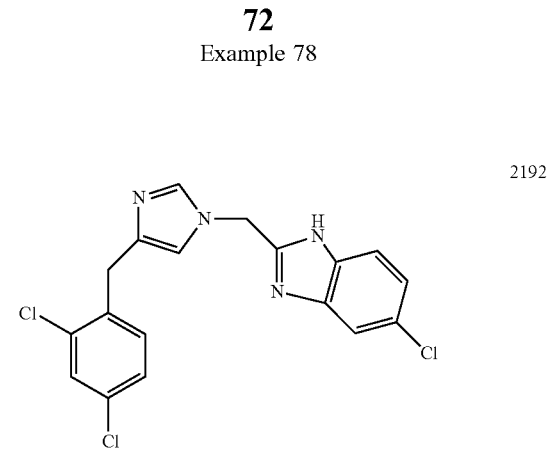

2192

The synthetic procedure of compound 2192 (6-chlor₀₋₂-({4-[(2,4-dichlorophenyl)-methyl]-1H-imidazol-1-yl}methyl)-1H-1,3-benzodiazole) was the same as 2189 via using 4-Chloro-benzene-1,2-diamine. LC/MS: (ESI) (M+H)⁺=392.8.

Examples 79

Scheme 21

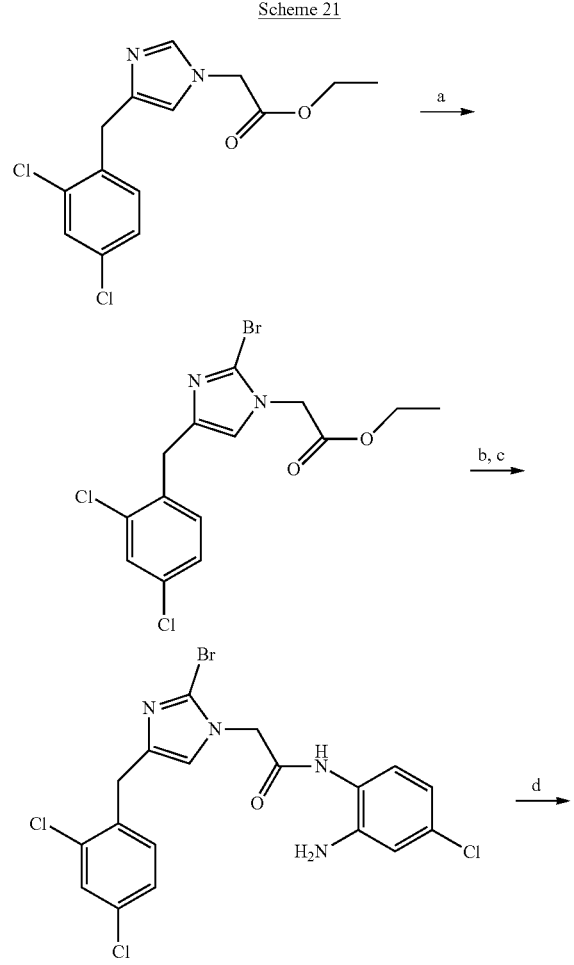

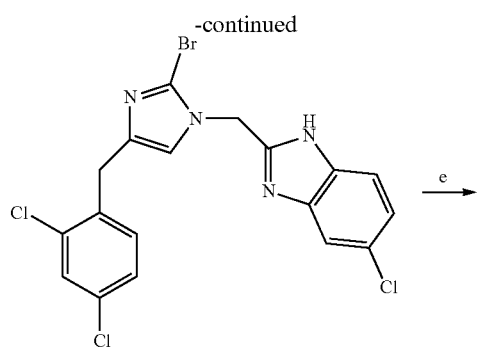

2194

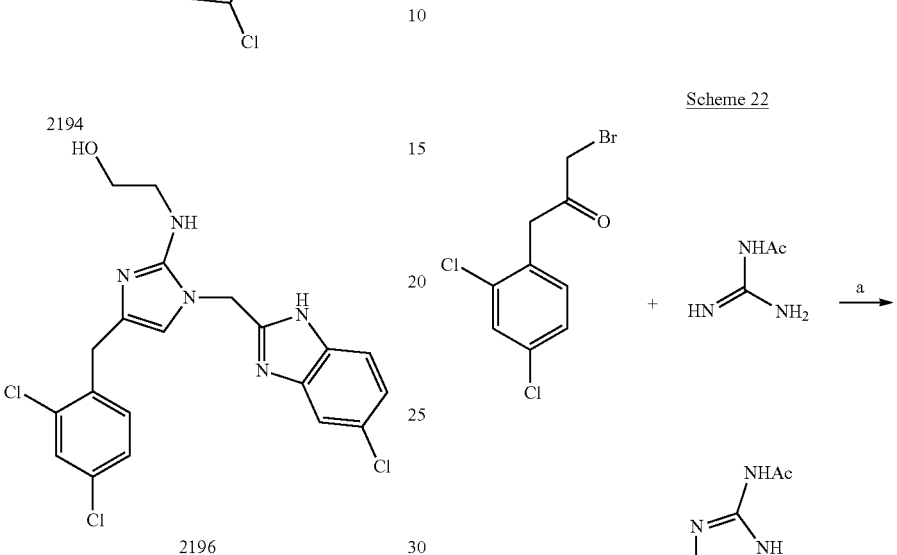

Reagents and conditions: (a) NBS; (b) LiOH, EtOH/H$_2$O; (c) EDC, 4-chloro-benzene-1,2-diamine, pyridine; (d) HOAc, microwave irradiation; (e) 2-amino-ethanol, microwave irradiation A solution of [4-(2,4-dichloro-benzyl)-imidazol-1-yl]-acetic acid ethyl ester (72 mg, 0.23 mmol) in THF was added N-bromosuccinimide (45 mg, 0.253 mmol). The mixture was stirred at room temperature overnight. After the solvent was removed, the residue was purified by flash chromatography to give 35 mg of [2-bromo-4-(2,4-dichloro-benzyl)-imidazol-1-yl]-acetic acid ethyl ester.

[2-bromo-4-(2,4-dichloro-benzyl)-imidazol-1-yl]-acetic acid ethyl ester (25 mg, 0.064 mmol) was added in 2 ml of ethanol and 4 ml of water, mixed with LiOH (6.1 mg, 0.26 mml) and stirred for 50 min at room temperature. The solution was acidified with 0.2 N hydrochloric acid and the solvent was completely removed in vacuo. The residue was dissolved in 1 ml of pyridine, then 4-chloro-benzene-1,2-diamine (0.1 mmol) and EDC hydrochloride (24.6 mg, 0.13 mmol) were added. The mixture was stirred at room temperature overnight. The solvent was removed on the rotary evaporator. The residue was dissolved in EtOAc (30 ml) and washed with water and brine. The organic layer was dried over Na$_2$SO$_4$ and concentrated in vacuo. The residue was dissolved in 1 ml of acetic acid and the solution was microwave irradiated at 60° C. for 20 min. After the solvent was removed on the rotary evaporator, the residue was purified by flash column chromatography (DCM/MeOH), giving 10.5 mg of 2194 (2-({2-bromo-4-[(2,4-dichlorophenyl)methyl]-1H-imidazol-1-yl}methyl)-6-chloro-1H-1,3-benzodiazole) in 35% yield. LC/MS: (ESI) (M+H)$^+$=471.0.

Examples 80

The solution of 2194 (6 mg, 0.013 mmol) in 0.2 ml of 2-amino-ethanol was microwave irradiated at 200° C. for 1 hour. The mixture was dilated with EtOAc and washed with water and brine. The organic layer was dried over Na$_2$SO$_4$ and concentrated in vacuo, the residue was purified by flash column chromatography (DCM/MeOH), giving 2.7 mg of 2196 (2-({1-[(6-chloro-1H-1,3-benzodiazol-2-yl)methyl]-4-[(2,4-dichlorophenyl)methyl]-1H-imidazol-2-yl}amino)ethan-1-ol) in 46% yield. LC/MS: (ESI) (M+H)$^+$=451.6.

Example 81

Scheme 22

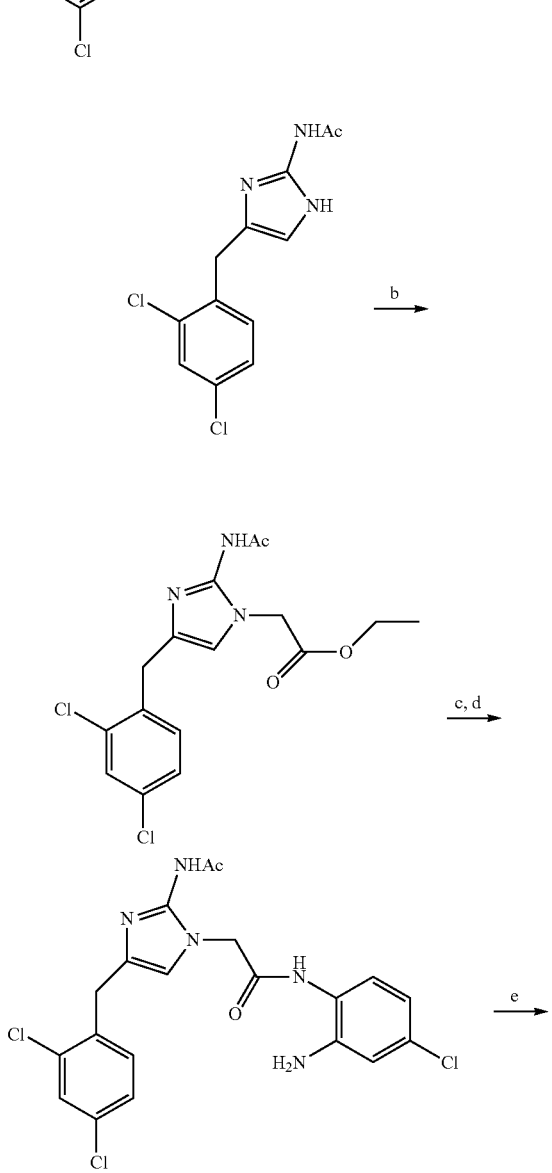

-continued

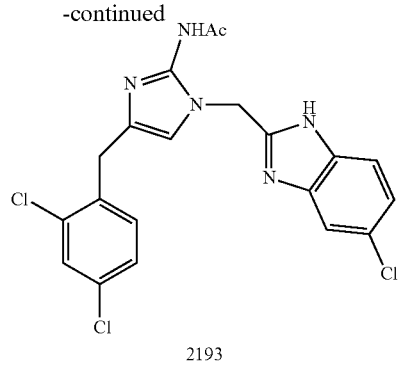

2193

Reagents and conditions: (a) MeCN, microwave irradiation; (b) K₂CO₃, ethyl bromoacetate; (c) LiOH, EtOH/H₂O; (d) EDC, 4-chloro-benzene-1,2-diamine, pyridine; (e) HOAc, microwave irradiation To a solution of 1-bromo-3-(2,4-dichloro-phenyl)-propan-2-one (185 mg, 0.66 mmol) in MeCN (5 ml) was added N-acetyl-guanidine (199 mg, 1.98 mmol). The mixture was microwave irradiated at 100° C. for 20 min. After the solvent was removed, the residues was dissolved with EtOAc and washed successively with water and brine. The organic layer was dried over Na₂SO₄ and concentrated in vacuo. The residue was purified by flash chromatography to give 159 mg of N-[4-(2,4-dichloro-benzyl)-1H-imidazol-2-yl]-acetamide.

To a solution of N-[4-(2,4-dichloro-benzyl)-1H-imidazol-2-yl]-acetamide (67 mg, 0.273 mmol) in 2 ml of anhydrous DMF were added K₂CO₃ (45.2 mg, 0.33 mmol) and ethyl bromoacetate (27.3 μl, 0.246 mmol). The mixture was stirred at 55° C. overnight. After most solvent was removed, the residues was dissolved with EtOAc and washed successively with water and brine. The organic layer was dried over Na₂SO₄ and concentrated in vacuo. The residue was purified by flash chromatography to give 56 mg of [2-acetylamino-4-(2,4-dichloro-benzyl)-imidazol-1-yl]-acetic acid ethyl ester.

[2-acetylamino-4-(2,4-dichloro-benzyl)-imidazol-1-yl]-acetic acid ethyl ester (23.7 mg, 0.064 mmol) was added in 1 ml of ethanol and 2 ml of water, mixed with LiOH (6.1 mg, 0.26 mml) and stirred for 50 min at room temperature. The solution was acidified with 0.2 N hydrochloric acid and the solvent was completely removed in vacuo. The residue was dissolved in 1 ml of pyridine, then 4-chloro-benzene-1,2-diamine (0.1 mmol) and EDC hydrochloride (24.6 mg, 0.13 mmol) were added. The mixture was stirred at room temperature overnight. The solvent was removed on the rotary evaporator. The residue was dissolved in EtOAc (30 ml) and washed with water and brine. The organic layer was dried over Na₂SO₄ and concentrated in vacuo. The residue was dissolved in 1 ml of acetic acid and the solution was microwave irradiated at 60° C. for 20 min. After the solvent was removed on the rotary evaporator, the residue was purified by flash column chromatography (DCM/MeOH), giving 16.1 mg of 2193 (N-{1-[(6-chloro-1H-1,3-benzodiazol-2-yl)methyl]-4-[(2,4-dichlorophenyl)methyl]-1H-imidazol-2-yl}acetamide) in 56% yield. LC/MS: (ESI) (M+H)⁺=449.8.

Example 82

Scheme 23

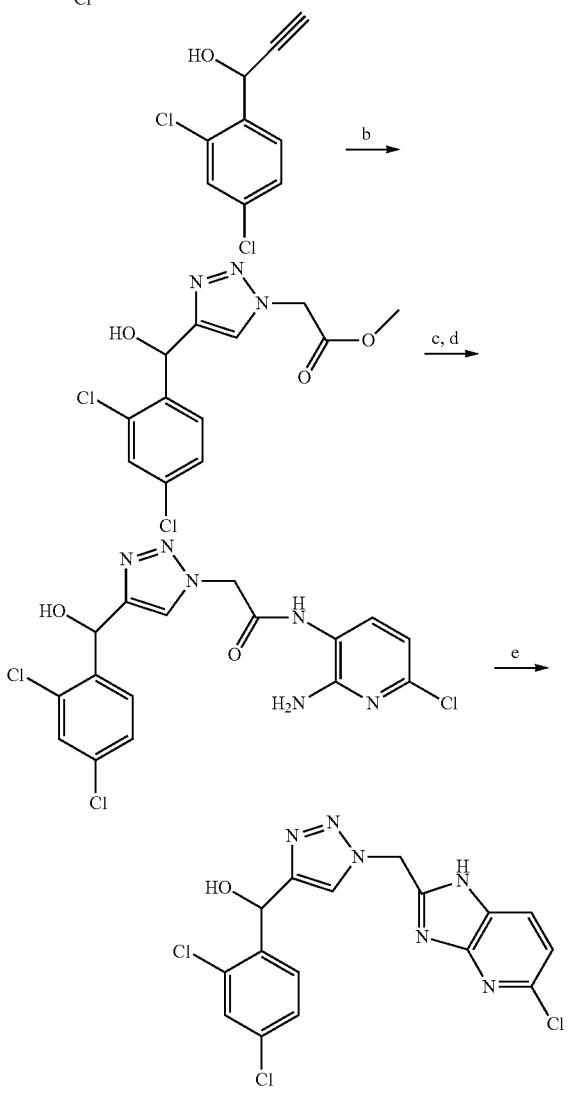

2198

Reagents and conditions: (a) THF; (b) methyl azidoacetate, CuSO₄, sodium ascorbate; (b) K₂CO₃, ethyl bromoacetate; (c) LiOH, MeOH/H₂O; (d) EDC, 6-chloropyridine-2,3-diamine, pyridine; (e) HOAc, microwave irradiation To a solution of 2,4-dichloro-benzaldehyde (48 mg, 0.27 mmol) in anhydrous THF (5 ml) at −78° C. was added ethynylmagnesium bromide (0.33 mmol, 0.5 M in THF). The mixture was warm up to room temperature and stirred for 1 hour. After the solvent was removed, the residues was dissolved with EtOAc and washed successively with saturated NH₄Cl and brine. The organic layer was dried over Na₂SO₄ and concentrated in vacuo to give 1-(2,4-dichlorophenyl)-prop-2-yn-1-ol which was directly used without further purification. The solution of 1-(2,4-dichloro-phenyl)-prop-2-yn-1-ol in 4 ml of methanol and 2 ml of H₂O was added methyl azidoacetate (24 μl, 0.243 mmol), 6.7 mg of CuSO₄ and 11 mg of sodium ascorbate. The mixture was stirred at room temperature overnight. After most solvent was removed, the residues was dissolved with EtOAc and washed successively with water and brine. The organic layer was dried over Na₂SO₄ and concentrated in vacuo. The residue was purified by flash chromatography to give 33.3 mg of {4-[(2,4-Dichloro-phenyl)-hydroxy-methyl]-[1,2,3]triazol-1-yl}-acetic acid methyl ester.

{4-[(2,4-Dichloro-phenyl)-hydroxy-methyl]-[1,2,3]triazol-1-yl}-acetic acid methyl ester (20.2 mg, 0.064 mmol) was added in 1 ml of methanol and 2 ml of water, mixed with LiOH (6.1 mg, 0.26 mml) and stirred for 50 min at room temperature. The solution was acidified with 0.2 N hydrochloric acid and the solvent was completely removed in vacuo. The residue was dissolved in 1 ml of pyridine, then 6-chloropyridine-2,3-diamine (0.1 mmol) and EDC hydrochloride (24.6 mg, 0.13 mmol) were added. The mixture was stirred at room temperature overnight. The solvent was removed on the rotary evaporator. The residue was dissolved in EtOAc (30 ml) and washed with water and brine. The organic layer was dried over Na₂SO₄ and concentrated in vacuo. The residue was dissolved in 1 ml of acetic acid and the solution was microwave irradiated at 125° C. for 1 hour. After the solvent was removed on the rotary evaporator, the residue was purified by flash column chromatography (DCM/MeOH), giving 8.6 mg of 2198 in 33% yield. LC/MS: (ESI) (M+H)⁺=410.8.

Example 83

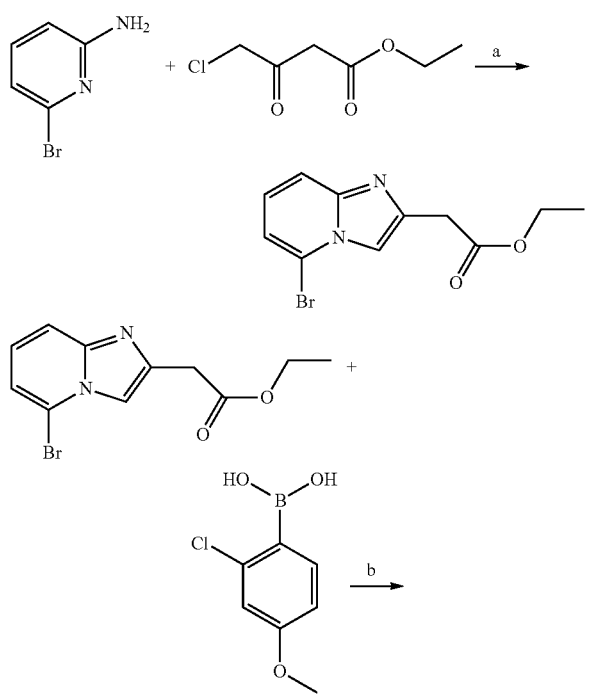

Scheme 24

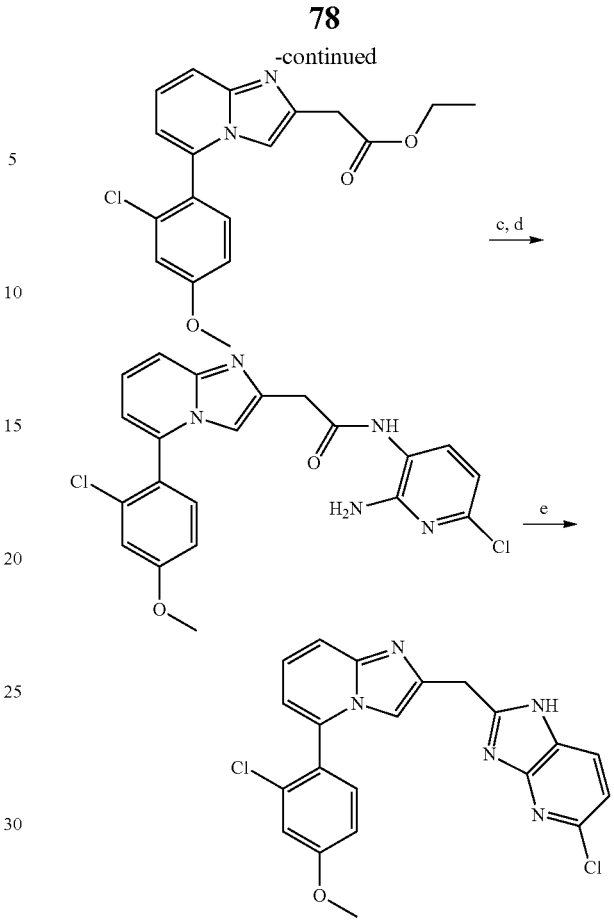

Reagents and conditions (a) ethanol, refluxing; (b) K₂CO₃, Pd(PPh₃)₄, DME, H₂O, microwave irradiation; (c) LiOH, ethanol/water; (d) EDC, 6-chloropyridine-2, 3-diamine, pyridine; (e) HOAc, microwave irradiation General Procedure 7 (2119, 2122, 2126-2135, 2144-2146, 2164-2166, 2236, 2268):

A mixture of ethyl 4-chloroacetoacetate (271 μl, 2 mmol) and 6-bromoylpyridin-2-amine (364 mg, 2 mmol) in EtOH (20 mL) was refluxed overnight. After the solution was cooled down, the white precipitate was collected and washed with cold EtOH. Ethyl 2-(5-bromoH-imidazo[1,2-a]pyridin-2-yl)acetate HCl salt (311 mg) was obtained and directly used.

A mixture of ethyl 2-(5-bromoH-imidazo[1,2-a]pyridin-2-yl)acetate (93 mg, 0.29 mmol) 2-chloro-4-methoxyphenylboronic acid (82 mg, 0.44 mmol), potassium carbonate (162 mg, 1.16 mmol) and tetrakis(triphenylphosphine)palladium(0) (16.8 mg, 0.0145 mmol) in water (1 mL) and DME (3 mL) was microwave irradiated at 100° C. for 20 min. After organic solvent was removed in vacuo, the residue was extracted with EtOAc and washed successively with water and brine. The organic layer was dried over Na₂SO₄ and concentrated in vacuo. The residue was purified by flash chromatography on silica gel (hexane/EtOAc) to obtain ethyl 2-(5-(2-chloro-4-methoxyphenyl)-H-imidazo[1,2-a]pyridin-2-yl)acetate (75 mg, 75%).

Ethyl 2-(5-(2-chloro-4-methoxyphenyl)H-imidazo[1,2-a]pyridin-2-yl)acetate (18.2 mg, 0.0528 mmol) was added in 1 ml of ethanol and 3 ml of water, mixed with LiOH (5.1 mg, 0.211 mmol) and stirred for 50 min at room temperature. The solution was acidified with 0.2 N hydrochloric acid and the solvent completely removed in vacuo. The residue was dissolved in 3 ml of pyridine, then 6-chloropyridine-2,3-diamine (9.0 mg, 0.063 mmol) and EDC hydrochloride (21 mg, 0.11 mmol) were added. The mixture was stirred at room temperature overnight. The solvent was removed on a rotary evaporator. The residue was dissolved in EtOAc (30 ml) and washed with water and brine. The organic layer was dried over Na$_2$SO$_4$ and concentrated in vacuo. The residue was purified by flash chromatography on silica gel to give N-(2-amino-6-chloropyridin-3-yl)-2-(5-(2-chloro-4-methoxyphenyl)H-imidazo[1,2-a]pyridin-2-yl)acetamide (16.3 mg, 0.034 mmol). N-(2-amino-6-chloropyridin-3-yl)-2-(5-(2-chloro-4-methoxyphenyl)H-imidazo[1,2-a]pyridin-2-yl)acetamide (16.3 mg, 0.034 mmol) was dissolved in 2 ml of acetic acid and the solution was microwave irradiated at 125° C. for 1 h. After the solvent was removed on a rotary evaporator, the residue was purified by flash column chromatography (DCM/MeOH), yielding 2119 (2-({5-chloro-1H-imidazo[4,5-b]pyridin-2-yl}methyl)-5-(2-chloro-4-methoxyphenyl)imidazo[1,2-a]pyridine) in 71% yield (10.2 mg). LC/MS: (ESI) (M+H)$^+$=425.4.

Example 84

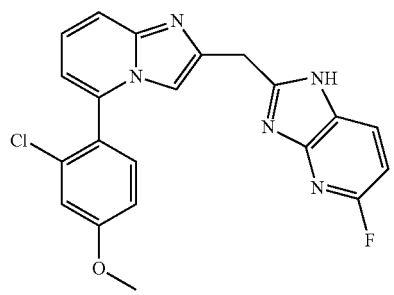

2122 (5-(2-chloro-4-methoxyphenyl)-2-({5-fluoro-1H-imidazo[4,5-b]pyridin-2-yl}methyl)imidazo[1,2-a]pyridine) was synthesized using 6-fluoropyridine-2,3-diamine following General Procedure 7. LC/MS: (ESI) (M+H)$^+$=408.7.

Example 85

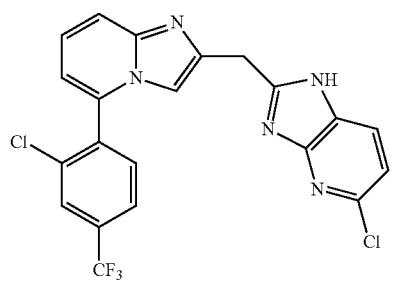

2126 (2-({5-chloro-1H-imidazo[4,5-b]pyridin-2-yl}methyl)-5-[2-chloro-4-(trifluoromethyl)phenyl]imidazo[1,2-a]pyridine) was synthesized using 2-chloro-4-(trifluoromethyl)phenylboronic acid following General Procedure 7. LC/MS: (ESI) (M+H)$^+$=463.7.

Example 86

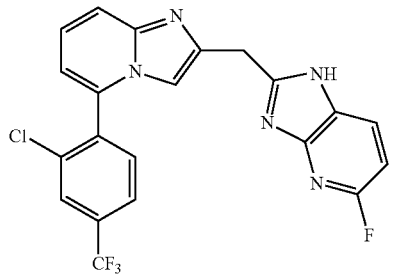

2127 (5-[2-chloro-4-(trifluoromethyl)phenyl]-2-({5-fluoro-1H-imidazo[4,5-b]pyridin-2-yl}methyl)imidazo[1,2-a]pyridine) was synthesized using 2-chloro-4-(trifluoromethyl)-phenylboronic acid and 6-fluoropyridine-2,3-diamine in General Procedure 7. LC/MS: (ESI) (M+H)$^+$=446.9.

Example 87

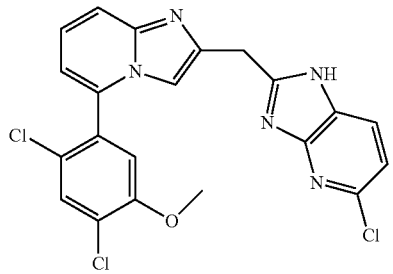

2128 (2-({5-chloro-1H-imidazo[4,5-b]pyridin-2-yl}methyl)-5-(2,4-dichloro-5-methoxyphenyl)imidazo[1,2-a]pyridine) was synthesized using 2,4-dichloro-5-methoxyphenylboronic acid following General Procedure 7. $^1$H NMR (MeOD) δ 7.64 (d, J=8.3 Hz, 1H), 7.46-7.35 (m, 2H), 7.28-7.18 (m, 2H), 7.07 (s, 1H), 7.00 (d, J=8.3 Hz, 1H), 6.77 (d, J=6.9 Hz, 1H), 4.27(s, 2H), 3.72 (s, 3H). LC/MS: (ESI) (M+H)$^+$=459.7.

Example 88

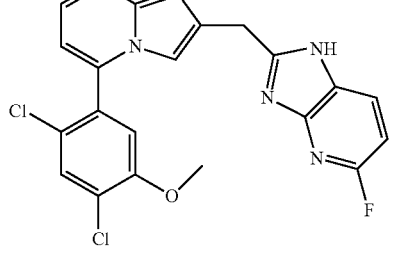

2129 (5-(2,4-dichloro-5-methoxyphenyl)-2-({5-fluoro-1H-imidazo[4,5-b]pyridin-2-yl}methyl)imidazo[1,2-a]pyridine) was synthesized using 2,4-dichloro-5-methoxyphenyl-boronic acid and 6-fluoropyridine-2,3-diamine following General Procedure 7. $^1$H NMR (MeOD) δ 7.83 (t, J=7.8 Hz, 1H), 7.54 (s, 1H), 7.47 (d, J=9.0 Hz, 1H), 7.36-7.28 (m, 1H), 7.26 (s, 1H), 7.15 (s, 1H), 6.84 (d, J=6.9 Hz, 1H), 6.75 (d, J=8.5 Hz, 1H), 4.31(s, 2H), 3.79 (s, 3H). LC/MS: (ESI) (M+H)$^+$=443.5.

Example 89

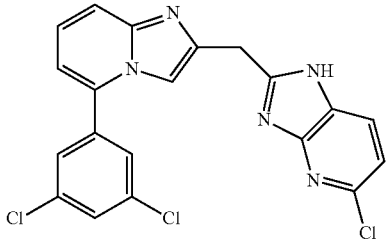

2130

2130 (2-({5-chloro-1H-imidazo[4,5-b]pyridin-2-yl}methyl)-5-(3,5-dichlorophenyl)-imidazo[1,2-a]pyridine) was synthesized using 3,5-dichlorophenylboronic acid following General Procedure 7. LC/MS: (ESI) (M+H)$^+$=429.7.

Example 90

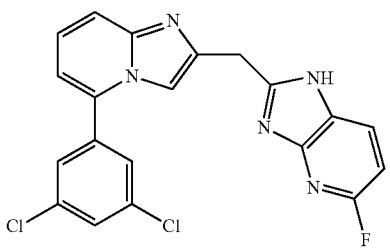

2131

2131 (5-(3,5-dichlorophenyl)-2-({5-fluoro-1H-imidazo[4,5-b]pyridin-2-yl}methyl)-imidazo[1,2-a]pyridine) was synthesized using 3,5-dichlorophenylboronic acid and 6-fluoropyridine-2,3-diamine following General Procedure 7. LC/MS: (ESI) (M+H)$^+$=413.4.

Example 91

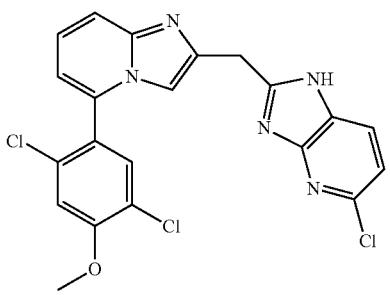

2132

2132 (2-({5-chloro-1H-imidazo[4,5-b]pyridin-2-yl}methyl)-5-(2,5-dichloro-4-methoxyphenyl)imidazo[1,2-a]pyridine) was synthesized using 2,5-dichloro-4-methoxy-phenylboronic acid following General Procedure 7. LC/MS: (ESI) (M+H)$^+$=459.7.

Example 92

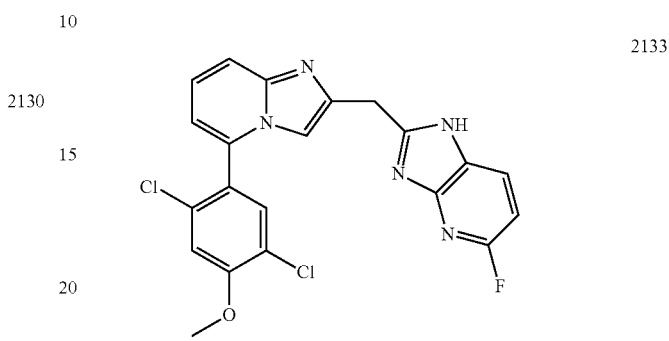

2133

2133 (5-(2,5-dichloro-4-methoxyphenyl)-2-({5-fluoro-1H-imidazo[4,5-b]pyridin-2-yl}methyl)imidazo[1,2-a]pyridine) was synthesized using 2,5-dichloro-4-methoxyphenyl-boronic acid and 6-fluoropyridine-2,3-diamine following General Procedure 7. LC/MS: (ESI) (M+H)$^+$=443.4.

Example 93

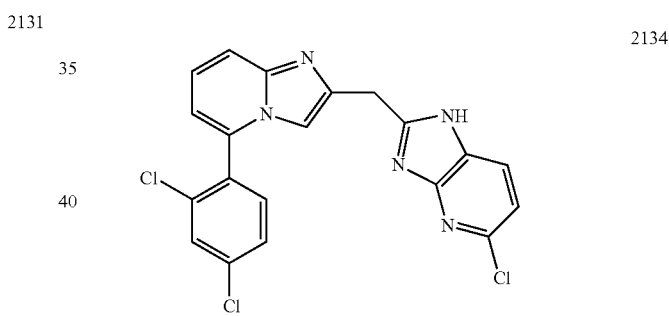

2134

2134 (2-({5-chloro-1H-imidazo[4,5-b]pyridin-2-yl}methyl)-5-(2,4-dichlorophenyl)-imidazo[1,2-a]pyridine) was synthesized using 2,4-dichlorophenylboronic acid following General Procedure 7. LC/MS: (ESI) (M+H)$^+$=429.8.

Example 94

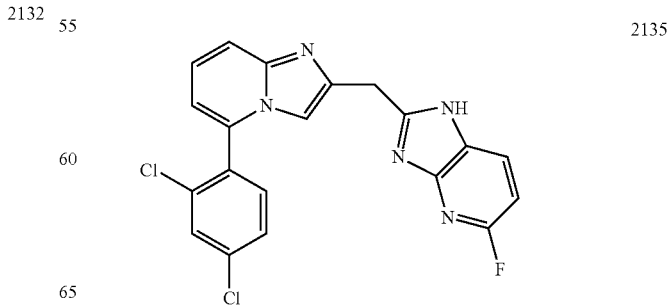

2135

2135 (5-(2,4-dichlorophenyl)-2-({5-fluoro-1H-imidazo[4,5-b]pyridin-2-yl}methyl)imidazo[1,2-a]pyridine) was synthesized using 2,4-dichlorophenylboronic acid and 6-fluoropyridine-2,3-diamine following General Procedure 7. LC/MS: (ESI) (M+H)$^+$=413.3.

Example 95

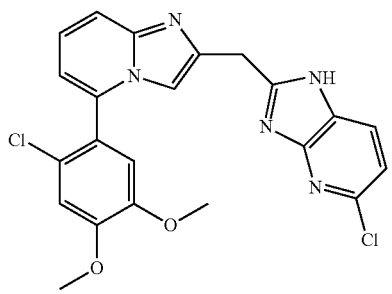

2144 (2-({5-chloro-1H-imidazo[4,5-b]pyridin-2-yl}methyl)-5-(2-chloro-4,5-dimethoxyphenyl)imidazo[1,2-a]pyridine) was synthesized using 2-chloro-4,5-dimethoxyphenylboronic acid following General Procedure 7. $^1$H NMR (MeOD) δ 7.70 (d, J=8.3 Hz, 1H), 7.42 (d, J=9.0 Hz, 1H), 7.34-7.25 (m, 1H), 7.24 (s, 1H), 7.08 (d, J=8.3 Hz, 1H), 6.94 (s, 1H), 6.78 (d, J=6.7 Hz, 1H), 4.31(s, 2H), 3.77 (s, 2H), 3.69 (s, 3H). LC/MS: (ESI) (M+H)$^+$=455.4.

Example 96

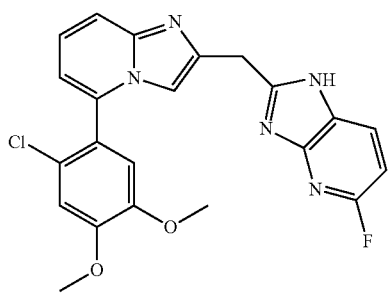

2145 (5-(2-chloro-4,5-dimethoxyphenyl)-2-({5-fluoro-1H-imidazo[4,5-b]pyridin-2-yl}methyl)imidazo[1,2-a]pyridine) was synthesized using 2-chloro-4,5-dimethoxyphenylboronic acid and 6-fluoropyridine-2,3-diamine following General Procedure 7. $^1$H NMR (MeOD) δ 7.84-7.75 (m, 1H), 7.40 (d, J=9.1 Hz, 1H), 7.29-7.27 (m, 1H), 7.20 (s, 1H), 7.02 (s, 1H), 6.93 (s, 1H), 6.76-7.71 (m, 1H), 4.28 (s, 2H), 3.75 (s, 3H), 3.67 (s, 3H). LC/MS: (ESI) (M+H)$^+$=439.0.

Example 97

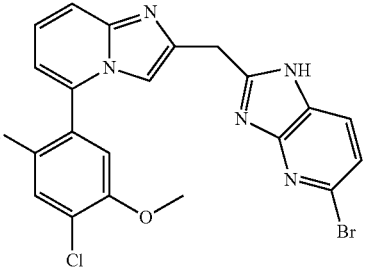

2146 (2-({5-bromo-1H-imidazo[4,5-b]pyridin-2-yl}methyl)-5-(2,4-dichloro-5-methoxyphenyl)imidazo[1,2-a]pyridine) was synthesized using 2,4-dichloro-5-methoxyphenylboronic acid and 6-bromopyridine-2,3-diamine following General Procedure 7. LC/MS: (ESI) (M+H)$^+$=504.1.

Example 98

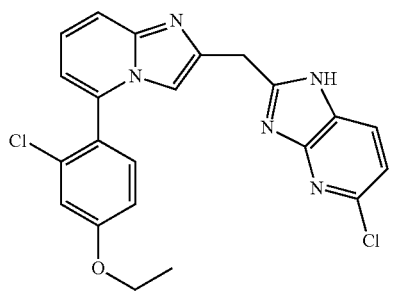

2164 (2-({5-chloro-1H-imidazo[4,5-b]pyridin-2-yl}methyl)-5-(2-chloro-4-ethoxyphenyl)imidazo[1,2-a]pyridine) was synthesized using 2-chloro-4-ethoxyphenylboronic acid following General Procedure 7. LC/MS: (ESI) (M+H)$^+$=439.4.

Example 99

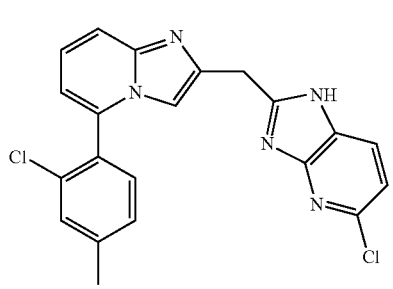

2165 (2-({5-chloro-1H-imidazo[4,5-b]pyridin-2-yl}methyl)-5-(2-chloro-4-methylphenyl)imidazo[1,2-a]pyridine) was synthesized using 2-chloro-4-methylphenylboronic acid following General Procedure 7. LC/MS: (ESI) (M+H)$^+$=409.4.

Example 100

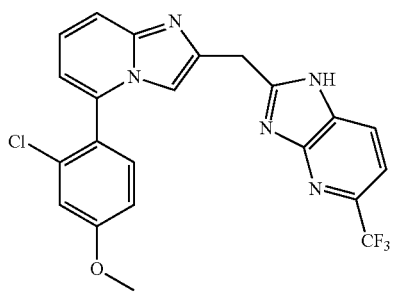

2166 (5-(2-chloro-4-methoxyphenyl)-2-{[5-(trifluoromethyl)-1H-imidazo[4,5-b]pyridin-2-yl]methyl}imidazo[1,2-a]pyridine) was synthesized using 6-trifluoromethylpyridine-2,3-diamine following General Procedure 7. LC/MS: (ESI) (M+H)⁺=458.9.

Example 101

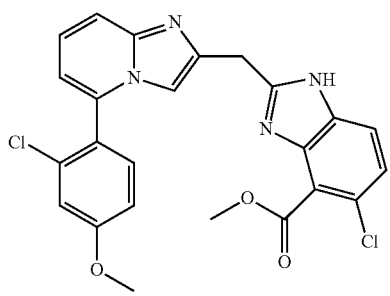

2236 (methyl 5-chloro-2-{[5-(2-chloro-4-methoxyphenyl)imidazo[1,2-a]pyridin-2-yl]methyl}-1H-1,3-benzodiazole-4-carboxylate) was synthesized using methyl 2,3-diamino-6-chlorobenzoate following General Procedure 7. LC/MS: (ESI) (M+H)⁺=482.3.

Example 102

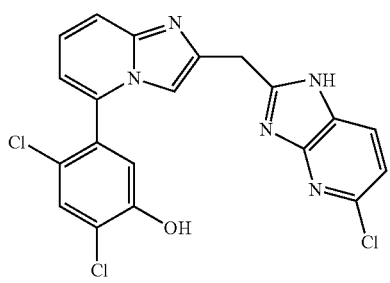

2268 (2,4-dichloro-5-[2-({5-chloro-1H-imidazo[4,5-b]pyridin-2-yl}methyl)imidazo[1,2-a]pyridin-5-yl]phenol) was synthesized using 2,4-dichloro-5-hydroxyphenylboronic acid following General Procedure 7. LC/MS: (ESI) (M+H)⁺=445.7.

Example 103

Scheme 25

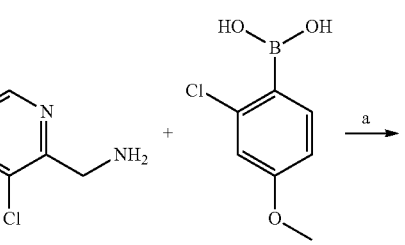

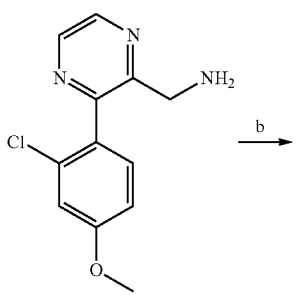

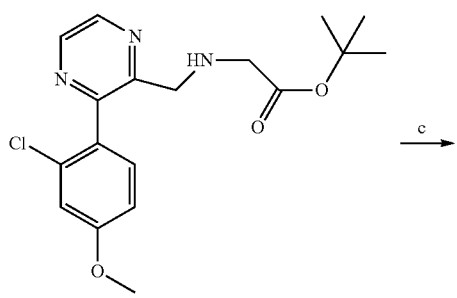

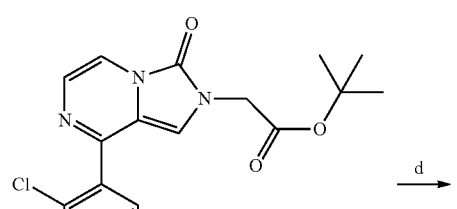

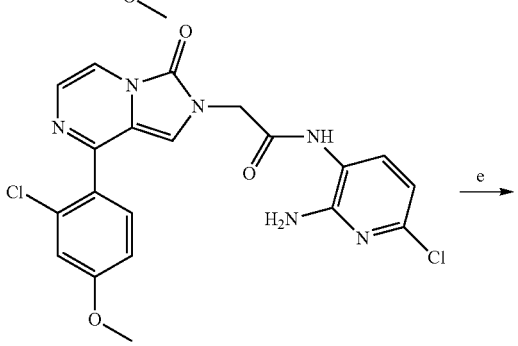

87

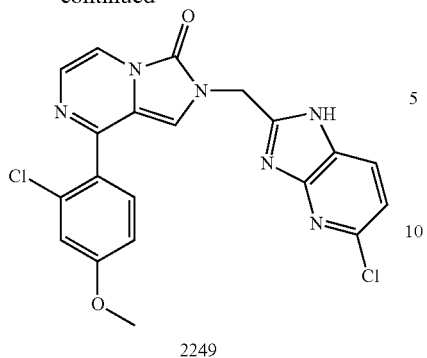

2249

Reagents and conditions (a) K₂CO₃, Pd(PPh₃)₄, DME, H₂O, microwave irradiation; (b) K₂CO₃, bromo-acetic acid tert-butyl ester; (c) triphosgen; (d), TFA, DCM; (e) HATU, 6-chlororopyridine-2, 3-diamine, DIPEA; (e) HOAc, microwave irradiation General Procedure 8 (2249, 2254, 2250):

(3-Chloropyrazin-2-yl)methanamine hydrochloride (157 mg, 0.873 mmol), 2-chloro-4-methoxyphenylboronic acid (325 mg, 1.75 mmol), potassium carbonate (482 mg, 3.49 mmol) and tetrakis(triphenylphosphine)palladium(0) (50 mg, 0.043 mmol) in water (1.5 mL) and DME (4.5 mL) was microwave irradiated at 110° C. for 30 min. After organic solvent was removed in vacuo, the residue was extracted with EtOAc and washed successively with water and brine. The organic layer was dried over Na₂SO₄ and concentrated in vacuo. The residue was purified by flash chromatography on silica gel (MeOH/DCM) to obtain 64 mg of [3-(2-chloro-4-methoxy-phenyl)-pyrazin-2-yl]-methylamine.

To a solution of [3-(2-chloro-4-methoxy-phenyl)-pyrazin-2-yl]-methylamine (64 mg, 0.257 mmol) in 5 ml of DMF was added potassium carbonate (177 mg, 1.285 mmol) and bromo-acetic acid tert-butyl ester (34 µl, 0.308 mmol). The mixture was microwave irradiated at 80° C. for 30 min. After organic solvent was removed in vacuo, the residue was purified by flash chromatography on silica gel (MeOH/DCM) to obtain 30 mg of {[3-(2-chloro-4-methoxy-phenyl)-pyrazin-2-ylmethyl]-amino}-acetic acid tert-butyl ester.

To a solution of {[3-(2-chloro-4-methoxy-phenyl)-pyrazin-2-ylmethyl]-amino}-acetic acid tert-butyl ester (10 mg, 0.028 mmol) in 5 ml of anhydrous DCM at 0° C. was added DIPEA (12 µl, 0.069 mmol) and triphosgen (1.7 µl, 0.01 mmol). The mixture was stirred at 0° C. for 40 min then room temperature for 1 hour. The solvent was removed on a rotary evaporator. The residue was purified by flash column chromatography (DCM/MeOH) to obtain 7.1 mg of [8-(2-Chloro-4-methoxy-phenyl)-3-oxo-imidazo[1,5-a]pyrazin-2-yl]-acetic acid tert-butyl ester.

[8-(2-Chloro-4-methoxy-phenyl)-3-oxo-imidazo[1,5-a]pyrazin-2-yl]-acetic acid tert-butyl ester (7.1 mg, 0.018 mmol) was treated with 1 ml of DCM and 1 ml of TFA. After the mixture was stirred at room temperature for 2 hours, solvents completely removed in vacuo. The residue was dissolved in DMF (2 ml). The solution was added DIPEA (20 ul), HATU (0.022 mmol) and 6-chlororopyridine-2,3-diamine (3.1 mg, 0.022 mmol). The mixture was stirred at room temperature for 3 hours. The solvent was removed on a rotary evaporator. The residue was dissolved in EtOAc (20 ml) and washed with water and brine. The organic layer was dried over Na₂SO₄ and concentrated in vacuo. The residue was dissolved in 1 ml of acetic acid and the solution was microwave irradiated at 125° C. for 1 h. After the solvent was removed on a rotary evaporator, the residue was purified by flash column chromatography (DCM/MeOH), yielding

88

2249 (2-({5-chloro-1H-imidazo[4,5-b]pyridin-2-yl}methyl)-8-(2-chloro-4-methoxyphenyl)-2H,3H-imidazo[1,5-a]pyrazin-3-one) (3.2 mg). LC/MS: (ESI) (M+H)⁺=442.2.

Example 104

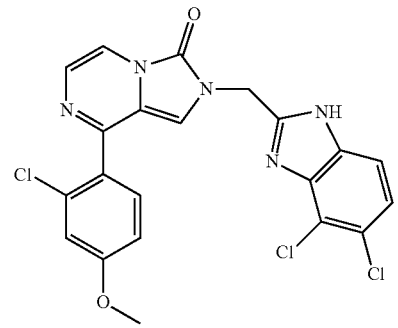

2254

2254 (8-(2-chloro-4-methoxyphenyl)-2-[(6,7-dichloro-1H-1,3-benzodiazol-2-yl)methyl]-2H,3H-imidazo[1,5-a]pyrazin-3-one) was synthesized using 3,4-dichloro-benzene-1,2-diamine following General Procedure 8. LC/MS: (ESI) (M+H)⁺=475.8.

Example 105

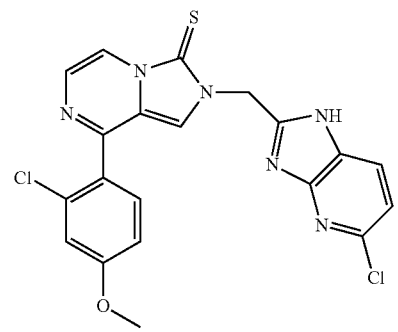

2250

2250 (2-({5-chloro-1H-imidazo[4,5-b]pyridin-2-yl}methyl)-8-(2-chloro-4-methoxyphenyl)-2H,3H-imidazo[1,5-a]pyrazine-3-thione) was synthesized using thiophosgen following General Procedure 8. LC/MS: (ESI) (M+H)⁺=458.5.

Example 106

Scheme 26

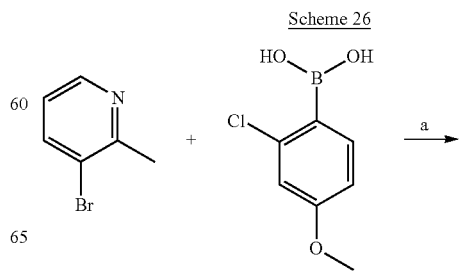

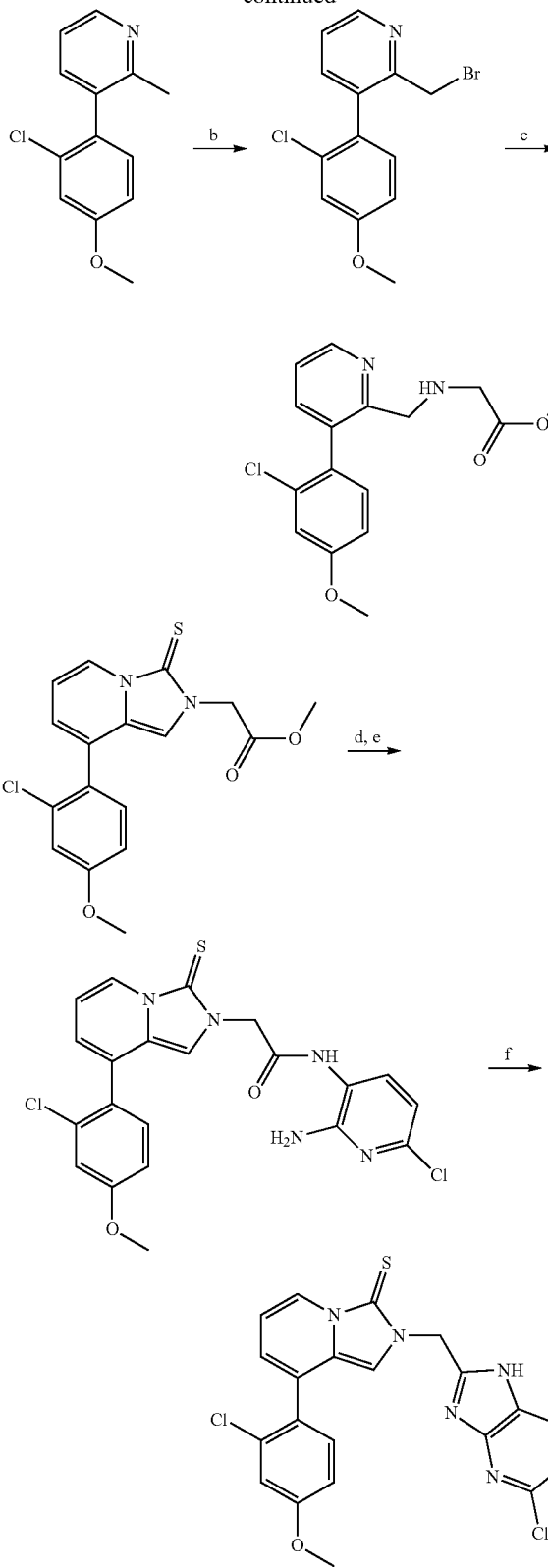

Reagents and conditions (a) K$_2$CO$_3$, Pd(PPh$_3$)$_4$, DME, H$_2$O, microwave irradiation; (b), NBS, benzoyl peroxide; (c) K$_2$CO$_3$, glycine methyl ester; (d) thiophosgen; (e), LiOH, MeOH, H$_2$O; (f) HATU, 6-chlororopyridine-2,3-diamine, DIPEA; (g) HOAc, microwave irradiation 3-brom$_{0-2}$-methyl-pyridine (50 μl, 0.44 mmol), 2-chloro-4-methoxyphenylboronic acid (124 mg, 0.66 mmol), potassium carbonate (182 mg, 1.32 mmol) and tetrakis(triphenylphosphine)palladium(0) (26 mg, 0.022 mmol) in water (0.5 mL) and DME (1.5 mL) was microwave irradiated at 110° C. for 30 min. After organic solvent was removed in vacuo, the residue was extracted with EtOAc and washed successively with water and brine. The organic layer was dried over Na$_2$SO$_4$ and concentrated in vacuo. The residue was purified by flash chromatography on silica gel (MeOH/DCM) to obtain 82 mg of 3-(2-Chloro-4-methoxy-phenyl)-2-methyl-pyridine To a solution of 3-(2-Chloro-4-methoxy-phenyl)-2-methyl-pyridine (82 mg, 0.35 mmol) in 4 ml of CCl$_4$ was added benzoyl peroxide (4 mg). The mixture was refluxed for 4 hours. After organic solvent was removed in vacuo, the residue was purified by flash chromatography on silica gel (MeOH/DCM) to obtain 88 mg of 2-bromomethyl-3-(2-chloro-4-methoxy-phenyl)-pyridine.

To a solution of 2-bromomethyl-3-(2-chloro-4-methoxyphenyl)-pyridine (88 mg, 0.28 mmol) in 5 ml of DMF was added potassium carbonate (232 mg, 1.68 mmol) and glycine methyl ester HCl (144 mg, 1.12 mmol). The mixture was stirred at 80° C. overnight. After organic solvent was removed in vacuo, the residue was purified by flash chromatography on silica gel (MeOH/DCM) to obtain 45 mg of {[3-(2-chloro-4-methoxy-phenyl)-pyridin-2-ylmethyl]-amino}-acetic acid methyl ester.

To a solution of {[3-(2-chloro-4-methoxy-phenyl)-pyridin-2-ylmethyl]-amino}-acetic acid methyl ester (10 mg, 0.031 mmol) in 5 ml of anhydrous DCM at 0° C. was added DIPEA (12 μl, 0.069 mmol) and thiophosgen (0.031 mmol). The mixture was stirred at room temperature for 3 hour. The solvent was removed on a rotary evaporator. The residue was purified by flash column chromatography (DCM/MeOH) to obtain 6.8 mg of [8-(2-Chloro-4-methoxy-phenyl)-3-thioxo-imidazo[1,5-a]pyridin-2-yl]-acetic acid methyl ester.

{[8-(2-Chloro-4-methoxy-phenyl)-3-thioxo-imidazo[1,5-a]pyridin-2-yl]-acetic acid methyl ester (6.8 mg, 0.019 mmol) was added in 1 ml of methanol and 2 ml of water, mixed with LiOH (1.8 mg, 0.075 mml) and stirred for 50 min at room temperature. The solution was acidified with 0.2 N hydrochloric acid and the solvent was completely removed in vacuo. The residue was dissolved in 2 ml of DMF. The solution was added DIPEA (20 ul), HATU (0.022 mmol) and 6-chloropyridine-2,3-diamine (3.1 mg, 0.022 mmol). The mixture was stirred at room temperature for 3 hours. The solvent was removed on a rotary evaporator. The mixture was stirred at room temperature overnight. The solvent was removed on the rotary evaporator. The residue was dissolved in EtOAc (20 ml) and washed with water and brine. The organic layer was dried over Na$_2$SO$_4$ and concentrated in vacuo. The residue was dissolved in 1 ml of acetic acid and the solution was microwave irradiated at 125° C. for 1 hour. After the solvent was removed on the rotary evaporator, the residue was purified by flash column chromatography (DCM/MeOH), giving 4.3 mg of 2243 (2-({5-chloro-1H-imidazo[4,5-b]pyridin-2-yl}methyl)-8-(2-chloro-4-methoxyphenyl)-2H,3H-imidazo[1,5-a]pyridine-3-thione). LC/MS: (ESI) (M+H)$^+$=457.6.

Example 107

Scheme 27

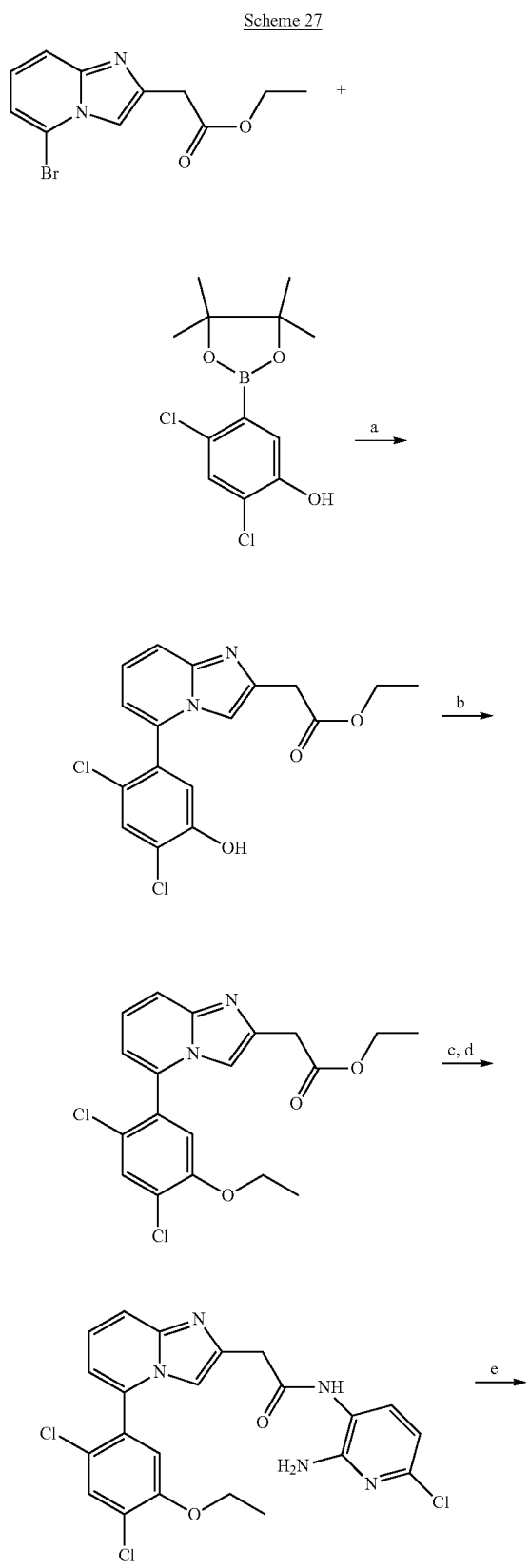

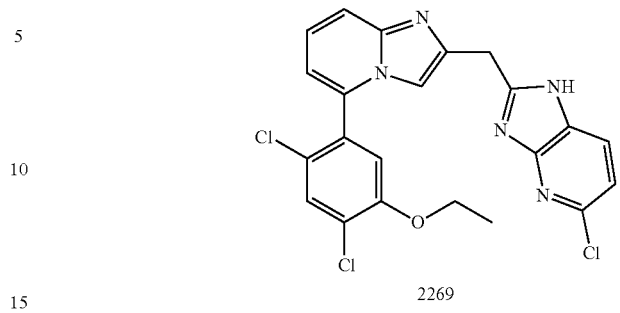

2269

Reagents and conditions (a) K₂CO₃, Pd(PPh₃)₄, DME, H₂O; (b) K₂CO₃, bromoethane, DMF; (c) LiOH, ethanol/water; (d) EDC, 6-chloropyridine-2,3-diamine, pyridine; (e) HOAc, microwave irradiation Ethyl 2-(5-bromoH-imidazo[1,2-a]pyridin-2-yl)acetate (80 mg, 0.28 mmol), 2,4-dichloro-5-(4,4,5,5-tetramethyl-1,3,2-dioxaborolan-2-yl)phenol (122 mg, 0.42 mmol), potassium carbonate (97 mg, 0.71 mmol) and tetrakis(triphenylphosphine)palladium(0) (16 mg, 0.014 mmol) in water (0.5 mL) and DME (1.5 mL) was microwave irradiated at 100° C. for 30 min. After organic solvent was removed in vacuo, the residue was extracted with EtOAc and washed successively with water and brine. The organic layer was dried over Na₂SO₄ and concentrated in vacuo. The residue was purified by flash chromatography on silica gel (hexane/EtOAc) to obtain 90 mg of ethyl 2-(5-(2,4-dichloro-5-hydroxyphenyl)H-imidazo[1,2-a]pyridin-2-yl)acetate.

To a solution of ethyl 2-(5-(2,4-dichloro-5-hydroxyphenyl)H-imidazo[1,2-a]pyridin-2-yl)acetate (6.7 mg, 0.018 mmol) in 1 ml of DMF was added potassium carbonate (3.3 mg, 0.024 mmol) and bromoethane (1.7 µl, 0.023 mmol). The mixture was microwave irradiated at 80° C. for 20 min. After organic solvent was removed in vacuo, the residue was purified by flash chromatography on silica gel (hexane/EtOAc) to obtain 6.7 mg of ethyl 2-(5-(2,4-dichloro-5-hydroxyphenyl)H-imidazo[1,2-a]pyridin-2-yl)acetate.

Ethyl 2-(5-(2,4-dichloro-5-hydroxyphenyl)H-imidazo[1,2-a]pyridin-2-yl)acetate (6.7 mg, 0.017 mmol) was added in 1 ml of ethanol and 3 ml of water, mixed with LiOH (1.6 mg, 0.068 mmol) and stirred for 50 min at room temperature. The solution was acidified with 0.2 N hydrochloric acid and the solvent completely removed in vacuo. The residue was dissolved in 3 ml of pyridine, then 6-chlororopyridine-2,3-diamine (3.7 mg, 0.026 mmol) and EDC hydrochloride (0.034 mmol) were added. The mixture was stirred at room temperature overnight. The solvent was removed on a rotary evaporator. The residue was dissolved in EtOAc (30 ml) and washed with water and brine. The organic layer was dried over Na₂SO₄ and concentrated in vacuo. The residue was dissolved in 2 ml of acetic acid and the solution was microwave irradiated at 125° C. for 1 h. After the solvent was removed on a rotary evaporator, the residue was purified by flash column chromatography (DCM/MeOH), yielding 2269 (2-({5-chloro-1H-imidazo[4,5-b]pyridin-2-yl}methyl)-5-(2,4-dichloro-5-ethoxyphenyl)imidazo[1,2-a]pyridine) (5.2 mg). LC/MS: (ESI) (M+H)⁺=473.9.

Examples 108

Scheme 28

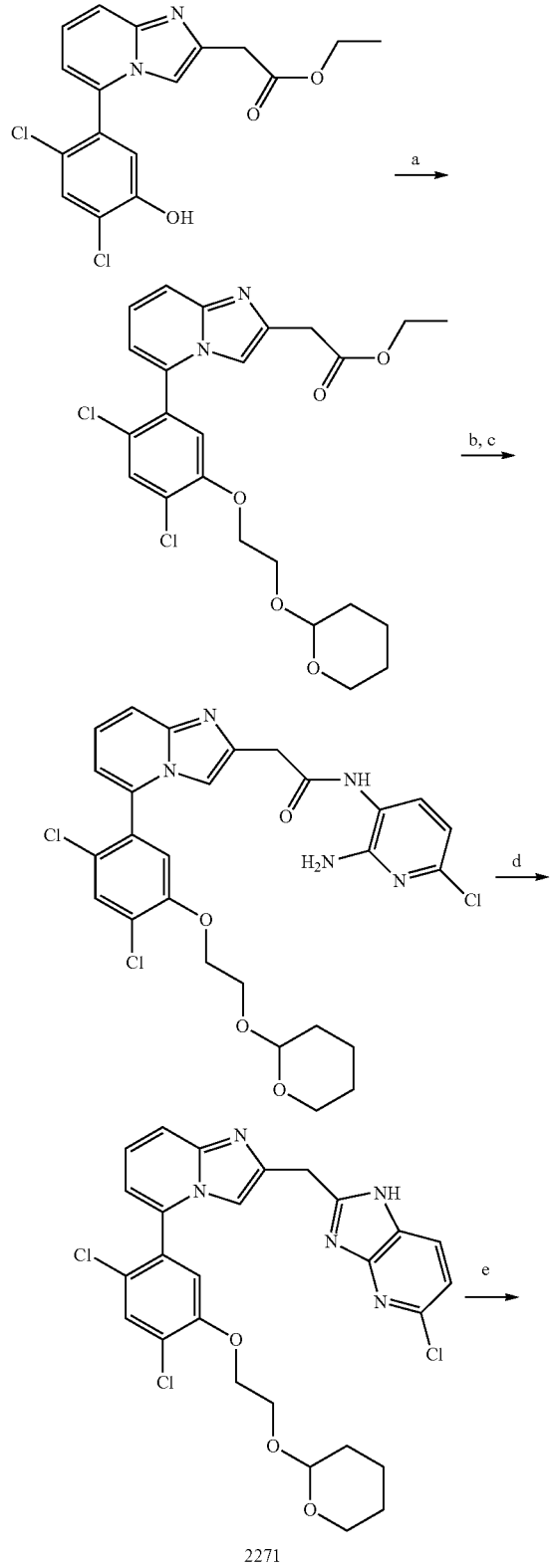

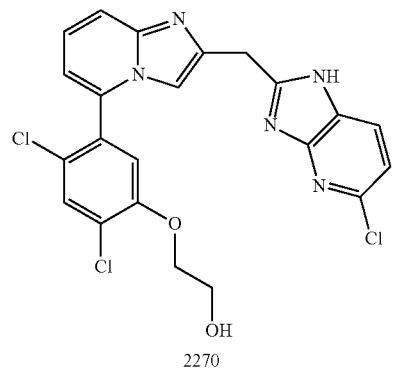

2270

Reagents and conditions (a) K$_2$CO$_3$, 2-(2-bromoethoxy)-tetrahydro-2H-pyran, DMF; (b) LiOH, ethanol/water; (c) EDC, 6-chloropyridine-2, 3-diamine, pyridine; (d) HOAC, microwave irradiation; (e) 2 N HCl, acetone, microwave irradiation To a solution of ethyl 2-(5-(2,4-dichloro-5-hydroxyphenyl)H-imidazo[1,2-a]pyridin-2-yl)acetate (41 mg, 0.11 mmol) in 1.5 ml of DMF was added potassium carbonate (5.7 mg, 0.041 mmol) and 2-(2-bromoethoxy)-tetrahydro-2 H-pyran (8.5 µl, 0.056 mmol). The mixture was microwave irradiated at 80° C. for 12 min. After organic solvent was removed in vacuo, the residue was purified by flash chromatography on silica gel (hexane/EtOAc) to obtain 25 mg of ethyl 2-(5-(2,4-dichloro-5-hydroxyphenyl)H-imidazo[1,2-a]pyridin-2-yl)acetate.

Ethyl 2-(5-(2,4-dichloro-5-hydroxyphenyl)H-imidazo[1,2-a]pyridin-2-yl)acetate (18 mg, 0.037 mmol) was added in 1 ml of ethanol and 3 ml of water, mixed with LiOH (3.5 mg, 0.15 mmol) and stirred for 50 min at room temperature. The solution was acidified with 0.2 N hydrochloric acid and the solvent completely removed in vacuo. The residue was dissolved in 3 ml of pyridine, then 6-chloropyridine-2,3-diamine (8.0 mg, 0.056 mmol) and EDC hydrochloride (0.074 mmol) were added. The mixture was stirred at room temperature overnight. The solvent was removed on a rotary evaporator. The residue was dissolved in EtOAc (30 ml) and washed with water and brine. The organic layer was dried over Na$_2$SO$_4$ and concentrated in vacuo. The residue was dissolved in 2 ml of acetic acid and the solution was microwave irradiated at 125° C. for 1 h. After the solvent was removed on a rotary evaporator, the residue was purified by flash column chromatography (DCM/MeOH), yielding 2271 (2-({5-chloro-1H-imidazo[4,5-b]pyridin-2-yl}methyl)-5-{2,4-dichloro-5-[2-(oxan-2-yloxy)ethoxy]phenyl}-imidazo[1,2-a]pyridine) (10.4 mg). LC/MS: (ESI) (M+H)$^+$=573.9.

Examples 109

The solution of 2271 (5.2 mg, 0.009 mmol) in 1 ml of acetone and 0.5 ml of 2 N HCl was microwave irradiated at 80° C. for 12 min. The solvent was removed on a rotary evaporator. The residue was purified by flash column chromatography (DCM/MeOH), yielding 2270 (2-{2,4-dichloro-5-[2-({5-chloro-1H-imidazo[4,5-b]pyridin-2-yl}methyl)imidazo[1,2-a]pyridin-5-yl]phenoxy}ethan-1-ol) (2.8 mg). LC/MS: (ESI) (M+H)$^+$=489.6.

Example 110

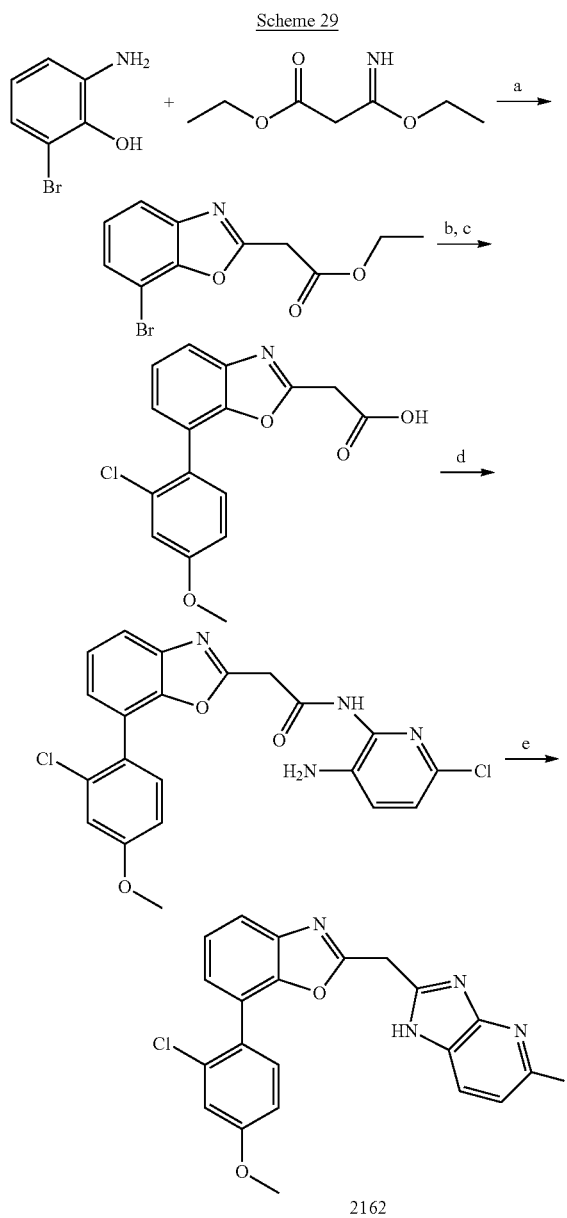

2162

Reagents and conditions (a) ethanol, microwave irradiation; (b) 2-chloro-4-methoxyphenylboronic acid, K$_2$CO$_3$, Pd(PPh$_3$)$_4$; (c) LiOH, ethanol/water; (d) EDC, 6-chloropyridine-2, 3-diamine, pyridine; (e) HOAc, microwave irradiation The mixture of ethyl ethoxycarbonylacetimidate hydrochloride (132 mg, 0.678 mmol) and 2-amino-6-bromophenol (85 mg, 0.452 mmol) in ethanol was microwave irradiation at 90° C. for 30 min. After the solution was cooled down to room temperature, the solid was removed and the filtrate was concentrated on a rotary evaporator. The residue was dissolved in EtOAc (20 ml) and washed with saturated Na$_2$CO$_3$ and brine. The organic layer was dried over Na$_2$SO$_4$ and concentrated in vacuo. The residue was purified by flash chromatography on silica gel to give ethyl 2-(7-bromobenzo[d]oxazol-2-yl)acetate (38.5 mg, 0.136 mmol).

A mixture of ethyl 2-(7-bromobenzo[d]oxazol-2-yl)acetate (38.5 mg, 0.136 mmol), 2-chloro-4-methoxyphenylboronic acid (38 mg, 0.204 mmol), potassium carbonate (38 mg, 0.272 mmol) and tetrakis(triphenylphosphine)palladium(0) (6 mg) in water (1 mL) and DME (3 mL) was microwave irradiated at 100° C. for 20 min. After organic solvent was removed in vacuo, the residue is extracted with EtOAc and washed successively with water and brine. The organic layer was dried over Na$_2$SO$_4$ and concentrated in vacuo. The residue was purified by flash chromatography on silica gel (DCM/MeOH) to give ethyl 2-(7-(2-chloro-4-methoxyphenyl)benzo[d]oxazol-2-yl)acetate (24.4 mg, 52%).

Ethyl 2-(7-(2-chloro-4-methoxyphenyl)benzo[d]oxazol-2-yl)acetate (24.4 mg, 0.071 mmol) was added in 1 ml of ethanol and 3 ml of water, mixed with LiOH (7 mg, 0.28 mml) and stirred for 50 min at room temperature. The solution was acidified with 0.2 N hydrochloric acid and the solvent was completely removed in vacuo. The residue was dissolved in 3 ml of pyridine, then 6-chlororopyridine-2,3-diamine (15.2 mg, 0.106 mmol) and EDC hydrochloride (27 mg, 0.142 mmol) were added. The mixture was stirred at room temperature overnight. The solvent was removed on a rotary evaporator. The residue was dissolved in EtOAc (30 ml) and washed with water and brine. The organic layer was dried over Na$_2$SO$_4$ and concentrated in vacuo. The residue was purified by flash chromatography on silica gel to give N-(3-amino-6-chloropyridin-2-yl)-2-(7-(2-chloro-4-methoxyphenyl)benzo[d]oxazol-2-yl)acetamide (18.8 mg, 0.043 mmol). N-(3-amino-6-chloropyridin-2-yl)-2-(7-(2-chloro-4-methoxyphenyl)benzo[d]oxazol-2-yl)acetamide (18.8 mg, 0.043 mmol) was dissolved in 2 ml of acetic acid and the solution was microwave irradiated at 125° C. for 1 h. After the solvent was removed on a rotary evaporator, the residue was purified by flash column chromatography (DCM/MeOH), yielding 2162 (2-({5-chloro-1H-imidazo[4,5-b]pyridin-2-yl}methyl)-7-(2-chloro-4-methoxyphenyl)-1,3-benzoxazole) in 45% yield (8.2 mg). LC/MS: (ESI) (M+H)$^+$=426.4.

Example 111

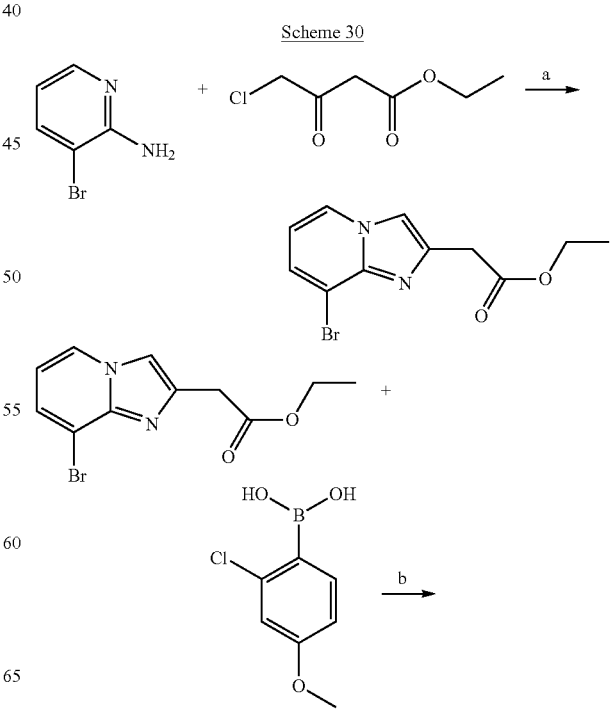

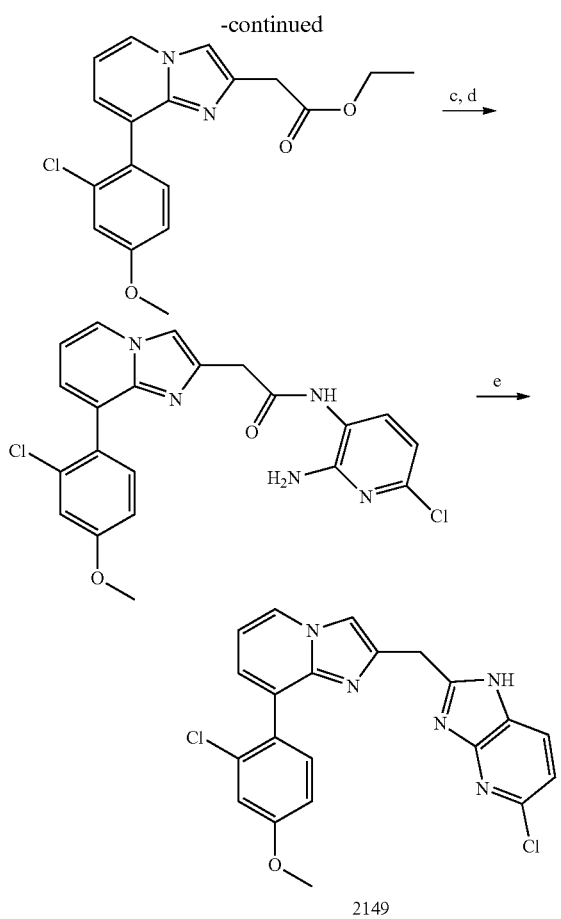

2149

Reagents and conditions (a) ethanol, refluxing; (b) K₂CO₃, Pd(PPh₃)₄, DME, H₂O, microwave irradiation; (c) LiOH, ethanol/water; (d) EDC, 6-chloropyridine-2,3-diamine, pyridine; (e) HOAc, microwave irradiation General Procedure 8 (2149, 2148):

A mixture of ethyl 4-chloroacetoacetate (389 μl, 2.88 mmol) and 3-bromopyridin-2-amine (437 mg, 2.4 mmol) in EtOH (20 mL) was refluxed overnight. After the solvent was removed on a rotary evaporator, the residue was dissolved in EtOAc (30 ml) and washed with saturated Na₂CO₃ and brine. The organic layer was dried over Na₂SO₄ and concentrated in vacuo. The residue was purified by flash chromatography on silica gel to give ethyl 2-(8-bromoH-imidazo[1,2-a]pyridin-2-yl)acetate (317 mg, 1.12 mmol).

Ethyl 2-(8-bromoH-imidazo[1,2-a]pyridin-2-yl)acetate (61 mg, 0.22 mmol), chloro-4-methoxyphenylboronic acid (82 mg, 0.44 mmol), potassium carbonate (60 mg, 0.44 mmol) and tetrakis(triphenylphosphine)palladium(0) (8 mg, 0.007 mmol) in water (0.5 mL) and DME (1.5 mL) was microwave irradiated at 100° C. for 20 min. After organic solvent was removed in vacuo, the residue was extracted with EtOAc and washed successively with water and brine. The organic layer was dried over Na₂SO₄ and concentrated in vacuo. The residue was purified by flash chromatography on silica gel (hexane/EtOAc) to obtain ethyl 2-(8-(2-chloro-4-methoxyphenyl)H-imidazo[1,2-a]pyridin-2-yl)acetate (53 mg, 70%).

Ethyl 2-(8-(2-chloro-4-methoxyphenyl)H-imidazo[1,2-a]pyridin-2-yl)acetate (22 mg, 0.063 mmol) was added in 1 ml of ethanol and 3 ml of water, mixed with LiOH (6.1 mg, 0.25 mml) and stirred for 50 min at room temperature. The solution was acidified with 0.2N hydrochloric acid and the solvent was completely removed in vacuo. The residue was dissolved in 3 ml of pyridine, then 6-chloropyridine-2,3-diamine (10.8 mg, 0.076 mmol) and EDC hydrochloride (25 mg, 0.132 mmol) were added. The mixture was stirred at room temperature overnight. The solvent was removed on a rotary evaporator. The residue was dissolved in EtOAc (30 ml) and washed with water and brine. The organic layer was dried over Na₂SO₄ and concentrated in vacuo. The residue was purified by flash chromatography on silica gel to give N-(2-amino-6-chloropyridin-3-yl)-2-(8-(2-chloro-4-methoxyphenyl)H-imidazo[1,2-a]pyridin-2-yl)acetamide (18 mg, 0.037 mmol). N-(2-amino-6-chloropyridin-3-yl)-2-(8-(2-chloro-4-methoxyphenyl)H-imidazo[1,2-a]pyridin-2-yl)acetamide (18 mg, 0.037 mmol) was dissolved in 2 ml of acetic acid and the solution was microwave irradiated at 125° C. for 1 h. After the solvent was removed on a rotary evaporator, the residue was purified by flash column chromatography (DCM/MeOH), yielding 2149 (2-({5-chloro-1H-imidazo[4,5-b]pyridin-2-yl}methyl)-8-(2-chloro-4-methoxyphenyl)imidazo[1,2-a]pyridine) in 75% yield (12 mg). LC/MS: (ESI) (M+H)⁺=425.4.

Example 112

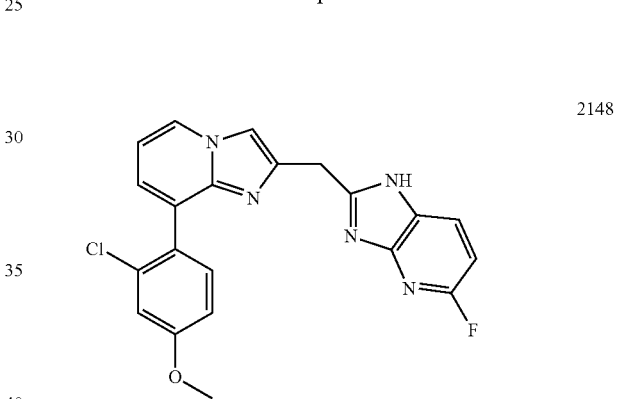

2148

2148 (8-(2-chloro-4-methoxyphenyl)-2-({5-fluoro-1H-imidazo[4,5-b]pyridin-2-yl}methyl)imidazo[1,2-a]pyridine) was synthesized using 6-fluoropyridine-2,3-diamine following General Procedure 8. LC/MS: (ESI) (M+H)⁺=408.8.

Example 113

Scheme 31

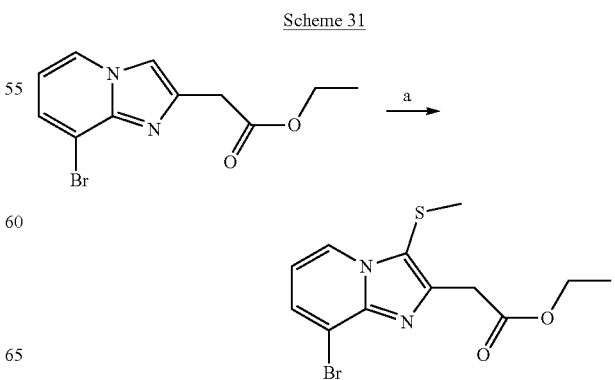

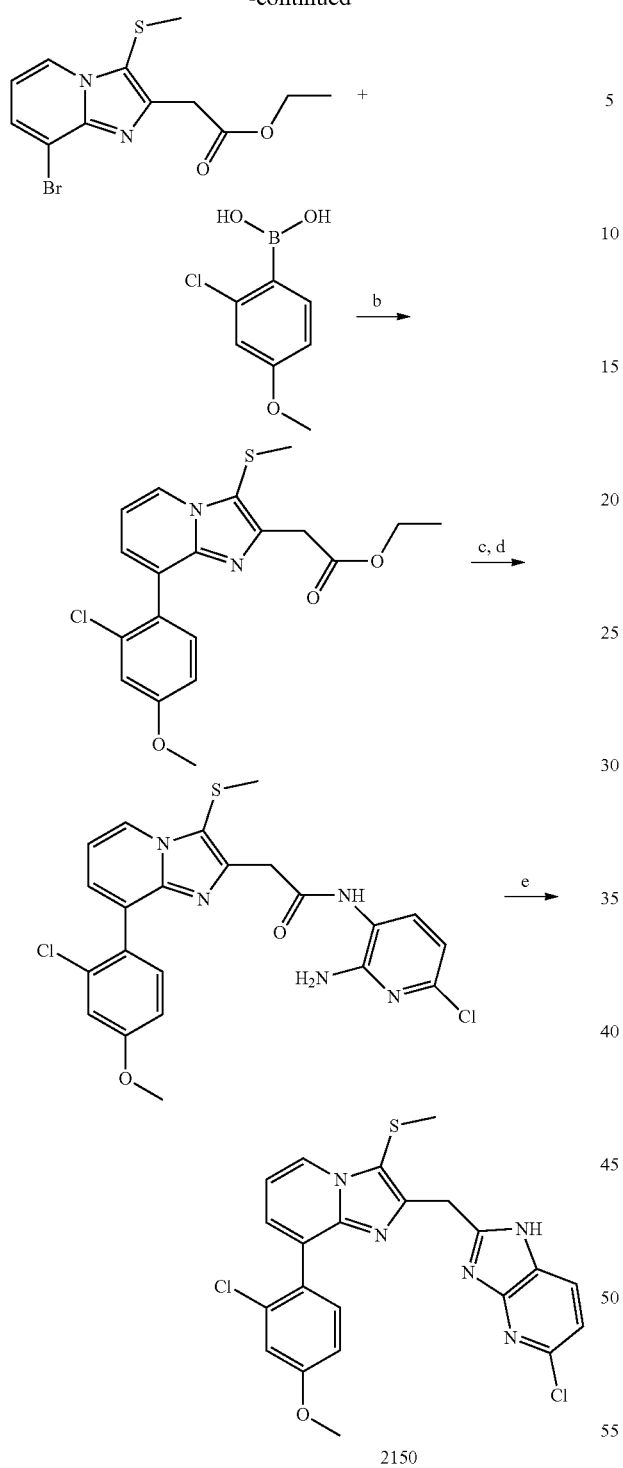

2150

Reagents and conditions (a) POCl₃, DMSO; (b) K₂CO₃, Pd(PPh₃)₄, DME, H₂O, microwave irradiation; (c) LiOH, ethanol/water; (d) EDC, 6-chloropyridine-2,3-diamine, pyridine; (e) HOAc, microwave irradiation.

A solution of ethyl 2-(8-bromoH-imidazo[1,2-a]pyridin-2-yl)acetate (61 mg, 0.22 mmol), POCl₃ (44 μl, 0.33 mmol) in 1 ml of DMSO was heated at 50° C. for 4 days. The solution was diluted with EtOAc and washed with water and brine. The organic layer was dried over Na₂SO₄ and concentrated in vacuo. The residue was purified by flash chromatography on silica gel to give ethyl 2-(8-bromo-3-(methylthio)H-imidazo[1,2-a]pyridin-2-yl)acetate (30 mg, 0.09 mmol).

Ethyl 2-(8-bromo-3-(methylthio)H-imidazo[1,2-a]pyridin-2-yl)acetate (30 mg, 0.09 mmol), chloro-4-methoxyphenylboronic acid (34 mg, 0.18 mmol), potassium carbonate (25 mg, 0.18 mmol) and tetrakis(triphenylphosphine)palladium(0) (4 mg, 0.0035 mmol) in water (0.5 mL) and DME (1.5 mL) was microwave irradiated at 100° C. for 20 min. After organic solvent was removed in vacuo, the residue was extracted with EtOAc and washed successively with water and brine. The organic layer was dried over Na₂SO₄ and concentrated in vacuo. The residue was purified by flash chromatography on silica gel (hexane/EtOAc) to obtain ethyl 2-(8-(2-chloro-4-methoxyphenyl)-3-(methylthio)H-imidazo[1,2-a]pyridin-2-yl)acetate (26 mg, 0.067 mmol).

Ethyl ethyl 2-(8-(2-chloro-4-methoxyphenyl)-3-(methylthio)H-imidazo[1,2-a]pyridin-2-yl)acetate (26 mg, 0.067 mmol) was added in 1 ml of ethanol and 3 ml of water, mixed with LiOH (6.5 mg, 0.26 mml) and stirred for 50 min at room temperature. The solution was acidified with 0.2 N hydrochloric acid and the solvent was completely removed in vacuo. The residue was dissolved in 3 ml of pyridine, then 6-chlororopyridine-2,3-diamine (12 mg, 0.082 mmol) and EDC hydrochloride (27 mg, 0.142 mmol) were added. The mixture was stirred at room temperature overnight. The solvent was removed on a rotary evaporator. The residue was dissolved in EtOAc (30 ml) and washed with water and brine. The organic layer was dried over Na₂SO₄ and concentrated in vacuo. The residue was purified by flash chromatography on silica gel to give N-(2-amino-6-chloropyridin-3-yl)-2-(8-(2-chloro-4-methoxyphenyl)-3-(methylthio)H-imidazo[1,2-a]pyridin-2-yl)acetamide (15.5 mg, 0.032 mmol). N-(2-amino-6-chloropyridin-3-yl)-2-(8-(2-chloro-4-methoxyphenyl)-3-(methylthio)H-imidazo[1,2-a]pyridin-2-yl)acetamide (15.5 mg, 0.032 mmol) was dissolved in 2 ml of acetic acid and the solution was microwave irradiated at 125° C. for 1 h. After the solvent was removed on a rotary evaporator, the residue was purified by flash column chromatography (DCM/MeOH), yielding 2150 (2-({5-chloro-1H-imidazo[4,5-b]pyridin-2-yl}methyl)-8-(2-chloro-4-methoxyphenyl)-3-(methylsulfanyl)imidazo[1,2-a]pyridine) in 70% yield (11 mg). LC/MS: (ESI) (M+H)⁺=471.4.

Example 114

Scheme 32

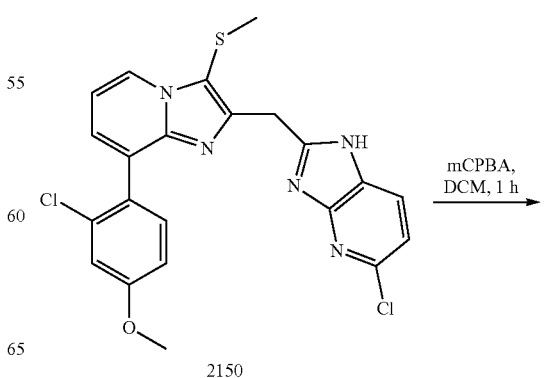

2150

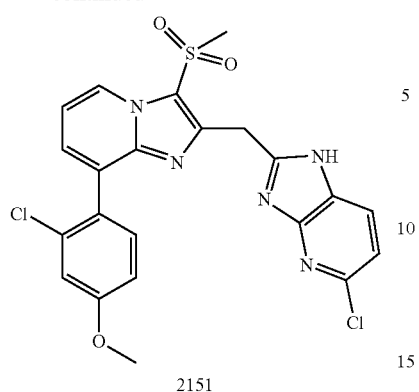

2151

To a solution of 2150 (6.0 mg, 0.013 mmol) in DCM (10 mL) was added mCPBA (7 mg, 0.04 mmol) at 0° C. The mixture was stirred at room temperature for 1 h, and washed with 10 mL of saturated NaHCO₃ twice. Methylene chloride layer was separated, washed with brine, and dried over anhydrous Na₂SO₄. The solvent was evaporated under reduced pressure. The residue was purified by silica gel column chromatography to give 2151 (2-({5-chloro-1H-imidazo[4,5-b]pyridin-2-yl}methyl)-8-(2-chloro-4-methoxyphenyl)-3-methanesulfonylimidazo[1,2-a]pyridine) (5.1 mg, 0.01 mmol). LC/MS: (ESI) (M+H)⁺=503.6.

Example 115

Scheme 33

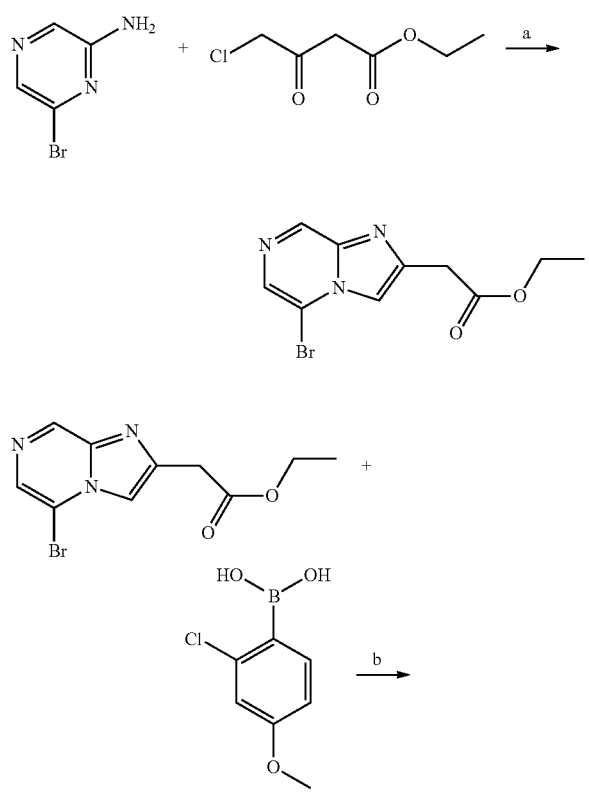

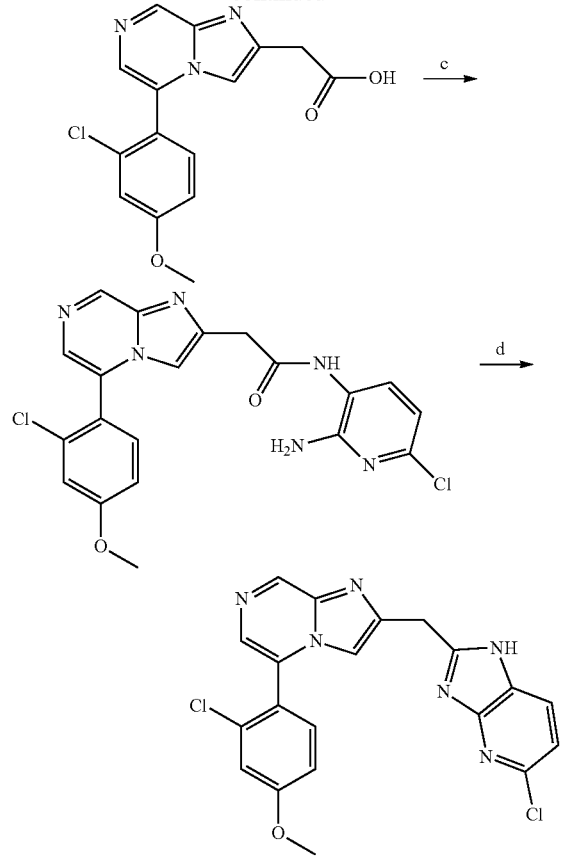

2156

Reagents and conditions (a) ethanol, microwave irradiation; (b) K₂CO₃, Pd(PPh₃)₄, DME, H₂O, microwave irradiation; (c) EDC, 6-chloropyridine-2,3-diamine, pyridine; (d) HOAc, microwave irradiation A mixture of ethyl 4-chloroacetoacetate (200 μl, 1.48 mmol) and 6-bromopyrazin-2-amine (100 mg, 0.575 mmol) in EtOH (1 mL) was microwave irradiated at 90° C. for 40 min. After organic solvent was removed in vacuo, the residue was extracted with EtOAc and washed successively with saturated Na₂CO₃ and brine. The organic layer was dried over Na₂SO₄ and concentrated in vacuo. The residue was purified by flash chromatography on silica gel (DCM/MeOH) to obtain ethyl 2-(5-bromoimidazo[1,2-a]pyrazin-2-yl)acetate (49 mg, 0.173 mmol).

A mixture of ethyl 2-(5-bromoimidazo[1,2-a]pyrazin-2-yl)acetate (49 mg, 0.173 mmol), 2-chloro-4-methoxyphenylboronic acid (48 mg, 0.26 mmol), potassium carbonate (72 mg, 0.519 mmol) and tetrakis(triphenylphosphine)palladium(0) (10 mg) in water (0.4 mL) and DME (1.2 mL) was microwave irradiated at 110° C. for 50 min. The solution was acidified with 0.2 N HCl. After most of organic solvent was removed in vacuo, the mixture was extracted with EtOAc and washed successively with water and brine. The organic layer was dried over Na₂SO₄ and concentrated in vacuo. The residue was purified by flash chromatography on silica gel (DCM/MeOH) to obtain 2-(5-(2-chloro-4-methoxyphenyl)imidazo[1,2-a]pyrazin-2-yl)acetic acid (36 mg, 65%).

2-(5-(2-chloro-4-methoxyphenyl)imidazo[1,2-a]pyrazin-2-yl)acetic acid (12 mg, 0.038 mmol) was dissolved in 2 ml of pyridine, then 6-chloropyridine-2,3-diamine (8.2 mg, 0.057 mmol) and EDC hydrochloride (14.5 mg, 0.076 mmol) were added. The mixture was stirred at room temperature overnight. The solvent was removed on a rotary evaporator. The residue was purified by flash chromatography on silica gel to give N-(2-amino-6-chloropyridin-3-yl)-2-(5-(2-chloro-4-methoxyphenyl)imidazo[1,2-a]pyrazin-2-yl)acetamide (14 mg, 0.032 mmol). N N-(2-amino-6-chloropyridin-3-yl)-2-(5-(2-chloro-4-methoxyphenyl) imidazo[1,2-a]pyrazin-2-yl)acetamide (14 mg, 0.032 mmol) was dissolved in 2 ml of acetic acid and the solution was microwave irradiated at 125° C. for 1 h. After the solvent was removed on a rotary evaporator, the residue was purified by flash column chromatography (DCM/MeOH), yielding 2156 (2-({5-chloro-1H-imidazo[4,5-b]pyridin-2-yl}methyl)-5-(2-chloro-4-methoxyphenyl)imidazo[1,2-a]pyrazine) in 65% yield (13.6 mg). LC/MS: (ESI) $(M+H)^+$=436.3.

Example 116

Scheme 34

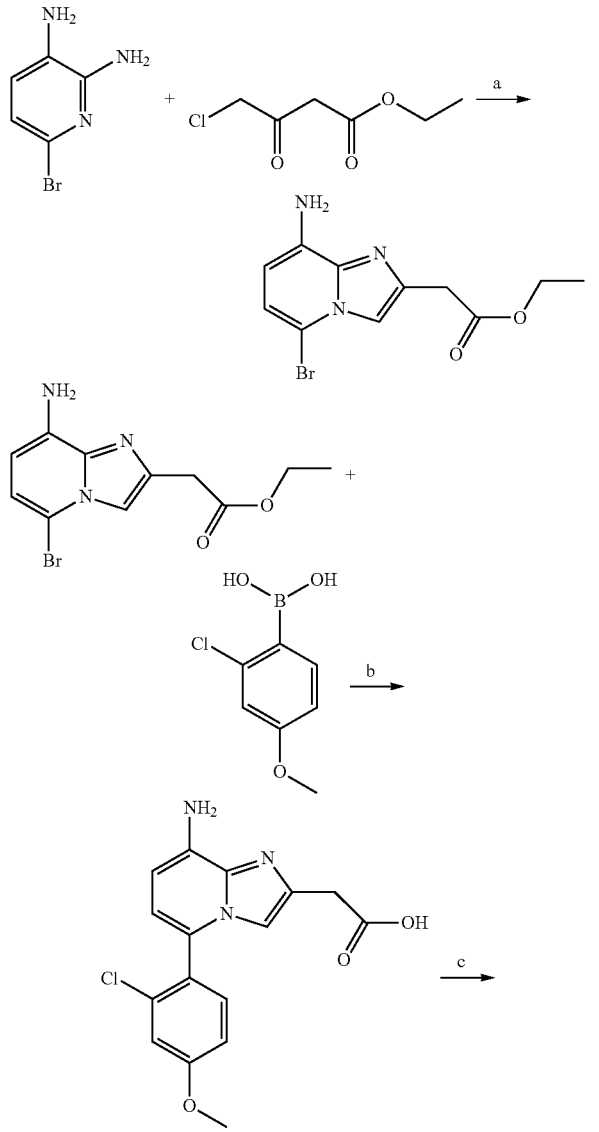

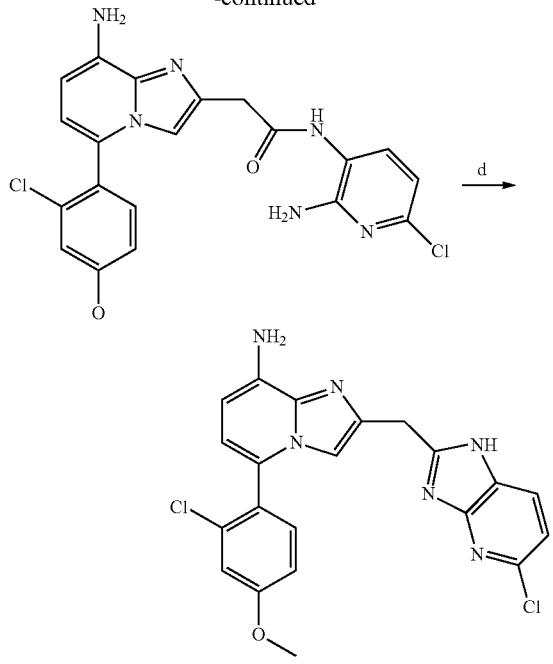

Reagents and conditions (a) ethanol, microwave irradiation; (b) $K_2CO_3$, Pd(PPh$_3$)$_4$, DME, H$_2$O, microwave irradiation; (c) EDC, 6-chloropyridine, 3-diamine, pyridine; (d) HOAc, microwave irradiation General Procedure 9 (2169, 2180, 2183, 2184):

A mixture of ethyl 4-chloroacetoacetate (205 μl, 1.51 mmol) and 6-bromo-pyridine-2,3-diamine (237 mg, 1.26 mmol) in EtOH (20 mL) was refluxed overnight. After the solvent was removed on a rotary evaporator, the residue was dissolved in EtOAc (30 ml) and washed with saturated Na$_2$CO$_3$ and brine. The organic layer was dried over Na$_2$SO$_4$ and concentrated in vacuo. The residue was purified by flash chromatography on silica gel to give ethyl 2-(8-bromoH-imidazo[1,2-a]pyridin-2-yl)acetate (263 mg, 0.88 mmol). $^1$H NMR (CDCl$_3$) δ 7.71 (s, 1H), 6.79 (d, J=7.8 Hz, 1H), 6.28 (d, J=7.8 Hz, 1H), 4.53 (br, 2H), 4.21(q, J=7.1 Hz, 2H), 3.86 (s, 2H), 1.29 (t, J=9.1 Hz, 3H).

Ethyl 2-(8-bromoH-imidazo[1,2-a]pyridin-2-yl)acetate (58.8 mg, 0.20 mmol), chloro-4-methoxyphenylboronic acid (56 mg, 0.3 mmol), potassium carbonate (82 mg, 0.60 mmol) and tetrakis(triphenylphosphine)palladium(0) (12 mg) in water (0.5 mL) and DME (1.5 mL) was microwave irradiated at 110° C. for 30 min. The solution was acidified with 0.2 N HCl. After most of organic solvent was removed in vacuo, the mixture was extracted with EtOAc and washed successively with water and brine. The organic layer was dried over Na$_2$SO$_4$ and concentrated in vacuo. The residue was purified by flash chromatography on silica gel (DCM/MeOH) to obtain [8-Amino-5-(2-chloro-4-methoxy-phenyl)-imidazo[1,2-a]pyridin-2-yl]-acetic acid (48 mg, 72%).

[8-Amino-5-(2-chloro-4-methoxy-phenyl)-imidazo[1,2-a]pyridin-2-yl]-acetic acid (19.2 mg, 0.058 mmol) was dissolved in 2 ml of pyridine, then 6-chloropyridine-2,3-diamine (16.5 mg, 0.116 mmol) and EDC hydrochloride (16.7 mg, 0.087 mmol) were added. The mixture was stirred at room temperature overnight. The solvent was removed on a rotary evaporator. The residue was purified by flash chromatography on silica gel to give 2-[8-Amino-5-(2-chloro-4-methoxy-phenyl)-imidazo[1,2-a]pyridin-2-yl]—

N-(2-amino-6-chloro-pyridin-3-yl)-acetamide (20 mg, 0.044 mmol). 2-[8-Amino-5-(2-chloro-4-methoxy-phenyl)-imidazo[1,2-a]pyridin-2-yl]—N-(2-amino-6-chloro-pyridin-3-yl)-acetamide (20 mg, 0.044 mmol) was dissolved in 2 ml of acetic acid and the solution was microwave irradiated at 140° C. for 1 h. After the solvent was removed on a rotary evaporator, the residue was purified by flash column chromatography (DCM/MeOH), yielding 2169 (N-[2-({5-chloro-1H-imidazo[4,5-b]pyridin-2-yl}methyl)-5-(2-chloro-4-methoxyphenyl)imidazo[1,2-a]pyridin-8-yl]acetamide) in 85% yield (18 mg). LC/MS: (ESI) (M+H)$^+$=482.3.

Example 117

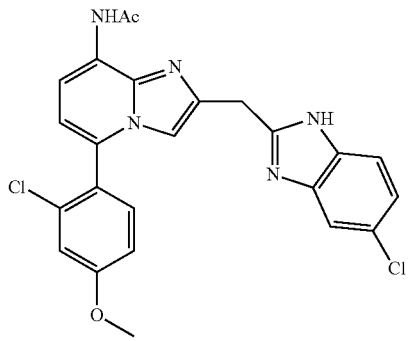

2180 (N-{2-[(6-chloro-1H-1,3-benzodiazol-2-yl)methyl]-5-(2-chloro-4-methoxyphenyl)imidazo[1,2-a]pyridin-8-yl}acetamide) was synthesized using 4-Chloro-benzene-1,2-diamine following General Procedure 9. LC/MS: (ESI) (M+H)$^+$=481.4.

Example 118

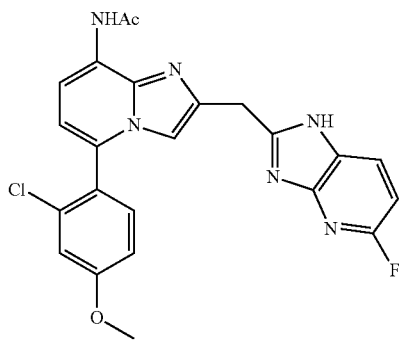

2183 (N-[5-(2-chloro-4-methoxyphenyl)-2-({5-fluoro-1H-imidazo[4,5-b]pyridin-2-yl}methyl)imidazo[1,2-a]pyridin-8-yl]acetamide) was synthesized using 6-fluoropyridine-2,3-diamine following General Procedure 9. LC/MS: (ESI) (M+H)$^+$=464.8.

Example 119

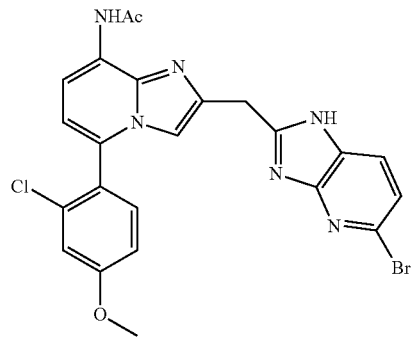

2184 (N-[2-({5-bromo-1H-imidazo[4,5-b]pyridin-2-yl}methyl)-5-(2-chloro-4-methoxyphenyl)imidazo[1,2-a]pyridin-8-yl]acetamide) was synthesized using 6-fluoropyridine-2,3-diamine following General Procedure 9. LC/MS: (ESI) (M+H)$^+$=426.9.

Example 120

Scheme 35

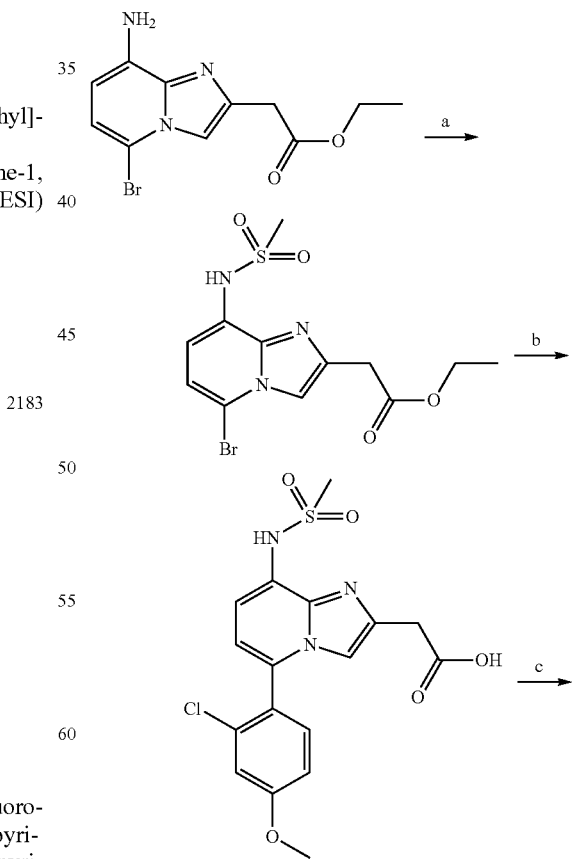

-continued

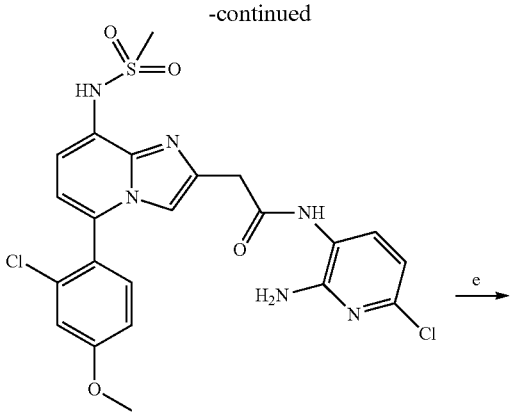

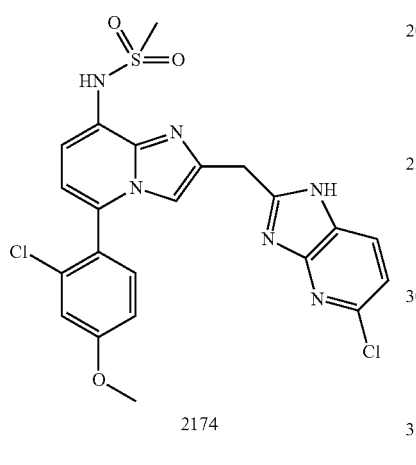

2174

Reagents and conditions (a) methanesulfonyl chloride, pyridine; (b) K₂CO₃, Pd(PPh₃)₄, DME, H₂O, micowave irradition; (c) EDC, 6-chloropyridine-2,3-diamine, pyridine; (d) HOAc, microwave irradiation To a solution of ethyl 2-(8-amino-5-bromoH-imidazo[1,2-a]pyridin-2-yl)acetate (20 mg, 0.067 mmol) in 1 ml of pyridine was added methanesulfonyl chloride (52 μl, 0.67 mmol). The mixture was stirred at room temperature overnight. After the solvent was removed, the residue was dissolved in EtOAc (30 ml) and washed with water and brine. The organic layer was dried over Na₂SO₄ and concentrated in vacuo. The residue was purified by flash chromatography on silica gel to give (5-Bromo-8-methanesulfonylamino-imidazo[1,2-a]pyridin-2-yl)-acetic acid ethyl ester (20 mg, 0.054 mmol).

(5-Bromo-8-methanesulfonylamino-imidazo[1,2-a]pyridin-2-yl)-acetic acid ethyl ester (20 mg, 0.054 mmol), chloro-4-methoxyphenylboronic acid (14.7 mg, 0.081 mmol), potassium carbonate (15 mg, 0.108 mmol) and tetrakis(triphenylphosphine)palladium(0) (3 mg) in water (0.5 mL) and DME (1.5 mL) was microwave irradiated at 110° C. for 30 min. The solution was acidified with 0.2 N HCl. After most of organic solvent was removed in vacuo, the mixture was extracted with EtOAc and washed successively with water and brine. The organic layer was dried over Na₂SO₄ and concentrated in vacuo. The residue was purified by flash chromatography on silica gel (DCM/MeOH) to obtain [5-(2-Chloro-4-methoxy-phenyl)-8-methanesulfonylamino-imidazo[1,2-a]pyridin-2-yl]-acetic acid (16.7 mg, 76%).

[5-(2-Chloro-4-methoxy-phenyl)-8-methanesulfonylamino-imidazo[1,2-a]pyridin-2-yl]-acetic acid (16.7 mg, 0.041 mmol) was dissolved in 2 ml of pyridine, then 6-chloropyridine-2,3-diamine (8.8 mg, 0.062 mmol) and EDC hydrochloride (15.7 mg, 0.082 mmol) were added. The mixture was stirred at room temperature overnight. The solvent was removed, the residue was purified by flash chromatography on silica gel to give N-(2-Amino-6-chloro-pyridin-3-yl)-2-[5-(2-chloro-4-methoxy-phenyl)-8-methanesulfonylamino-imidazo[1,2-a]pyridin-2-yl]-acetamide (17.5 mg, 0.033 mmol). N-(2-Amino-6-chloro-pyridin-3-yl)-2-[5-(2-chloro-4-methoxy-phenyl)-8-methanesulfonylamino-imidazo[1,2-a]pyridin-2-yl]-acetamide (17.5 mg, 0.033 mmol) was dissolved in 2 ml of acetic acid and the solution was microwave irradiated at 125° C. for 1 h. After the solvent was removed, the residue was purified by flash column chromatography (DCM/MeOH), yielding 2174 (N-[2-({5-chloro-1H-imidazo[4,5-b]pyridin-2-yl}methyl)-5-(2-chloro-4-methoxyphenyl)imidazo[1,2-a]pyridin-8-yl]methanesulfonamide) in 88% yield (14 mg). LC/MS: (ESI) $(M+H)^+=518.3$.

Example 121

Scheme 36

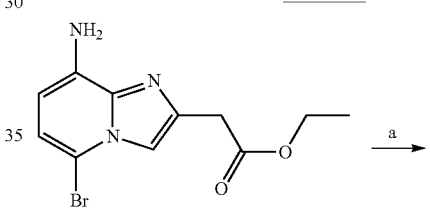

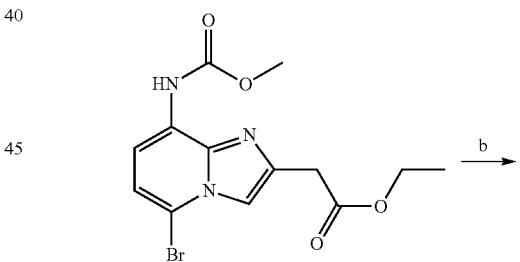

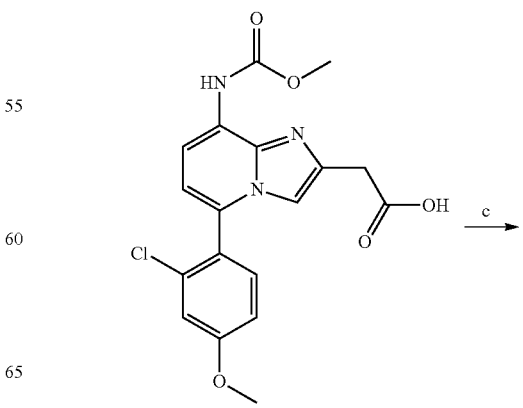

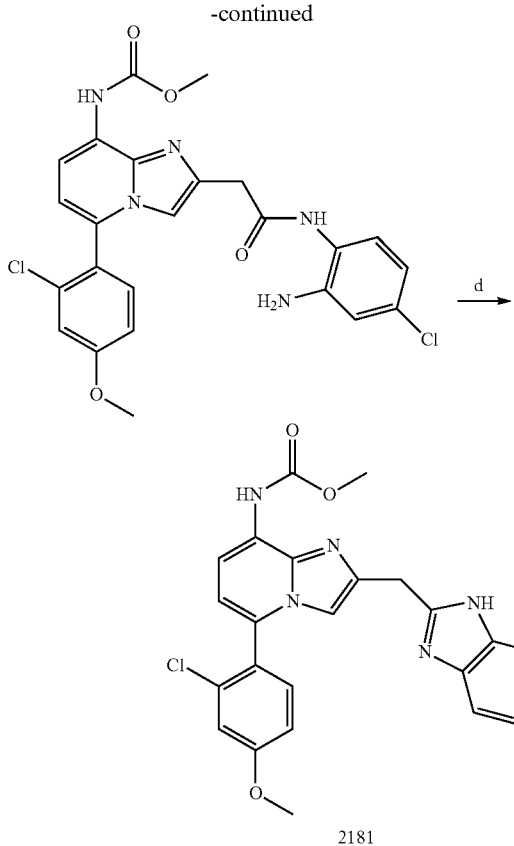

2181

Reagents and conditions (a) phosgene, DIPEA, methanol; (b) K₂CO₃, Pd(PPh₃)₄, DME, H₂O, microwave irradition; (c) EDC, 4-chlorobenzene-1,2-diamine, pyridine; (d) HOAc, microwave irradiation To a solution of ethyl 2-(8-amino-5-bromoH-imidazo[1,2-a]pyridin-2-yl)acetate (10.5 mg, 0.035 mmol), DIPEA (24 µl, 0.138 mmol) in 2 ml of DCM at 0° C. was added phosgene in 15 wt. % in toluene (30 µl, 0.042 mmol). The mixture was stirred at 0° C. for 50 min. Methanol (1 ml) was added and the mixture was stirred room temperature for 8 h. After the solvent was removed, the residue was dissolved in EtOAc (30 ml) and washed with water and brine. The organic layer was dried over Na₂SO₄ and concentrated in vacuo. The residue was purified by flash chromatography on silica gel to give methyl 2-((ethoxycarbonyl)methyl)-5-bromoH-imidazo[1,2-a]pyridin-8-ylcarbamate (11.3 mg, 0.032 mmol).

Ethyl 2-(5-bromo-8-(3-ethylureido)H-imidazo[1,2-a]pyridin-2-yl)acetate (11.3 mg, 0.032 mmol), chloro-4-methoxyphenylboronic acid (8.7 mg, 0.048 mmol), potassium carbonate (8.9 mg, 0.064 mmol) and tetrakis(triphenylphosphine)palladium(0) (1.9 mg) in water (0.5 mL) and DME (1.5 mL) was microwave irradiated at 100° C. for 20 min. The solution was acidified with 0.2 N HCl. After most of organic solvent was removed in vacuo, the mixture was extracted with EtOAc and washed successively with water and brine. The organic layer was dried over Na₂SO₄ and concentrated in vacuo. The residue was purified by flash chromatography on silica gel (DCM/MeOH) to obtain methyl 2-((carboxylic acid)methyl)-5-(2-chloro-4-methoxyphenyl)H-imidazo[1,2-a]pyridin-8-ylcarbamate (9.7 mg, 78%).

2-(5-(2-chloro-4-methoxyphenyl)-8-(3-ethylureido)H-imidazo[1,2-a]pyridin-2-yl)acetic acid (9.7 mg, 0.025 mmol) was dissolved in 2 ml of pyridine, then 4-chlorobenzene-1,2-diamine (5.3 mg, 0.0375 mmol) and EDC hydrochloride (9.4 mg, 0.05 mmol) were added. The mixture was stirred at room temperature overnight. The solvent was removed. The residue was purified by flash chromatography on silica gel to give methyl 2-((2-amino-4-chlorophenylcarbamoyl)methyl)-5-(2-chloro-4-methoxyphenyl)H-imidazo[1,2-a]pyridin-8-ylcarbamate (10.3 mg, 0.02 mmol). Methyl 2-((2-amino-4-chlorophenylcarbamoyl)methyl)-5-(2-chloro-4-methoxyphenyl)H-imidazo[1,2-a]pyridin-8-ylcarbamate (10.3 mg, 0.02 mmol) was dissolved in 2 ml of acetic acid and the solution was microwave irradiated at 60° C. for 20 min. After the solvent was removed, the residue was purified by flash column chromatography (DCM/MeOH), yielding 2181 (methyl N-{2-[(6-chloro-1H-1,3-benzodiazol-2-yl)methyl]-5-(2-chloro-4-methoxyphenyl)imidazo[1,2-a]pyridin-8-yl}carbamate) in 81% yield (8.0 mg). LC/MS: (ESI) (M+H)⁺=497.5.

Example 122

Scheme 37

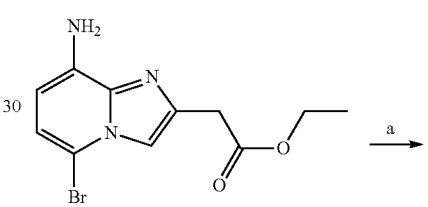

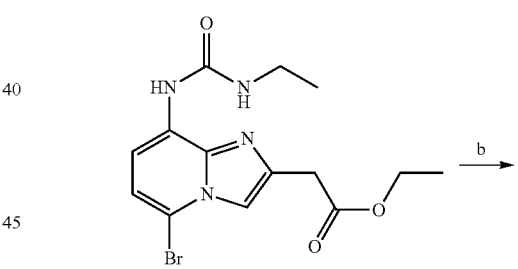

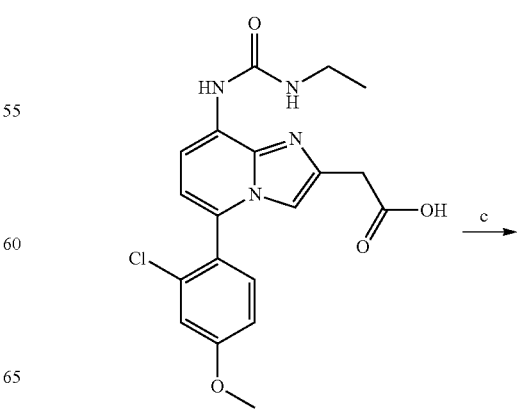

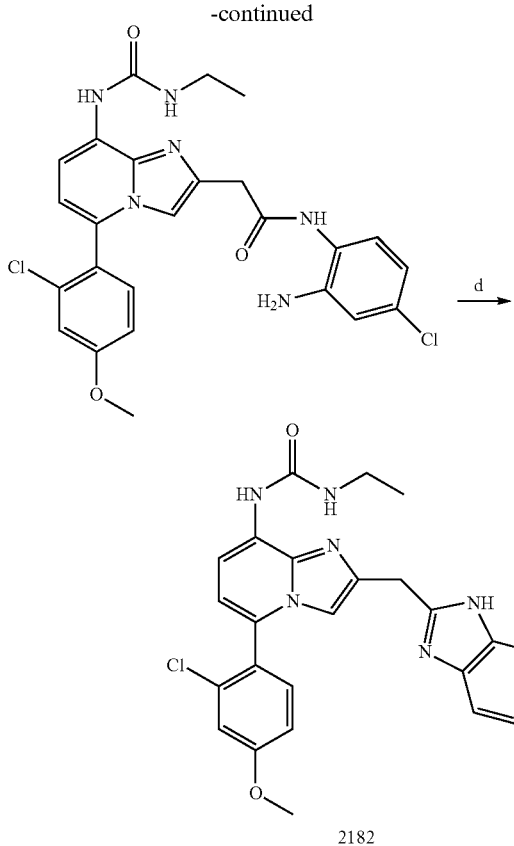

2182

Reagents and conditions (a) phosgene, DIPEA, ethylamine; (b) K₂CO₃, Pd(PPh₃)₄, DME, H₂O, microwave irradition; (c) EDC, 4-chlorobenzene-1,2-diamine, pyridine; (d) HOAc, microwave irradiation To a solution of ethyl 2-(8-amino-5-bromoH-imidazo[1,2-a]pyridin-2-yl)acetate (10.5 mg, 0.035 mmol), DIPEA (24 µl, 0.138 mmol) in 2 ml of DCM at 0° C. was added phosgene in 15 wt. % in toluene (30 µl, 0.042 mmol). The mixture was stirred at 0° C. for 50 min. 2 M ethylamine in THF (70 µl, 0.14 mmol) was added and the mixture was stirred room temperature for 8 h. After the solvent was removed, the residue was dissolved in EtOAc (30 ml) and washed with water and brine. The organic layer was dried over Na₂SO₄ and concentrated in vacuo. The residue was purified by flash chromatography on silica gel to give ethyl 2-(5-bromo-8-(3-ethylureido)H-imidazo[1,2-a]pyridin-2-yl)acetate (11 mg, 0.03 mmol).

Ethyl 2-(5-bromo-8-(3-ethylureido)H-imidazo[1,2-a]pyridin-2-yl)acetate (11 mg, 0.03 mmol), chloro-4-methoxyphenylboronic acid (8.2 mg, 0.045 mmol), potassium carbonate (8.3 mg, 0.06 mmol) and tetrakis(triphenylphosphine)palladium(0) (1.8 mg) in water (0.5 mL) and DME (1.5 mL) was microwave irradiated at 100° C. for 20 min. The solution was acidified with 0.2 N HCl. After most of organic solvent was removed in vacuo, the mixture was extracted with EtOAc and washed successively with water and brine. The organic layer was dried over Na₂SO₄ and concentrated in vacuo. The residue was purified by flash chromatography on silica gel (DCM/MeOH) to obtain 2-(5-(2-chloro-4-methoxyphenyl)-8-(3-ethylureido)H-imidazo[1,2-a]pyridin-2-yl)acetic acid (8.7 mg, 72%).

2-(5-(2-chloro-4-methoxyphenyl)-8-(3-ethylureido)H-imidazo[1,2-a]pyridin-2-yl)acetic acid (8.7 mg, 0.022 mmol) was dissolved in 2 ml of pyridine, then 4-chlorobenzene-1,2-diamine (4.7 mg, 0.033 mmol) and EDC hydrochloride (8.3 mg, 0.044 mmol) were added. The mixture was stirred at room temperature overnight. The solvent was removed on a rotary evaporator. The residue was purified by flash chromatography on silica gel to give 1-(2-((2-amino-4-chlorophenylcarbamoyl)methyl)-5-(2-chloro-4-methoxyphenyl)H-imidazo[1,2-a]pyridin-8-yl)-3-ethylurea (10.5 mg, 0.02 mmol). 1-(2-((2-amino-4-chlorophenylcarbamoyl)methyl)-5-(2-chloro-4-methoxyphenyl)H-imidazo[1,2-a]pyridin-8-yl)-3-ethylurea (10.5 mg, 0.02 mmol) was dissolved in 2 ml of acetic acid and the solution was microwave irradiated at 60° C. for 20 min. After the solvent was removed, the residue was purified by flash column chromatography (DCM/MeOH), yielding 2182 (1-{2-[(6-chloro-1H-1,3-benzodiazol-2-yl)methyl]-5-(2-chloro-4-methoxyphenyl)imidazo[1,2-a]pyridin-8-yl}-3-ethylurea) in 85% yield (8.6 mg). LC/MS: (ESI) (M+H)⁺=510.3.

Example 123

Scheme 38

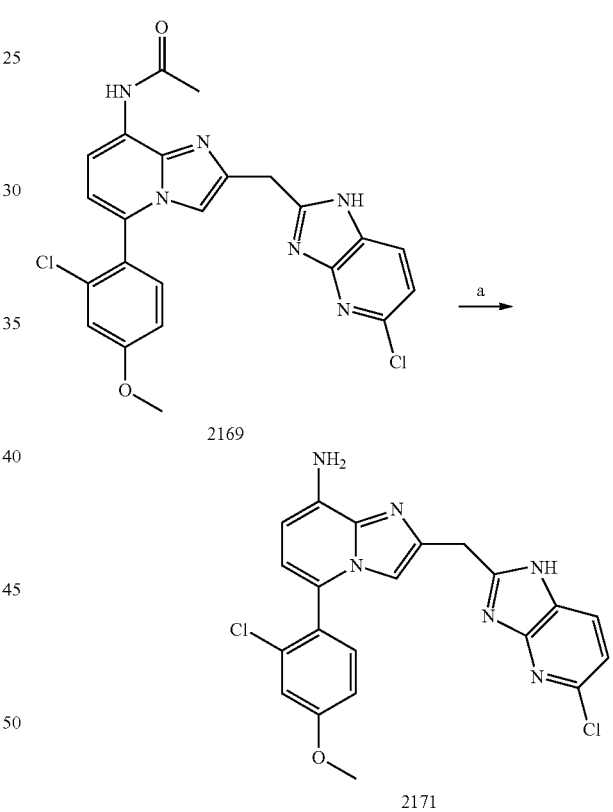

2171

Reagents and conditions (a) 6N HCl, MW 100° C., 15 min

General Procedure 10 (2171, 2179):

2169 (12 mg, 0.025 mmol) in 0.5 ml of 6 N HCl was microwave irradiated at 100° C. for 15 min. The solution was neutralized by solid Na₂CO₃ at 0° C. and extracted with EtOAc (3×10 ml). The combined organic layer was washed with water and brine, dried over Na₂SO₄ and concentrated in vacuo. The residue was purified by flash chromatography on silica gel (DCM/MeOH) to obtain 2171 (2-({5-chloro-1H-imidazo[4,5-b]pyridin-2-yl}methyl)-5-(2-chloro-4-methoxyphenyl)imidazo[1,2-a]pyridin-8-amine) (9.8 mg). LC/MS: (ESI) (M+H)⁺=440.3.

Example 124

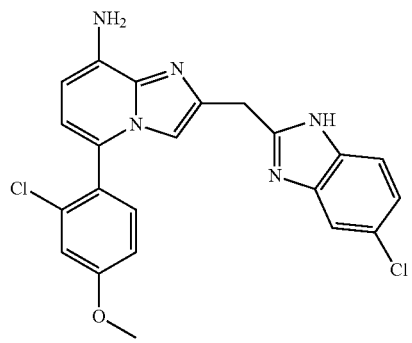

2179 (2-[(6-chloro-1H-1,3-benzodiazol-2-yl)methyl]-5-(2-chloro-4-methoxyphenyl)imidazo[1,2-a]pyridin-8-amine) was synthesized from 2108 following General Procedure 10. LC/MS: (ESI) (M+H)$^+$=439.3.

Example 125

Scheme 39

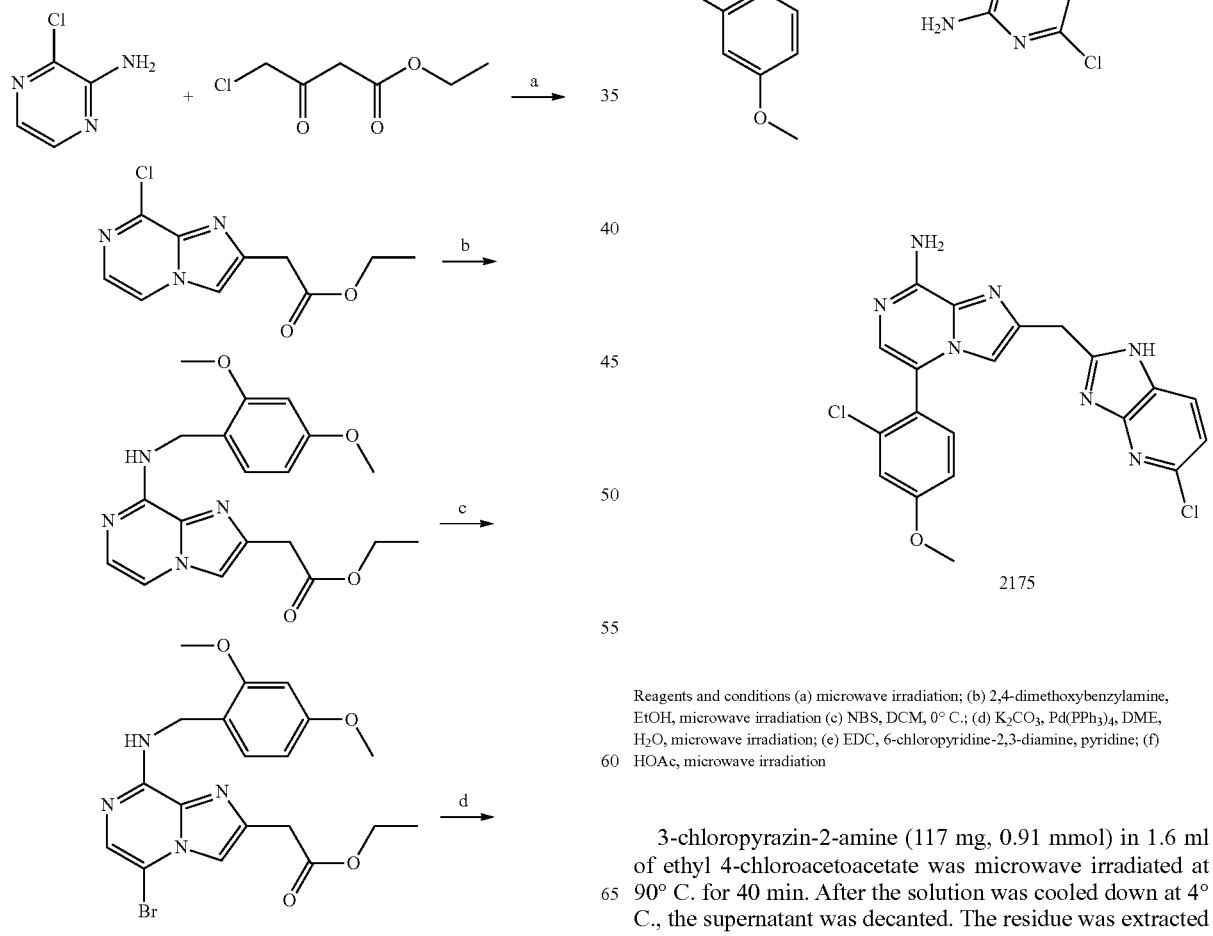

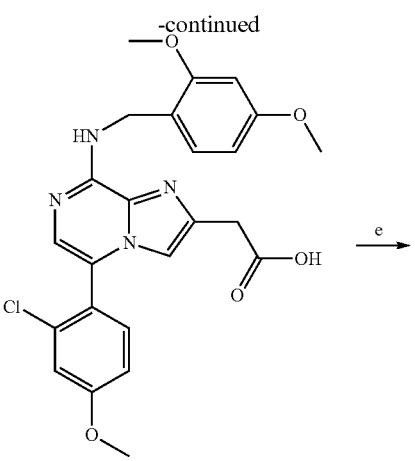

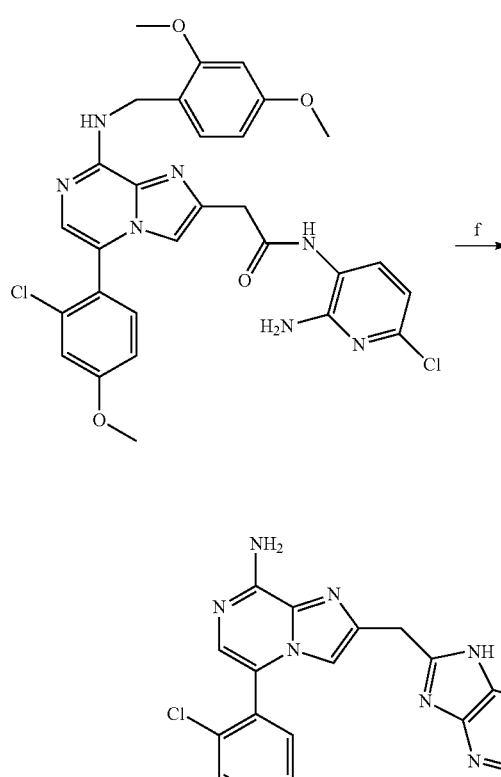

2175

Reagents and conditions (a) microwave irradiation; (b) 2,4-dimethoxybenzylamine, EtOH, microwave irradiation (c) NBS, DCM, 0° C.; (d) K$_2$CO$_3$, Pd(PPh$_3$)$_4$, DME, H$_2$O, microwave irradiation; (e) EDC, 6-chloropyridine-2,3-diamine, pyridine; (f) HOAc, microwave irradiation 3-chloropyrazin-2-amine (117 mg, 0.91 mmol) in 1.6 ml of ethyl 4-chloroacetoacetate was microwave irradiated at 90° C. for 40 min. After the solution was cooled down at 4° C., the supernatant was decanted. The residue was extracted with EtOAc and washed successively with saturated Na₂CO₃ and brine. The organic layer was dried over Na₂SO₄ and concentrated in vacuo. The residue was purified by flash chromatography on silica gel (DCM/MeOH) to obtain ethyl 2-(8-chloroimidazo[1,2-a]pyrazin-2-yl)acetate (62 mg, 0.259 mmol).

A solution of ethyl 2-(8-chloroimidazo[1,2-a]pyrazin-2-yl)acetate (49 mg, 0.205 mmol), DIPEA (213 μl, 1.23 mmol) and 2,4-dimethoxylbenzylamine (342 mg, 2.05 mmol) in 3 ml of ethanol was microwave irradiated at 125° C. for 1 hour. After the solvent was removed on a rotary evaporator, the residue was dissolved in EtOAc (30 ml) and washed with water and brine. The organic layer was dried over Na₂SO₄ and concentrated in vacuo. The residue was purified by flash chromatography on silica gel to give ethyl 2-(8-(2,4-dimethoxybenzylamino)imidazo[1,2-a]pyrazin-2-yl)acetate (70 mg, 0.19 mmol).

To the solution of ethyl 2-(8-(2,4-dimethoxybenzylamino)imidazo[1,2-a]pyrazin-2-yl)acetate (35 mg, 0.095 mmol) in 2 ml of DCM at 0° C. was added NBS (18.6 mg, 0.105 mmol). The mixture was stirred at 0° C. for 15 min. The solution was purified by flash chromatography on silica gel to give ethyl 2-(8-(2,4-dimethoxybenzylamino)-5-bromoimidazo[1,2-a]pyrazin-2-yl)acetate (38.2 mg, 0.085 mmol).

Ethyl 2-(8-(2,4-dimethoxybenzylamino)-5-bromoimidazo[1,2-a]pyrazin-2-yl)acetate (21.6 mg, 0.048 mmol), potassium carbonate (8.9 mg, 0.064 mmol) and tetrakis(triphenylphosphine)palladium(0) (1.9 mg) in water (0.5 mL) and DME (1.5 mL) was microwave irradiated at 100° C. for 20 min. The solution was acidified with 0.2 N HCl. After most of organic solvent was removed in vacuo, the mixture was extracted with EtOAc and washed successively with water and brine. The organic layer was dried over Na₂SO₄ and concentrated in vacuo. The residue was purified by flash chromatography on silica gel (DCM/MeOH) to obtain 2-(8-(2,4-dimethoxybenzylamino)-5-(2-chloro-4-methoxyphenyl)imidazo[1,2-a]pyrazin-2-yl)acetic acid (18.5 mg, 80%).

2-(8-(2,4-dimethoxybenzylamino)-5-(2-chloro-4-methoxyphenyl)imidazo[1,2-a]pyrazin-2-yl)acetic acid (18.5 mg, 0.0384 mmol) was dissolved in 2 ml of pyridine, then 6-chloropyridine-2,3-diamine (8.3 mg, 0.0575 mmol) and EDC hydrochloride (14.4 mg, 0.077 mmol) were added. The mixture was stirred at room temperature overnight. The solvent was removed on a rotary evaporator. The residue was purified by flash chromatography on silica gel to give 2-(8-(2,4-dimethoxybenzylamino)-5-(2-chloro-4-methoxyphenyl)imidazo[1,2-a]pyrazin-2-yl)—N-(2-amino-6-chloropyridin-3-yl)acetamide (17.6 mg, 0.029 mmol). 2-(8-(2,4-dimethoxybenzylamino)-5-(2-chloro-4-methoxyphenyl)imidazo[1,2-a]pyrazin-2-yl)—N-(2-amino-6-chloropyridin-3-yl)acetamide (17.6 mg, 0.029 mmol) was dissolved in 2 ml of acetic acid and the solution was microwave irradiated at 125° C. for 1 hour. After the solvent was removed, the residue was purified by flash column chromatography (DCM/MeOH), yielding 2175 (2-({5-chloro-1H-imidazo[4,5-b]pyridin-2-yl}methyl)-5-(2-chloro-4-methoxyphenyl)imidazo[1,2-a]pyrazin-8-amine) in 75% yield (9.6 mg). ¹H NMR (MeOD) δ 7.81 (d, J=8.3 Hz, 1H), 7.37 (d, J=8.5 Hz, 1H), 7.27 (s, 1H), 7.19 (d, J=8.4 Hz, 1H), 7.13 (d, J=2.5 Hz, 1H), 7.07 (s, 1H), 6.96-7.94 (m, 1H), 4.37(s, 2H), 3.81 (s, 3H). LC/MS: (ESI) (M+H)⁺=441.2.

Example 126

Scheme 40

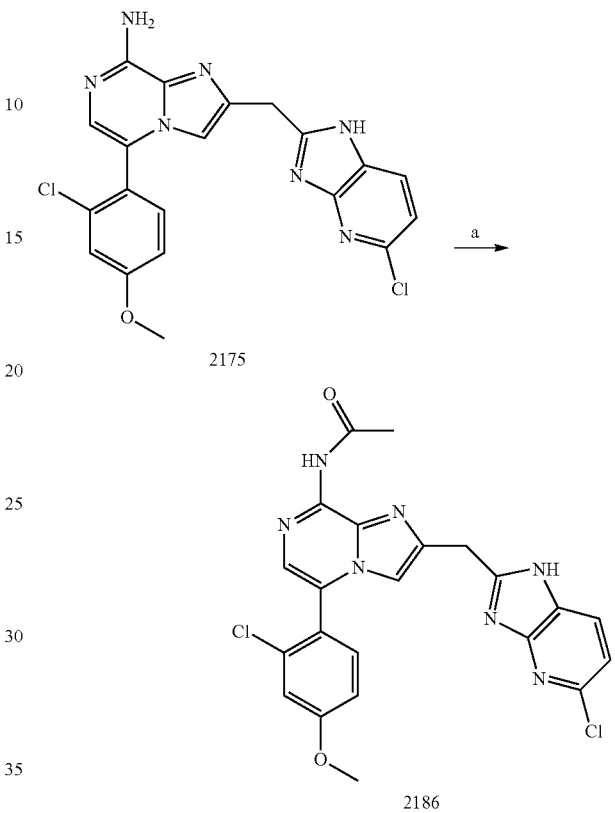

2175

2186

Reagents and conditions (a) HOAc, microwave irradiation 3-chloropyrazin-2-amine (7 mg, 0.016 mmol) (2175) in 1 ml of acetic acid was microwave irradiated at 150° C. for 5 h. After the solution was removed in vacuo, the residue was extracted with EtOAc and washed successively with saturated Na₂CO₃, brine. The organic layer was dried over Na₂SO₄ and concentrated in vacuo. The residue was purified by flash chromatography on silica gel (DCM/MeOH) to obtain 2186 (N-[2-({5-chloro-1H-imidazo[4,5-b]pyridin-2-yl}methyl)-5-(2-chloro-4-methoxyphenyl)imidazo[1,2-a]pyrazin-8-yl]acetamide) (2.3 mg, 0.0048 mmol). LC/MS: (ESI) (M+H)⁺=483.4.

Example 127

Scheme 41

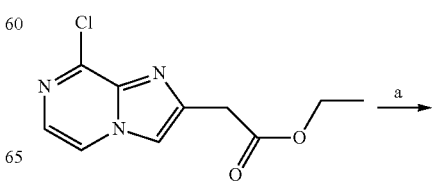

117
-continued

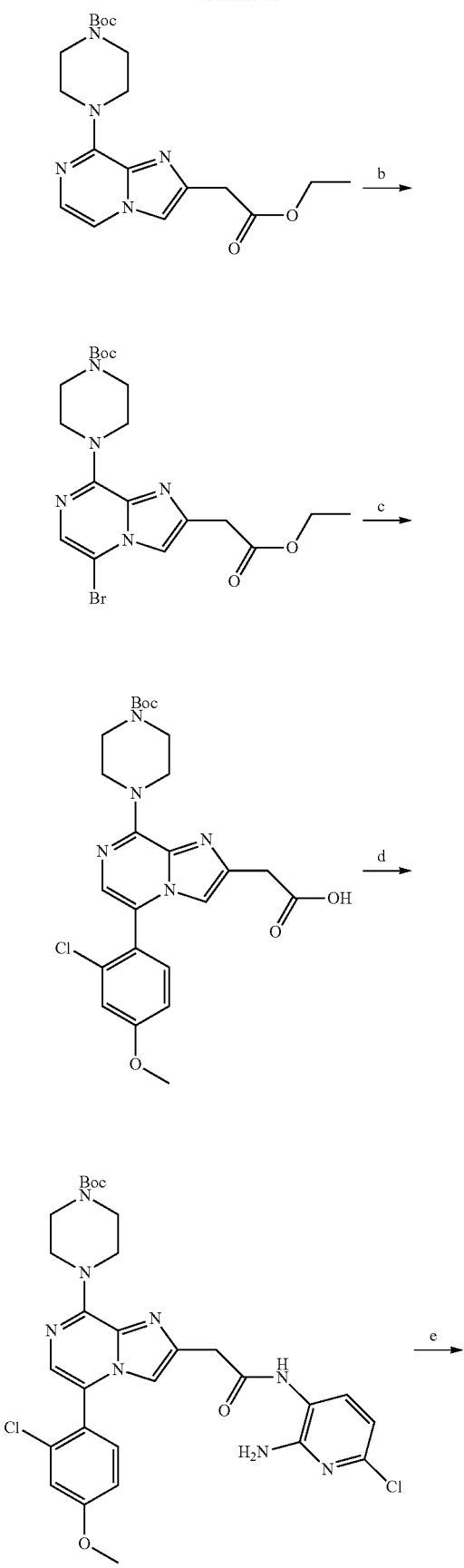

118
-continued

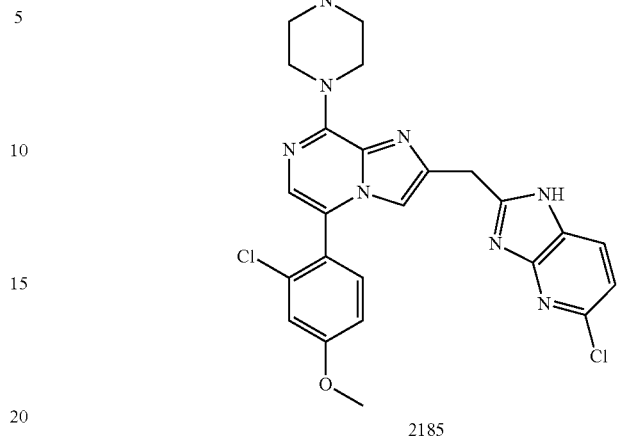

2185

Reagents and conditions (a) tert-butyl piperazine-1-carboxylate, ethanol, microwave irradiation; (b) 2, 4-dimethoxybenzylamine, EtOH, microwave irradiation (c) NBS, DCM, 0° C.; (d) K₂CO₃, Pd(PPh₃)₄, DME, H₂O, microwave irradiation; (c) EDC, 6-chloropyridine-2, 3-diamine, pyridine; (d) HOAc, microwave irradiation A solution of ethyl 2-(8-chloroimidazo[1,2-a]pyrazin-2-yl)acetate (24 mg, 0.10 mmol), DIPEA (104 µl, 0.60 mmol) and tert-butyl piperazine-1-carboxylate (186 mg, 1.0 mmol) in 2 ml of ethanol was microwave irradiated at 125° C. for 1 hour. After the solvent was removed on a rotary evaporator, the residue was dissolved in EtOAc (30 ml) and washed with water and brine. The organic layer was dried over Na₂SO₄ and concentrated in vacuo. The residue was purified by flash chromatography on silica gel to give tert-butyl 4-(2-((ethoxycarbonyl)methyl)imidazo[1,2-a]pyrazin-8-yl)piperazine-1-carboxylate (35 mg, 0.09 mmol).

To the solution of tert-butyl 4-(2-((ethoxycarbonyl)methyl)imidazo[1,2-a]pyrazin-8-yl)piperazine-1-carboxylate (35 mg, 0.09 mmol) in 2 ml of DCM at 0° C. was added NBS (17.6 mg, 0.099 mmol). The mixture was stirred at 0° C. for 15 min. The solution was purified by flash chromatography on silica gel to give tert-butyl 4-(2-((ethoxycarbonyl)methyl)-5-bromoimidazo[1,2-a]pyrazin-8-yl)piperazine-1-carboxylate (37.5 mg, 0.08 mmol).

tert-butyl 4-(2-((ethoxycarbonyl)methyl)-5-bromoimidazo[1,2-a]pyrazin-8-yl)piperazine-1-carboxylate (22.5 mg, 0.048 mmol), K₂CO₃ (8.9 mg, 0.064 mmol) and tetrakis(triphenylphosphine)palladium(0) (1.9 mg) in water (0.5 mL) and DME (1.5 mL) was microwave irradiated at 100° C. for 20 min. After most of organic solvent was removed in vacuo, the mixture was extracted with EtOAc and washed successively with water and brine. The organic layer was dried over Na₂SO₄ and concentrated in vacuo. The residue was purified by flash chromatography on silica gel (DCM/MeOH) to obtain 2-(8-(4-(tert-butoxycarbonyl)-piperazin-1-yl)-5-(2-chloro-4-methoxyphenyl)imidazo[1,2-a]pyrazin-2-yl)acetic acid (19.7 mg, 82%).

2-(8-(4-(tert-butoxycarbonyl)piperazin-1-yl)-5-(2-chloro-4-methoxyphenyl)imidazo[1,2-a]pyrazin-2-yl)acetic acid (19.7 mg, 0.039 mmol) was dissolved in 2 ml of pyridine, then 6-chloropyridine-2,3-diamine (8.4 mg, 0.0585 mmol) and EDC hydrochloride (14.6 mg, 0.078 mmol) were added. The mixture was stirred at room temperature overnight. The solvent was removed. The residue was purified by flash chromatography on silica gel to give tert-butyl 4-(2-((2-amino-6-chloropyridin-3-ylcarbamoyl)methyl)-5-(2-chloro- 4-methoxyphenyl)imidazo[1,2-a]pyrazin-8-yl)piperazine-1-carboxylate (18.8 mg, 0.03 mmol). tert-butyl 4-(2-((2-amino-6-chloropyridin-3-ylcarbamoyl)methyl)-5-(2-chloro-4-methoxyphenyl)imidazo[1,2-a]pyrazin-8-yl)piperazine-1-carboxylate (18.8 mg, 0.03 mmol) was dissolved in 2 ml of acetic acid and the solution was microwave irradiated at 125° C. for 1 hour. After the solvent was removed on the rotary evaporator, the residue was purified by flash column chromatography (DCM/MeOH), yielding 2185 (1-{4-[2-({5-chloro-1H-imidazo[4,5-b]pyridin-2-yl}methyl)-5-(2-chloro-4-methoxyphenyl)imidazo[1,2-a]pyrazin-8-yl]piperazin-1-yl}ethan-1-one) in 80% yield (13.2 mg). LC/MS: (ESI) $(M+H)^+=552.4$.

Example 128

To a solution of 5-(2-chloro-4,5-dimethoxyphenyl)H-imidazo[1,2-a]pyridin-2-amine (25 mg, 0.083 mmol) in 1 ml of pyridine was added 2-bromo-5-fluoro-1H-imidazo[4,5-b]pyridine (7 mg). The mixture was microwave irradiated at 100° C. for 30 min. The solvent was removed, and the residue dissolved in EtOAc (30 ml) and washed with water and brine. The organic layer was dried over $Na_2SO_4$ and concentrated in vacuo. The residue was purified by flash chromatography on silica gel to give 2267 (5-(2-chloro-4,5-dimethoxyphenyl)—N-{5-fluoro-1H-imidazo[4,5-b]pyridin-2-yl}imidazo[1,2-a]pyridin-2-amine) (2.8 mg). LC/MS: (ESI) $(M+H)^+=439.7$.

Example 129

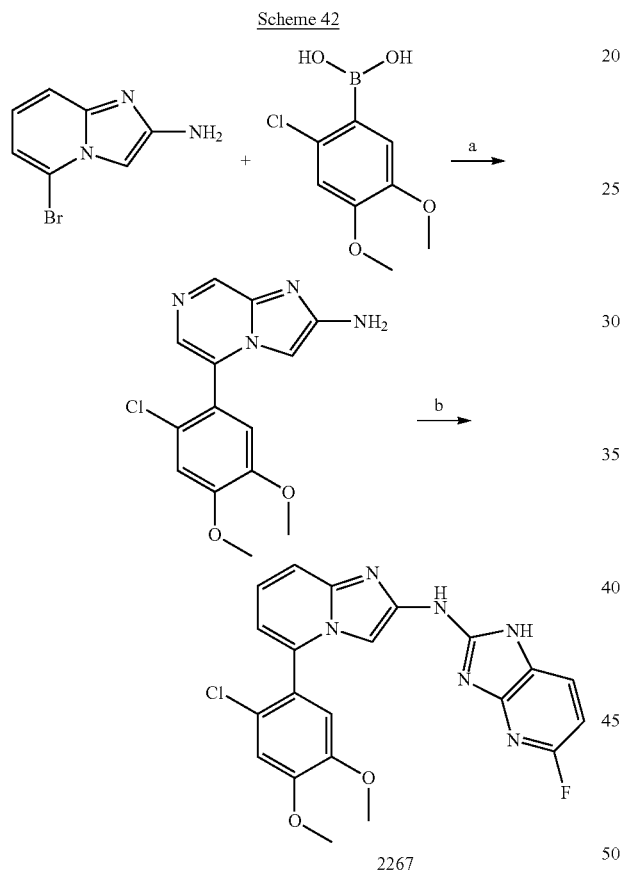

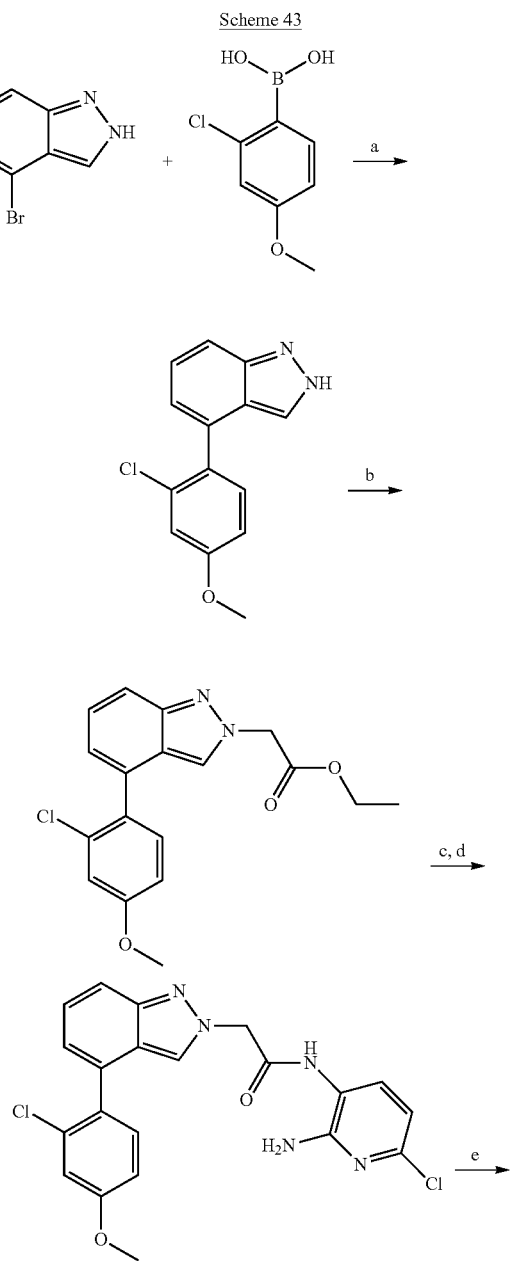

A mixture of 5-bromoH-imidazo[1,2-a]pyridin-2-amine (49.2 mg, 0.232 mmol) 2-chloro-4-methoxyphenylboronic acid (103 mg, 0.464 mmol), potassium carbonate (80 mg, 0.58 mmol) and tetrakis(triphenylphosphine)palladium(0) (13.4 mg) in water (0.25 mL) and DME (1 mL) was microwave irradiated at 100° C. for 30 min. After organic solvent was removed in vacuo, the residue was extracted with EtOAc and washed successively with water and brine. The organic layer was dried over $Na_2SO_4$ and concentrated in vacuo. The residue was purified by flash chromatography on silica gel (MeOH/DCM) to obtain 5-(2-chloro-4,5-dimethoxyphenyl)H-imidazo[1,2-a]pyridin-2-amine (51 mg, 72%).

-continued

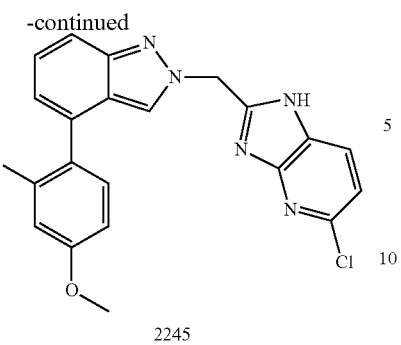

2245

Reagents and conditions (a) K₂CO₃, Pd(PPh₃)₄, DME, H₂O, microwave irradiation; (b) ethyl 2-bromoacetate, K₂CO₃, microwave irradiation; (c) LiOH, EtOH/H₂O; (d) EDC, 6-chloropyridine-2,3-diamine, pyridine; (d) HOAc, microwave irradiation A mixture of 4-brom$_{0-2}$H-indazole (125.2 mg, 0.64 mmol) 2-chloro-4-methoxyphenylboronic acid (177 mg, 0.96 mmol), potassium carbonate (263 mg, 1.92 mmol) and tetrakis(triphenylphosphine)palladium(0) (37 mg) in water (0.5 mL) and DME (1.5 mL) was microwave irradiated at 100° C. for 30 min. After organic solvent was removed in vacuo, the residue was extracted with EtOAc and washed successively with water and brine. The organic layer was dried over Na₂SO₄ and concentrated in vacuo. The residue was purified by flash chromatography on silica gel (MeOH/DCM) to obtain 4-(2-chloro-4-methoxyphenyl)-2H-indazole (167 mg).

To a solution of 4-(2-chloro-4-methoxyphenyl)-2H-indazole (93.3 mg, 0.36 mmol) in 2 ml of DMF was added potassium carbonate (198 mg, 1.44 mmol) and ethyl 2-bromoacetate (48 μl, 0.43 mmol). The mixture was microwave irradiated at 80° C. for 30 min. The solvent was removed on a rotary evaporator. The residue was dissolved in EtOAc (30 ml) and washed with water and brine. The organic layer was dried over Na₂SO₄ and concentrated in vacuo. The residue was purified by flash chromatography on silica gel to give ethyl 2-(4-(2-chloro-4-methoxyphenyl)-2H-indazol-2-yl)acetate (28 mg).

Ethyl 2-(4-(2-chloro-4-methoxyphenyl)-2H-indazol-2-yl) acetate (22.1 mg, 0.064 mmol) was added in 1 ml of ethanol and 2 ml of water, mixed with LiOH (6.1 mg, 0.26 mml) and stirred for 50 min at room temperature. The solution was acidified with 0.2 N hydrochloric acid and the solvent was completely removed in vacuo. The residue was dissolved in 1 ml of pyridine, then 6-chloropyridine-2,3-diamine (0.1 mmol) and EDC hydrochloride (24.6 mg, 0.13 mmol) were added. The mixture was stirred at room temperature overnight. The solvent was removed on the rotary evaporator. The residue was dissolved in EtOAc (30 ml) and washed with water and brine. The organic layer was dried over Na₂SO₄ and concentrated in vacuo. The residue was dissolved in 1 ml of acetic acid and the solution was microwave irradiated at 125° C. for 1 hour. After the solvent was removed on the rotary evaporator, the residue was purified by flash column chromatography (DCM/MeOH), giving 8.2 mg of 2245 (2-({5-chloro-1H-imidazo[4,5-b]pyridin-2-yl}methyl)-4-(2-chloro-4-methoxyphenyl)-2H-indazole). LC/MS: (ESI) (M+H)⁺=425.4.

Example 130

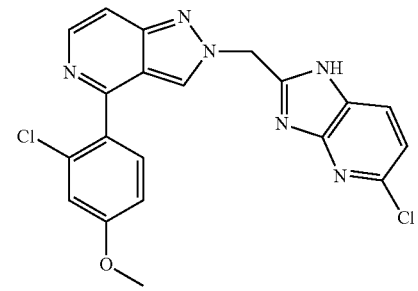

2247

2247 (2-({5-chloro-1H-imidazo[4,5-b]pyridin-2-yl}methyl)-4-(2-chloro-4-methoxyphenyl)-2H-pyrazolo[4,3-c]pyridine) was synthesized via the same procedure as 2245 by using 4-brom$_{0-2}$H-pyrazolo[4,3-c]pyridine. LC/MS: (ESI) (M+H)⁺=426.4.

Example 131

Scheme 44

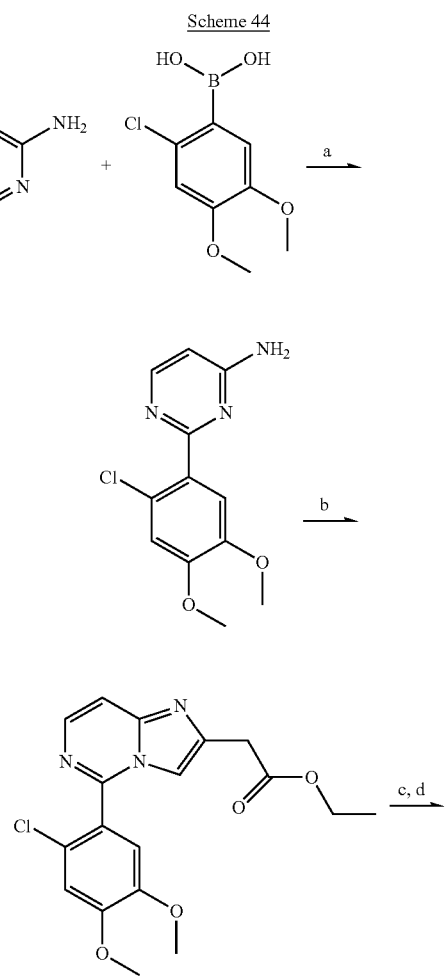

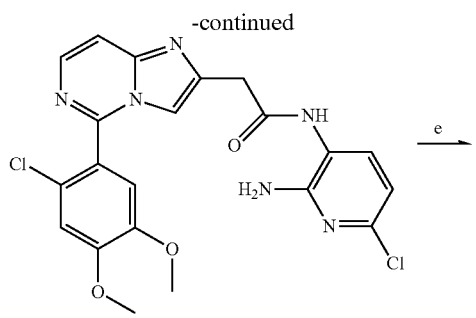

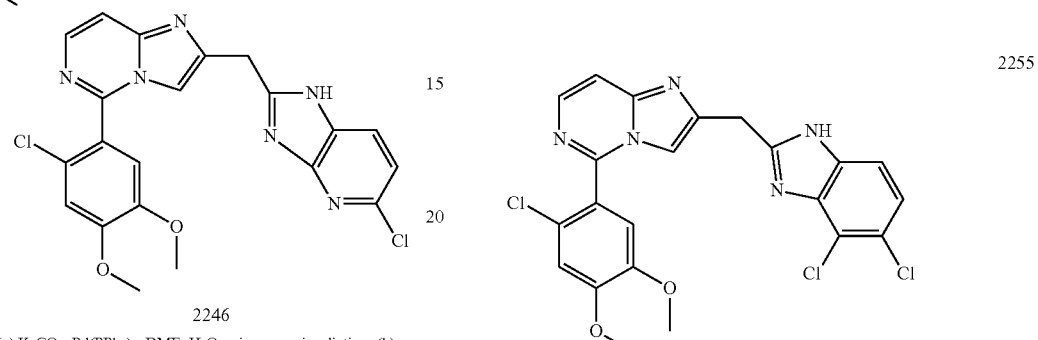

2246

Reagents and conditions (a) K$_2$CO$_3$, Pd(PPh$_3$)$_4$, DME, H$_2$O, microwave irradiation; (b) 4-chloro-3-oxo-butyric acid ethyl ester, microwave irradiation; (c) LiOH, EtOH/H$_2$O; (d) EDC, 6-chloropyridine-2, 3-diamine, pyridine; (d) HOAc, microwave irradiation General Procedure 11 (2246, 2255, 2256):

A mixture of 2-chloro-pyrimidin-4-ylamine (123 mg, 0.95 mmol), 2-chloro-4,5-dimethoxyphenylboronic acid (307 mg, 1.42 mmol), potassium carbonate (260 mg, 1.90 mmol) and tetrakis(triphenylphosphine)palladium(0) (55 mg) in water (1 mL) and DME (3 mL) was microwave irradiated at 110° C. for 1 hour. After organic solvent was removed in vacuo, the residue was extracted with EtOAc and washed successively with water and brine. The organic layer was dried over Na$_2$SO$_4$ and concentrated in vacuo. The residue was purified by flash chromatography on silica gel (MeOH/DCM) to obtain 2-(2-chloro-4,5-dimethoxy-phenyl)-pyrimidin-4-ylamine (113 mg).

2-(2-Chloro-4,5-dimethoxy-phenyl)-pyrimidin-4-ylamine (72 mg, 0.27 mmol) in 4 ml of 4-chloro-3-oxo-butyric acid ethyl ester was microwave irradiated at 110° C. for 2 hours. After the mixture was cooled to 0° C., 4 ml of pyridine was added. The mixture was stirred at room temperature for 2 hours and 400 ml of EtOAc was added. The solution was washed with 50 ml of water three times and brine. The organic layer was dried over Na$_2$SO$_4$ and concentrated in vacuo. The residue was purified by flash chromatography on silica gel to give [5-(2-chloro-4,5-dimethoxy-phenyl)-imidazo[1,2-c]pyrimidin-2-yl]-acetic acid ethyl ester (18 mg).

[5-(2-Chloro-4,5-dimethoxy-phenyl)-imidazo[1,2-c]pyrimidin-2-yl]-acetic acid ethyl ester (18 mg, 0.048 mmol) was added in 1 ml of ethanol and 2 ml of water, mixed with LiOH (4.6 mg, 0.19 mml) and stirred for 50 min at room temperature. The solution was acidified with 0.2 N hydrochloric acid and the solvent was completely removed in vacuo. The residue was dissolved in 1 ml of pyridine, then 6-chloropyridine-2,3-diamine (10.4 mg, 0.072 mmol) and EDC hydrochloride (18.5 mg, 0.096 mmol) were added. The mixture was stirred at room temperature overnight. The solvent was removed on the rotary evaporator. The residue was dissolved in EtOAc (30 ml) and washed with water and brine. The organic layer was dried over Na$_2$SO$_4$ and concentrated in vacuo. The residue was dissolved in 1 ml of acetic acid and the solution was microwave irradiated at 125° C. for 1 hour. After the solvent was removed on the rotary evaporator, the residue was purified by flash column chromatography (DCM/MeOH), giving 8.2 mg of 2246 (2-({5-chloro-1H-imidazo[4,5-b]pyridin-2-yl}methyl)-5-(2-chloro-4,5-dimethoxyphenyl)imidazo[1,2-c]pyrimidine). LC/MS: (ESI) (M+H)$^+$=456.4.

Example 132

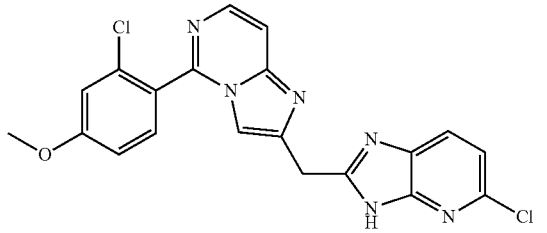

2255

2255 (6,7-dichloro-2-{[5-(2-chloro-4,5-dimethoxyphenyl)imidazo[1,2-c]pyrimidin-2-yl]methyl}-1H-1,3-benzodiazole) was synthesized using 3,4-dichloro-benzene-1,2-diamine following General Procedure 11. LC/MS: (ESI) (M+H)$^+$=489.6

Example 133

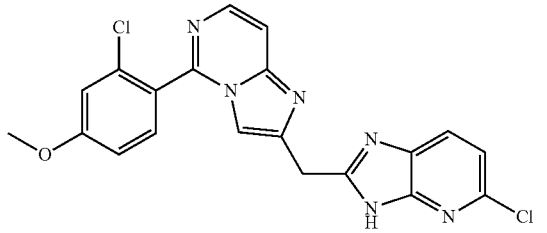

2256

2256 (2-({5-chloro-1H-imidazo[4,5-b]pyridin-2-yl}methyl)-5-(2-chloro-4-methoxyphenyl)imidazo[1,2-c]pyrimidine) was synthesized using 2-chloro-4-methoxyphenylboronic acid following General Procedure 11. LC/MS: (ESI) (M+H)$^+$=426.4

Example 134

Scheme 45

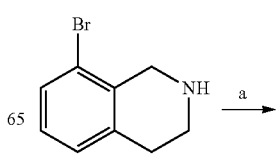

-continued

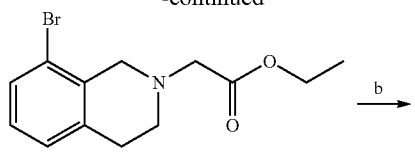

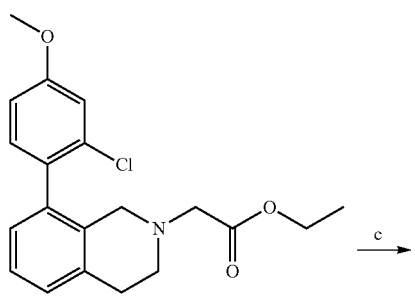

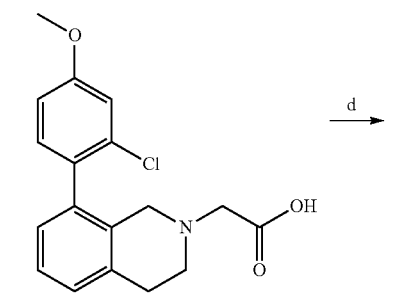

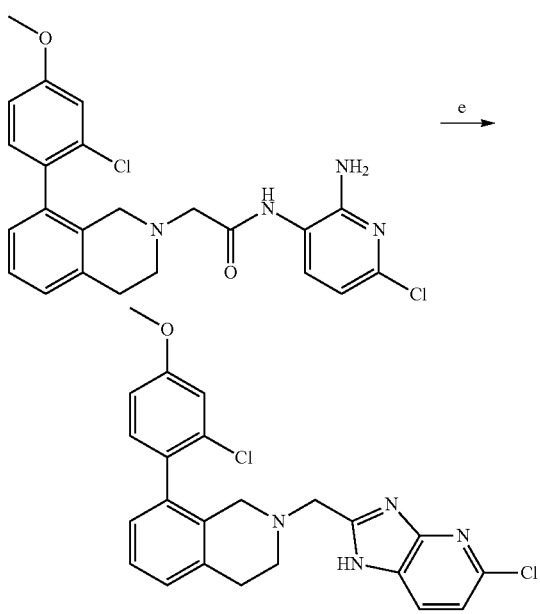

2161

Reagents and conditions: (a) ethyl 2-bromoacetate, K₂CO₃, acetonitrile, r.t., overnight; (b) (2-chloro-4-methoxyphenyl) boronic acid, Pd(PPh₃)₄, K₂CO₃, Dioxane/H₂O, MW, 120° C., 30 min; (c) LiOH, CH₃OH/H₂O, r.t., over night; (d) 6-chloropyridine-2, 3-diamine, EDC, Pyridine, r.t., over night; (f) AcOH, MW, 140° C., 60 min.

General Procedure 12:

(a) 8-bromo-1,2,3,4-tetrahydroisoquinoline (64 mg, 0.3 mmol) was dissolved in acetonitrile, K₂CO₃ (166 mg, 1.2 mmol) and ethyl 2-bromoacetate (40 µL, 0.36 mmol) were added. The mixture was stirred at r.t. over night. The solvent was evaporated off, and the residue was extracted with ethyl acetate. The organic layer was dried over anhydrous sodium sulfate, filtered and concentrated in vacuum. Purification through flash chromatography on silica gel eluted with 30% ethyl acetate in hexane gave intermediate ethyl 2-(8-(2-chloro-4-methoxyphenyl)-3,4-dihydroisoquinolin-2(1H)-yl) acetate 73 mg as a brown oil, yield: 86.8%. LC/MS: (ESI) $[M+H]^+=299.2$ (b) A mixture of ethyl 2-(8-(2-chloro-4-methoxyphenyl)-3,4-dihydroisoquinolin-2(1H)-yl)acetate (28.4 mg, 0.1 mmol), 2-chloro-4-methoxyphenylboronic acid (28 mg, 0.15 mmol), potassium carbonate (41 mg, 0.3 mmol) and tetrakis(triphenylphosphine)palladium(0) (17 mg, 0.015 mmol) in water (0.5 mL) and DME (2 mL) was microwave irradiated at 120° C. for 30 min. The organic solvent was removed in vacuo, and the residue was extracted with EtOAc and washed successively with water and brine. The organic layer was dried over Na₂SO₄, filtered and concentrated in vacuo. The residue was used for the next step without purification. LC/MS: (ESI) $[M+H]^+=360.8$ (c) Ethyl 2-(8-(2-chloro-4-methoxyphenyl)-3,4-dihydroisoquinolin-2(1H)-yl)acetate obtained from above was dissolved in MeOH/H₂O (4:1), LiOH (7.2 mg, 0.3 mM) was added and the mixture was stirred at r.t. 2 h. The solution was acidified with 0.2 N hydrochloric acid and completely dried in vacuo. The residue was purified through flash chromatography on silica gel eluted with 20% MeOH in DCM to gave intermediate 2-(8-(2-chloro-4-methoxyphenyl)-3,4-dihydroisoquinolin-2(1H)-yl)acetic acid 130 mg as gray solid, yield: 39.2% over two steps. LC/MS: (ESI) $[M+H]^+=333.0$ (d) A mixture of 2-(8-(2-chloro-4-methoxyphenyl)-3,4-dihydroisoquinolin-2(1H)-yl)acetic acid (33 mg, 0.1 mmol), and 6-chloropyridine-2,3-diamine (14.2 mg, 0.11 mmol) in pyridine was added EDC hydrochloride (23 mg, 0.12 mmol). The mixture was stirred at room temperature overnight. The solvent was removed and the residue was dissolved in EtOAc (30 ml) and washed with water and brine. The organic layer was dried over Na₂SO₄ and concentrated in vacuo. The residue was purified by flash chromatography on silica gel eluted with DCM to give N-(2-amino-6-chloropyridin-3-yl)-2-(8-(2-chloro-4-methoxyphenyl)-3,4-dihydroisoquinolin-2(1H)-yl)acetamide 14 mg, yield: 21.9%. LC/MS: (ESI) $(M+H)^+=458.4$ (e) N-(2-amino-6-chloropyridin-3-yl)-2-(8-(2-chloro-4-methoxyphenyl)-3,4-dihydroisoquinolin-2(1H)-yl)acetamide (14 mg) was dissolved in 2 ml of acetic acid and the solution was microwave irradiated at 140° C. for 1 h. After the solvent was removed on a rotary evaporator, the residue was dissolved in DCM and washed with water and brine. The organic layer was dried over Na₂SO₄ and concentrated in vacuo. Purification by flash column chromatography on silica gel eluted with 4% MeOH in DCM gave 2161 (2-({5-chloro-1H-imidazo[4,5-b]pyridin-2-yl}methyl)-8-(2-chloro-4-methoxyphenyl)-1,2,3,4-tetrahydroisoquinoline) 6.0 mg, yield: 62.4%. LC/MS: (ESI) $(M+H)^+=440.3$.

Example 135

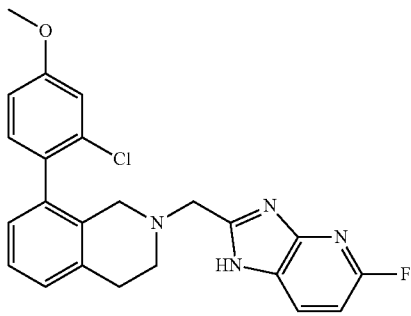

2167: 8-(2-chloro-4-methoxyphenyl)-2-((5-fluoro-1H-imidazo[4,5-b]pyridin-2-yl)methyl)-1,2,3,4-tetrahydroisoquinoline was synthesized using 6-fluoropyridine-2,3-diamine following General Procedure 11. $^1$H NMR (MeOD) δ 8.19 (t, J=7.2 Hz, 1H), 7.45 (t, J=7.3 Hz, 1H), 7.39 (d, J=7.5 Hz, 1H), 7.17 (dd, J=16.1, 7.8 Hz, 2H), 7.07 (d, J=10.3 Hz, 2H), 6.96 (d, J=8.3 Hz, 1H), 4.78 (s, 2H), 4.34 (s, 2H), 3.86 (s, 3H), 3.42-3.36 (m, 4H). LC/MS: (ESI) (M+H)$^+$=423.8.

Example 136

Scheme 46

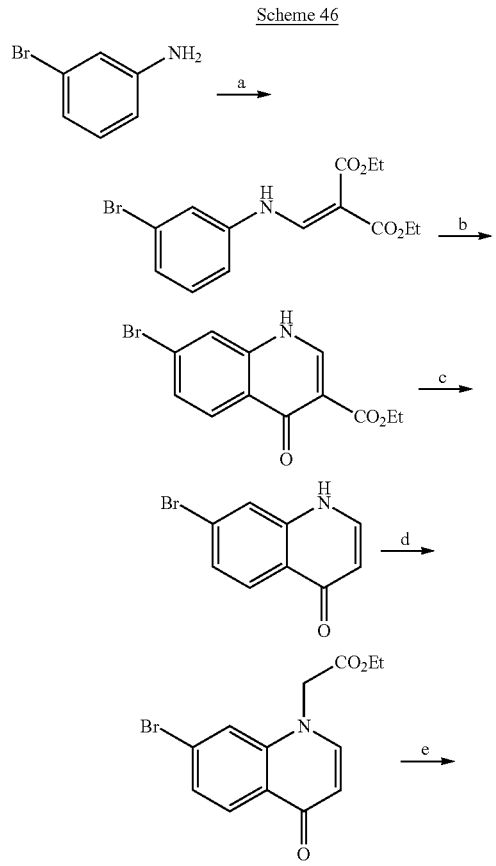

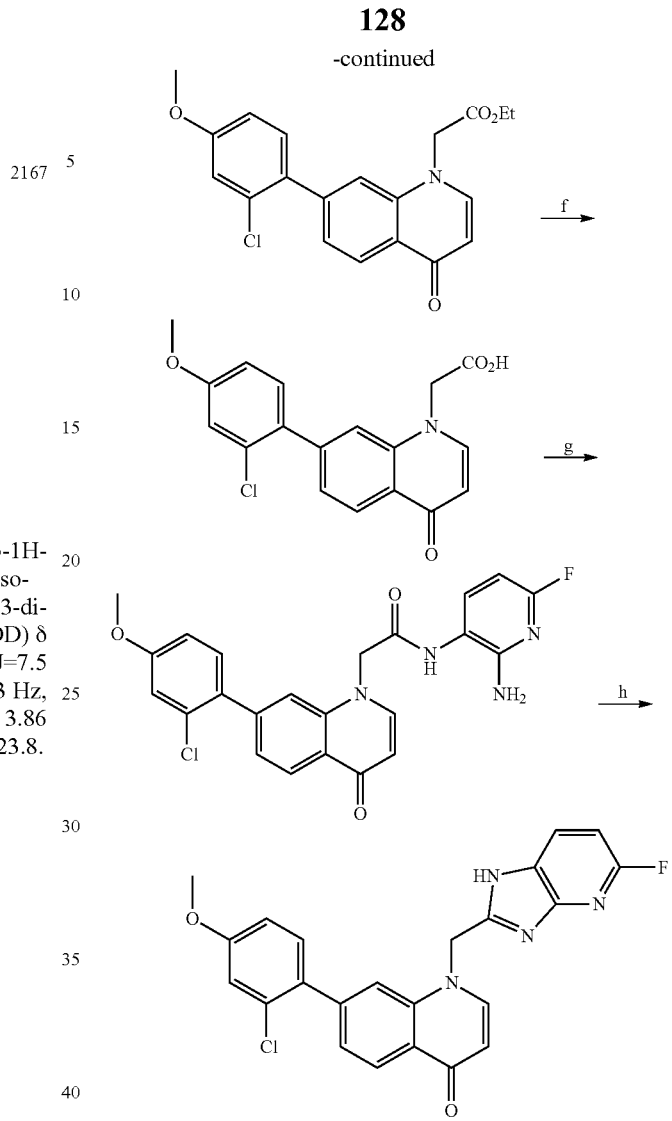

Reagents and conditions; (d) ethyl 2-bromoacetate, K$_2$CO$_3$, Acetonitrile, 60° C.,3 h; (e) (2-chloro-4-methoxyphenyl)boronic acid, Pd(PPh$_3$)$_4$, K$_2$CO$_3$, DMF/H$_2$O, 80° C., 60 min; (f) LiOH, CH$_3$OH/H$_2$O, r.t., over night; (g) 6-fluoropyridine-2,3-diamine, EDC, Pyridine, r.t., over night; (h) AcOH, MW, 140° C., 30 min.

Procedure 13:

(a,b,c) The synthesis of intermediate 7-bromoquinolin-4(1H)-one was following procedures reported (Devine, W., et.al. Journal of Medicinal Chemistry 58, (14), 5522).

(d) Intermediate 7-bromoquinolin-4(1H)-one (225 mg, 1 mmol) was dissolved in ACN, K$_2$CO$_3$ (414 mg, 3 mmol) and ethyl 2-bromoacetate (275 uL, 2.5 mmol) were added. The mixture was heated at 60° C. for 3 h. The solvent was evaporated off, and the residue was extracted with DCM. The organic layer was dried over anhydrous sodium sulfate, filtered and concentrated in vacuum. Purification through flash chromatography on silica gel eluted with 5% MeOH in DCM (0.5% ammonia hydroxide) gave intermediate ethyl 2-(7-bromo-4-oxoquinolin-1(4H)-yl) acetate 220 mg as gray solid, yield: 71.0%. LC/MS: (ESI) [M+H]$^+$=311.6

(e, f) Intermediate ethyl 2-(7-bromo-4-oxoquinolin-1(4H)-yl)acetate (80 mg, 0.26 mmol), (2-chloro-4-methoxyphenyl)boronic acid (75 mg, 0.4 mmol) were dissolved in a mixture of DMF:H$_2$O=4:1. Catalyst Pd(PPh$_3$)$_4$ (25 mg), ligand DavePhose (25 mg) and base K$_2$CO$_3$ (80 mg, 0.58 mmol) were added. The mixture was heated at 80° C. for 1 h under N$_2$. The solvent was removed under reduced pressure, the residue was acidified by 1 N HCl and extracted with DCM. The organic layer was dried over sodium sulfate, concentrated in vacuum, and the residue was purified through flash chromatography on silica gel eluted with 80% MeOH in DCM to give 35 mg of compound 2-(7-(2-chloro-4-methoxyphenyl)-4-oxoquinolin-1(4H)-yl)acetic acid as a yellow solid, yield: 36.5% over two steps. LC/MS: (ESI) [M+H]$^+$=344.8

(g) To a solution of intermediate 2-(7-(2-chloro-4-methoxyphenyl)-4-oxoquinolin-1(4H)-yl)acetic acid (34.5 mg, 0.1 mmol) and 6-fluoropyridine-2,3-diamine (12.7 mg, 0.1 mmol) in pyridine (2 mL) was added EDC (23 mg, 0.12 mmol). The mixture was stirred at r.t. overnight, and pyridine was then removed under reduced pressure. After addition of saturated aqueous sodium bicarbonate to the residue, the mixture was extracted with DCM. The organic layer was dried over anhydrous sodium sulfate, and concentrated in vacuum. Purification through flash chromatography on silica gel eluted with 8% MeOH in DCM (0.5% ammonia hydroxide) gave intermediate N-(2-amino-6-fluoropyridin-3-yl)-2-(7-(2-chloro-4-methoxyphenyl)-4-oxoquinolin-1(4H)-yl)acetamide 18 mg as brown solid, yield: 39.7%.

(h) N-(2-amino-6-fluoropyridin-3-yl)-2-(7-(2-chloro-4-methoxyphenyl)-4-oxoquinolin-1(4H)-yl)acetamide obtained from above step was dissolved in glacial acetic acid (1.5 mL). The mixture was microwave irradiated at 140° C. for 0.5 hour. The reaction mixture was concentrated in vacuum and the residue was partitioned between saturated sodium bicarbonate and DCM. The organic extract was dried over anhydrous sodium sulfate, and concentrated in vacuum. Purification through flash chromatography on silica gel eluted with 6% MeOH in DCM (0.5% ammonia hydroxide) gave 2.4 mg (yield: 13.9%) target compound 2168: 7-(2-chloro-4-methoxyphenyl)-1-((5-fluoro-1H-imidazo[4,5-b]pyridin-2-yl)methyl)quinolin-4(1H)-one. $^1$H NMR (MeOD) δ 8.43 (d, J=8.5 Hz, 1H), 8.33 (d, J=7.5 Hz, 1H), 8.01-7.93 (m, 1H), 7.83 (s, 1H), 7.56 (d, J=8.2 Hz, 1H), 7.44 (s, 1H), 7.23 (d, J=8.5 Hz, 1H), 6.98 (d, J=2.4 Hz, 1H), 6.90 (dd, J=11.2, 5.3 Hz, 1H), 6.63 (d, J=7.5 Hz, 1H), 5.82 (s, 2H), 3.84 (s, 3H). LC/MS: (ESI) [M+H]$^+$=435.9

Example 137

Scheme 47

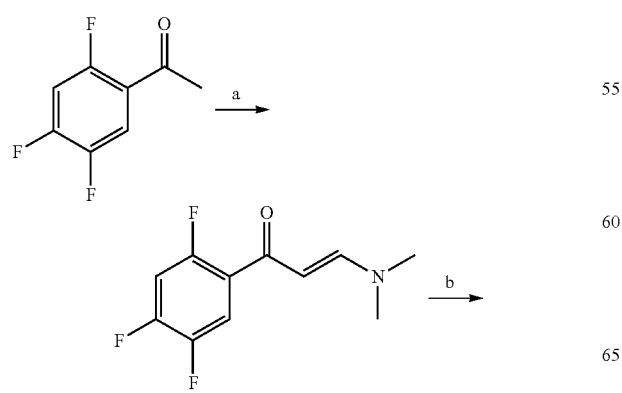

-continued

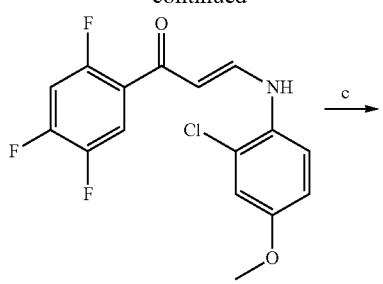

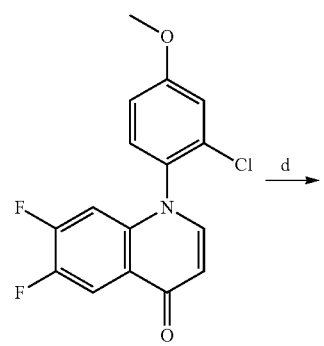

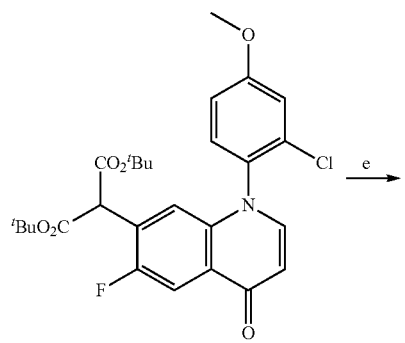

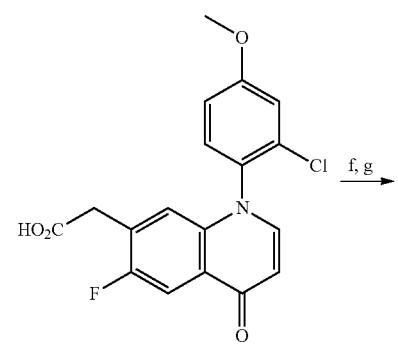

-continued

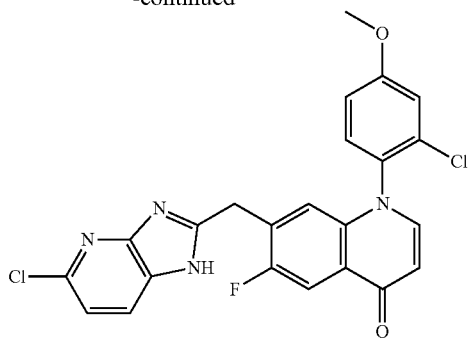

2178

Reagents and conditions: (a) DMADA (N, N-dimethylacetamide dimethyl acetal), MW, 120° C., 20 min; (b) 2-chloro-4-methoxyaniline, AcOH, 50° C., 2 h; (c) K$_2$CO$_3$, DMF, 80° C., 30 min; (d) di-*tert*-butyl malonate, NaH, DMF, 0° C.-80° C., 3 h; (e) TFA, DCM, r.t. overnight; (f) 6-chloropyridine-2, 3-diamine, EDC, Pyridine, r.t., over night; (g) AcOH, MW, 140° C., 30 min.

Procedure 14:

(a) 1-(2,4,5-trifluorophenyl)ethanone (348 mg, 2 mmol) was dissolved in DMADA (800 μL), the mixture was microwave irradiated at 120° C. for 20 min. The reaction mixture was concentrated in vacuum and hexane was added. The solid was filtered and washed with hexane to give 3-(dimethylamino)-1-(2,4,5-trifluorophenyl)prop-2-en-1-one 458 mg as a yellow solid, yield: 100%. LC/MS: (ESI) [M+H]$^+$=230.3

(b) A mixture of 3-(dimethylamino)-1-(2,4,5-trifluorophenyl)prop-2-en-1-one (115 mg, 0.5 mmol) and 2-chloro-4-methoxyaniline (80 mg, 0.5 mmol) in AcOH was heated at 50° C. for 4 h. The reaction mixture was concentrated in vacuum and the residue was partitioned between saturated sodium bicarbonate and DCM. The organic extract was dried over anhydrous sodium sulfate, and concentrated in vacuum to obtain 3-((2-chloro-4-methoxyphenyl)amino)-1-(2,4,5-trifluorophenyl)prop-2-en-1-one 210 mg, which was used for next step without further purification. LC/MS: (ESI) [M+H]$^+$=343.8

(c) 3-((2-chloro-4-methoxyphenyl)amino)-1-(2,4,5-trifluorophenyl)prop-2-en-1-one (100 mg, 0.29 mmol) was dissolved in DMF, K$_2$CO$_3$ (81 mg, 0.59 mmol) was added and the mixture was heated at 80° C. for 30 min. The solvent was evaporated off and the residue was extracted with DCM. The organic extract was dried over anhydrous sodium sulfate, and concentrated in vacuum. Purification through flash chromatography on silica gel eluted with 60% ethyl acetate in hexane gave 1-(2-chloro-4-methoxyphenyl)-6,7-difluoroquinolin-4(1H)-one 85 mg, yield: 89.7%. LC/MS: (ESI) [M+H]$^+$=323.7

(d) A suspension of NaH (60%, 25 mg, 0.62 mmol) in dried DMF was cooled to 0° C. Di-tert-butyl malonate (135 μL, 0.62 mmol) was added and the mixture stirred at r.t. for 10 min. 1-(2-chloro-4-methoxyphenyl)-6,7-difluoroquinolin-4(1H)-one (50 mg, 0.155 mmol) in DMF was added to the above solution dropwise at r.t., and the mixture heated to 80° C. for 3 h. After being cooled to r.t. the reaction mixture was poured into ice-water and extracted with ethyl acetate. The organic extract was dried over anhydrous sodium sulfate, and concentrated in vacuum. Purification through flash chromatography on silica gel eluted with 80% ethyl acetate in hexane gave di-tert-butyl 2-(1-(2-chloro-4-methoxyphenyl)-6-fluoro-4-oxo-1,4-dihydroquinolin-7-yl)malonate 48 mg, yield: 59.8%. LC/MS: (ESI) [M+H]$^+$=518.9

(e) To a solution of di-tert-butyl 2-(1-(2-chloro-4-methoxyphenyl)-6-fluoro-4-oxo-1,4-dihydroquinolin-7-yl)malonate (48 mg, 0.093 mM) in DCM (2 mL) was added TFA (2 mL) at 0° C. The mixture was stirred at r.t. overnight. The solvent was evaporated off and the residue was purified through flash chromatography on silica gel eluted with 60% MeOH in DCM to give 2-(1-(2-chloro-4-methoxyphenyl)-6-fluoro-4-oxo-1,4-dihydroquinolin-7-yl)acetic acid 30 mg, yield: 89.3%. LC/MS: (ESI) [M+H]$^+$=363.3

(f) To a solution of 2-(1-(2-chloro-4-methoxyphenyl)-6-fluoro-4-oxo-1,4-dihydroquinolin-7-yl)acetic acid (15 mg, 0.045) and 6-chloropyridine-2,3-diamine (8 mg, 0.056 mM) in pyridine was added EDC (13 mg, 0.068 mM). The mixture was stirred at r.t. overnight, and the solvent was removed under reduced pressure. After addition of saturated aqueous sodium bicarbonate to the residue, the mixture was extracted with DCM. The organic layer was dried over anhydrous sodium sulfate, and concentrated in vacuum. Purification through flash chromatography on silica gel eluted with 3% MeOH in DCM (0.5% ammonia hydroxide) gave N-(2-amino-6-chloropyridin-3-yl)-2-(1-(2-chloro-4-methoxyphenyl)-6-fluoro-4-oxo-1,4-dihydroquinolin-7-yl) acetamide 8 mg as pink solid, yield: 36.8% . LC/MS: (ESI) [M+H]$^+$=488.5

(g) N-(2-amino-6-chloropyridin-3-yl)-2-(1-(2-chloro-4-methoxyphenyl)-6-fluoro-4-oxo-1,4-dihydroquinolin-7-yl) acetamide (8 mg, 0.016 mM) obtained from above step was dissolved in glacial acetic acid (1.5 mL). The mixture was microwave irradiated at 140° C. for 0.5 hour. The reaction mixture was concentrated in vacuum and the residue was partitioned between saturated sodium bicarbonate and DCM. The organic extract was dried over anhydrous sodium sulfate, and concentrated in vacuum. Purification through flash chromatography on silica gel eluted with 5% MeOH in DCM (0.5% ammonia hydroxide) gave 6.3 mg (yield: 36.5%) target compound 2178: 7-((5-chloro-1H-imidazo[4,5-b]pyridin-2-yl)methyl)-1-(2-chloro-4-methoxyphenyl)-6-fluoroquinolin-4(1H)-one. $^1$H NMR (300 MHz, CDCl$_3$) δ 7.93 (d, J=8.3 Hz, 1H), 7.61 (d, J=9.6 Hz, 1H), 7.52 (d, J=7.6 Hz, 1H), 7.34-7.22 (m, 2H), 6.97 (s, 1H), 6.87 (d, J=8.6 Hz, 1H), 6.77 (s, 1H), 6.35 (d, J=7.6 Hz, 1H), 4.51 (s, 2H), 3.88 (s, 3H). LC/MS: (ESI) [M+H]$^+$=470.3

Example 138

Scheme 48

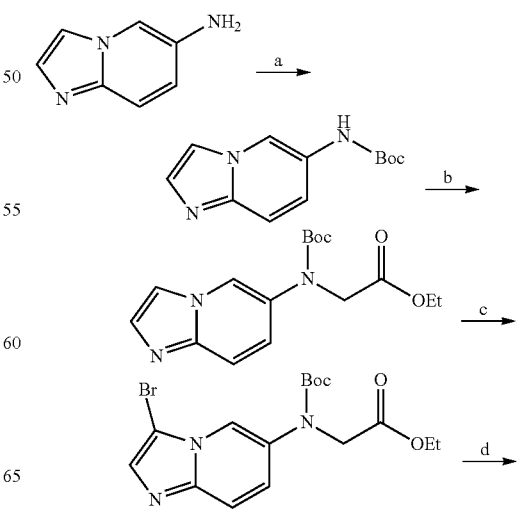

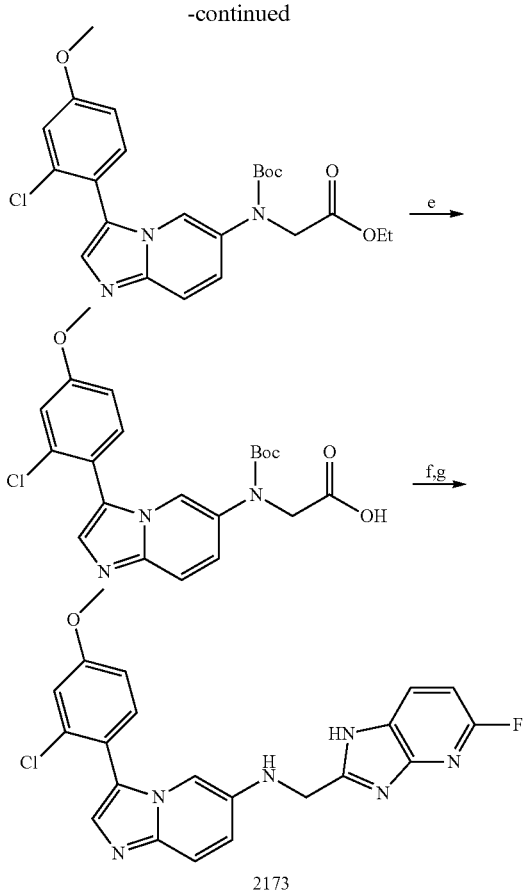

Reagents and conditions: (a) (Boc)₂O, DIPEA, DMAP, DCM, r.t. overnight; (b) ethyl 2-bromoacetate, K₂CO₃, DMF, reflux, 4 h; (c) NBS, DCM, r.t., 2 h; (d) (2-chloro-4-methoxyphenyl)boronic acid, PdCl₂(dppf). DCM, K₂CO₃, DMF/H₂O, 105° C., 60 min; (e) LiOH, MeOH/H₂O, r.t., 4 h; (f) 6-fluoropyridine-2,3-diamine, EDC, Pyridine, r.t., over night; (g) AcOH, MW, 140° C., 30 min.

Procedure 15:

(a) Imidazo[1,2-a]pyridin-6-amine (400 mg, 3 mM) was dissolved in DCM, (Boc)₂O (0.98 g,4.5 mM), DIPEA (0.5 mL, 4.5 mM) and catalytic amount of DMAP were added. The mixture was stirred at r.t. overnight and diluted by DCM followed by washing with H₂O and brine. The organic extract was dried over anhydrous sodium sulfate, and concentrated in vacuum. Purification through flash chromatography on silica gel eluted with 4% MeOH in DCM (0.5% ammonia hydroxide) gave tert-butyl imidazo[1,2-a]pyridin-6-ylcarbamate 300 mg, yield: 42.9%. LC/MS: (ESI) [M+H]⁺=234.4

(b) To a solution of tert-butyl imidazo[1,2-a]pyridin-6-ylcarbamate (23 mg, 0.1 mM) in DMF was added K₂CO₃ (28 mg, 0.2 mM) and ethyl 2-bromoacetate (17 μL, 0.15 mM), and the mixture was refluxed for 4 h. The reaction mixture was concentrated in vacuum and the residue was partitioned between saturated sodium bicarbonate and DCM. The organic extract was dried over anhydrous sodium sulfate, and concentrated in vacuum. Purification through flash chromatography on silica gel eluted with 2% MeOH in DCM (0.5% ammonia hydroxide) gave ethyl 2-((tert-butoxycarbonyl)(imidazo[1,2-a]pyridin-6-yl)amino)acetate 16 mg, yield: 49.6%. LC/MS: (ESI) [M+H]⁺=320.3

(c) A mixture of ethyl 2-((tert-butoxycarbonyl)(imidazo[1,2-a]pyridin-6-yl)amino)acetate (170 mg, 0.53 mmol) and NBS (95 mg, 0.53 mmol) in DCM was stirred at r.t. for 1 h. After diluted with DCM, the solution was washed successively with water and brine. The organic layer was dried over sodium sulfate, concentrated in vacuum, and the residue was purified through flash chromatography on silica gel eluted with 3% MeOH in DCM to give 98 mg of ethyl 2-((3-bromoimidazo[1,2-a]pyridin-6-yl)(tert-butoxycarbonyl)amino)acetate as a brown oil, yield: 46.4%. LC/MS: (ESI) [M+H]⁺=399.5

(d) Ethyl 2-((3-bromoimidazo[1,2-a]pyridin-6-yl)(tert-butoxycarbonyl)amino)acetate (8 mg, 0.02 mmol) and (2-chloro-4-methoxyphenyl)boronic acid (5.2 mg, 0.028 mmol) were dissolved in a mixture of DMF:H₂O=4:1. To the mixture, PdCl₂(dppf).DCM (2 mg) and K₂CO₃ (5.6 mg, 0.04 mmol) were added. The mixture was heated at 105° C. for 1 h under N₂. The solvent was removed under reduced pressure, and the residue was extracted with DCM. The organic layer was dried over sodium sulfate, concentrated in vacuum, and the residue was purified through flash chromatography on silica gel eluted with 80% ethyl acetate in hexane to give ethyl 2-((tert-butoxycarbonyl)(3-(2-chloro-4-methoxyphenyl)imidazo[1,2-a]pyridin-6-yl)amino)acetate 8 mg, yield: 87.0%. LC/MS: (ESI) [M+H]⁺=460.8

(e, f, g) Steps (e, f, g) were performed following Procedure 12. 2173: 3-(2-chloro-4-methoxyphenyl)—N-((5-fluoro-1H-imidazo[4,5-b]pyridin-2-yl)methyl)imidazo[1,2-a]pyridin-6-amine. ¹H NMR (MeOD) δ 8.34-8.26 (m, 1H), 7.99 (s, 1H), 7.91 (d, J=9.7 Hz, 1H), 7.79 (d, J=9.7 Hz, 1H), 7.47 (d, J=8.5 Hz, 1H), 7.32 (d, J=8.7 Hz, 1H), 7.09 (dd, J=8.5, 2.4 Hz, 1H), 7.05 (s, 1H), 7.02 (d, J=2.4 Hz, 1H), 4.93 (d, J=7.9 Hz, 2H), 3.96 (s, 3H). LC/MS: (ESI) [M+H]⁺=423.

Example 139

Scheme 49

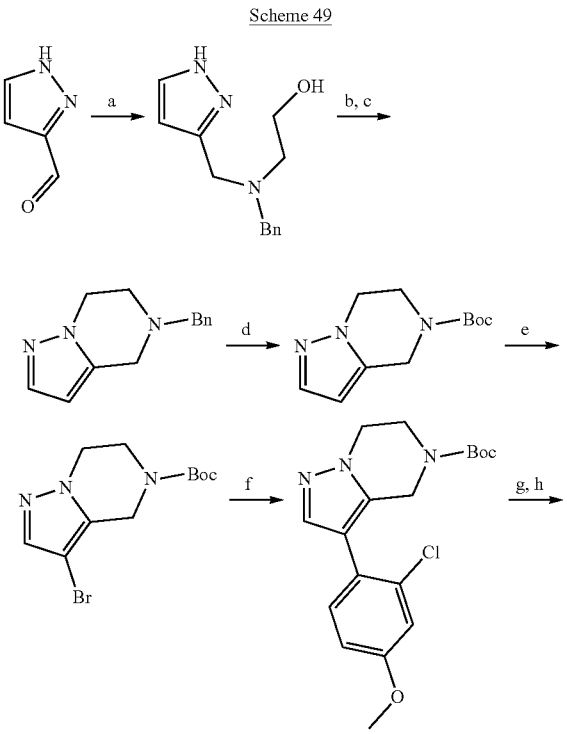

-continued

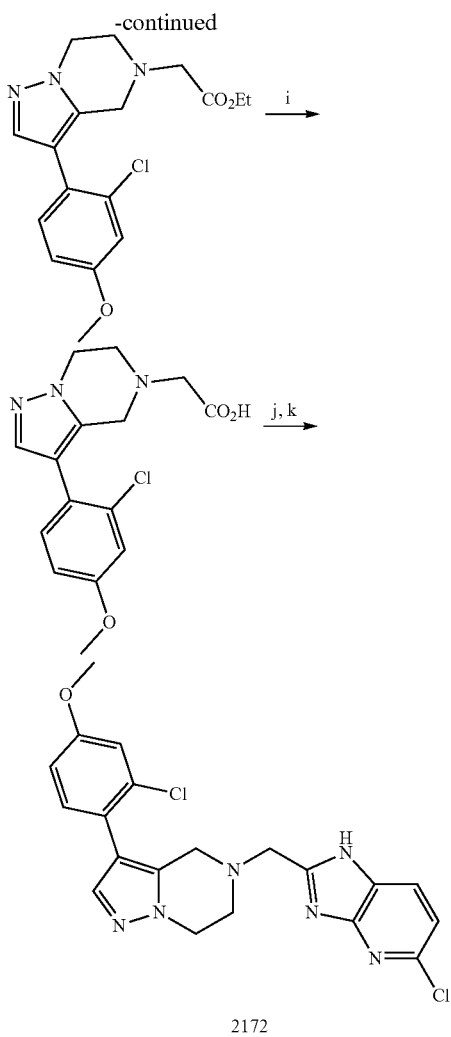

2172

Reagents and conditions: (a) 2-(benzylamino) ethanol, NaBH$_3$CN, AcOH, MeOH, r.t. overnight; (b) SOCl$_2$, DCM, 0° C.-r.t., overnight; (c) NaH, DMF, r.t., 1 h; (d) (Boc)$_2$O, Pd(OH)$_2$, H$_2$, MeOH, r.t., overnight; (e) NBS, DCM, r.t., 2 h; (f) 2-chloro-4-methoxyphenyl) boronic acid, PdCl$_2$(dppf). DCM, K$_2$CO$_3$, DMF/H$_2$O, 105° C., 60 min; (g) TFA, DCM, r.t., (h) ethyl 2-bromoacetate, K$_2$CO$_3$, ACN, reflux, 1 h; (i) LiOH, CH$_3$OH/H$_2$O, r.t., 4 h; (j) 6-chloropyridine-2, 3-diamine, EDC, Pyridine, r.t., over night; (k) AcOH, MW, 140° C., 30 min.

General Procedure 16:

tert-butyl 6,7-dihydropyrazolo[1,5-a]pyrazine-5(4H)-carboxylate was synthesized following reported procedures (Barsanti, P. A. et. al. *ACS Medicinal Chemistry Letters* 6, (1), 37).

(a) A solution of 1H-pyrazole-5-carbaldehyde (192 mg, 2 mmol) and 2-(benzylamino)ethanol (302 mg, 2 mmol) in MeOH was stirred at r.t. for 1 hour. To the mixture was added sodium cyanoborohydride (190 mg, 3 mmol) followed by AcOH (0.2 ml, 4 mmol). The reaction mixture was stirred at r.t. overnight. The reaction mixture was quenched with 2 mL of water and then concentrated. The residue was partitioned between saturated aqueous NaHCO$_3$ and EtOAc. The organic layer was dried over sodium sulfate, concentrated in vacuum, and the residue was used for next step without further purification. LC/MS: (ESI) [M+H]$^+$=232.3

(b,c) To a solution of 2-(((1H-pyrazol-5-yl)methyl)(benzyl)amino)ethanol (390 mg, 1.69 mmol) in DCM at 0° C. was added thionyl chloride (0.88 mL, 11.8 mmol). The mixture was warmed to r.t. and stirred overnight. The solvent was removed under reduced pressure. The residue was dissolved in DMF, NaH (60%, 200 mg, 5 mmol) was added, and the reaction mixture was stirred at r.t. for 1 h. The solvent was removed under reduced pressure, the residue was extracted with ethyl acetate. The organic layer was dried over sodium sulfate, concentrated in vacuum, and the residue was purified through flash chromatography on silica gel eluted with 50% ethyl acetate in hexane to give 250 mg of 5-benzyl-4,5,6,7-tetrahydropyrazolo[1,5-a]pyrazine as a yellow oil, yield: 75.1%. LC/MS: (ESI) [M+H]$^+$=214.5

(d) To a solution of 5-benzyl-4,5,6,7-tetrahydropyrazolo[1,5-a]pyrazine (213 mg, 1 mmol) in MeOH were added Pd(OH)$_2$ (100 mg, 0.1 mmol) and Boc$_2$O (650 mg, 0.3 mmol). The reaction mixture was stirred under an atmosphere of H$_2$ at r.t. overnight. The reaction mixture was filtered through Celite, and the filtrate was concentrated. The residue was purified through flash chromatography on silica gel eluted with 50% ethyl acetate in hexane to obtain 130 mg of tert-butyl 6,7-dihydropyrazolo[1,5-a]pyrazine-5(4H)-carboxylate, yield: 58.2%. LCMS: (ESI) [M+H]$^+$=224.6

(e) A mixture of tert-butyl 6,7-dihydropyrazolo[1,5-a]pyrazine-5(4H)-carboxylate (223 mg, 1 mmol) and NBS (190 mg, 1.05 mmol) in DCM was stirred at r.t. for 2 h. The mixture was diluted with DCM followed by washing successively with water and brine. The organic layer was dried over sodium sulfate, concentrated in vacuum, and the residue was purified through flash chromatography on silica gel eluted with 40% ethyl acetate in hexane to give 260 mg of tert-butyl 3-bromo-6,7-dihydropyrazolo[1,5-a]pyrazine-5(4H)-carboxylate as a colorless oil, yield: 86.1%. LC/MS: (ESI) [M+H]$^+$=303.4

(f) tert-Butyl 3-bromo-6,7-dihydropyrazolo[1,5-a]pyrazine-5(4H)-carboxylate (30.2 mg, 0.1 mmol), (2-chloro-4-methoxyphenyl)boronic acid (26 mg, 0.14 mmol) were dissolved in a mixture of DMF:H$_2$O=4:1. To the mixture, PdCl$_2$(dppf).DCM (10 mg), Na$_2$CO$_3$ (21 mg, 0.17 mmol) were added. The mixture was heated at 105° C. for 1 h under N$_2$. The solvent was removed under reduced pressure; the residue was extracted with DCM. The organic layer was dried over sodium sulfate, concentrated in vacuum, and the residue was purified through flash chromatography on silica gel eluted with 40% ethyl acetate in hexane to give 25 mg of tert-butyl 3-(2-chloro-4-methoxyphenyl)-6,7-dihydropyrazolo[1,5-a]pyrazine-5(4H)-carboxylate, yield: 68.7%. LC/MS: (ESI) [M+H]$^+$=365.1

(g) To a solution of tert-butyl 3-(2-chloro-4-methoxyphenyl)-6,7-dihydropyrazolo[1,5-a]pyrazine-5(4H)-carboxylate (25 mg, 0.069 mM) in DCM 2 mL was added TFA (200 µL) at 0° C. The mixture was stirred at r.t. overnight. The solvent was evaporated off and the residue was used for next step directly. LC/MS: (ESI) [M+H]$^+$=264.9

(h) To a solution of 3-(2-chloro-4-methoxyphenyl)-4,5,6,7-tetrahydropyrazolo[1,5-a]pyrazine (100 mg, 0.38 mmol) in acetonitrile were added K$_2$CO$_3$ (157 mg, 1.1 mmol) and ethyl 2-bromoacetate (63 µL, 0.57 mmol). The mixture was refluxed for 1 h. The solvent was evaporated off, and the residue was extracted with ethyl acetate. The organic layer was dried over anhydrous sodium sulfate, filtered and concentrated in vacuum. Purification through flash chromatography on silica gel eluted with 60% ethyl acetate in hexane gave ethyl 2-(3-(2-chloro-4-methoxyphenyl)-6,7-dihydropyrazolo[1,5-a]pyrazin-5(4H)-yl)acetate 52 mg as brown oil, yield: 56.4%. LC/MS: (ESI) [M+H]$^+$=350.9

(h, i, j) Steps (h, i, j) were performed following Procedure 13.

2172: 5-chlor$_{0-2}$-((3-(2-chloro-4-methoxyphenyl)-6,7-dihydropyrazolo[1,5-a]pyrazin-5(4H)-yl)methyl)-1H-imidazo

[4,5-b]pyridine. ¹H NMR (CDCl₃) δ 7.93 (d, J=8.2 Hz, 1H), 7.62 (s, 1H), 7.23 (d, J=8.2 Hz, 1H), 7.07 (d, J=8.4 Hz, 1H), 6.95 (s, 1H), 6.79 (d, J=8.4 Hz, 1H), 4.23 (s, 2H), 4.16 (s, 2H), 3.81 (s, 3H), 3.52-3.49 (br, 4H), 3.14 (s, 2H). LC/MS: (ESI) [M+H]⁺=430.2

Example 140

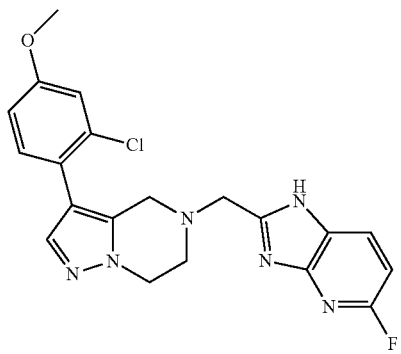

2170

2170: 2-((3-(2-chloro-4-methoxyphenyl)-6,7-dihydropyrazolo[1,5-a]pyrazin-5(4H)-yl)methyl)-5-fluoro-1H-imidazo[4,5-b]pyridine was synthesized using 6-fluoropyridine-2,3-diamine following General Procedure 15. ¹H NMR (CDCl₃) δ 8.04 (t, J=7.0 Hz, 1H), 7.61 (s, 1H), 7.26 (s, 1H), 7.06 (d, J=8.3 Hz, 1H), 6.93 (s, 1H), 6.83 (d, J=8.4 Hz, 1H), 6.77 (d, J=8.5 Hz, 1H), 4.20(s, 2H), 4.04 (s, 2H), 3.51-3.76 (m, 4H), 3.74 (s, 3H), 3.07 (s, 2H). LC/MS: (ESI) (M+H)⁺=414.6.

Example 141

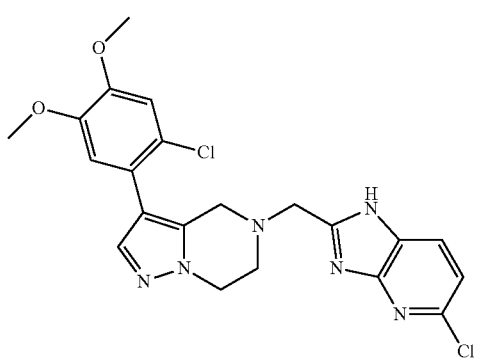

2205

2205: 5-chlor₀₋₂-((3-(2-chloro-4,5-dimethoxyphenyl)-6,7-dihydropyrazolo[1,5-a]pyrazin-5(4H)-yl)methyl)-1H-imidazo[4,5-b]pyridine was synthesized using (2-chloro-4,5-dimethoxyphenyl)boronic acid following General Procedure 15. LC/MS: (ESI) (M+H)⁺=459.5, HPLC purity: 97.8%.

Example 142

Scheme 50

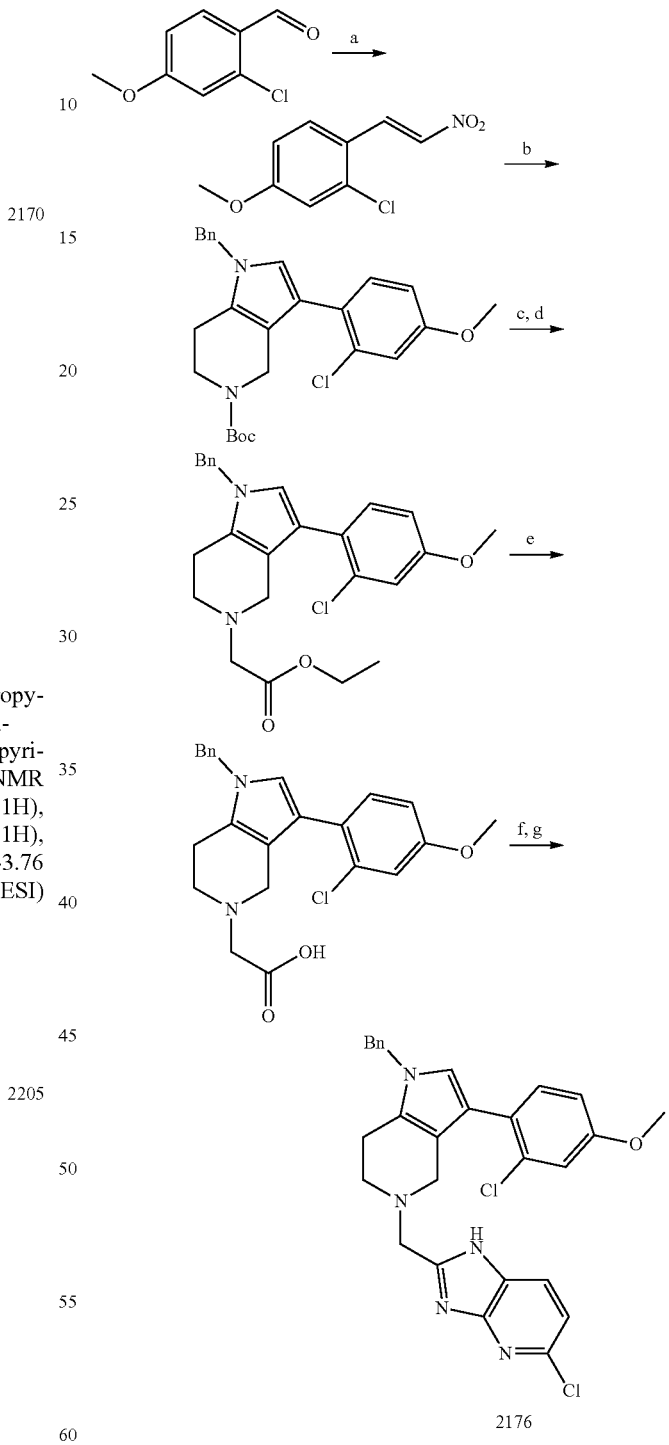

2176

Reagents and conditions: (a) CH₃NO₂, NH₄Ac, AcOH, 110° C., 2 h; (b) tert-butyl 4-oxopiperidine-1-carboxylate, phenylmathanamine, SiO2, tolune, MW, 60° C., 20 min, then 2-chloro-4-methoxy-1-(2-nitrovinyl) benzene, r.t., overnight; (d) TFA, DCM, r.t., (e) ethyl 2-bromoacetate, K₂CO₃, ACN, reflux, 1 h; (i) LiOH, CH₃OH/H₂O, r.t., 4 h; (j) 6-chloropyridine-2, 3-diamine, EDC, Pyridine, r.t., over night; (k) AcOH, MW, 140° C., 30 min.

General Procedure 17:

(a) A mixture of 2-chloro-4-methoxybenzaldehyde (170 mg, 1 mmol), $CH_3NO_2$ (500 μL), $NH_4Ac$ (231 mg, 3 mmol) in AcOH (3 mL) was heated at 110° C. for 2 h. The mixture was cooled and poured into ice water and the solid was filtered and washed by cold water. The solid was dried to get 2-chloro-4-methoxy-1-(2-nitrovinyl)benzene 106 mg as yellow solid, which was used for next step directly. LC/MS: (ESI) $(M+H)^+=214.5$ (b) This step was conducted following reported procedure with modification {Rudolph, D. A. et. al. *Bioorganic & Medicinal Chemistry Letters* 21, (1), 42}. To a solution of 4-oxo-piperidine-1-carboxylic acid tert-butyl ester (20 mg, 0.1 mmol) in toluene was added phenylmethanamine (11 μL, 0.1 mmol) followed by $SiO_2$ (30 mg). This mixture was microwave irradiated at 60° C. for 20 min. 2-chloro-4-methoxy-1-(2-nitrovinyl)benzene (22 mg, 0.1 mmol) obtained above was added and the mixture was stirred at r.t. overnight. The mixture was filtered through Celite and concentrated in vacuo. The residue was purified through flash chromatography on silica gel eluted with 30% ethyl acetate in hexane, yielding tert-butyl 1-benzyl-3-(2-chloro-4-methoxyphenyl)-6,7-dihydro-1H-pyrrolo[3,2-c]pyridine-5(4H)-carboxylate 18.3 mg as a yellow solid, yield: 40.4%. LC/MS: (ESI) $[M+H]^+=454.3$ Steps (c,d,e,f,g) were conducted following General Procedure 16.

2176: 2-((1-benzyl-3-(2-chloro-4-methoxyphenyl)-6,7-dihydro-1H-pyrrolo[3,2-c]pyridin-5(4H)-yl)methyl)-5-chloro-1H-imidazo[4,5-b]pyridine. Purification through flash chromatography on silica gel eluted with DCM gave target compound. LC/MS: (ESI) $[M+H]^+=519.2$ Example 143

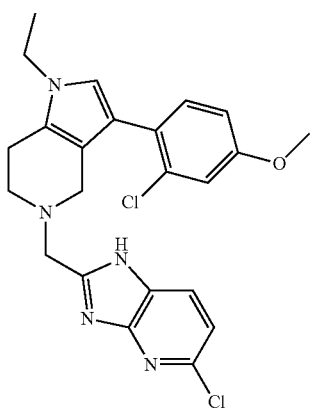

2177: 5-chlor$_{0-2}$-((3-(2-chloro-4-methoxyphenyl)-1-ethyl-6,7-dihydro-1H-pyrrolo[3,2-c]pyridin-5(4H)-yl)methyl)-1H-imidazo[4,5-b]pyridine was synthesized using ethylamine following General Procedure 17. Purification through flash chromatography on silica gel eluted with DCM gave target compound. $^1$H NMR (300 MHz, CDCl$_3$) δ 7.85 (s, 1H), 7.23 (d, J=8.4 Hz, 1H), 7.13 (d, J=8.5 Hz, 1H), 6.94 (d, J=2.5 Hz, 1H), 6.76 (dd, J=8.5, 2.6 Hz, 1H), 6.72 (s, 1H), 4.51-4.11 (br, 2H), 3.85 (dd, J=14.7, 7.3 Hz, 2H), 3.84-3.80 (br, 2h), 3.79 (s, 3H), 3.36-3.03 (br, 2H), 3.06-2.76 (br, 2H), 1.42 (t, J=7.3 Hz, 3H). LC/MS: (ESI) $[M+H]^+=457.1$ Example 144

Scheme 51

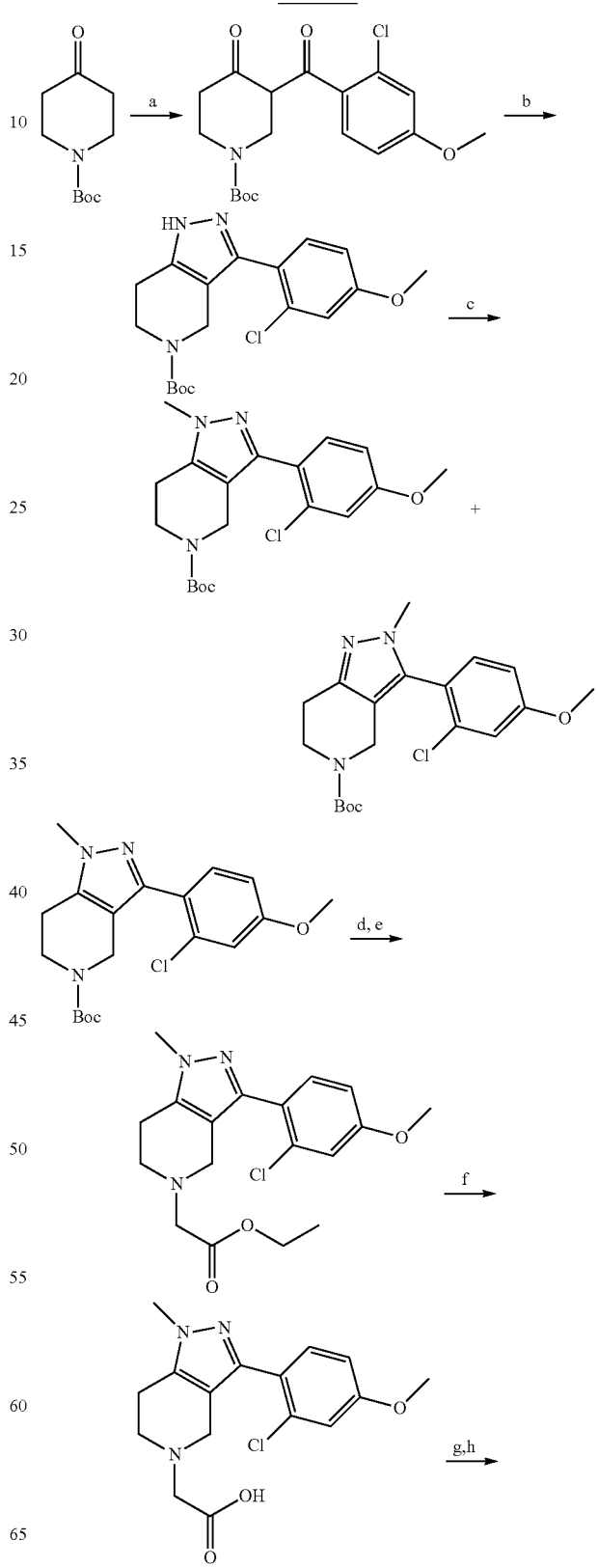

2177

-continued

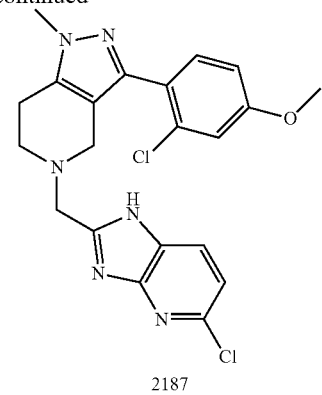

2187

Reagents and conditions: (a) 2-chloro-4-methoxybenzoyl chloride, KHMDS, toluene, 0° C.-r.t., 1 h; (b) Hydrazine, EtOH, 0° C.-r.t., overnight; (c) CH$_3$I, Cs$_2$CO$_3$, 0° C.-r.t., overnight; (d) TFA, DCM, r.t., (e) ethyl 2-bromoacetate, K$_2$CO$_3$, ACN, reflux, 1 h; (i) LiOH, CH$_3$OH/H$_2$O, r.t., 4 h; (j) 6-chloropyridine-2,3-diamine, EDC, Pyridine, r.t., over night; (k) AcOH, MW, 140° C., 30 min.

General Procedure 18:

(a) tert-Butyl 4-oxopiperidine-1-carboxylate (150 mg, 0.75 mmol) was dissolved in toluene and was cooled to 0° C. under N$_2$. Potasium hexamethyldisilazide (0.5 M in THF, 220 μL, 0.11 mmol) was added and the mixture was stirred for 5 min. 2-chloro-4-methoxybenzoyl chloride (11 mg, 0.05 mmol) in toluene was added and the mixture was stirred at r.t. for 1 h. The solvent was evaporated off, and the residue was extracted with ethyl acetate. The organic layer was dried over anhydrous sodium sulfate, filtered and concentrated in vacuum to give tert-butyl 3-(2-chloro-4-methoxybenzoyl)-4-oxopiperidine-1-carboxylate as brown oil 250 mg, yield: 93.0%.

(b) The crude product obtained above was dissolved in EtOH at 0° C., hydrazine (72 μL, 2.3 mM) was added and the mixture was stirred at r.t. overnight. The solvent was evaporated off, and the residue was purified through flash chromatography on silica gel eluted with 80% ethyl acetate in hexane, yielding tert-butyl 3-(2-chloro-4-methoxyphenyl)-6,7-dihydro-1H-pyrazolo[4,3-c]pyridine-5(4H)-carboxylate 160 mg as a white solid, yield: 47.3%. LC/MS: (ESI) [M+H]$^+$=365.1

(c) tert-Butyl 3-(2-chloro-4-methoxyphenyl)-6,7-dihydro-1H-pyrazolo[4,3-c]pyridine-5(4H)-carboxylate (73 mg, 0.2 mmol) was dissolved in DMF, Cs$_2$CO$_3$ (78 mg, 0.24 mmol) was added and the mixture was cooled to 0° C. CH$_3$I (19 μL, 0.3 mmol) was added and the mixture was stirred at r.t. overnight. The solvent was evaporated off, and the residue was extracted with ethyl acetate. The organic layer was dried over anhydrous sodium sulfate, filtered and concentrated in vacuum. Purification through flash chromatography on silica gel eluted with 80% ethyl acetate in hexane gave tert-butyl 3-(2-chloro-4-methoxyphenyl)-1-methyl-6,7-dihydro-1H-pyrazolo[4,3-c]pyridine-5(4H)-carboxylate 40 mg (yield: 52.5%), and tert-butyl 3-(2-chloro-4-methoxyphenyl)-2-methyl-6,7-dihydr$_{0-2}$H-pyrazolo[4,3-c]pyridine-5 (4H)-carboxylate 36 mg (yield: 47.5%).

Steps (c,d,e,f,g) were conducted following General Procedure 16.

2187: 5-((5-chloro-1H-imidazo[4,5-b]pyridin-2-yl)methyl)-3-(2-chloro-4-methoxyphenyl)-1-methyl-4,5,6,7-tetrahydro-1H-pyrazolo[4,3-c]pyridine. Purification through flash chromatography on silica gel eluted with 6% MeOH in DCM gave target compound. $^1$H NMR (CDCl$_3$) δ 7.87 (d, J=8.1 Hz, 1H), 7.21 (d, J=8.3 Hz, 1H), 7.13 (d, J=8.5 Hz, 1H), 7.00 (d, J=2.5 Hz, 1H), 6.84 (dd, J=8.5, 2.5 Hz, 1H), 4.28-4.08 (br, 2H), 3.82 (s, 3H), 3.72-3.65 (m, 2H), 3.64 (s, 3H), 3.15-2.98 (br, 2H), 2.94 (s, 2H). LC/MS: (ESI) [M+H]$^+$=444.2

Example 145

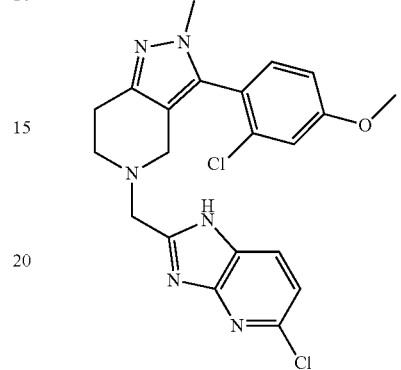

2188

2188: 5-((5-chloro-1H-imidazo[4,5-b]pyridin-2-yl)methyl)-3-(2-chloro-4-methoxyphenyl)-2-methyl-4,5,6,7-tetrahydr$_{0-2}$H-pyrazolo[4,3-c]pyridine was synthesized using tert-butyl 3-(2-chloro-4-methoxyphenyl)-2-methyl-6,7-dihydr$_{0-2}$H-pyrazolo[4,3-c]pyridine-5(4H)-carboxylate following General Procedure 18. Purification through flash chromatography on silica gel eluted with 6% MeOH in DCM gave target compound. $^1$H NMR (CDCl$_3$) δ 7.88 (d, J=6.7 Hz, 1H), 7.32 (d, J=8.6 Hz, 1H), 7.22 (d, J=8.4 Hz, 1H), 6.92 (d, J=2.5 Hz, 1H), 6.82 (dd, J=8.6, 2.5 Hz, 1H), 4.39-4.13 (br, 2H), 3.87-3.77 (br, 2H), 3.81 (s, 3H), 3.79 (s, 3H), 3.28-3.03 (br, 2H), 2.99-2.81 (br, 2H). LC/MS: (ESI) [M+H]$^+$=444.1

Example 146

Scheme 52

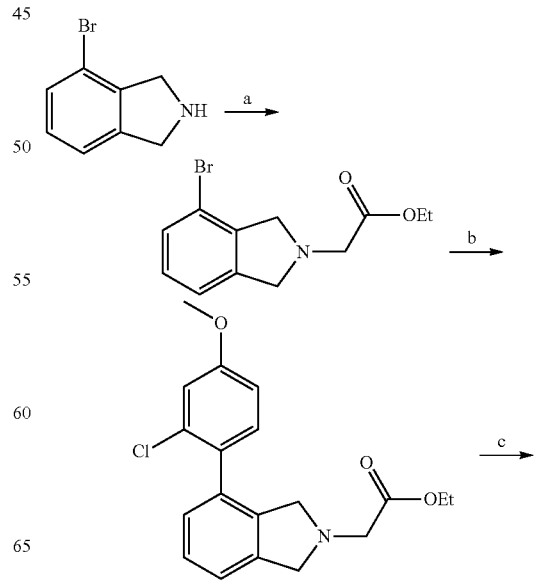

-continued

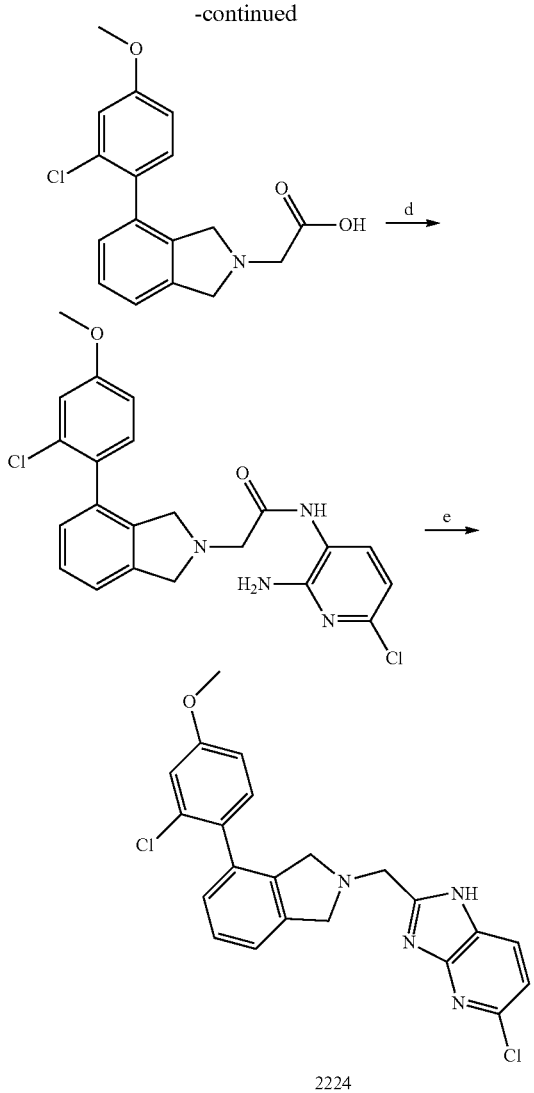

2224

Reagents and conditions: (a) ethyl 2-bromoacetate, K₂CO₃, acetonitrile, reflux, 1 h; (b) (2-chloro-4-methoxyphenyl)boronic acid, PdCl₂(dppf).DCM, K₂CO₃, DMF/H₂O, 105° C., 60 min; (c) LiOH, CH₃OH/H₂O, r.t., 4 h; (d) 6-chloropyridine-2,3,-diamine, EDC, pyridine, r.t., over night; (e) AcOH, MW, 140° C., 30 min.

General Procedure 19:

(a) To a solution of 4-bromoisoindoline (48 mg, 0.2 mmol) in acetonitrile were added K$_2$CO$_3$ (55 mg, 0.4 mmol) and ethyl 2-bromoacetate (26 µL, 0.24 mmol). The mixture was refluxed for 1 h. The solvent was evaporated off, and the residue was extracted with ethyl acetate. The organic layer was dried over anhydrous sodium sulfate, filtered and concentrated in vacuum. Purification through flash chromatography on silica gel eluted with 8% menthol in methylene chloride gave ethyl 2-(4-bromoisoindolin-2-yl)acetate 58 mg as a brown gel, yield: 100%. LC/MS: (ESI) [M+H]$^+$=285.2

(b) Ethyl 2-(4-bromoisoindolin-2-yl) (58.0 mg, 0.2 mmol) and (2-chloro-4-methoxyphenyl)boronic acid (52 mg, 0.28 mmol) were dissolved in a mixture of DMF:H$_2$O (v/v 4:1). To the mixture, PdCl$_2$(dppf).DCM (16 mg) and K$_2$CO$_3$ (55 mg, 0.4 mmol) were added. The mixture was heated at 105° C. for 1 h under N$_2$. The solvent was removed under reduced pressure; the residue was extracted with DCM. The organic layer was dried over sodium sulfate, concentrated in vacuum, and the residue was purified through flash chromatography on silica gel eluted with 4% methanol in methylene chloride to give 55 mg of ethyl 2-(4-(2-chloro-4-methoxyphenyl)isoindolin-2-yl)acetate as a brown solid, yield: 79.5%. LC/MS: (ESI) [M+H]$^+$=346.8

(c) Ethyl 2-(4-(2-chloro-4-methoxyphenyl)isoindolin-2-yl)acetate (55 mg, 0.16 mmol) was dissolved in MeOH/H$_2$O (4:1), LiOH (8 mg, 0.32 mmol) was added and the mixture was stirred at r.t. for 4 h. The solution was acidified with 0.2 N hydrochloric acid and completely dried in vacuo. The residue was used for the next step directly. LC/MS: (ESI) [M+H]$^+$=319.0

(d) To a solution of 2-(4-(2-chloro-4-methoxyphenyl) isoindolin-2-yl)acetic acid (16.2 mg, 0.05 mmol) and 6-chloropyridine-2,3-diamine (7.2 mg, 0.05 mmol) in pyridine (2 mL) was added EDC (15 mg, 0.075 mmol). The mixture was stirred at r.t. overnight, and pyridine was then removed under reduced pressure. After addition of saturated aqueous sodium bicarbonate to the residue, the mixture was extracted with DCM. The organic layer was dried over anhydrous sodium sulfate, and concentrated in vacuum. Purification through flash chromatography on silica gel eluted with 100% DCM gave N-(2-amino-6-chloropyridin-3-yl)-2-(4-(2-chloro-4-methoxyphenyl)isoindolin-2-yl)acetamide 16 mg as a brown solid, yield: 72.2%. LC/MS: (ESI) [M+H]$^+$=444.4

(e) N-(2-amino-6-chloropyridin-3-yl)-2-(4-(2-chloro-4-methoxyphenyl)isoindolin-2-yl)acetamide (16 mg, 0.036 mmol) was dissolved in glacial acetic acid (1.5 mL). The mixture was microwave irradiated at 140° C. for 0.5 hour. The reaction mixture was concentrated in vacuum and the residue was partitioned between saturated sodium bicarbonate and DCM. The organic extract was dried over anhydrous sodium sulfate, and concentrated in vacuum. Purification through flash chromatography on silica gel eluted with 3% MeOH in DCM (0.5% ammonia hydroxide) gave 10.6 mg (yield: 69.3%) of the target compound 2224: 5-chlor$_{0-2}$-((4-(2-chloro-4-methoxyphenyl)isoindolin-2-yl)methyl)-1H-imidazo[4,5-b]pyridine. LC/MS: (ESI) [M+H]$^+$=426.4, HPLC purity: 95.0%.

Example 147

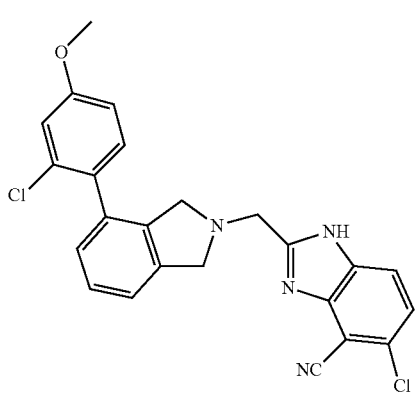

2229

2229: 5-chlor$_{0-2}$-((4-(2-chloro-4-methoxyphenyl)isoindolin-2-yl)methyl)-1H-benzo[d]imidazole-4-carbonitrile was synthesized using 2,3-diamino-6-chlorobenzonitrile following General Procedure 19. LC/MS: (ESI) (M+H)$^+$=451.2, HPLC purity: 97.5%.

Example 148

Scheme 53

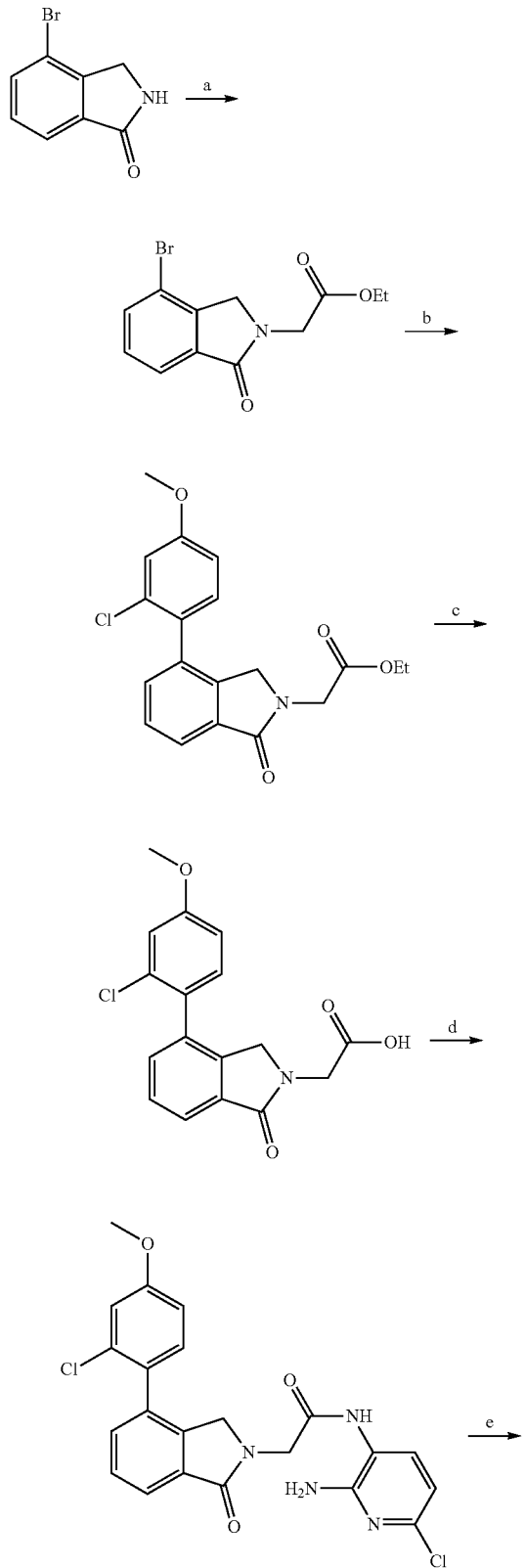

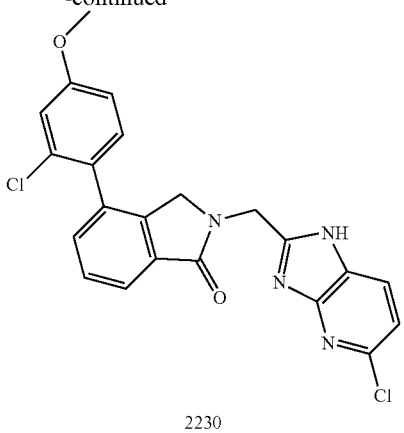

2230

Reagents and conditions: (a) ethyl 2-bromoacetate, $K_2CO_3$, acetonitrile, reflux, over night; (b) (2-chloro-4-methoxyphenyl)boronic acid, $PdCl_2(dppf)$, DCM, $K_2CO_3$, DMF/$H_2O$, 105° C., 60 min; (c) (i) LiOH, $CH_3OH$/$H_2O$, r.t., 4 h; (d) 6-chloropyridine-2,3-diamine, EDC, pyridine, r.t., over night; (e) AcOH, MW, 140° C., 30 min.

General Procedure 20:

(a) To a solution of 4-bromoisoindolin-1-one (106 mg, 0.5 mmol) in acetonitrile were added $K_2CO_3$ (110 mg, 0.8 mmol) and ethyl 2-bromoacetate (52 µL, 0.5 mmol). The mixture was refluxed overnight. The solvent was evaporated off, and the residue was extracted with ethyl acetate. The organic layer was dried over anhydrous sodium sulfate, filtered and concentrated in vacuum. Purification through flash chromatography on silica gel eluted with 8% menthol in methylene chloride gave ethyl 2-(4-bromo-1-oxoisoindolin-2-yl)acetate 150 mg as a brown gel, yield: 100%. LC/MS: (ESI) $[M+H]^+$=300.4

(b, c, d, e) Steps b, c, d, e were conducted following General Procedure 19.

2230: 2-((5-chloro-1H-imidazo[4,5-b]pyridin-2-yl)methyl)-4-(2-chloro-4-methoxyphenyl)isoindolin-1-one. Purification through flash chromatography on silica gel eluted with 2% MeOH in DCM gave the target compound. LC/MS: (ESI) $(M+H)^+$=440.7, HPLC purity: 97.8%.

Example 149

2231

2231: 2-((5-chloro-1H-imidazo[4,5-b]pyridin-2-yl)methyl)-4-(2-chloro-4,5-dimethoxyphenyl)isoindolin-1-one. Compound 2231 was synthesized using (2-chloro-4,5- dimethoxyphenyl)boronic acid following general procedure 20. Purification through flash chromatography on silica gel eluted with 60% EA in Hexanes gave the target compound. LC/MS: (ESI) (M+H)+=470.4, HPLC purity: 97.0%.

Example 150

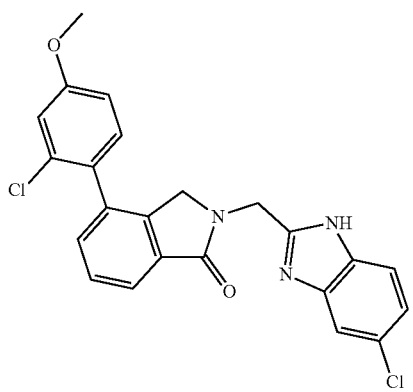

2232

2232: 2-((5-chloro-1H-benzo[d]imidazol-2-yl)methyl)-4-(2-chloro-4-methoxyphenyl)isoindolin-1-one. Compound 2232 was synthesized using 4-chlorobenzene-1,2-diamine following general procedure 20. Purification through flash chromatography on silica gel eluted with 2% MeOH in DCM gave the target compound. LC/MS: (ESI) (M+H)+=439.5, HPLC purity: 95.0%.

Example 151

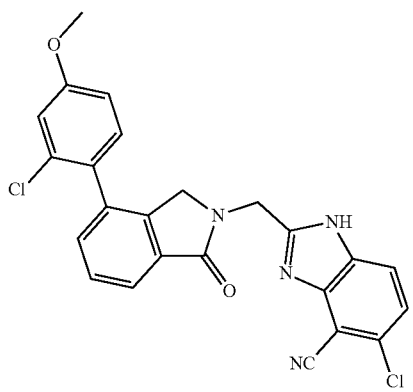

2233

2233: 5-chloro-2-((4-(2-chloro-4-methoxyphenyl)-1-oxoisoindolin-2-yl)methyl)-1H-benzo[d]imidazole-4-carbonitrile. Compound 2233 was synthesized using 2,3-diamino-6-chlorobenzonitrile following general procedure 20. Purification through flash chromatography on silica gel eluted with 4% MeOH in DCM gave the target compound. LC/MS: (ESI) (M+H)+=464.2, HPLC purity: 97.1%.

Example 152

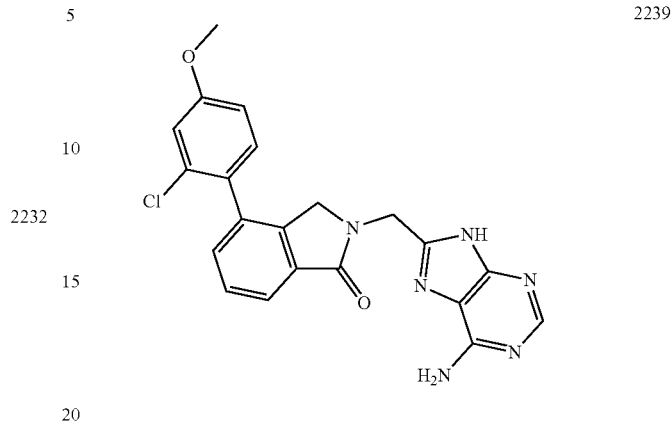

2239

2239: 2-((6-amino-9H-purin-8-yl)methyl)-4-(2-chloro-4-methoxyphenyl)isoindolin-1-one. Compound 2239 was synthesized using pyrimidine-4,5,6-triamine following general procedure 20. Purification through flash chromatography on silica gel eluted with 12% MeOH in DCM gave the target compound. LC/MS: (ESI) (M+H)+=426.0, HPLC purity: 95.9%.

Example 153

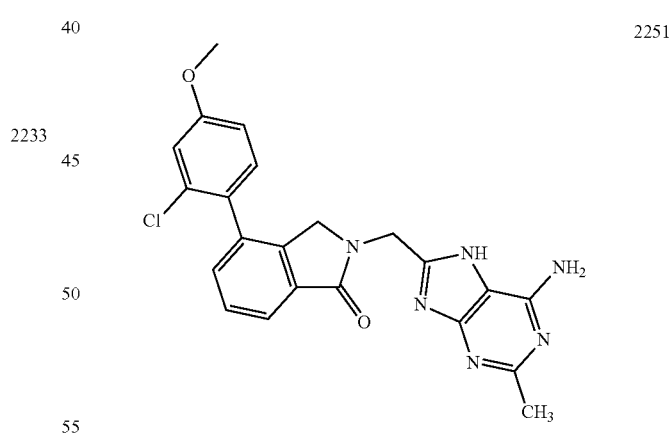

2251

2251: 2-((6-amino-2-methyl-7H-purin-8-yl)methyl)-4-(2-chloro-4-methoxyphenyl)isoindolin-1-one. Compound 2251 was synthesized using 2-methylpyrimidine-4,5,6-triamine following general procedure 20. Purification through flash chromatography on silica gel eluted with 20% MeOH in DCM gave the target compound. LC/MS: (ESI) (M+H)+=436.7.

Example 154

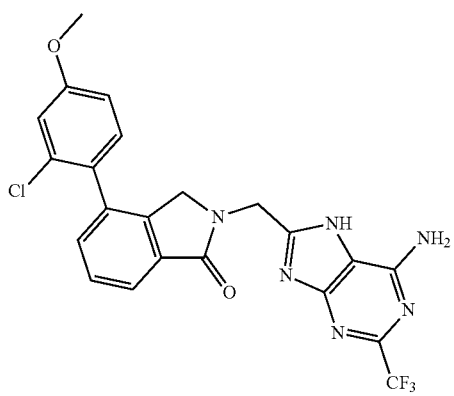

2252: 2-((6-amino-2-(trifluoromethyl)-7H-purin-8-yl)methyl)-4-(2-chloro-4-methoxyphenyl)isoindolin-1-one. Compound 2252 was synthesized using 2-(trifluoromethyl)pyrimidine-4,5,6-triamine following general procedure 20. Purification through flash chromatography on silica gel eluted with 20% MeOH in DCM gave the target compound. LC/MS: (ESI) (M+H)$^+$=489.8, HPLC purity: 97.9%.

Example 155

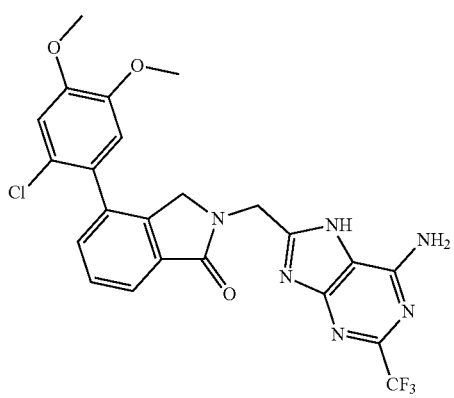

2253: 2-((6-amino-2-methyl-7H-purin-8-yl)methyl)-4-(2-chloro-4,5-dimethoxyphenyl)isoindolin-1-one. Compound 2253 was synthesized using 2-methylpyrimidine-4,5,6-triamine and (2-chloro-4,5-dimethoxyphenyl)boronic acid following general procedure 19. Purification through flash chromatography on silica gel eluted with 8% MeOH in DCM gave the target compound. LC/MS: (ESI) (M+H)$^+$=466.1.

Example 156

Scheme 54

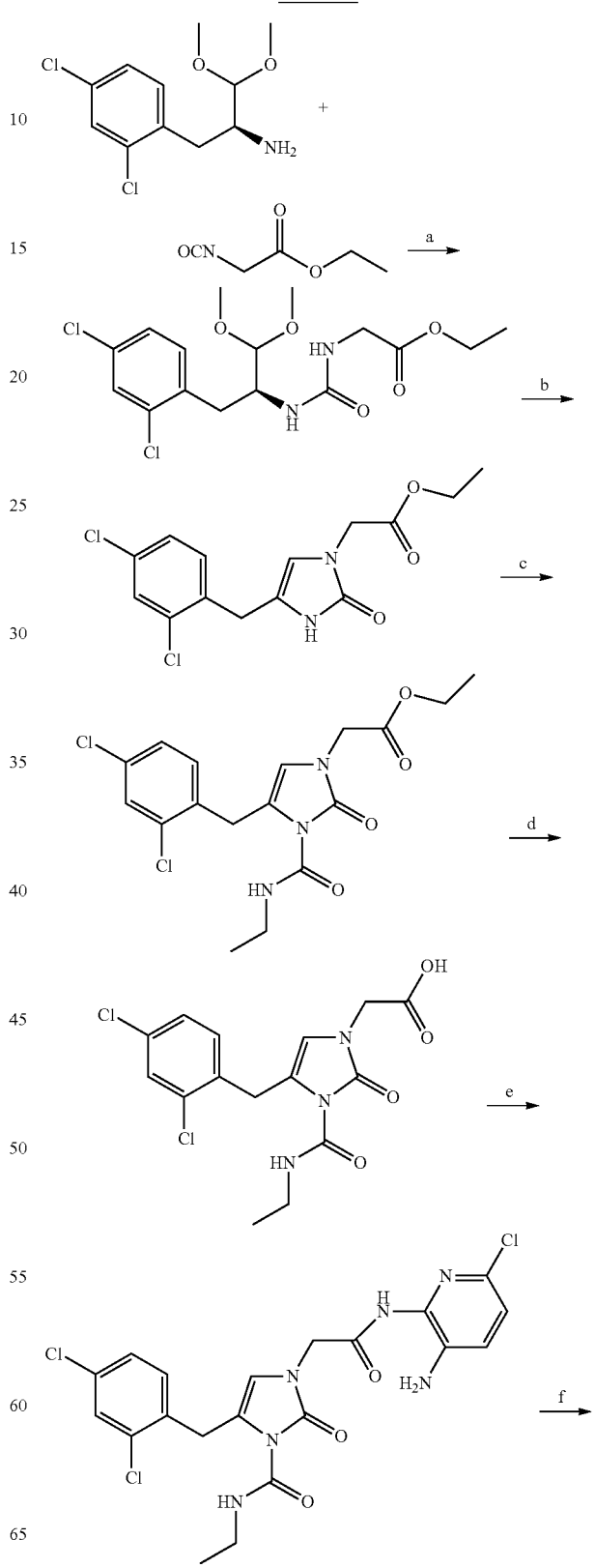

-continued

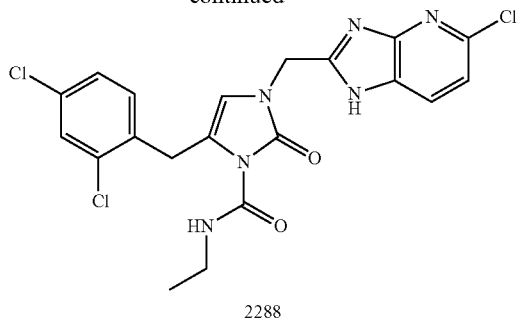

2288

Reagents and conditions (a) DCM; (b) HCOOH, 50° C.; (c) Cs₂CO₃, ethyl isocyanate, 0° C.; (d) LiOH; (e) HATU, DIPEA, 6-chloropyridine-2,3-diamine; (f) HOAc, microwave irradiation.

A solution of 1-(2,4-Dichloro-benzyl)-2,2-dimethoxyethylamine (0.159 mmol) from Scheme 6 in anhydrous DCM was added DIPEA (28 µl, 0.159 mmol) and ethyl isocyanatoacetate (18.2 µl, 0.159 mmol) at 0° C. The mixture was stirred at 0° C. for 20 min then room temperature for 1.5 h. Purification by chromatography afforded {3-[1-(2,4-Dichloro-benzyl)-2,2-dimethoxy-ethyl]-ureido}-acetic acid ethyl ester (51.7 mg, 0.132 mmol). {3-[1-(2,4-Dichloro-benzyl)-2,2-dimethoxy-ethyl]-ureido}-acetic acid ethyl ester (51.7 mg, 0.132 mmol) in formic acid was stirred at 50° C. overnight. After solvent was removed, the residue was purified using silica gel chromatography, eluted with MeOH/DCM to give [4-(2,4-Dichloro-benzyl)-2-oxo-2,3-dihydro-imidazol-1-yl]-acetic acid ethyl ester (36 mg, 0.109 mmol). [4-(2,4-Dichloro-benzyl)-2-oxo-2,3-dihydro-imidazol-1-yl]-acetic acid ethyl ester (11 mg, 0.033 mmol) was dissolved in 2 ml anhydrous DMF and treated with ethyl isocyante (4 µl, 0.05 mmol) and cessium carbonate (33 mg, 0.101 mmol) at 0° C. The mixture was stirred for 30 min at 0° C. After the reaction solvent was evaporated, the residue was purified by flash chromatography on silica gel (dichloromethane/methanol) to obtain [4-(2,4-Dichloro-benzyl)-3-ethylcarbamoyl-2-oxo-2,3-dihydro-imidazol-1-yl]-acetic acid ethyl ester (8.1 mg, 0.020 mmol).

[4-(2,4-Dichloro-benzyl)-3-ethylcarbamoyl-2-oxo-2,3-dihydro-imidazol-1-yl]-acetic acid ethyl ester (8.1 mg, 0.020 mmol) was added in 1 ml of ethanol and 2 ml of water, mixed with LiOH (2 mg, 0.08 mmol) and stirred for 80 min at room temperature. The solution was neutralized with 0.2 N hydrochloric acid and the solvent was completely removed in vacuo. The residue was dissolved in 2 ml of DMF, then HATU (9 mg, 0.024 mmol), DIPEA (10 µl, 0.06 mmol) and 6-chloropyridine-2,3-diamine (4.4 mg, 0.03 mmol) were added. The mixture was stirred at room temperature overnight. The solvent was removed on the rotary evaporator. The residue was dissolved in EtOAc (30 ml) and washed with water and brine. The organic layer was dried over Na₂SO₄ and concentrated in vacuo. The residue was purified by flash chromatography on silica gel to give 3-[(3-amino-6-chloro-pyridin-2-ylcarbamoyl)-methyl]-5-(2,4-dichloro-benzyl)-2-oxo-2,3-dihydro-imidazole-1-carboxylic acid ethylamide. 3-[(3-Amino-6-chloro-pyridin-2-ylcarbamoyl)-methyl]-5-(2,4-dichloro-benzyl)-2-oxo-2,3-dihydro-imidazole-1-carboxylic acid ethylamide was dissolved in 2 ml of acetic acid and the solution was microwave irradiated at 125° C. for 1 h. After the solvent was removed, the residue was purified by flash column chromatography on silica gel (DCM/MeOH), giving 5 mg of 2288 (3-({5-chloro-1H-imidazo[4,5-b]pyridin-2-yl}methyl)-5-[(2,4-dichlorophenyl)methyl]—N-ethyl-2-oxo-2,3-dihydro-1H-imidazole-1-carboxamide). LC/MS: (ESI) (M+H)⁺=480.9

Examples 157-162

The following compounds were prepared substantially according to the procedures described above.

| Ex. No | Compd. | Structure | Name |
|---|---|---|---|
| 157 | 2218 | 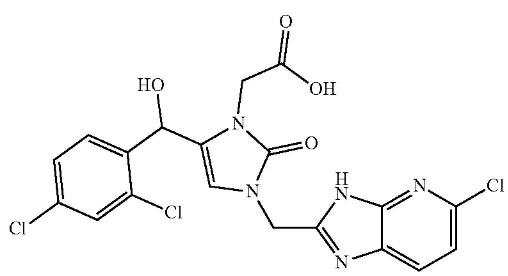 [SMILES: O=C(O)Cn1c(C(O)c2ccc(Cl)cc2Cl)cn(Cc2nc3ccc(Cl)nc3[nH]2)c1=O] | 2-(3-((5-chloro-3H-imidazo[4,5-b]pyridin-2-yl)methyl)-5((2,4-dichlorophenyl)(hydroxy)methyl)-2-oxo-2,3-dihydro-1H-imidazol-1-yl)acetic acid |
| 158 | 2217 | 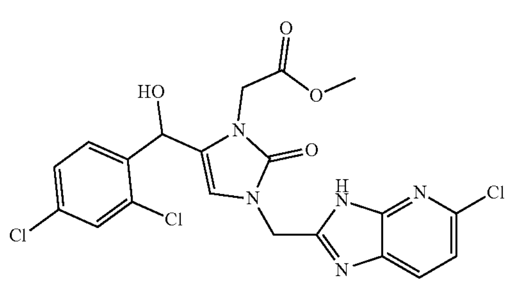 [SMILES: COC(=O)Cn1c(C(O)c2ccc(Cl)cc2Cl)cn(Cc2nc3ccc(Cl)nc3[nH]2)c1=O] | methyl 2-(3-((5-chloro-3H-imidazo[4,5-b]pyridin-2-yl)methyl)-5-((2,4-dichlorophenyl)(hydroxy)methyl)-2-oxo-2,3-dihydro-1H-imidazol-1-yl)acetate |

-continued

| Ex. No | Compd. | Structure | Name |
|---|---|---|---|
| 159 | 2214 | 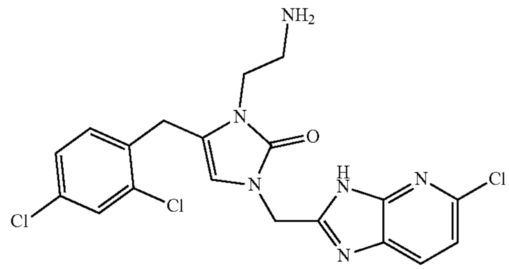 [SMILES: NCCn1c(Cc2ccc(Cl)cc2Cl)cn(Cc2nc3ccc(Cl)nc3[nH]2)c1=O] | 3-(2-aminoethyl)-1-((5-chloro-3H-imidazo[4,5-b]pyridin-2-yl)methyl)-4-(2,4-dichlorobenzyl)-1,3-dihydro-2H-imidazol-2-one |
| 160 | 2211 | 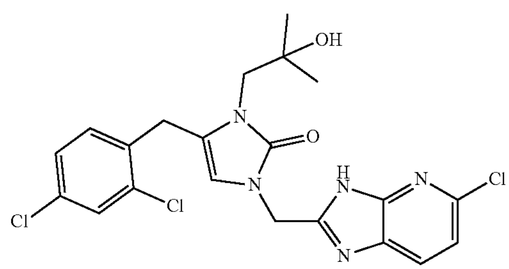 [SMILES: CC(C)(O)Cn1c(Cc2ccc(Cl)cc2Cl)cn(Cc2nc3ccc(Cl)nc3[nH]2)c1=O] | 1-((5-chloro-3H-imidazo[4,5-b]pyridin-2-yl)methyl)-4-(2,4-dichlorobenzyl)-3-(2-hydroxy-2-methylpropyl)-1,3-dihydro-2H-imidazol-2-one |
| 161 | 2203 | 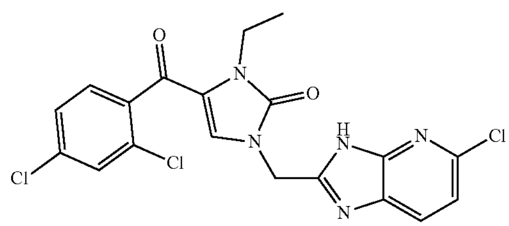 [SMILES: CCn1c(C(=O)c2ccc(Cl)cc2Cl)cn(Cc2nc3ccc(Cl)nc3[nH]2)c1=O] | 1-((5-chloro-3H-imidazo[4,5-b]pyridin-2-yl)methyl)-4-(2,4-dichlorobenzoyl)-3-ethyl-1,3-dihydro-2H-imidazol-2-one |
| 162 | 2226 | 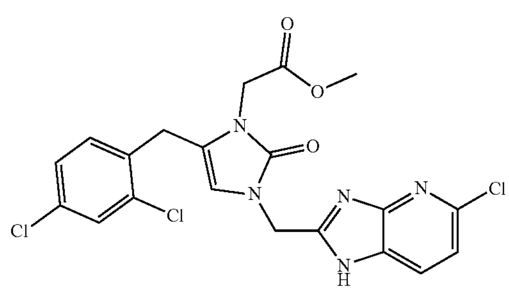 [SMILES: COC(=O)Cn1c(Cc2ccc(Cl)cc2Cl)cn(Cc2nc3nc(Cl)ccc3[nH]2)c1=O] | 1-({5-chloro-1H-imidazo[4,5-b]pyridin-2-yl}methyl)-4-[(2,4-dichlorophenyl)methyl]-3-[(1-hydroxycyclopropyl)methyl]-2,3-dihydro-1H-imidazol-2-one |

Example 163

Materials and Methods

Sequence alignments. Global pairwise amino acid sequence alignments were generated with NCBI alignment tool, CLUSTAL omega.

Media and culture conditions. Mueller Hinton broth (MHB), cation adjusted Mueller Hinton broth (CA-MHB), and Brain Heart Infusion broth (BHI) were purchased from Becton Dickinson (Franklin Lakes, N.J.). Tryptic soy agar (TSA) plates, TSA with 5% sheep blood plates, and CA-MHB with 3% laked horse blood were purchased from Remel (San Diego, Calif.). MHB was used to assay all *Staphylococcus aureus* strains. CA-MHB was used for *Staphylococcus epidermidis, Enterococcus faecalis, Enterococcus faecium, Escherichia coli*, and *Pseudomonas aeruginosa*. CA-MHB supplemented with 3% laked horse blood was used for *Streptococcus pneumoniae* and *Streptococcus pyogenes*. *Staphylococcus, Enterococcus, Escherichia*, and *Pseudomonas* strains were cultured at 37° C. with ambient air. *Streptococcus* strains were cultured in 37° C. with 5% $CO_2$. Separate conditions for radiolabeled precursor uptake assays are described below.

Compounds, reagents, and radiochemicals. The synthesis methods for the following compounds have been previously described: 1312, 1575, 1614, 1717, and 1962 (structures shown below). 1312, 1575, 1614, and 1717 were described in Shibata et al. 2011. *Antimicrob.Agents Chemother.* 55:1982-1989, and Zhang et al. 2016. *ACS Infect.Dis.* 2:399-404. 1962 was described in Faghih et al. 2017. *Antimicrob. Agents Chemother.* 61:e00999-17, and International Patent Publication No. WO 2016/029146.

1312 (2-((3-((3,5-dichlorobenzyl)amino)propyl)amino)quinolin-4(1H)-one):

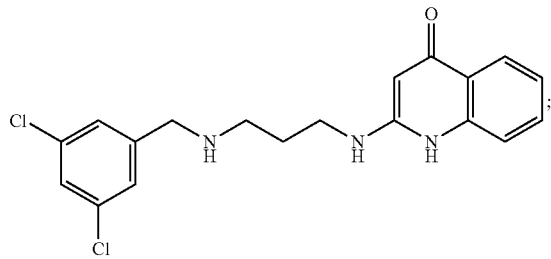 [SMILES: O=c1cc(NCCCNCc2cc(Cl)cc(Cl)c2)[nH]c2ccccc12]

1575 (N1-(3,5-dichlorobenzyl)—N3-(1H-imidazo[4,5-b]pyridin-2-yl)propane-1,3-diamine):

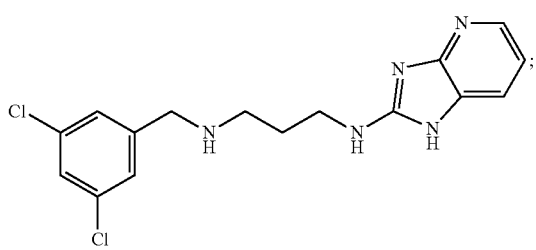 [SMILES: Clc1cc(Cl)cc(CNCCCNc2nc3ncccc3[nH]2)c1]

1614 ([(3,5-dichlorophenyl)methyl][3-({5-fluoro-3H-imidazo[4,5-b]pyridin-2-yl}amino)propyl]amine):

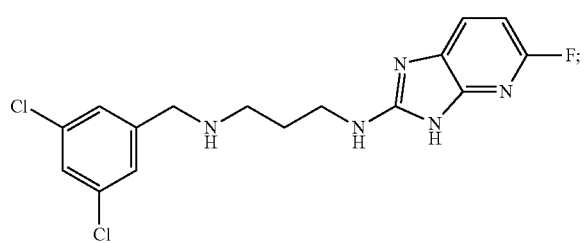 [SMILES: Fc1ccc2nc(NCCCNCc3cc(Cl)cc(Cl)c3)[nH]c2n1]

1717 ((4R)-6,8-dichloro—N-[3-({5-fluoro-3H-imidazo[4,5-b]pyridin-2-yl}amino)propyl]-1,2,3,4-tetrahydroquinolin-4-amine):

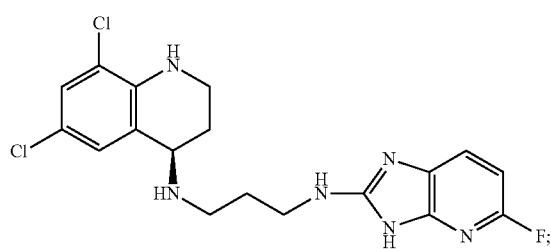 [SMILES: Fc1ccc2nc(NCCCN[C@@H]3CCNc4c(Cl)cc(Cl)cc43)[nH]c2n1]

and 1962 (4-(2,4-dichlorobenzyl)-1-((5-fluoro-3H-imidazo[4,5-b]pyridin-2-yl)methyl)-1,3-dihydro-2H-imidazol-2-one):

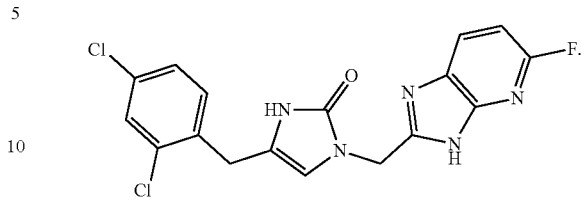

The following antibiotics were purchased commercially: vancomycin (Sigma-Aldrich, St. Louis, Mo.), linezolid (Chem-Impex International, Wood Dale, Ill.), rifampicin (Chem-Impex International, Wood Dale, Ill.), ciprofloxacin (Acros Organics, Geel, Belgium), and novobiocin (Promega, Madison, Wis.). Ketoprofen was purchased from Sigma Aldrich (St. Louis, Mo.). Human pooled serum was purchased from Thermo Fisher Scientific (Waltham, Mass.). Dulbecco's phosphate buffered saline with calcium and magnesium (dPBS) was purchased from Lonza (Basel, Switzerland). [Methyl-3H]-thymidine (2% EtOH, 69.7 Ci/mmol) and [5,6-3H]-uridine (sterile water, 60 Ci/mmol) were purchased from American Radiolabeled Chemicals (St. Louis, Mo.). L-[4,5-3H(N)]-lysine (2% EtOH, 82.4 Ci/mmol) was purchased from PerkinElmer (Waltham, Mass.).

Production of recombinant *S. aureus* MetRSs. The SaMetRS gene (UniProtKB—A0A0H$_2$XID2) was PCR amplified (Sense 5'-GGGTCCTGGTTCGGCTAAAGAAA-CATT CTATATAACAACCCCAATATAC-3' (SEQ ID NO: 1) and Antisense 5'-CTTGTTCGTGC TGTTTATTATT-TAATCACTGCACCATTTGGAATTG-3' (SEQ ID NO:2)) from genomic DNA isolated from *S. aureus* (ATCC 29213) cultures. The PCR product was then cloned into the AVA0421 plasmid and sequence verified. The expression of recombinant protein was performed as previously described. The N-terminal 6-His fusion proteins were purified by nickel affinity chromatography followed by size exclusion gel chromatography (Superdex 75 26/60; GE Biosciences, Piscataway, N.J.).

Enzyme assays. Inhibition of SaMetRS was measured using the ATP depletion assay as previously described with some modifications. Compounds were pre-incubated for 15 minutes at room temperature in a 96-well plate with 400 µg/mL bulk *E. coli* tRNA, 25 nM SaMetRS, 0.1 U/mL pyrophosphatase, 0.2 mM spermine, 0.1 mg/mL bovine serum albumin, 2.5 mM dithiothreitol, 25 mM HEPES-KOH pH 7.9, 10 mM MgCl$_2$, 50 mM KCl, and 2% DMSO. Reagents were purchased from Sigma-Aldrich or Roche. The reaction was started with the addition of 150 nM ATP and 20 µM L-methionine and after 120 minute incubation was stopped by the addition of an equal volume (50 µL) of Kinase-Glo® (Promega). Percent inhibition=100×(test compound−AVG low control)/(AVG high control−AVG low control) where the low control is all reagents except the compound and the high control is all reagents except the compounds and L-methionine. IC$_{50}$ values were calculated by non-linear regression, sigmoidal-dose response, in Prism 3.0.

Bacterial strains. Strains with ATCC designations were either obtained directly from the American Type Culture Collection (Manassas, Va.) or were kindly provided by the University of Washington Clinical Microbiology laboratory. *Escherichia coli* permeability mutants (properties shown in Table 1) were provided as a gift from Dr. Katherine Young at Merck (Rahway, N.J.).

TABLE 1

Properties of E. coli strains

| Strain | Relevant markers | Reference |
|---|---|---|
| MB4827 | wt for outer membrane permeability and efflux | Young K and Silver L. L. 1991. Leakage of periplasmic enzymes from envA1 strains of |
| MB4902 | lpx::Tn10 | Escherichia coli. J. Bacteriol. 173: 3609-3614 |
| MB5746 | lpxC, tolC::Tn10 | Kodali et al. 2005. Determination of selectivity and efficacy of fatty acid synthesis inhibitors. J.Biol.Chem. 280: 1669-1677 |
| MB5747 | tolC::Tn10 | |

Macromolecular synthesis assays: Methods for measuring uptake of radiolabeled precursors by S. aureus (ATCC strain 29213) were adapted from previous publications. For these assays, bacteria were grown in defined media (DM): RPMI-1640 pH 7.3±0.1 without phenol red or L-glutamine (Lonza, Basel, Switzerland) supplemented with 4 mM L-glutamine (Lonza, Basel, Switzerland), 10 mM HEPES (Lonza, Basel, Switzerland), and 1% (w/v) D-glucose (Sigma Aldrich, St. Louis, Mo.). Fresh overnight cultures grown in DM at 37° C. were diluted 1:50 in pre-warmed DM and grown at 37° C. with shaking (150 rpm) until reaching an $OD_{600}$ of 0.420 correlating to ~1*10$^9$ CFUs/mL in mid-log phase. Each compound was assayed in quadruplicate with an 11-point three-fold serial dilution per radioisotope. A pre-warmed 96-well V-bottom plate (Corning 3894; Corning, Corning, Mass.) containing 25 μL of 4× final concentration of test compound was inoculated with 65 μL of mid-log phase bacteria ($OD_{600}$ of 0.420). Both positive and negative control wells received 25 μL untreated DM and 65 μL of inoculum at the same time. After one minute, 10 μL of radiolabeled precursor (10× final concentration in DM) was added to samples and positive control wells. Final isotope concentrations for assay of [3H]-lysine (protein), [3H]-thymidine (DNA), and [3H]-uridine (RNA) were 10 μCi/mL, 2 μCi/mL, and 2 μCi/mL respectively. The plates were incubated at 37° C. for 25 minutes and terminated by the addition of 50 μL of 30% trichloroacetic acid (TCA)/70% ethanol to all test and control wells. After termination, 10 μL of 10× radiolabeled precursor was added to negative control wells. The negative control consisted of adding radiolabeled precursors after termination of the bacterial incubation in order to represent background measurement of the isotope. Plates were sealed with plate tape (Thermo Fischer Scientific, Waltham, Mass.) and shaken at 250 rpm for one hour at room temperature. Aliquots of 125 μL were transferred from the 96-well V-bottom plates to 96-well filter plates (Merck Millipore, Billerica, Mass.). To bind macromolecules, the samples were passed through the filter membrane (0.45 μM hydrophilic Durapore PVDF membrane) with a vacuum manifold, then the filter was washed with 4×200 μL 10% TCA and 1×150 μL of 95% ethanol, and dried overnight in vacuum at room temperature. 25 μL Ultima Gold scintillation fluid (Perkin Elmer, Waltham, Mass.) was added to each well and DPM was quantified using a MicroBeta$^2$-2450 (Perkin Elmer, Waltham, Mass.) scintillation counter. The percent incorporation was determined by subtracting each well by the average negative background and dividing by the average positive incorporation×100. Error bars represent SEM between replicates. The assay was run twice with similar results.

Susceptibility testing: Minimum inhibitory concentration (MIC) determinations were performed in triplicate in 96-well round bottom microtiter plates (Corning, Corning N.Y.) as described by the Clinical and Laboratory Standards Institute (CLSI). Serial two-fold dilutions of compounds were added to plates in 50 μL volumes. An additional 50 μL of media containing bacterial cells (1×10$^6$ CFUs/mL) was then added to each well. Maximum DMSO concentrations were 0.5%. Plates were incubated at 37° C. for at least 18 h before reading the susceptibility result by optical absorbance ($OD_{600}$) using a BioTek ELx800. The lowest concentration causing ≥90% growth inhibition compared to the untreated control was recorded as the MIC (and also corresponded to the visual MIC). MICs were measured at least twice and the higher value (if different) was recorded herein.

MBC determinations (defined as the concentration killing 99.9% of the inoculum) were performed according to published methods. Using glass tubes (16×100-mm), serial twofold dilutions of 2× compound were generated from DMSO stocks in singlicate 1 mL volumes. Maximum DMSO concentrations were 0.5%. An additional 1 mL of media with 1*10$^6$ CFUs/mL was added per sample. Each experiment's inoculum was serially diluted and plated on TSA to count competent cells. Cultures were incubated at 37° C. for at least 20 h and plated on TSA for CFU determination. Additionally, each concentration was sampled after the 20 h incubation for MIC determination as above.

Cytotoxicity testing on mammalian cells: Compounds were assayed for cytotoxicity against CRL-8155 (human lymphoblasts) and HepG2 cells (human hepatocellular carcinoma). Cells were exposed to serial dilutions of compounds for 48 hours and toxicity was quantified using AlamarBlue (ThermoFisher Scientific, Waltham, Mass.). Assays were performed in quadruplicate and $EC_{50}$ values were calculated with non-linear regression methods using software by the Collaborative Drug Database (Burlingame, Calif. www.collaborativedrug.com)

Resistance frequency rates determination: The spontaneous resistance frequency rates to test compounds was determined according to published methods. Agar selection plates were made by adding compound from DMSO stocks into molten Mueller Hinton agar in a 55° C. water bath. Each compound used four plates (P5981-100EA, 150×15 mm; Sigma Aldrich, St. Louis, Mo.) containing 8× the MIC of the compound. The final DMSO concentration was <0.1% per plate. Plates were dried in a sterile hood for 30 minutes prior to overnight storage at 4° C., and pre-warmed in the 37° C. incubator for 1 hour prior to assay.

A fresh overnight culture was diluted 1:50 in MHB and grown at 37° C. with shaking (150 rpm) until reaching an $OD_{600}$ of 0.4 correlating to ~2×10$^9$ CFUs/mL. Approximately 3 mL for a total of 6*10$^9$ CFUs were distributed onto 4 plates for each compound. Plates were incubated at 37° C. for 72 h prior to counting of colonies. The starting inoculum was also serially diluted and plated to quantify initial bacterial load. The resistance frequency was determined as the number of compound-resistant colonies divided by the total colonies plated.

Serum shift assays: To assess the role of protein binding on compound susceptibility, MIC determinations were performed in triplicate in the presence and absence of 50% human serum. Serial threefold dilutions of 2× compound were generated in MHB and aliquoted onto 96 well plates with a DMSO limit of 0.5%. Bacteria were adjusted to 1*10$^8$ CFUs/mL in MHB, then further diluted 1:100 in MHB and 100% heat deactivated filter sterilized pooled human serum. Fifty microliters were added to each well of the corresponding plates, and the plates were incubated at 37° C. for ~20 h. The lowest concentration causing ≥90% growth inhibition was recorded as the MIC.

Protein binding assays: Compound binding to mouse plasma proteins was determined using 96-well equilibrium dialyzer plates (SDIS 9610EN, Nest Group, Inc.). Mouse plasma (MSEPLLIHP-SW-F, BioreclamationIVT, Westbury, N.Y.) containing compound (final concentration 1 µM) was added to a donor chamber as a 150 µL volume. The buffer solution (0.2 mM phosphate buffer, 150 µL) was added to the reciprocal acceptor chamber. Each compound was tested in triplicate. To prepare calibration solution for compound quantifications, blank wells were prepared containing only mouse plasma in a donor well and buffer solution in its acceptor well. The equilibrium dialysis was carried out by rocking the plate for 22 hours in 37° C. Once equilibrium was reached, the plasma and buffer solution from both wells were carefully removed for further analysis with liquid chromatography-tandem mass spectrometry. Plasma solution and internal standard were mixed in the presence of 80% acetonitrile. After centrifuging the solution, the supernatant was transferred to an insert. Similarly, the buffer solution from the acceptor side was prepared containing 40% acetonitrile. Calibration standards for donor and acceptor sides were prepared with compound concentrations of 50 nM, 100 nM, 250 nM, 500 nM, and 1 µM. The compound concentrations from each well were calculated from the calibration curves using Microsoft Excel. The percentage of the test compound bound was determined as follows:

% Free=(Concentration buffer chamber/Concentration plasma chamber)×100%

% Bound=100%−% Free

Microsome stability. Liver microsome stability assays were done by contract research laboratory, Wuxi AppTec Co. (Hubei, China). Briefly, compounds at 1 µM concentration were incubated in singlet with human or CD-1 mouse liver microsomes for 6 time points (0, 5, 10, 20, 30, and 60 min). Loss of parent compound was quantified by liquid chromatography/tandem mass spectrometry.

Murine pharmacokinetics studies. The methods were performed as previously described. Briefly, test compounds were administered to mice by oral gavage (3 mice per compound) followed by tail blood sampling at intervals of 30, 60, 120, 240, 360, 480, and 1440 min. Blood samples were analyzed by extracting dried blood spots in acetonitrile for measurements of compound concentrations by liquid chromatography/tandem mass spectrometry.

Murine thigh infection model. Animal studies were approved by the Institutional Animal Care and Use Committee at the University of Washington, Seattle. Female specific pathogen free CD1 mice were obtained from Charles River (Wilmington, Mass.) weighing 23-27 grams and allowed at least 3 days to acclimate prior to study. Mice had access to food and water ad libitum. Neutropenia was induced by administering cyclophosphamide monohydrate (Sigma Aldrich C7397; St. Louis, Mo.) via IP injection 4 days (at 150 mg/kg) and 1 day (at 100 mg/kg) prior to infection. Neutropenic status was confirmed by neutrophil count <100 cells/mm$^3$.

Overnight culture of *S. aureus* (ATCC strain 29213) was diluted 1:100 in MHB and incubated until reaching mid-log phase ($OD_{600}$<0.750). The inoculum was prepared by pelleting log-phase culture and re-suspending in sterile dPBS. The culture was adjusted to $OD_{600}$ of 0.200 and diluted 1:100 in sterile dPBS correlating to an inoculum of ~5*10$^5$ CFU/50 µL. The mice were infected by an intramuscular injection of 50 µL in the right posterior thigh while under isoflurane gas anesthesia. At 1 h post infection, one vehicle group was sacrificed for determination of initial inoculum (status level of infection). Mice were dosed at 2 and 12 h post-infection with test compounds (below); they received a SC dose of 5 mg/kg ketoprofen at 2 h post-infection for pain management. Mice were sacrificed at 24 h post-infection; the thigh muscle was sterilely removed, weighed, homogenized in 5 mLs dPBS, serially diluted, plated on tryptic soy agar in duplicate, and incubated overnight at 37° C. Colonies were counted to quantify the bacterial load in CFUs per gram of thigh tissue.

Vancomycin was given at 100 mg/kg SC in 100 µL in a 0.9% saline solution. Linezolid was administered 75 mg/kg PO in 200 ul of 0.5% methylcellulose, cP400 (Sigma Aldrich, St. Louis, Mo.), 0.5% Tween80 (Sigma Aldrich, St. Louis, Mo.) in distilled water. Test compounds were administered PO in 200 µL of vehicle containing 60% Phosal 53 MCT (Lipoid, Ludwigshafen Germany), 30% PEG400 (Sigma Aldrich, St. Louis, Mo.), and 10% EtOH (Decon Laboratories, King of Prussia, Pa.).

Example 164

Protein sequence analysis. Using coordinates from the *T. brucei* MetRS complex with inhibitor 1312 (PDB #4EG5), the residues in the binding site of the inhibitor were aligned for various species (Table 2). The *S. aureus* MetRS (UniProtKB—A0A0H$_2$XID2, strain USA300) has extremely high sequence conservation with the *Trypanosoma brucei* MetRS with 22 of 25 identical amino acids (and potentially 23 identical amino acids since position 456 could either be a Leu or His, but is ambiguous in the model due to loop length). This confirms that many inhibitors of the *T. brucei* MetRS will likely inhibit the *S. aureus* MetRS. MetRS from the human mitochondrial MetRS was compared with the *S. aureus* sequence and identified four different amino acid residues (at positions 249, 291, 470, and 471). Three of these changes occur in pocket q that binds the quinolone moiety of 1312.

TABLE 2

| | | | | | | | | | | | | |
|---|---|---|---|---|---|---|---|---|---|---|---|---|
| Inhibitor binding site amino acid residues for MetRS enzymes ||||||||||||| 
| Seq. No.[a] | 247 | 248 | 249 | 250 | 287 | 289 | 290 | 291 | 292 | 456 | 460 | 461 |
| Pocket[b] | b | b | B | L | q | q | q | q | q | q | q | q |
| *T. brucei* | Pro | Ile | Tyr | Tyr | Asp | His | Gly | Gln | Lys | Leu | Ala | Ile |
| *S. aureus* | Pro | Ile | Tyr | Tyr | Asp | His | Gly | Gln | Lys | | Gly | Val/Ile* |
| *H. sapiens* - mitochondrial | Pro | Ile | Phe | Tyr | Asp | His | Gly | Leu | Lys | | Gly | Ile |

TABLE 2-continued

Inhibitor binding site amino acid residues for MetRS enzymes

| Seq. No.[a] | 470 | 471 | 472 | 473 | 474 | 476 | 477 | 478 | 480 | 481 | 519 | 522 | 523 |
|---|---|---|---|---|---|---|---|---|---|---|---|---|---|
| Pocket[b] | q | q | q | Q | B | q | b | b | b | b | b | B | b |
| T. brucei | Cys | Val | Tyr | Val | Trp | Asp | Ala | Leu | Asn | Tyr | Ile | Phe | His |
| S. aureus | Val | Val | Tyr | Val | Trp | Asp | Ala | Leu | Asn | Tyr | Ile | Phe | His |
| H. sapiens/mito | Thr | Ile | Tyr | Val | Trp | Asp | Ala | Leu | Asn | Tyr | Ile | Phe | His |

[a] Sequence numbers refer to the T. brucei sequence;
[b] l = linker zone, b = benzyl pocket, q = quinolone pocket.
*This residue is Val in all S. aureus sequences in UNIPROT except for A0A033UAT9 (strain C0673), where it is an Ile.
¶ Due to a different loop length it is unclear what the equivalent residue is.

Example 165

MetRS inhibitors and lead optimization. The aminoquinolone scaffold exemplified by 1312 was originally reported by investigators at GlaxoSmithKline to have potent activity on Gram positive bacteria but had poor oral bioavailability. This restricted development of 1312 (pre—New Drug Application) to topical use for skin infections and to oral use for Clostridium difficile infection where oral absorption was not needed. In separate research to develop MetRS inhibitors as antiprotozoan drugs, the evolution of this compounds included changing the aminoquinolone group to a fluorinated-imidazopyridine (e.g. 1614) that improved oral bioavailability. Subsequent changes to the linker region reported previously have further optimized potency and pharmacological properties of the series. The results of testing the MetRS inhibitors against recombinant S. aureus MetRS, bacterial cultures, and mammalian cells are shown in Table 3. All compounds tested had $IC_{50}$ values on the S. aureus MetRS below the level of sensitivity of the assay (25 nM). The MetRS inhibitors have potent activity on a variety of Gram positive bacterial strains, but essentially no activity on Gram negative bacteria (E. coli and Pseudomonas aeruginosa). Potent activities were documented against strains of S. aureus (including MSSA, MRSA, and VISA), S. epidermidis, E. faecalis, and E. faecium (including VSE and VRE strains). The compounds with the lowest MICs were 1717, 2093, and 2144 which were >10-times more potent than the control drugs vancomycin or linezolid against many strains. These compounds are the subject of further investigations discussed below. Higher MICs were seen against S. pyogenes and no activity seen on S. pneumoniae. The selectivity on Staphylococci versus mammalian cells (comparing MIC to $CC_{50}$) was at least 35-fold for these three most potent compounds.

TABLE 3

Assay results of representative MetRS inhibitors. The second column shows the $IC_{50}$ values against recombinant S. aureus MetRS enzyme.

| Cmpd Name | MetRS S. aureus (enzyme) $IC_{50}$ (μM)* | S. aureus MSSA (ATCC 29213) MIC (μg/ml) | S. aureus MSSA (ATCC 19636) MIC (μg/ml) | S. aureus MRSA (ATCC 43300) MIC (μg/ml) | S. aureus MRSA (ATCC 33591) MIC (μg/ml) | S. aureus VISA (ATCC 700699) MIC (μg/ml) | E. faecalis (ATCC 29212) MIC (μg/ml) |
|---|---|---|---|---|---|---|---|
| 1312 | <0.025 | 2.5 | | 5 | | | 0.313 |
| 1575 | <0.025 | 10 | | >10 | | | 1.25 |
| 1614 | <0.025 | 2.5 | 2.5 | 5 | 5 | 10 | 1.25 |
| 1717 | <0.025 | 0.156 | 0.078 | 0.156 | 0.078 | 0.156 | 0.078 |
| 1962 | <0.025 | 2.5 | | 5 | | | 5 |
| 2062 | <0.025 | 0.078 | | | | | 1.25 |
| 2093 | <0.025 | 0.039 | 0.313 | 0.313 | 0.313 | 0.313 | 0.156 |
| 2114 | <0.025 | 0.313 | | | | | 0.625 |
| 2144 | <0.025 | 0.0195 | 0.078 | 0.039 | 0.039 | 0.039 | 0.0195 |
| VAN | >10.0 | 1.25 | 1.25 | 1.25 | 1.25 | 10 | 5 |
| CIP | >10.0 | 0.156 | 0.078 | 0.156 | 0.313 | >10 | 1.25 |
| LNZ | >10.0 | 2.5 | 1.25 | 2.5 | 1.25 | 1.25 | 2.5 |

| Cmpd Name | E. faecium (ATCC 19434) MIC (μg/ml) | E. faecium VRE (ATCC 51559) MIC (μg/ml) | S. epidermidis (ATCC 49134) MIC (μg/ml) | S. epidermidis (ATCC 12228) MIC (μg/ml) | S. pyogenes (ATCC 19615) MIC (μg/ml) | S. pneumoniae (ATCC 49619) MIC (μg/ml) |
|---|---|---|---|---|---|---|
| 1312 | 0.156 | 0.156 | | | | |
| 1575 | | 0.625 | | | >10 | >10 |
| 1614 | 0.625 | 0.625 | 10 | 5 | >10 | >10 |
| 1717 | 0.039 | 0.156 | 0.313 | 0.156 | 2.5 | >20 |
| 1962 | 1.25 | 1.25 | | | | |
| 2062 | 0.313 | 0.313 | 1.25 | | | |
| 2093 | 0.078 | 0.078 | 1.25 | 0.625 | 1.25 | >20 |
| 2114 | 0.078 | 0.156 | 1.25 | 1.25 | | |
| 2144 | 0.0195 | 0.0195 | 0.313 | 0.156 | 1.25 | >20 |
| VAN | 0.625 | >10 | 2.5 | 2.5 | 0.625 | 0.313 |

TABLE 3-continued

Assay results of representative MetRS inhibitors. The second column shows the $IC_{50}$ values against recombinant *S. aureus* MetRS enzyme.

| CIP | 5 | 5 | 0.313 | 0.156 | 0.625 | 1.25 |
|---|---|---|---|---|---|---|
| LNZ | 2.5 | 1.25 | 0.625 | 0.625 | 1.25 | 1.25 |

| Cmpd Name | *E. coli* (ATCC 25922) MIC (µg/ml) | *P. aeruginosa* (ATCC 27853) MIC (µg/ml) | Mamm. cells (CRL8155) CC50 (µg/ml) | Mamm. cells (HepG2) CC50 (µg/ml) |
|---|---|---|---|---|
| 1312 | | | >7.5 | >7.5 |
| 1575 | >10 | >10 | 12.2 | >17.5 |
| 1614 | >10 | >10 | 14.8 | >18.4 |
| 1717 | >10 | >10 | 5.8 | 10.4 |
| 1962 | | | >19.6 | >19.6 |
| 2062 | | | >21.0 | >21.0 |
| 2093 | | | >21.6 | >21.6 |
| 2114 | | | >20.8 | >20.8 |
| 2144 | | | >11.3 | >11.3 |
| VAN | | | >145 | >145 |
| CIP | 0.039 | 0.313 | >33 | >33 |
| LNZ | | | >33.7 | >33.7 |

*Lower limit of detection for assay is 0.025 µM. (All the listed inhibitors have low- or subnanomolar activity on the SaMetRS enzyme).
Abbreviations: CIP (ciprofloxacin), LNZ (linezolid), MSSA (methicillin sensitive *Staphylococcus aureus*), MRSA (methicillin resistant *Staphylococcus aureus*), VAN (vancomycin), VISA (vancomycin intermediate *Staphylococcus aureus*).

TABLE 4

MICs (µg/mL) of selected MetRS inhibitors against "permeability strains" of *E. coli*

| Comd. | MB4827 (wild-type) | MB4902 (lpxC) | MB5747 (tolC) | MB5746 (lpxC, tolC) |
|---|---|---|---|---|
| 1717 | >20 | >20 | >20 | >20 |
| 2093 | >20 | >20 | >20 | >20 |
| 2144 | >20 | >20 | >20 | >20 |
| CIP | 0.0156 | 0.0078 | 0.0078 | 0.0078 |

Example 166

Microbiological Characterization of Selected Compounds.

Macromolecular synthesis assays: In order to verify that the compounds are acting by the expected mechanism of action, radioisotope incorporation assays were performed (FIG. 1). Incorporation of the amino acid ($^3$H-Lysine) was profoundly inhibited by the MetRS inhibitors (1717, 2093, and 2144), consistent with inhibition of protein synthesis. The findings were similar to those seen with linezolid (FIG. 1, panel A) which is known to inhibit protein synthesis by interfering with the bacterial ribosome. In contrast, the MetRS inhibitors had less effect on both the incorporation of $^3$H-uridine (a measure of RNA synthesis) and the incorporation of $^3$H-thymidine (a measure of DNA synthesis). Ciprofloxacin showed selective inhibition of DNA synthesis (panel B) consistent with its mechanism as an inhibitor of DNA topoisomerases. Finally, rifampicin showed selective inhibition of RNA synthesis (panel C) consistent with its mechanism as an inhibitor of bacterial RNA polymerase.

Activity on permeable *E. coli* strains: The purpose of these experiments was to determine if the non-susceptibility of Gram negative strains (e.g. *E. coli* ATCC 25922, shown in Table 3) was due to inability of the MetRS inhibitors to penetrate the Gram-negative cell wall. The mutant MB4902 is an outer membrane permeable *E. coli* strain and showed no greater susceptibility to three MetRS inhibitors (1717, 2093, and 2144) than to the wild-type *E. coli* strain (MB4827). Similarly, the efflux negative strain MB5747 showed no increased susceptibility to the MetRS inhibitors, nor did the mutant containing both mutations (MB5746).

MIC/MBC: Measurements of minimum bactericidal concentrations (MBCs) were done with the *S. aureus* strain ATCC 29213 (Table 5). The MBC is defined as the drug concentration that reduces bacterial growth by ≥99.9%. Compounds exhibiting an MBC/MIC ratio of ≤4 are generally considered bactericidal, while an MBC/MIC ratio >4 is considered bacteriostatic. The data indicates that 1717, 2093, and 2144 have bacteriostatic activity similar to linezolid.

TABLE 5

MICs and MBCs against *S. aureus* (ATCC 29213)

| Molecule name | MIC (µg/mL) | MBC (µg/mL) | MBC/MIC ratio | Published mechanism* |
|---|---|---|---|---|
| 1717 | 0.156 | 5 | 32 | |
| 2093 | 0.078 | 1.25 | 16 | |
| 2144 | 0.010 | 0.313 | 32 | |
| LNZ | 2.5 | 160 | 64 | Static |
| VAN | 1.25 | 5 | 4 | Cidal |
| NOV | 0.156 | 5 | 32 | Static |
| CIP | 0.313 | 1.25 | 4 | Cidal |

*Mandell, G. L., J. E. Bennett, and R. Dolin. 2010. Principles and Practice of Infectious Diseases. Churchill Livingston Elsevier Resistance frequency rates: The propensity for *S. aureus* to develop resistance to MetRS inhibitors was also studied (Table 6). This was done by plating high numbers ($3.8 \times 10^9$ in Expt. 1 and $5.5 \times 10^9$ in Expt. 2) of *S. aureus* on TSA plates impregnated with compound at concentrations of 8× the MIC and incubating for 72 h. The resistance frequency rates for 1717, 2093, and 2144 were in the range of $2 \times 10^{-8}$ to $4 \times 10^{-9}$. These rates are comparable to test drug novobiocin, but higher than the rates found for ciprofloxacin or linezolid.

TABLE 6

Resistance frequency rates occurring at 8× the MIC (two independent experiments and average)

| Compound | Resistance frequency (Expt. 1) | Resistance frequency (Expt. 2) | Resistance frequency (average or greater #) |
|---|---|---|---|
| NOV | ND | $1.58 \times 10^{-8}$ | $1.58 \times 10^{-8}$ |
| CIP | $<2.63 \times 10^{-10}$ | $<1.81 \times 10^{-10}$ | $<2.63 \times 10^{-10}$ |
| LNZ | $<2.63 \times 10^{-10}$ | $<1.81 \times 10^{-10}$ | $<2.63 \times 10^{-10}$ |
| 1717 | $2.89 \times 10^{-9}$ | $5.43 \times 10^{-9}$ | $4.16 \times 10^{-9}$ |
| 2093 | $1.60 \times 10^{-8}$ | $2.58 \times 10^{-8}$ | $2.10 \times 10^{-8}$ |
| 2144 | $3.15 \times 10^{-9}$ | $2.45 \times 10^{-8}$ | $1.38 \times 10^{-8}$ |

Serum shift and protein binding assays. Serum shift assays were done to analyze the impact of protein binding on the MICs (Table 7). The MIC shifts in the presence of 50% human serum are significant for the MetRS inhibitors which is consistent with high protein binding (e.g. 95.4% for 1717). Although the shifts are much higher than the shift for vancomycin (1.7-fold), the absolute MICs for some compounds in serum (e.g. 1717 and 2144) are still comparable to that of vancomycin (in the range of 2 µg/mL).

TABLE 7

Serum shift assays.

| Compd. | # expts | Avg MIC ± SEM (no serum) µg/mL | Avg MIC ± SEM (+50% serum) µg/mL | Avg Fold-shift of MIC | % binding to mouse plasma | % binding to human plasma |
|---|---|---|---|---|---|---|
| VAN | 10 | 0.714 ± 0.05 | 1.213 ± 0.12 | 1.7 | 25 (49) | 55* |
| NOV | 8 | 0.081 ± 0.02 | 12.913 ± 1.97 | 158.6 | | 95* |
| LNZ | 2 | 1.575 ± 0.1 | 1.89 ± 0.1 | 1.2 | 39.5 | 31* |
| CIP | 2 | 0.145 ± 0.001 | 0.152 ± 0.01 | 1.0 | | |
| 1614 | 2 | 2.47 ± 0.35 | 42.7 ± 4.1 | 17.3 | 96.5 | |
| 1717 | 7 | 0.088 ± 0.02 | 2.066 ± 0.19 | 23.5 | 97.6 | 95.4 |
| 2062 | 2 | 0.057 ± 0.004 | 11.77 ± 4.03 | 208.1 | 99.4 | |
| 2069 | 2 | 0.036 ± 0.03 | 18.3 ± 2.2 | 506.9 | 99.6 | |
| 2093 | 2 | 0.036 ± 0.01 | 9.59 ± 1.71 | 267.9 | 99.9 | |
| 2144 | 2 | 0.036 ± 0.01 | 2.055 ± 0.51 | 56.5 | 98.4 | |

*Data from Drugbank (www.drugbank.ca)

Example 167

Pharmacological studies: Compounds were incubated with murine or human liver microsomes to evaluate stability to hepatic metabolic enzymes (Table 8).

TABLE 8

Molecular weights, calculated Log P scores, and liver microsome stability half-lives.

| Compd. | MW (g/mol) | cLog P | Microsome stability: Human T½ (minutes) | Microsome stability: Mouse T½ (minutes) |
|---|---|---|---|---|
| 1614 | 368.24 | 3.73 | 9.8 | 6.6 |
| 1717 | 409.29 | 3.15 | 10.3 | 10.3 |
| 1962 | 392.21 | 3.69 | 25.86 | 26.96 |
| 2062 | 420.27 | 4.23 | 12.6 | 8.4 |
| 2093 | 432.30 | 3.76 | 8.3 | 3.2 |
| 2114 | 415.85 | 3.47 | 15.2 | 7.7 |
| 2144 | 454.31 | 4.18 | 16.4 | 6.5 |

Pharmacokinetics studies: Selected compounds were administered to mice in single oral doses at 50 mg/kg and tail blood was sampled at time intervals out to 24 h to assess blood exposure (Table 9).

TABLE 9

Mouse pharmacokinetics

| Compd. | Mouse Oral PK DBS: Dose Concentration (mg/kg) | Mouse Oral PK DBS: Average Cmax (µg/mL) | Mouse Oral PK DBS: Average $AUC_{(0-24\ h)}$ (min*µg/mL) | Mouse Oral PK DBS: Vehicle Composition |
|---|---|---|---|---|
| 1717 | 50 | 1.47 ± 0.53 | 942 ± 354 | 60% Phosal 53 MCT, 30% PEG400, 10% EtOH |
| 2093 | 50 | 7.57 ± 2.29 | 1222 ± 267 | 60% Phosal 53 MCT, 30% PEG400, 10% EtOH |
| 2114 | 50 | 5.45 ± 0.75 | 899 ± 71 | 60% Phosal 53 MCT, 30% PEG400, 10% EtOH |
| 2144 | 50 | 8.95 ± 1.38 | 3791 ± 1440 | 60% Phosal 53 MCT, 30% PEG400, 10% EtOH |
| LNZ | 50 | 26.5 ± 15.2 | 5661 ± 768 | 0.5% methylcellulose, 0.5% Tween80 in distilled water |

Example 168

Efficacy studies in mice: Selected compounds were tested for in vivo efficacy in the neutropenic *S. aureus* thigh infection model (9). Mice were immunosuppressed with cyclophosphamide then infected in a thigh with 5×10⁵ *S. aureus* (ATCC 29213). Compounds were dosed orally with 75 mg/kg at 2 and 12 h post-infection. At 24 h, thighs were harvested for CFU counts. MetRS inhibitors (1717 and 2144) resulted in a ~3-4-log decrease in CFUs compared to the vehicle group, similar to vancomycin and linezolid (FIG.

2). Note the drop is below the stasis level which was determined by harvesting a group of mice at 1 hour post-infection.

Discussion of Examples 163-168

The essential enzyme, methionyl-tRNA synthetase, was targeted for antibiotic drug discovery against Gram positive bacteria. The research capitalizes on progress to develop antimicrobial agents against pathogenic protozoa including *Trypanosoma brucei* and *Giardia intestinalis*. In particular, challenges with poor oral bioavailability observed with early aminoquinolone compounds such as 1312 were dramatically improved with the fluoroimidazopyridine derivatives (1614-2144). Compounds of this scaffold were optimized for activity against the *T. brucei* MetRS (a type 1 enzyme). The comparison of the protein sequences of the MetRS enzymes of *T. brucei* and *S. aureus* shows identity of 22 of 25 amino acid residues in the inhibitor binding site (Table 2) suggesting that cross activity from *T. brucei* to *S. aureus* was likely. In fact, all the compounds tested for inhibitory activity against recombinant *S. aureus* MetRS enzyme (Table 3) demonstrated $IC_{50}$ values below 25 nM, the sensitivity limit of the assay. Further titration below this concentration was not possible with the applied methods due to the need for 25 nM enzyme to give a suitable signal for measurement. The assays against live bacterial cultures demonstrated the excellent potency of the MetRS inhibitors against *S. aureus* and other Gram positive bacteria (Table 3). Of the compounds with the "linear linker" structure (e.g., 1312-1717), compound 1717 was the most potent with a MIC of 0.156 µg/mL. Guided by the crystal structures of MetRS, the ring systems to the "linker" region of the scaffold were introduced (e.g. 1962-2144) and this led to two compounds (2093 and 2144) with even lower MIC values against *S. aureus* (Table 3). Compound 2093 contains a single ring in the linker (an imidazole-2-one) whereas compound 2144 contains a fused imidazo[1,2-a]pyridine ring system in the linker region.

The spectrum of activity of the MetRS inhibitors was explored against ATCC strains of pathogenic Gram positive and Gram negative bacteria. As was predicted, the antibiotic activity is restricted to bacteria dependent upon the type 1 MetRS enzyme, i.e. Gram positive bacteria. Gram negative bacteria (i.e., *Escherichia coli* and *Pseudomonas aeruginosa*), which are known to contain the type 2 MetRS enzyme, were insensitive to all the tested compounds at the highest concentration of 10 µg/mL. The selectivity for Gram positive organisms is potentially advantageous in that the MetRS inhibitor developed as a drug will not add to resistance of non-targeted Gram negative bacteria. Sensitive Gram positive strains were *S. aureus, Enterococcus faecium, Enterococcus faecalis,* and *Staphylococcus epidermidis*. Furthermore, these included drug-resistant strains such as MRSA, VISA, and VRE whose mechanisms of resistance to semisynthetic penicillins and glycopeptide antibiotics are unrelated to the cellular processes inhibited by the MetRS inhibitors. The MICs of the MetRS inhibitors to *S. pyogenes* (ATCC 19615) was higher than to *S. aureus* and *Enterococcus* strains, which likely is due to the need to grow *S. pyogenes* in media containing lysed blood. The effects of plasma protein binding on MICs of the compounds is shown in Table 7. With the shift observed with blood, the MIC for 2144 (1.25 µg/mL) is about the same as MICs observed with vancomycin and linezolid (0.625 and 1.25 µg/mL). The gram positive coccus, *Streptococcus pneumoniae* (ATCC 49619), was resistant to the MetRS inhibitors (MICs >10 µg/mL). This is consistent with previous reports that ~45% of *S. pneumoniae* strains are resistant to type 1 MetRS inhibitors due to the presence of a second (type 2) MetRS inhibitor in the genome. It is likely that MetRS inhibitors would need to be used with caution for treatment of pneumonia or other clinical syndromes in which *S. pneumoniae* is commonly found, at least until cultures rule out *S. pneumoniae* as the cause of the infection. Future studies will investigate a broader collection of *S. pneumoniae* isolates to assess the MIC range against this pathogen. The issue of a secondary MetRS gene has not been described in other Gram positive bacteria, so this is unlikely to be a broader concern. It is expected that MetRS inhibitors will be active against many other bacteria containing the type 1 MetRS enzyme including species of *Clostridia, Corynebacterium, Bacillus, Propionibacterium, Actinomyces*, and others. Various species of these are, of course, pathogenic in humans and their susceptibility will be tested in future studies. An exception to the Gram positive rule mentioned above is *Brucella* (a Gram negative rod) which is known to contain a type 1 MetRS and is susceptible to MetRS inhibitors.

In order to address the question about target of action in living bacteria, macromolecular synthesis assays were run with MetRS inhibitors and various control drugs (FIG. 1). As was expected, MetRS inhibitors resulted in rapid dose-dependent decreases in uptake of radiolabeled amino acid (Lys) consistent with disruption of protein synthesis. The changes were similar to those seen with the protein synthesis inhibitor, linezolid. At the same time, effects on RNA and DNA synthesis were not affected by MetRS inhibitors until concentrations above the MIC were used while the control drugs, rifampicin and ciprofloxacin, caused inhibition of these pathways, respectively, in the anticipated manner. These studies provide assurance that the compounds are likely to be mediating their antibiotic effects through inhibiting the MetRS target in vivo.

In a similar vein, selected MetRS inhibitors were tested on strains of *E. coli* with defects in cell wall permeability and/or efflux (Table 4). The purpose of these experiments was to show that resistance of *E. coli* was not due to exclusion of the MetRS inhibitors by the Gram negative cell wall or efflux, but rather due to inherent resistance. The findings that the cell permeable strains were resistant to the three most potent MetRS inhibitors (1717, 2093, and 2144) is consistent with the understanding that *E. coli* contains a type 2 MetRS enzyme which is not inhibited by the compounds under development. Furthermore, it indicates that off target mechanisms of action are not at play, at least with this species of bacteria.

Minimum bactericidal concentrations of 1717, 2093, and 2144 were determined against the *S. aureus* ATCC 29213 strain. The MBC/MIC ratio was between 16 and 32 for these three compounds. A ratio of 4 or less is considered bactericidal thus the MetRS inhibitors would be considered bacteriostatic against this strain of *S. aureus*. An MBC/MIC ratio of 64 was observed with the clinical drug linezolid (known to be bacteriostatic), whereas the ratio for vancomycin was 4, consistent with its bactericidal mechanism.

Resistance frequency rates of *S. aureus* (ATCC 29213) to MetRS inhibitors were determined on agar plates containing MetRS inhibitors at concentrations 8-times times their MICs. The resistance frequency rates for MetRS inhibitors were between $2\times10^{-8}$ and $4\times10^{-9}$ which is higher than observed for ciprofloxacin and linezolid (Table 6). Resistance frequency rates in the $10^{-6}$ to $10^{-9}$ range are indicative of a single drug target within the cell which is consistent with the understanding of the mechanism of action of these compounds. Drugs such as rifampicin have even higher rates ($2\times10^{-7}$), but are generally used in combination with other drugs to avoid generating resistance. Vancomycin and linezolid are known to have low resistance frequency rates ($<10^{-11}$) and, along with this characteristic, relatively little resistance (at least from Staphylococci) has developed in the clinic. Further research will be necessary to find out if the rates of resistance to MetRS inhibitors are problematic for their clinical development as monotherapy agents. If the risk for resistance developing appears high, then developing the compounds with a partner antibiotic may be an attractive option to mitigate the problem.

The MetRS inhibitors characterized in this report exhibit high protein binding properties (95-99.9%). The low unbound concentration of compounds translates to substantial effects when MICs are measured in the presence of serum (Table 7). Serum shifts ranging from 17-fold to 507-fold were observed with the series of tested compounds. For perspective, vancomycin only demonstrates about a 1.7-fold serum shift (Table 7) whereas fusidic acid is reported to have 97% protein binding and a 130-fold increase in MIC to S. aureus in the presence of 50% serum. Due to the remarkable potency of the MetRS inhibitors, the MIC of compound 2144 in the presence of 50% serum (2.06 µg/mL) is comparable to the MIC for vancomycin (1.21 µg/mL).

Incubation of the MetRS inhibitors with mouse or human liver microsomes showed variable rates of metabolism, although generally half-lives were relatively short (<20 min for human microsomes and <10 min for mouse) (Table 8). However, presumably due to high protein binding, the plasma levels in mice were rather good following oral dosing at 50 mg/kg (Table 9). For 1717 and 2144, the maximum plasma concentrations were approximately 1.5 and 9 µg/mL, respectively, followed by sustained levels above 1 ug/mL for at least 8 hours. As will be discussed with the efficacy results, the combined properties of the compounds (particularly 1717 and 2144) appear to be sufficient to clear bacteria from infected mice with similar efficiency as vancomycin or linezolid.

The results of the efficacy experiments are very encouraging towards the prospects of developing MetRS inhibitors as antibiotics. A pilot experiment (not shown) and two independent experiments showed the reproducibility of the S. aureus thigh infection model in mice made neutropenic by cyclophosphamide pre-treatment. The model represents a soft tissue infection which resembles the disease process (skin and skin structure infection) for which clinical development of the compounds would initially be targeted. Both compounds 1717 and 2144 demonstrated significant reduction of bacterial load below the stasis level at least as effectively as the comparator drugs vancomycin and linezolid. The approximately 2-log reduction below stasis levels in a neutropenic mouse is noteworthy in light of the bacteriostatic activity observed in vitro (Table 5). This shows that tissue levels at the site of infection were sufficient to substantially reduce bacteria levels even in the absence of neutrophils. Many bacteriostatic antibiotics (including linezolid) are widely and successfully used in the clinic, so the bacteriostatic characteristic of the MetRS inhibitors may not be a significant liability. Interestingly, compound 2093 was found to have weaker activity than the other MetRS inhibitors evaluated. The explanation probably relates to the particularly high protein binding of this compound that presumably reduce the levels of unbound compound below the threshold needed to exceed the MBC at the site of infection. Future dose response experiments will help determine the relative potency of 1717 and 2144 compared to each other and additional MetRS inhibitors under development.

Figure 3:
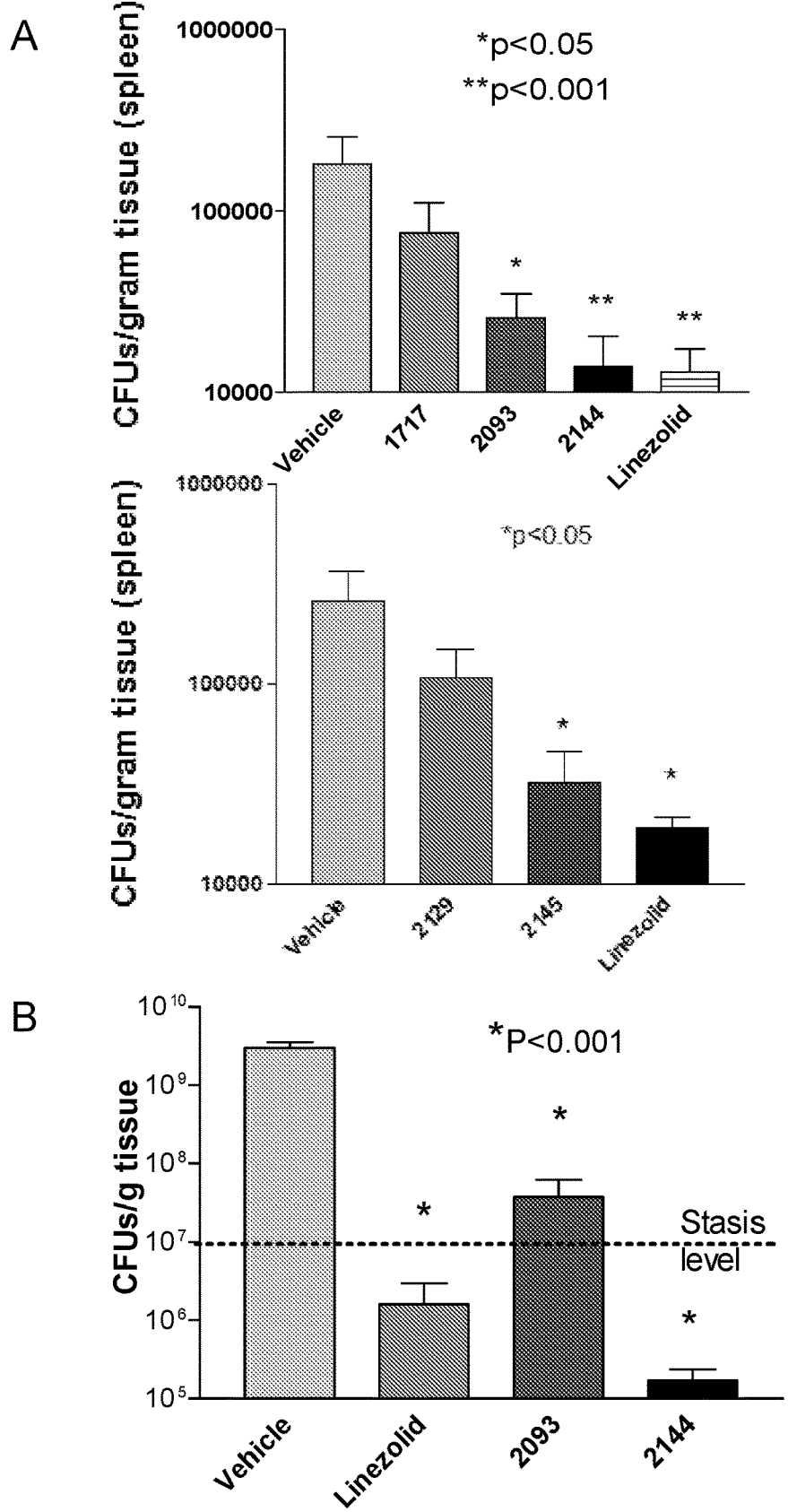
FIG. 3 illustrates efficacy of MetRS inhibitors in neutropenic mouse *S. aureus* thigh infection model. Error bars are SEMs. (A) Activity of MetRS inhibitors and linezolid in two different experiments. The MetRS inhibitors were given at 75 mg/kg by oral gavage×2 doses (1 h and 12 h post-infection). Spleens harvested at 24 h p.i. (B) Mice were immunosuppressed with cyclophosphamide then infected in a thigh with 5×10$^5$ *S. aureus* (ATCC 29213). Compounds were dosed orally with 75 mg/kg at 2 and 12 h post-infection. At 24 h, thighs were harvested for CFU counts. Stasis level determined from untreated mice sacrificed 1 hr p.i.

Additional compounds of the disclosure were tested in S. aureus thigh infection model, and these results are illustrated in FIG. 3.

To date, no apparent side-effects of the MetRS inhibitors given to mice were observed. In this study, uninfected mice received single dose (50 mg/kg) of compounds for PK analysis had no acute reactions during the 24 hour observation period. In a previous publication, compounds 1614 and 1717 were administered to mice infected with T. brucei for 10 days at 50 mg/kg PO twice-per-day with no deleterious effects on weight, grooming, or body condition. Cytotoxicity against mammalian cells was low for the MetRS inhibitors (Table 3). For example, the ratio of $CC_{50}$ to MIC for compounds 2093 and 2144 were >500 demonstrating a wide therapeutic window. A potential toxicity concern for the MetRS inhibitors is inhibition of the mammalian mitochondrial MetRS enzyme which bears close homology to the S. aureus MetRS (Table 2). Manifestations of this potential toxicity have not been evident with in vitro cytotoxicity testing (the 48 h assay against a lymphocyte and hepatocyte cell lines) nor in mice as described above. Many antibiotics acting as protein synthesis inhibitors are known to inhibit mitochondrial protein synthesis as an off-target effect. These include widely used drugs such as tetracycline, erythromycin, aminoglycosides, and linezolid. Instead of directly affecting mitochondrial oxidative phosphorylation, these drugs interfere with mitochondrial biogenesis and are relatively slow to result in clinical problems, often with tissue specific toxicity depending on the particular drug. Linezolid for example is known to cause hematologic disturbances, peripheral neuropathy, and metabolic acidosis when it is administered for more than a 28-day period. The fact that these side effects are slow to manifest makes them more tolerable for antibiotics since treatment course are typically relatively short (<10 days). Studies of the effects on MetRS inhibitors on mammalian mitochondrial function will be part of future investigations.

With the aid of structure-based drug design, the disclosure provides new MetRS inhibitors having potent and broad spectrum activity against bacteria and protozoa. Macromolecule labeling studies demonstrate the inhibition of protein synthesis, consistent with the designed mechanism of action. As with other protein synthesis inhibitors such as oxazolidinones, tetracyclines, and lincosamides, the MetRS inhibitors have bacteriostatic properties against S. aureus in vitro. The compounds are highly protein bound which may help sustain plasma levels in vivo by limiting availability to CYP metabolism. The MetRS inhibitors of the disclosure displayed excellent activity in the neutropenic mouse thigh infection model (comparable to linezolid) which indicates that the free fraction of compound is sufficient to inhibit bacterial growth. In fact, the bacterial load decreased by 1-2 logs below the status level indicating that the in vivo activity was not just bacteriostatic, but bactericidal. These studies and previous reports have shown that the MetRS inhibitors have little in vitro toxicity and appear well-tolerated when dosed to mice for up to 10 days. The MetRS inhibitor compounds of the disclosure having good oral bioavailability represent a class of compounds acting by a novel mechanism with excellent potential for clinical development.

Example 169: Additional In Vitro Data

The compounds of the disclosure were further evaluated according to the methods disclosed above. The complete results are provided in Table 10, where column (A) represents results in MetRS (*T. brucei*) $IC_{50}$ (nM), column (B) represents results in MetRS (*S. aureus*) $IC_{50}$ (nM), column (C) represents results in MetRS (*C. parvum*) $IC_{50}$ (nM), column (D) represents results in *T. brucei* $EC_{50}$ (nM), column (E) represents results in *T. cruzi* $EC_{50}$ (nM), column (F) represents results in *S. aureus* (ATCC 29213) MIC (μg/ml), column (G) represents results in MRSA (ATCC33591) MIC (μg/mL), column (H) represents results in *S. pyogenes* (ATCC 19615) MIC (μg/ml), column (I) represents results in *E. faecium* (ATCC 51559) MIC (μg/ml), column (J) represents results in *C. parvum* $EC_{50}$ (μM), and column (K) represents results in *G. lamblia* (ATCC GL50803) $EC_{50}$ (μM).

TABLE 10

| Compd. Name | (A) | (B) | (C) | (D) | (E) | (F) | (G) | (H) | (I) | (J) | (K) |
|---|---|---|---|---|---|---|---|---|---|---|---|
| 2056 | <40 | | 195 | 242 | 3723 | | | | | | |
| 2062 | <40 | <25 | <40.0 | <9.08, 3.48, 3.15, 3.48 | 85.22, 98.87, 90.84 | 0.0527, 0.161, 0.0521, 0.0610 | | | 0.0464, 0.269 | | |
| 2067 | <40 | <25 | <40.0 | <0.91, 1.76, 2.16, 1.31, 1.55, 1.28 | 16.66, 32.29 | 5.80E-03, 2.85E-03, 3.39E-03, <3.05E-03 | 1.35, 1.16 | >2.00, 0.792 | >2.00 | 0.610, 0.205 | 0.67 |
| 2068 | <40 | | <40.0 | 40.18 | 1002.93 | | | | | | |
| 2069 | <40 | <25 | <40.0 | <0.91, 5.13, 6.45, 3.78 | 91.31, 176.49 | 0.0976, 0.0106, 0.0193, 0.0616, 0.173 | 0.445 | | >2.00 | 0.599, 0.223 | |
| 2070 | <40 | | <40.0 | 3.80, 7.57, 9.41 | 132.62 | 0.0609, 0.0371 | | | 0.0246 | >2.000 | |
| 2071 | <40 | | <40.0 | 6.16, 22.37, 20.39 | 525.81 | >2.50 | | | | >2.000 | |
| 2077 | <40 | <25 | <40.0 | 1.35, 3.47 | 215.02 | 0.818 | >2.50 | | | 0.475, 0.283 | |
| 2079 | <40 | <25 | <40.0 | <0.91, 1.79 | 25.96, 22.52 | 0.0440, 0.0391 | >2.50 | | | | |
| 2080 | <40 | | <40.0 | 1.01, 3.52 | 220.42 | 0.999 | 1.4 | | | 0.610, 0.434 | 3.85 |
| 2081 | <40 | | <40.0 | <0.91, 3.55 | 437.9 | 1.33 | | | | | |
| 2082 | <40 | <25 | <40.0 | <0.91, 2.01 | 145.02 | 0.18 | 1.54 | | 0.238 | | |
| 2084 | <40 | | <40.0 | 4.93, 20.33 | 607.94 | 2.04 | | | | | |
| 2085 | <40 | | <40.0 | 4.56, 9.03 | 513.81 | 1.71 | | | | 0.834, 0.683 | |
| 2086 | <40 | | 41.2 | 5.94, 7.64 | 552.1 | 0.964 | >2.50 | | | | |
| 2087 | <40 | <25 | <40.0 | 1.18, 4.85 | 358.77 | 0.254 | 1.67 | | | | |
| 2088 | <40 | <25 | <40.0 | <0.91, 3.48 | 262.93 | 0.424 | 1.5 | | | | |
| 2091 | <40 | <25 | <40.0 | 2.8 | 58.95, 40.62 | 0.199 | >2.50 | | | 0.598 | |
| 2092 | <40 | | 47.5 | 11.65, 32.80 | 501.96 | >2.50 | | | | | |
| 2093 | <40 | <25 | <40.0 | <0.91, 0.41, 0.52, 1.21, 0.85, 1.11, 1.92, 1.97 | 8.28, 5.81 | <0.0391, 0.0207, 0.102, 0.0221, 0.0483 | 0.123, 0.225 | 0.678 | 0.0507, 0.0387 | 0.038, 0.033 | 0.01 |
| 2102 | <40 | <25 | <40.0 | 2.60, 6.63 | 421.94 | 1.48 | | | >2.00 | | |
| 2103 | 63 | | 175.4 | 112.73 | 2928.81 | | | | | | |
| 2104 | <40 | | 40.3 | 73.39 | 1480.43 | | | | | | |
| 2105 | <40 | <25 | 108.8 | 71.46 | 867.2 | 2.15 | | | | | |
| 2109 | <40 | | <40.0 | 53.52 | 329.07 | | | | | | |
| 2110 | <40 | <25 | 98.6 | 19.4 | 177.61 | 0.795 | 2.36 | >4.00 | 1.99 | 1.27 | |
| 2111 | <40 | <25 | 145.5 | 54.59 | 445.37 | 1.25 | | | | | |
| 2112 | <40 | | <40.0 | 9.56 | 176.1 | 0.254 | 0.405 | | | 0.62 | |
| 2113 | 2000 | | >1000.0 | 1932.84 | | | | | | | |
| 2114 | <40 | <25 | <40.0 | 1.4 | 25.90, 23.23 | 0.129, 0.192 | 1.53 | 0.754 | 0.0328, 0.130 | 0.053 | |

TABLE 10-continued

| Compd. Name | (A) | (B) | (C) | (D) | (E) | (F) | (G) | (H) | (I) | (J) | (K) |
|---|---|---|---|---|---|---|---|---|---|---|---|
| 2119 | <40 | <25 | <40.0 | 17.95, 29.34 | 195.86 | 0.285 | 1.04 | >2.00, >8.00 | 0.727 | 0.480, 0.633 | 0.06 |
| 2120 | <40 | <25 | <40.0 | 13.57 | 295.26 | 1.26 | | >4.00 | 0.336 | 1.23 | |
| 2121 | 41 | | 476.2 | 1343.07 | | | | | | | |
| 2122 | <40 | <25 | <40.0 | 58.54 | 703.16 | 0.419 | 0.909 | >2.00, 4.38 | 0.263 | 0.976, 0.597 | 0.22 |
| 2126 | 40 | | >1000.0 | 1780.15 | | | | | | | |
| 2127 | 63 | | >1000.0 | >2000.00 | | | | | | | |
| 2128 | <40 | <25 | <40.0 | 3.62, 3.40 | 5.88, 10.81 | <0.0195, 0.0166, 0.0509 | 0.0311, 0.0974 | | 0.24 | 1.68 | |
| 2129 | <40 | <25 | <40.0 | 5.33, 11.84 | 102.48, 82.05 | <0.0195, <508E−06, 0.0566 | <9.77E−03, 0.0830 | | 0.0467, 0.0131 | 0.696, >2.000, 2.000 | |
| 2130 | 190 | | >1000.0 | 195.78 | | | | | | | |
| 2131 | 325 | | 806.1 | 197.03 | | | | | | | |
| 2132 | <40 | | 656.4 | 507.96 | | | | | | | |
| 2133 | <40 | | 354.1 | 848.53 | | | | | | | |
| 2134 | <40 | <25 | 58.8 | 63.98 | 685.11 | 0.162 | 0.268, 0.331 | | 0.259 | | |
| 2135 | <40 | <25 | 56.7 | 99.34 | 2156.52 | 0.592 | | | 1.33 | | |
| 2138 | <40 | <25 | <40.0 | 2.46, 3.48 | 26.74, 53.10 | 0.062 | 0.553 | | 0.596 | 0.276, 0.632 | |
| 2139 | <40 | <25 | <40.0 | 3.21 | 85.36, 190.20 | 0.0776 | 0.307 | | | 0.193 | |
| 2142 | <40 | | 89.4 | 489.02 | | | | | | | |
| 2143 | <40 | | 96.6 | 805.76 | | | | | | | |
| 2144 | <40 | <25 | 40.9 | 2.38, 5.72, 2.36, 2.44, 2.69, 3.06 | 7.79, 13.54 | <0.0195, 0.00725, 0.0143, 0.0200, 0.0236, 0.0274, 0.0439 | 0.0216, 0.0330 | 1.09, 0.504 | 0.0140, 0.0126 | >2.000 | |
| 2145 | <40 | <25 | 74.7 | 6.82, 3.67, 11.77, 6.32 | 66.73, 128.66 | 0.0537, 0.0222, 0.0291, 0.0189, 0.0423 | 0.342, 0.0220, 0.0948 | | 0.110, 0.0289, 0.0143 | >2.000 | |
| 2146 | <40 | <25 | 92.4 | 1.71, 11.20 | 19.52, 29.70 | 0.0281, 0.0939, 0.286 | 0.127, 0.165, 0.179 | | 0.141 | 1.99 | |
| 2148 | 60 | | 992.9 | >2000.00 | | | | | | | |
| 2149 | 45 | | >1000.0 | >2000.00 | | | | | | | |
| 2150 | <40 | | 468.5 | 896.59 | | | | | | | |
| 2151 | <40 | | 614 | 364 | | | | | | | |
| 2156 | <40 | | <40.0 | 32.02 | 319.17 | 1.10, 0.946 | 0.285 | | 1.49 | 1.29 | |
| 2157 | <40 | | 107.2 | >200.00 | | | | | | | |
| 2161 | <40 | | 251.9 | 1050.44 | | | | | | | |
| 2162 | <40 | | 90.4 | 174.81 | | | | | | | |
| 2164 | 143 | | >1000.0 | 1909.37 | | | | | | | |
| 2165 | <40 | | 325.5 | >200.00 | | | | | | | |
| 2166 | <40 | 177 | >1000.0 | >200.00 | 596.3 | >1.25 | | | >2.50 | | |
| 2167 | 203 | | 504.8 | >2000.00 | | | | | | | |
| 2168 | <40 | <25 | <40.0 | >200.00 | 6145.1 | >1.25 | | | >2.50 | | |
| 2169 | <40 | | <40.0 | <0.91, 3.10, 9.19, 1.50 | 23.62, 55.22 | 0.259 | | | | 0.144, 0.195 | 0.01 |
| 2170 | <40 | | <40.0 | 64.48 | 1333.62 | | | | | 1.78 | |
| 2171 | <40 | | 75.3 | 28.98 | 302.41 | 1.16 | 1.87 | | | | |
| 2172 | <40 | | <40.0 | 29.29, 35.03 | 212.53 | 1.69, 0.898 | 1.32 | | 0.467 | 0.830, >2.000, 1.900 | |
| 2173 | 57 | | 185 | >2000.00 | | | | | | | |
| 2174 | <40 | <25 | <40.0 | 3.16, 9.29 | 195.15 | 0.158 | 0.319 | | 0.318 | 1.19 | |
| 2175 | 72.00, <40 | | 41.7 | 108.77, 61.04, 361.07 | 680.63, 638.02 | | | | | | |
| 2176 | <40 | <25 | 80 | 40.65 | 282.6 | >0.500 | >2.50 | | | | |
| 2177 | <40 | | <40.0 | 92.48 | 408.57 | | | | | | |
| 2178 | 116 | | 881 | 5662.92 | | | | | | | |
| 2179 | <40 | | 76 | 183.46 | | | | | | | |
| 2180 | <40 | | <40.0 | 18.49 | 178.63 | 0.362 | 0.515 | | 0.357 | 0.656, 0.640 | |

TABLE 10-continued

| Compd. Name | (A) | (B) | (C) | (D) | (E) | (F) | (G) | (H) | (I) | (J) | (K) |
|---|---|---|---|---|---|---|---|---|---|---|---|
| 2181 | <40 | | 52.9 | 61.06 | 537.66 | | 0.822 | | 0.694 | | |
| 2182 | <40 | | 42.1 | 84.01 | 647.48 | | | | | | |
| 2183 | <40 | | <40.0 | <0.91, 3.57, 5.92 | 115.76 | 0.245 | | | | 0.629 | |
| 2184 | <40 | <25 | <40.0 | <0.91, 3.23 | 29.27, 23.15 | 0.201 | 0.435 | | 0.286 | 0.719 | |
| 2185 | <40 | <25 | <40.0 | <0.91, 8.79 | 71.57, 90.90 | 0.358 | 1.2 | | | 0.243 | |
| 2186 | 59 | | 49.2 | 24.99 | 359.9 | 3.80, 3.21 | | | | | |
| 2187 | 117 | | 112.7 | >2000.00 | | | | | | | |
| 2188 | <40 | | 443 | 808.02 | | | | | | | |
| 2189 | <40 | | <40.0 | 7.9 | 155.96 | 0.676 | 0.596 | | 0.704 | 2 | |
| 2190 | <40 | | 91.7 | 174.17 | | | | | | | |
| 2192 | <40 | | 113.7 | 85.21 | 516.36 | | | | | >2.000 | |
| 2193 | <40 | | 232 | 256.79 | | | | | | | |
| 2194 | >10000.00 | | >1000.0 | >2000.00 | | | | | | | |
| 2196 | 1279 | | >1000.0 | >2000.00 | | | | | | | |
| 2201 | <40 | | 72.2 | 4.88 | 207.41 | 0.863, 0.946 | 0.701 | >2.00, >8.00 | 0.979 | >2.000 | |
| 2202 | 55 | | 212.8 | 45.27 | 2706.69 | >10.0, 13.2 | | >2.00, >8.00 | | 0.663, >2.000, >2.000 | |
| 2203 | <40 | | 99.4 | 1.73 | 34.71, 45.24 | 0.34 | 0.359 | >2.00, 4.83 | 0.172 | >2.000 | |
| 2204 | 53 | | 82.5 | 6.38 | 365.66 | 1.11, 0.927 | 0.293 | >2.00, >8.00 | 0.167 | 1.92 | |
| 2205 | <40 | | 65.2 | 12.44 | 108.55 | 0.652, 0.441, 0.450 | 0.265 | | 0.0839 | >2.000 | |
| 2207 | <40 | | <40.0 | <0.91, 0.38 | <2.29, 11.38 | 0.218, 0.424 | 0.334 | | | 0.129 | 0.03 |
| 2208 | <40 | | <40.0 | 1.27, 4.20 | 296.65 | 2.40, 1.53 | 1.8 | | 0.28 | >2.000 | |
| 2209 | 380.00, 781.00 | | | 93.13, 199.02 | 4620.23 | | | | | >2.000 | |
| 2210 | <40 | | <40.0 | 6.72 | 108.05 | 0.285 | 0.298 | | 0.166 | >2.000 | |
| 2211 | <40 | | 50.2 | <0.91, 1.16 | 21.74, 22.07 | 0.493, 0.590 | 0.489 | | 0.389, 0.281 | 1.17 | |
| 2212 | <40 | | 45.7 | 3.03 | 236.41 | 1.72, 1.33, 1.65 | 0.771, 1.56 | | 0.512, 0.426 | >2.000 | |
| 2213 | <40 | | <40.0 | 2.12 | 63.36, 71.27 | 0.422, 0.574 | 0.52 | | 0.272 | 1.91 | |
| 2214 | <40 | | 74.5 | 3.73 | 367.18 | >2.50 | | | | >2.000 | |
| 2215 | <40 | | <40.0 | <0.91, 0.46 | 14.79, 25.37 | 0.298 | 0.26 | | 0.272 | >2.000 | |
| 2216 | <40 | | 53.2 | 287.11 | >5000.00 | | | | | >2.000 | |
| 2217 | <40 | | 59.3 | 11.62 | 2597.77 | >2.50, 3.12, 3.27 | 1.17, 3.73 | | 0.691 | >2.000 | |
| 2218 | <40 | | 40.1 | 717.57 | >5000.00 | | | | | | |
| 2224 | 52 | | <40.0 | 23.66 | 173.6 | 1.07, 1.37 | 1.17 | | 0.995 | >2.000 | |
| 2225 | | | 49.2 | 14.48, 26.86 | 244.89 | >2.50, 3.02 | 1.35, 3.17 | | 1.52 | 1.84 | |
| 2226 | | | <40.0 | 10.31, 14.70 | 292.05 | 1.76, 2.26 | 0.824, 2.43 | | 1.33 | >2.000 | |
| 2227 | | | <40.0 | <0.91, 1.47 | 818.97 | 1.07 | 0.482 | | 0.175 | >2.000 | |
| 2228 | | | <40.0 | <0.91, 1.29 | 27.30, 31.83 | 0.484 | 0.562 | | 0.0999, 0.224 | 0.395, 0.141 | 0.17 |
| 2229 | | | 84.7 | 91.39 | 650.24 | 0.926 | 0.762 | | 0.327 | 1.98 | |
| 2230 | | | <40.0 | <0.91, 5.12 | 28.03, 39.61 | 0.393, 0.304 | 0.165 | | 0.0765, 0.134 | 0.211, 0.196 | 0.01 |
| 2231 | | | <40.0 | <0.91, 0.66 | <2.29, 5.93, 10.00 | 0.0220, 0.151, 0.0505, 0.0223 | <7.81E−03 | | <7.81E−03, 3.58E−03, 0.0158 | 0.538, 0.220 | 0.01 |
| 2232 | | | 53.9 | 71.29 | 244.46 | 0.255, 0.570 | 0.448 | | 0.415 | >2.000 | |
| 2233 | | | <40.0 | 23.31, 27.76 | 207.26 | 0.126, 0.336 | 0.186 | | 0.147 | 0.677, 1.590 | 0.02 |

TABLE 10-continued

| Compd. Name | (A) | (B) | (C) | (D) | (E) | (F) | (G) | (H) | (I) | (J) | (K) |
|---|---|---|---|---|---|---|---|---|---|---|---|
| 2234 | | | <40.0 | 9.17, 7.98 | 2099.4 | >2.50, >8.00 | >8.00 | | 1.06 | >2.000 | |
| 2235 | | | >1000.0 | 1052.81 | | | | | | >2.000 | |
| 2236 | | | 335.3 | 1661.27 | | | | | | >2.000 | |
| 2237 | | | >1000.0 | 545.8 | | | | | | >2.000 | |
| 2238 | | | 127.2 | 173.76 | | | | | | >2.000 | |
| 2239 | <40 | | <40.0 | 266.58 | 3879 | >2.00 | >2.00 | | | >2.000 | |
| 2240 | | | <40.0 | <0.91, 0.68 | 5.70, 6.83 | 0.0213, 0.0679 | 0.0578 | | 0.0141, 0.0122 | 0.190, 0.430 | 0.02 |
| 2241 | | | <40.0, <40.0 | 2.12, 1.52, 1.80, 1.71 | 6.56, 10.65, 12.70, 14.99 | 0.0270, 0.0489, 0.185, 0.195, 0.162, 0.223 | 0.104, 0.113 | 0.847 | 0.0277, 0.0206, 0.0160, 0.0189 | 1.600, >2.000 | |
| 2242 | | | <40.0 | 8.97, 11.84 | 112.26 | 0.597, 1.92, 2.08, 1.71 | 1.81 | | 0.599, 0.847 | 0.531, 0.800 | 0.05 |
| 2243 | | | | 7.55, 18.24 | 96.88, 171.86 | 0.101, 0.292 | | | | 0.753, 1.440 | |
| 2244 | | | <40.0 | 3.25, 1.40 | 541.08 | 1.66, 1.66, 2.21 | 1.57 | | 0.531, 0.555 | >2.000 | |
| 2245 | | | <40.0 | 25.37, 17.31 | 43.71, 141.54, 53.98 | 0.0924, 0.0526, 0.0902 | 0.0378 | | 0.0162, 0.0673 | >2.000, 2.000 | |
| 2246 | | | 55.6 | 6.68, 5.68 | 17.85, 20.64 | 0.277, 0.497 | 0.115 | | 0.0248, 0.0669, 0.0628 | 0.359, 0.300 | |
| 2247 | | | | 218.4 | 199.78 | 1651.1 | 1.18, 1.43 | 1.46, 1.58 | | 1.08 | >2.000 | |
| 2248 | | | | 40.8 | 81.78 | 490.63 | >2.00, 6.26 | >2.00, 7.06 | | 1.98, 2.23 | >2.000 | |
| 2249 | | | | 122 | 30.86, 31.65 | 76.40, 114.08 | >2.00, 3.33, 3.16 | 0.784, 3.05 | | >2.00, 0.529 | 1.068, 1.200, 1.140, >2.000 | 1.2 |
| 2250 | | | | | 28.87 | 135.50, 344.49 | 1.26, 2.59 | 0.461, 2.59 | | 1.35, 1.01 | | |
| 2251 | | | <40.0 | 166.12 | 811.23 | >2.00, >16.0 | >2.00, >16.0 | | >4.00 | >2.000 | |
| 2252 | | | | 430.7 | 267.88 | 629.62 | >2.00, >16.0 | >2.00 | | | | |
| 2253 | | | | 110 | 114.71 | | >2.00, >16.0, >16.0 | >2.00 | | | | |
| 2254 | | | | 138.2 | 167.82 | | >2.00, 12.0 | >2.00 | | | | |
| 2255 | | | | 277.2 | 71.53 | 164.61 | 1.82, 2.93 | 1.82 | | | >2.000 | |
| 2256 | | | | | 12.32, 20.30 | 76.45, 77.23 | 1.97, 3.04, >8.00 | >2.00, 1.59 | | | 1.94 | |
| 2257 | | | | | 1.11, 3.35 | 8.03, 8.17 | 0.646, 0.856, 2.23 | 0.876 | | | 0.310, 0.219 | |
| 2258 | | | | | <0.91, 1.35 | 5.39, 5.96 | 0.415 | 1.74, 0.425, 0.591 | | | 0.188, 0.193 | |
| 2259 | | | | | <0.91, 2.92 | 32.16, 41.40 | 0.422 | 1.99, 0.0300, 0.816 | | | 0.197, 0.071 | |
| 2261 | | | | | 28.59, <9.08, 20.51 | 214.41 | | | | | 0.340, 0.561 | |
| 2262 | | | | | 18.85, 25.63 | 126.36 | 0.557 | | | | 1.5 | |
| 2263 | | | | | 64.38, 69.10 | 365.76 | 3.29 | | | | >2.000 | |
| 2264 | | | | | 39.94, 73.09 | 133.37 | 1.22 | | | | >2.000 | |
| 2265 | | | | | 3.70, 7.54 | 324.66 | 1.62 | | | | 1.84 | |

TABLE 10-continued

| Compd. Name | (A) | (B) | (C) | (D) | (E) | (F) | (G) | (H) | (I) | (J) | (K) |
|---|---|---|---|---|---|---|---|---|---|---|---|
| 2267 | | | | >2000.00 | | >2.00 | | | | | |
| 2268 | | | | 186.08 | | 0.690, 0.345 | | | | | |
| 2269 | | | | 102.27 | | 1.77, 1.44 | | | | | |
| 2270 | | | | 43.25 | 705.65 | >2.00, >8.00 | | | | >2.000 | |
| 2271 | | | | 53.94 | 494.26 | >2.00, >8.00 | | | | >2.000 | |
| 2275 | | | | <0.91 | | | | | | | |
| 2286 | | | | >2000.00 | | >2.00, >8.00 | | | | | |
| 2288 | | | | 1.79 | 183.32 | 1.16 | >2.00 | >2.00 | | | |
| 2293 | | | | 830.52 | | >8.00 | | >8.00 | | | |
| 2294 | | | | 30.37 | 3327.63 | >8.00 | | >8.00 | | | |
| 2295 | | | | <0.91, 0.71 | 5.30, 4.59 | 0.124 | | 1.16 | | | |
| 2296 | | | | <0.91, 0.78 | 5.26, 7.44 | 0.21 | | 0.455 | | 0.062 | |
| 2297 | | | | 7.12 | 53.78, 79.66 | 2.98 | | >8.00 | | 0.203 | |

Example 170: Results C. parvum and T. cruzi Infection Models

Figure 4:
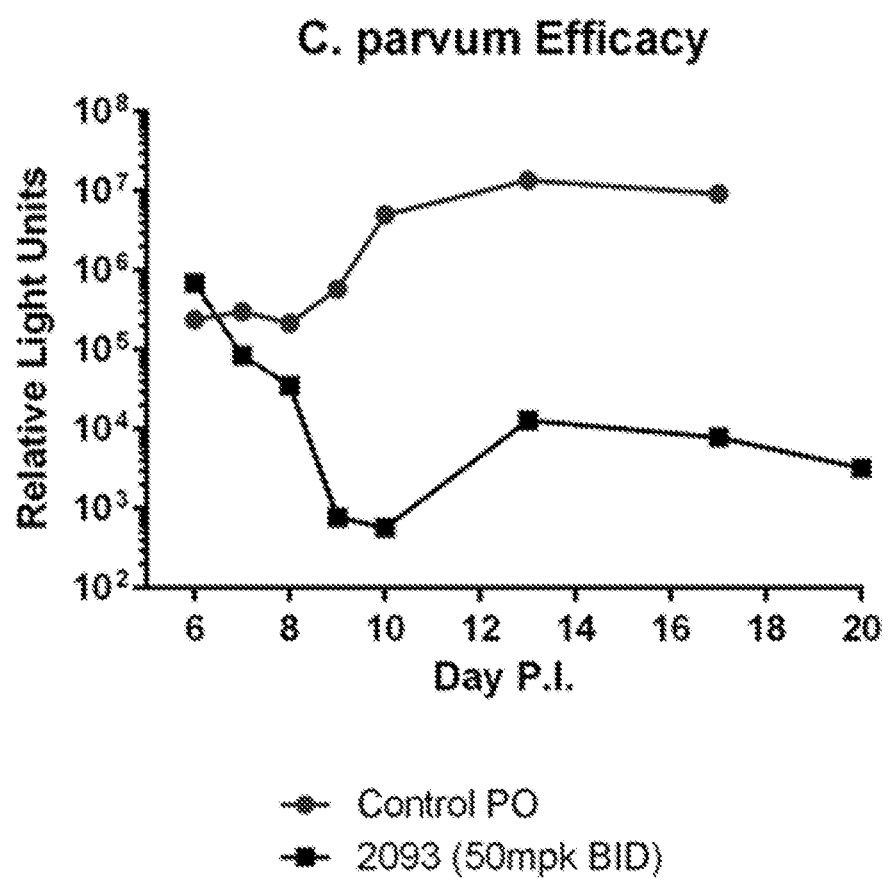
FIG. 4 illustrates efficacy of MetRS inhibitors in a parasite burden model of *Cryptosporidium parvum* infection. About 1,000-fold reduction of parasite burden was observed after treatment by 2093.
Figure 5:
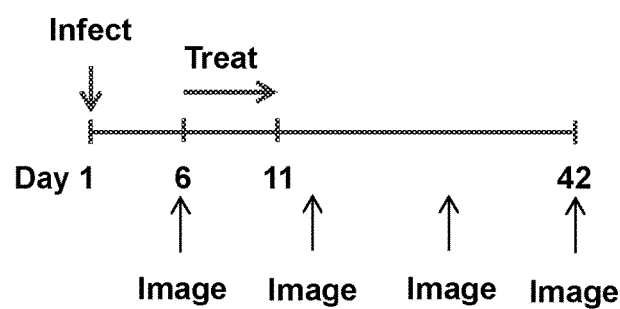
FIG. 5 illustrates efficacy of a MetRS inhibitor in acute *T. cruzi* infection model. (A) Study protocol. Compounds were dosed orally with 50 mg/kg twice a day for five days, and the images were taken of day 6, 13, and 24. (B) Images and (C) graphs of the fluorescence results.
Figure 5:
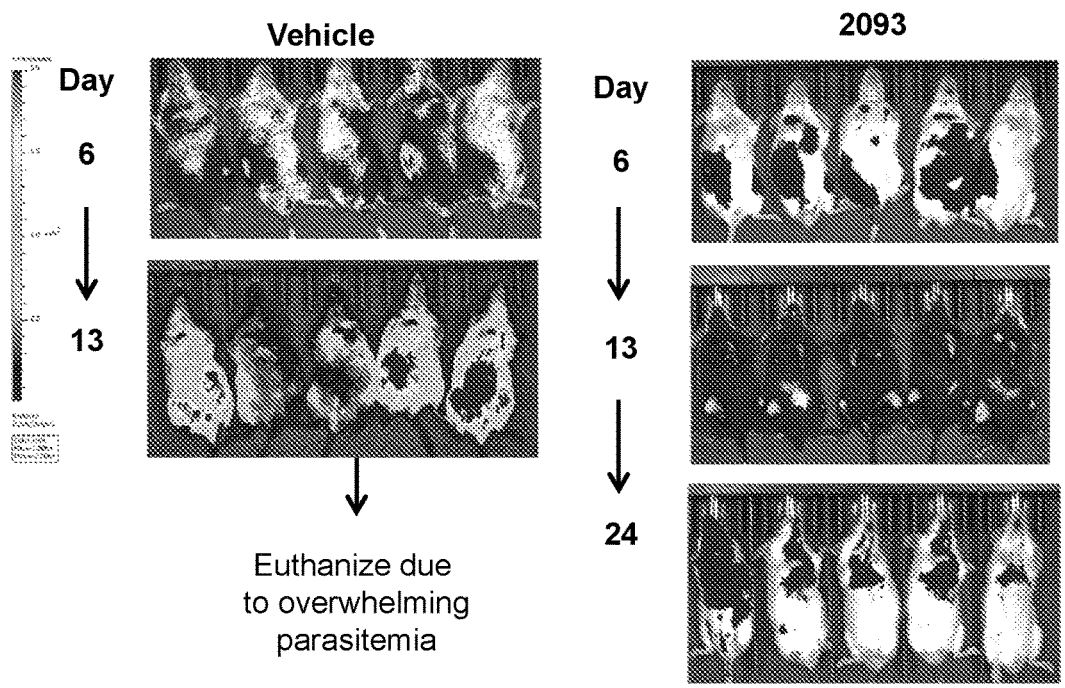
Figure 5:
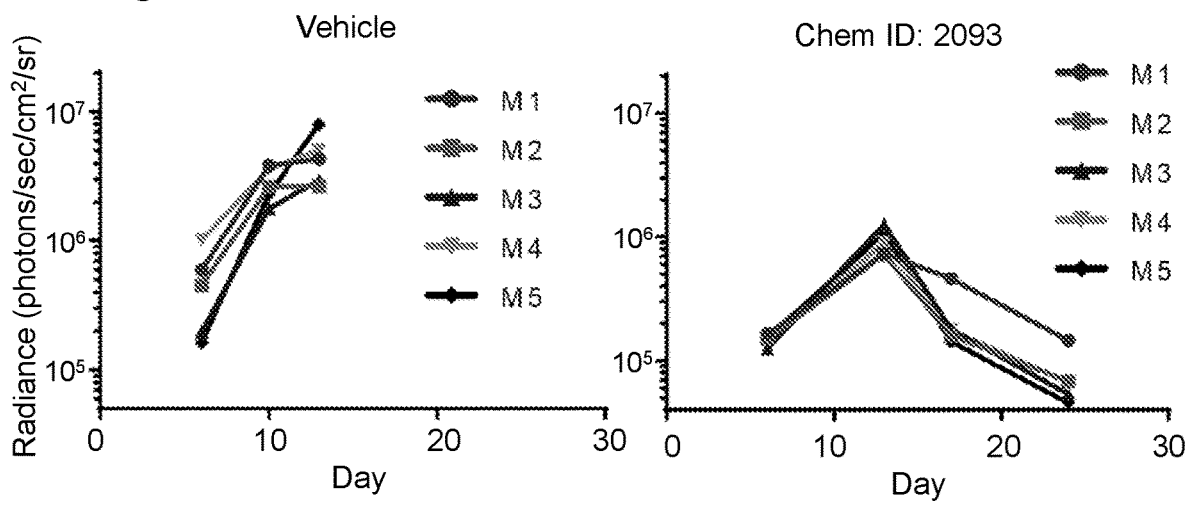

Several compounds of the disclosure were also evaluated in vivo in C. parvum infection model and in acute T. cruzi infection model. Immunosuppressed mice (NOD SCID Gamma) with Cryptosporidium infection were treated for 5 days with test compounds. Cryptosporidium oocysts were quantified in stool by PCR. Compound 2093 resulted in over 99% suppression of infection. In FIG. 4, gamma-IFN knockout mice were used and, similarly, treated for 5 days with the test compound 2093. Again, a high degree of anti-Cryptosporidium activity (>4 log drop in fecal parasites) was demonstrated using a bioluminescence readout. With respect to the T. cruzi, an efficacy model was employed in which the infection was monitored using bioluminescent T. cruz. With vehicle treatment, all mice died by day 14 post-infection. In contrast, mice treated with compound 2093 had dramatic suppression of tissue parasites (FIGS. 5B and 5C) combined with 100% survival, demonstrating potent anti-trypanosomal activity.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A compound of the formula:

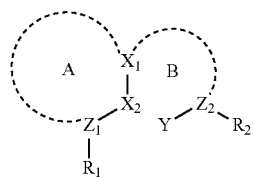

or a pharmaceutically acceptable salt thereof, wherein

A and B together form a fused ring system AB selected from the group consisting of:

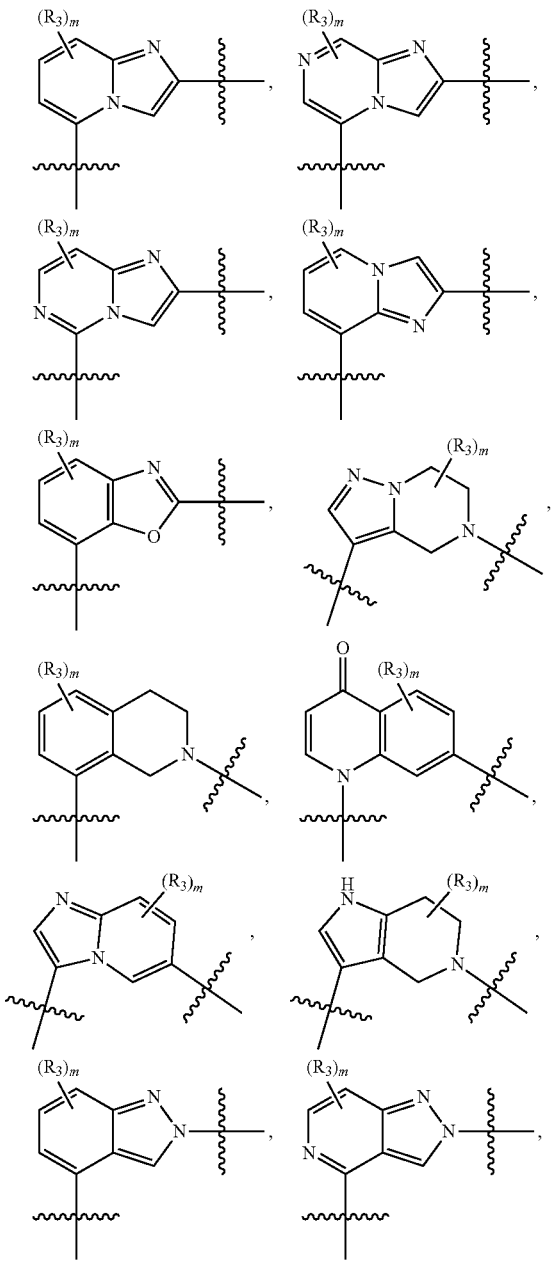

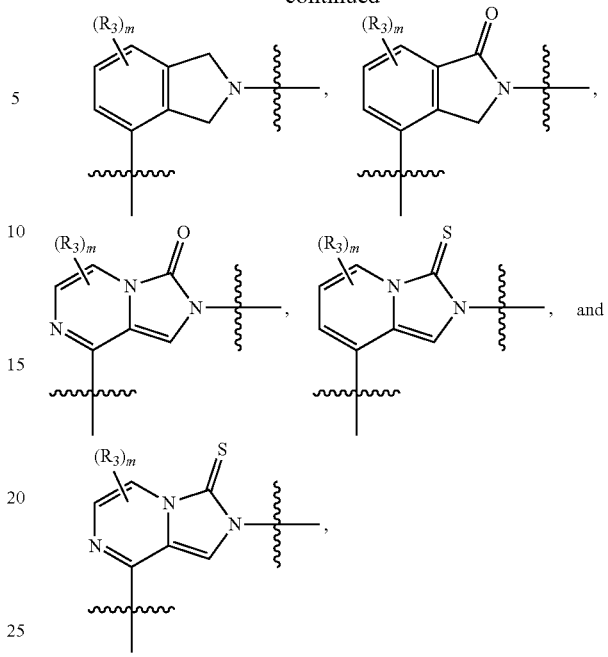

in which m is zero, one, two or three;

each $R_3$ is independently selected from halogen, —$NO_2$, —CN, $C_1$-$C_6$ alkyl, $C_1$-$C_6$ haloalkyl, —$NH_2$, —NH($C_1$-$C_6$ alkyl), —NH(aryl), —N($C_1$-$C_6$ alkyl)$_2$, —N(aryl)$_2$, —N($C_1$-$C_6$ alkyl)(aryl), —OH, $C_1$-$C_6$ alkoxy, $C_1$-$C_6$ haloalkoxy, aryloxy, —SH, —S($C_1$-$C_6$ alkyl), —S(aryl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—NH(aryl), —$CH_2$—N($C_1$-$C_6$ alkyl)$_2$, —$CH_2$N(aryl)$_2$, —$CH_2$—N($C_1$-$C_6$ alkyl)(aryl), —$CONH_2$, —CONH($C_1$-$C_6$ alkyl), —CONH(aryl), —CON($C_1$-$C_6$ alkyl)$_2$, —CON(aryl)$_2$, —CON($C_1$-$C_6$ alkyl)(aryl), —CONH—OH, —CONH—$NH_2$, —C(O)H, —$CO_2$H, —$CO_2$($C_1$-$C_6$ alkyl), —OCO($C_1$-$C_6$ alkyl), —NHCO($C_1$-$C_6$ alkoxy), —NHCO($C_1$-$C_6$ alkyl), —NHCO(aryl), —$NHCONH_2$, —NHCONH($C_1$-$C_6$ alkyl), —NHCONH(aryl), —S(O)$_{1-2}$—($C_1$-$C_6$ alkyl), —NH—S(O)$_{0-2}$—($C_1$-$C_6$ alkyl), —NH—S(O)$_{0-2}$-aryl, —NH—S(O)$_{0-2}$-heteroaryl, aryl($C_0$-$C_6$ alkyl), heteroaryl($C_0$-$C_6$ alkyl), heterocyclyl($C_0$-$C_6$ alkyl), —$CH_2$—$NHCONH_2$, —$CH_2$—NHCONH($C_1$-$C_6$ alkyl), —$CH_2$—NHCONH(aryl), and —$CH_2$—OCO($C_1$-$C_6$ alkyl), or two $R_3$ substituents when attached to the same atom form an oxo or a thioxo group, and wherein each alkyl, aryl, heteroaryl, or heterocyclyl moiety is optionally substituted with one or more $R_5$;

each $R_5$ is independently selected from halogen, —NO2, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—N($C_1$-$C_6$ alkyl)$_2$, —$CONH_2$, —CONH($C_1$-$C_6$ alkyl), —CON($C_1$-$C_6$ alkyl)$_2$, —CONH—OH, —CONH—$NH_2$, —COH, —$CO_2$H, —$CO_2$($C_1$-$C_6$ alkyl), —CO($C_1$-$C_6$ alkyl), —OCO ($C_1$-$C_6$ alkyl), —NHCO($C_1$-$C_6$ alkoxy), —NHCO($C_1$-$C_6$ alkyl), —$NHCONH_2$, —NHCONH($C_1$-$C_6$ alkyl), —NH—S(O)$_{0-2}$—($C_1$-$C_6$ alkyl), —NH—S(O)$_{0-2}$-aryl, —NH—S(O)$_{0-2}$-heteroaryl, —CH$_2$—NHCONH$_2$, —CH$_2$—NHCONH(C$_1$-C$_6$ alkyl), and —CH$_2$—OCO (C$_1$-C$_6$ alkyl);

X$_1$ and X$_2$, the fusion positions, are independently C or N;

Y is CH, CH$_2$, N, or O;

Z$_1$ and Z$_2$ are independently C or N;

R$_1$ is phenyl optionally substituted with one or more R$_7$; and

R$_2$ is —CH$_2$—R$_6$ or —NH—CH$_2$—R$_6$;

wherein R$_6$ represents a 9-member heteroaryl optionally substituted with one or more R$_7$;

each R$_7$ is independently selected from halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —N(aryl)$_2$, —N(C$_1$-C$_6$ alkyl)(aryl), —OH, C$_1$-C$_6$ alkoxy, C$_1$-C$_6$ haloalkoxy, —SH, —S(C$_1$-C$_6$ alkyl), —S(aryl), hydroxy(C$_1$-C$_6$ alkyl), alkoxy(C$_1$-C$_6$ alkyl), amino(C$_1$-C$_6$ alkyl), —CH$_2$—NH(C$_1$-C$_6$ alkyl), —CH$_2$—NH(aryl), —CH$_2$—N(C$_1$-C$_6$ alkyl)$_2$, —CH$_2$N(aryl)$_2$, —CH$_2$—N(C$_1$-C$_6$ alkyl)(aryl), —CONH$_2$, —CONH(C$_1$-C$_6$ alkyl), —CONH(aryl), —CON(C$_1$-C$_6$ alkyl)$_2$, —CON(aryl)$_2$, —CON(C$_1$-C$_6$ alkyl)(aryl), —CONH—OH, —CONH—NH$_2$, —COH, —CO$_2$H, —CO$_2$(C$_1$-C$_6$ alkyl), —OCO(C$_1$-C$_6$ alkyl), —NHCO(C$_1$-C$_6$ alkoxy), —NHCO(C$_1$-C$_6$ alkyl), —NHCO(aryl), —NHCONH$_2$, —NHCONH(C$_1$-C$_6$ alkyl), —NHCONH(aryl), —NH—S(O)$_{0-2}$-(C$_1$-C$_6$ alkyl), —NH—S(O)$_{0-2}$-aryl, —NH—S(O)$_{0-2}$-heteroaryl, —CH$_2$—NHCONH$_2$, —CH$_2$—NHCONH(C$_1$-C$_6$ alkyl), —CH$_2$—NHCONH(aryl), and —CH$_2$—OCO(C$_1$-C$_6$ alkyl).

2. The compound of claim 1, wherein the fused ring system AB is selected from the group consisting of:

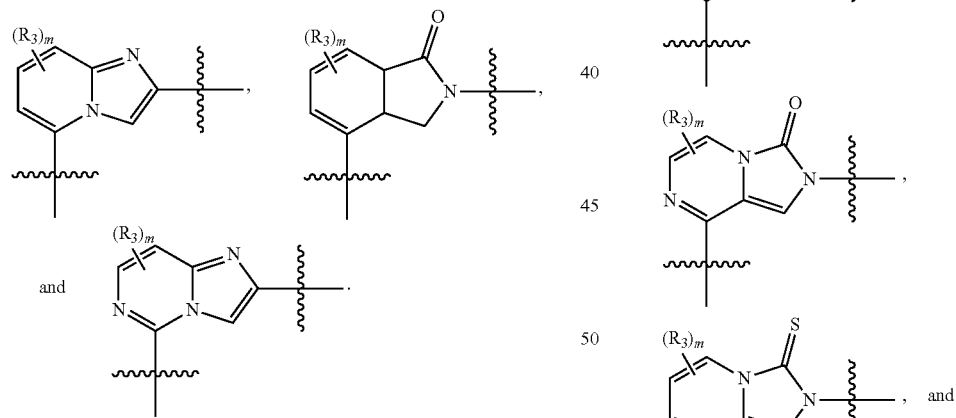

3. The compound of claim 1, wherein the fused ring AB is selected from the group consisting of:

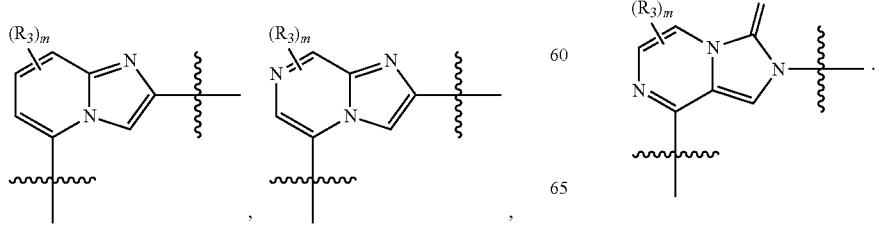

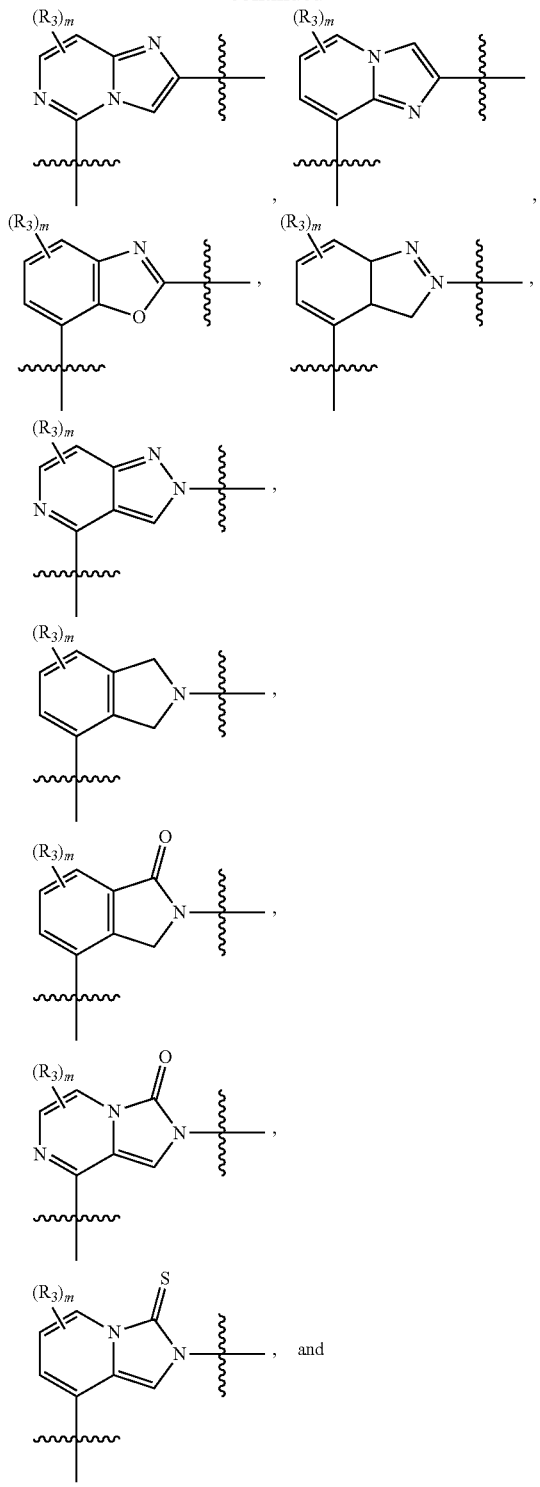

4. The compound of claim 1, wherein the fused ring AB is unsubstituted.

5. The compound of claim 1, wherein m is one or two, and wherein each $R_3$ is independently selected from halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —S($C_1$-$C_6$ alkyl), hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—N($C_1$-$C_6$ alkyl)$_2$, —$CONH_2$, —CONH($C_1$-$C_6$ alkyl), —CON($C_1$-$C_6$ alkyl)$_2$, —CONN—OH, —CONN—$NH_2$, —COH, —$CO_2$H, —$CO_2$($C_1$-$C_6$ alkyl), —NHCO($C_1$-$C_6$ alkyl), —NHCO($C_1$-$C_6$ alkoxy), —NH—S(O)$_{0-2}$—($C_1$-$C_6$ alkyl), —S(O)$_{1-2}$—($C_1$-$C_6$ alkyl), —NHCONH($C_1$-$C_6$ alkyl), 4-acetyl-piperazin-1-yl, and benzyl, or two $R_3$ substituents when attached to the same atom form oxo or thioxo, and wherein each alkyl, aryl, heteroaryl, or heterocyclyl moiety is optionally substituted with one or more $R_5$.

6. The compound of claim 5, wherein each $R_3$ is independently selected from halogen, $C_1$-$C_6$ alkyl, —$NH_2$, —NH($C_1$-$C_6$ alkyl), —N($C_1$-$C_6$ alkyl)$_2$, —S($C_1$-$C_6$ alkyl), —NHCO($C_1$-$C_6$ alkyl), —NHCO($C_1$-$C_6$ alkoxy), —NH—S(O)$_2$-($C_1$-$C_6$ alkyl), —S(O)$_{1-2}$—($C_1$-$C_6$ alkyl), —NHCONH($C_1$-$C_6$ alkyl), 4-acetyl-piperazin-1-yl, and benzyl, or two $R_3$ substituents when attached to the same atom form oxo or thioxo, and wherein each alkyl, aryl, heteroaryl, or heterocyclyl moiety is optionally substituted with one or more $R_5$.

7. The compound of claim 1, wherein $R_2$ is —$CH_2$—$R_6$.

8. The compound of claim 1, wherein R2 is —NH—$CH_2$—$R_6$.

9. The compound of claim 1, wherein R6 represents imidazo[4,5-b]pyridine optionally substituted with one or more $R_7$.

10. The compound of claim 1, wherein the phenyl ring of $R_1$ is substituted with one or more $R_7$.

11. The compound of claim 10, wherein each $R_7$ is independently selected from halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl).

12. The compound of claim 1, wherein $R_6$ is imidazo[4,5-b]pyridine or benzo[d]imidazole, each optionally substituted with one or more $R_7$.

13. The compound of claim 12, wherein each $R_7$ is independently selected from halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl).

14. The compound of claim 1 of formula:

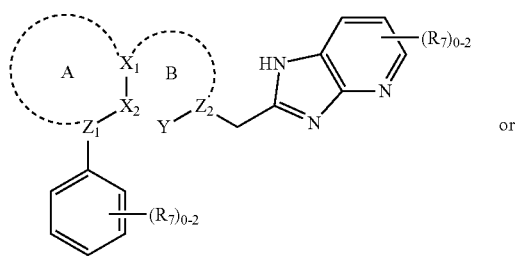

or

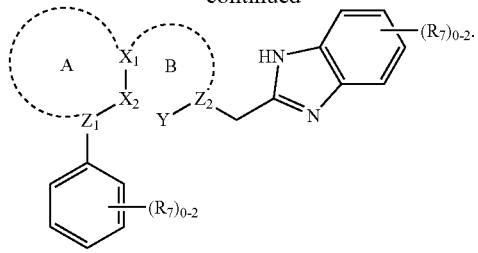

15. The compound, which is:
2-({5-chloro-1H-imidazo[4,5-b]pyridin-2-yl}methyl)-5-(2-chloro-4-methoxyphenyl)imidazo[1,2-a]pyridine;
5-(2-chloro-4-methoxyphenyl)-2-({5-fluoro-1H-imidazo[4,5-b]pyridin-2-yl}methyl)imidazo[1,2-a]pyridine;
2-({5-chloro-1H-imidazo[4,5-b]pyridin-2-yl}methyl)-5-[2-chloro-4-(trifluoromethyl)phenyl]imidazo[1,2-a]pyridine;
5-[2-chloro-4-(trifluoromethyl)phenyl]-2-({5-fluoro-1H-imidazo[4,5-a]pyridin-2-yl}methyl)imidazo[1,2-a]pyridine;
2-({5-chloro-1H-imidazo[4,5-a]pyridin-2-yl}methyl)-5-(2,4-dichloro-5-methoxyphenyl)imidazo[1,2-a]pyridine;
5-(2,4-dichloro-5-methoxyphenyl)-2-({5-fluoro-1H-imidazo[4,5-a]pyridin-2-yl}methyl)imidazo[1,2-a]pyridine;
2-({5-chloro-1H-imidazo[4,5-b]pyridin-2-yl}methyl)-5-(3,5-dichlorophenyl)imidazo[1,2-a]pyridine;
5-(3,5-dichlorophenyl)-2-({5-fluoro-1H-imidazo[4,5-b]pyridin-2-yl}methyl)imidazo[1,2-a]pyridine;
2-({5-chloro-1H-imidazo[4,5-b]pyridin-2-yl}methyl)-5-(2,5-dichloro-4-methoxyphenyl)imidazo[1,2-a]pyridine;
5-(2,5-dichloro-4-methoxyphenyl)-2-({5-fluoro-1H-imidazo[4,5-b]pyridin-2-yl}methyl)imidazo[1,2-a]pyridine;
2-({5-chloro-1H-imidazo[4, 5-b]pyridin-2-yl}methyl)-5-(2,4-dichlorophenyl)imidazo[1,2-a]pyridine;
5-(2,4-dichlorophenyl)-2-({5-fluoro-1H-imidazo[4,5-b]pyridin-2-yl}methyl)imidazo[1,2-a]pyridine;
2-({5-chloro-1H-imidazo[4,5-b]pyridin-2-yl}methyl)-5-(2-chloro-4,5-dimethoxyphenyl)imidazo[1,2-a]pyridine;
5-(2-chloro-4, 5-dimethoxyphenyl)-2-({5-fluoro-1H-imidazo[4, 5-b]pyridin-2-yl}methyl)imidazo[1,2-a]pyridine;
2-({5-bromo-1H-imidazo[4,5-b]pyridin-2-yl}methyl)-5-(2,4-dichloro-5-methoxyphenyl)imidazo[1,2-a]pyridine;
8-(2-chloro-4-methoxyphenyl)-2-({5-fluoro-1H-imidazo[4, 5-b]pyridin-2-yl}methyl)imidazo[1,2-a]pyridine;
2-({5-chloro-1H-imidazo[4, 5-b]pyridin-2-yl}methyl)-8-(2-chloro-4-methoxyphenyl)imidazo[1,2-a]pyridine;
2-({5-chloro-1H-imidazo[4,5-b]pyridin-2-yl}methyl)-8-(2-chloro-4-methoxyphenyl)-3-(methylsulfanyl)imidazo[1,2-a]pyridine;
2-({5-chloro-1H-imidazo[4,5-b]pyridin-2-yl}methyl)-8-(2-chloro-4-methoxyphenyl)-3-methanesulfonylimidazo[1,2-a]pyridine;
2-({5-chloro-1H-imidazo[4, 5-b]pyridin-2-yl}methyl)-5-(2-chloro-4-methoxyphenyl)imidazo[1,2-a]pyrazine;
2-({5-chloro-1H-imidazo[4, 5-b]pyridin-2-yl}methyl)-8-(2-chloro-4-methoxyphenyl)-1,2,3,4-tetrahydroisoquinoline;

2-({5-chloro-1H-imidazo[4, 5-b]pyridin-2-yl}methyl)-7-(2-chloro-4-methoxyphenyl)-1,3-benzoxazole;

2-({5-chloro-1H-imidazo[4, 5-b]pyridin-2-yl}methyl)-5-(2-chloro-4-ethoxyphenyl)imidazo[1,2-a]pyridine;

2-({5-chloro-1H-imidazo[4, 5-b]pyridin-2-yl}methyl)-5-(2-chloro-4-methylphenyl)imidazo[1,2-a]pyridine;

5-(2-chloro-4-methoxyphenyl)-2-{[5-(trifluoromethyl)-1H-imidazo[4, 5-b]pyridin-2-yl]methyl}imidazo[1,2-a]pyridine;

8-(2-chloro-4-methoxyphenyl)-2-({5-fluoro-1H-imidazo[4, 5-b]pyridin-2-yl}methyl)-1,2,3,4-tetrahydroisoquinoline;

7-(2-chloro-4-methoxyphenyl)-1-({5-fluoro-1H-imidazo[4, 5-b]pyridin-2-yl}methyl)-1,4-dihydroquinolin-4-one;

N42-({5-chloro-1H-imidazo[4, 5-b]pyridin-2-yl}methyl)-5-(2-chloro-4-methoxyphenyl)imidazo[1, 2-a]pyridin-8-yl)acetamide;

3-(2-chloro-4-methoxyphenyl)-5-({5-fluoro-1H-imidazo[4, 5-b]pyridin-2-yl}methyl)-4H, 5H, 6H, 7H-pyrazolo[1,5-a]pyrazine;

2-({5-chloro-1H-imidazo[4, 5-b]pyridin-2-yl}methyl)-5-(2-chloro-4-methoxyphenyl)imidazo[1,2-a]pyridin-8-amine;

5-({5-chloro-1H-imidazo[4, 5-b]pyridin-2-yl}methyl)-3-(2-chloro-4-methoxyphenyl)-4H, 5H, 6H, 7H-pyrazolo[1,5-a]pyrazine;

3-(2-chloro-4-methoxyphenyl)—N-({5-fluoro-1H-imidazo[4, 5-b]pyridin-2-yl}methyl)imidazo[1,2-a]pyridin-6-amine;

N42-({5-chloro-1H-imidazo[4, 5-b]pyridin-2-yl}methyl)-5-(2-chloro-4-methoxyphenyl)imidazo[1, 2-a]pyridin-8-yl)methanesulfonamide;

2-({5-chloro-1H-imidazo[4, 5-b]pyridin-2-yl}methyl)-5-(2-chloro-4-methoxyphenyl)imidazo[1,2-a]pyrazin-8-amine;

1-benzyl-5-({5-chloro-1H-imidazo[4, 5-b]pyridin-2-yl}methyl)-3-(2-chloro-4-methoxyphenyl)-1H,4H,5H,6H,7H-pyrrolo[3,2-c]pyridine;

5-({5-chloro-1H-imidazo[4, 5-b]pyridin-2-yl}methyl)-3-(2-chloro-4-methoxyphenyl)-1-ethyl-1H,4H, 5H,6H, 7H-pyrrolo[3,2-c]pyridine;

7-({5-chloro-1H-imidazo[4, 5-b]pyridin-2-yl}methyl)-1-(2-chloro-4-methoxyphenyl)-6-fluoro-1,4-dihydroquinolin-4-one;

2-[(6-chloro-1H-1,3-benzodiazol-2-yl)methyl]-5-(2-chloro-4-methoxyphenyl)imidazo[1,2-a]pyridin-8-amine;

N-{2-[(6-chloro-1H-1,3-benzodiazol-2-yl)methyl]-5-(2-chloro-4-methoxyphenyl)imidazo[1,2-a]pyridin-8-yl}acetamide;

methyl N-{2-[(6-chloro-1H-1,3-benzodiazol-2-yl)methyl]-5-(2-chloro-4-methoxyphenyl)imidazo[1,2-a]pyridin-8-yl}carbamate;

1-{2-[(6-chloro-1H-1,3-benzodiazol-2-yl)methyl]-5-(2-chloro-4-methoxyphenyl)imidazo[1,2-a]pyridin-8-yl-3-ethylurea;

N-[5-(2-chloro-4-methoxyphenyl)-2-({5-fluoro-1H-imidazo[4, 5-b]pyridin-2-yl}methyl)imidazo[1,2-a]pyridin-8-yl]acetamide;

N-[2-({5-bromo-1H-imidazo[4,5-b]pyridin-2-yl}methyl)-5-(2-chloro-4-methoxyphenyl)imidazo[1, 2-a]pyridin-8-yl]acetamide;

1-{442-({5-chloro-1H-imidazo[4, 5-b]pyridin-2-yl}methyl)-5-(2-chloro-4-methoxyphenyl)imidazo[1, 2-a]pyrazin-8-yl)piperazin-1-yl} ethan-1-one;

N-[2-({5-chloro-1H-imidazo[4,5-b]pyridin-2-yl}methyl)-5-(2-chloro-4-methoxyphenyl)imidazo[1, 2-a]pyrazin-8-yl]acetamide;

5-({5-chloro-1H-imidazo[4, 5-b]pyridin-2-yl}methyl)-3-(2-chloro-4-methoxyphenyl)-1-methyl-1H,4H, 5H,6H, 7H-pyrazolo[4,3-c]pyridine;

5-({5-chloro-1H-imidazo[4, 5-b]pyridin-2-yl}methyl)-3-(2-chloro-4-methoxyphenyl)-2-methyl-2H,4H, 5H, 6H,7H-pyrazolo[4,3-c]pyridine;

5-({5-chloro-1H-imidazo[4,5-b]pyridin-2-yl}methyl)-3-(2-chloro-4,5-dimethoxyphenyl)-4H, 5H, 6H,7H-pyrazolo[1,5-a]pyrazine;

2-({5-chloro-1H-imidazo[4, 5-b]pyridin-2-yl}methyl)-4-(2-chloro-4-methoxyphenyl)-2, 3-dihydro-1H-isoindole;

6-chlor-2-{[4-(2-chloro-4-methoxyphenyl)-2, 3-dihydro-1H-isoindol-2-yl]methyl 1-1H-1,3-benzodiazole-7-carbonitrile;

2-({5-chloro-1H-imidazo[4, 5-b]pyridin-2-yl}methyl)-4-(2-chloro-4-methoxyphenyl)-2, 3-dihydro-1H-isoindol-1-one;

2-({5-chloro-1H-imidazo[4, 5-b]pyridin-2-yl}methyl)-4-(2-chloro-4, 5-dimethoxyphenyl)-2,3-dihydro-1H-isoindol-1-one;

2-[(6-chloro-1H-1,3-benzodiazol-2-yl)methyl]-4-(2-chloro-4-methoxyphenyl)-2, 3-dihydro-1H-soindol-1-one;

6-chlor$_{0-2}$-{[4-(2-chloro-4-methoxyphenyl)-1-oxo-2,3-dihydro-1H-isoindol-2-yl]methyl-1H-1,3-benzodiazole-7-carbonitrile;

methyl 5-chloro-2-{[5-(2-chloro-4-methoxyphenyl)imidazo[1,2-a]pyridin-2-yl]methyl}-1H-1,3-benzodiazole-4-carboxylate;

2-[(6-amino-7H-purin-8-yl)methyl]-4-(2-chloro-4-methoxyphenyl)-2,3-dihydro-1H-isoindol-1-one;

2-({5-chloro-1H-imidazo[4, 5-b]pyridin-2-yl}methyl)-8-(2-chloro-4-methoxyphenyl)-2H, 3H-imidazo[1, 5-a]pyridine-3-thione;

2-({5-chloro-1H-imidazo[4, 5-b]pyridin-2-yl}methyl)-4-(2-chloro-4-methoxyphenyl)-2H-indazole;

2-({5-chloro-1H-imidazo[4,5-b]pyridin-2-yl}methyl)-5-(2-chloro-4,5-dimethoxyphenyl)imidazo[1,2-c]pyrimidine;

2-({5-chloro-1H-imidazo[4, 5-b]pyridin-2-yl}methyl)-4-(2-chloro-4-methoxyphenyl)-2H-pyrazolo[4,3-c]pyridine;

2-({5-chloro-1H-imidazo[4, 5-b]pyridin-2-yl}methyl)-8-(2-chloro-4-methoxyphenyl)-2H, 3H-imidazo[1, 5-a]pyrazin-3-one;

2-({5-chloro-1H-imidazo[4, 5-b]pyridin-2-yl}methyl)-8-(2-chloro-4-methoxyphenyl)-2H, 3H-imidazo[1, 5-a]pyrazine-3-thione;

2-[(6-amino-2-methyl-7H-purin-8-yl)methyl]-4-(2-chloro-4-methoxyphenyl)-2,3-dihydro-1H-isoindol-1-one;

2-{[6-amino-2-(trifluoromethyl)-7H-purin-8-yl]methyl-4-(2-chloro-4-methoxyphenyl)-2,3-dihydro-1H-isoindol-1-one;

2-[(6-amino-2-methyl-7H-purin-8-yl)methyl]-4-(2-chloro-4,5-dimethoxyphenyl)-2,3-dihydro-1H-isoindol-1-one;

8-(2-chloro-4-methoxyphenyl)-2-[(6,7-dichloro-1H-1,3-benzodiazol-2-yl)methyl]-2H,3H-imidazo[1,5-a]pyrazin-3-one;

6,7-dichloro-2-[5-(2-chloro-4, 5-dimethoxyphenyl)imidazo[1,2-c]pyrimidin-2-yl]methyl 1-1H-1,3-benzodiazole;

2-({5-chloro-1H-imidazo[4, 5-b]pyridin-2-yl}methyl)-5-(2-chloro-4-methoxyphenyl)imidazo[1,2-c]pyrimidine;

5-(2-chloro-4, 5-dimethoxyphenyl)—N-{5-fluoro-1H-imidazo[4, 5-b]pyridin-2-yl}imidazo[1,2-a]pyridin-2-amine;

2,4-dichloro-542-({5-chloro-1H-imidazo[4,5-b]pyridin-2-yl}methyl)imidazo[1,2-a]pyridin-5-yl]phenol;

2-({5-chloro-1H-imidazo[4,5-b]pyridin-2-yl}methyl)-5-(2,4-dichloro-5-ethoxyphenyl)imidazo[1,2-a]pyridine;

2-{2,4-dichloro-5-[2-({5-chloro-1H-imidazo[4,5-b]pyridin-2-yl}methyl)imidazo[1,2-a]pyridin-5-yl]phenoxy}ethan-1-ol;

2-({5-chloro-1H-imidazo[4,5-b]pyridin-2-yl}methyl)-5-{2,4-dichloro-5-[2-(oxan-2-yloxy)ethoxy]phenyl}imidazo[1,2-a]pyridine;

or a pharmaceutically acceptable salt thereof.

16. A method for treating a disease that is ameliorated by the inhibition of methionyl-tRNA synthetase (MetRS), the method comprising administering to a patient in need thereof a therapeutically effective amount of a compound according to claim 1, wherein the disease is a bacterial infection or a protozoan infection.

17. The compound of claim 1, wherein $R_6$ represents a 9-member heteroaryl optionally substituted with one or two $R_7$, wherein each $R_7$ is independently selected from halogen, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy.

18. A pharmaceutical composition comprising one or more of compounds according to claim 1 and a pharmaceutically acceptable carrier, diluent, or excipient.

19. The compound of claim 1, wherein $R_1$ represents a phenyl, which is 2,4-, 3,5- or 2,4,5-substituted.

20. The method of claim 16, wherein the disease is a protozoan infection selected from the group consisting of *Cryptosporidia, Cyclospora, Giardia, Leishmania, Trichomonas,* and *Trypanosoma*, or a bacterial infection caused by Gram positive bacteria, Gram negative bacteria, *Mycobacteria,* or *Mycoplasma.*

* * * * *

SEQUENCE LISTING

```
<160> NUMBER OF SEQ ID NOS: 2

<210> SEQ ID NO 1
<211> LENGTH: 49
<212> TYPE: DNA
<213> ORGANISM: Artificial Sequence
<220> FEATURE:
<223> OTHER INFORMATION: Synthetic

<400> SEQUENCE: 1
gggtcctggt tcggctaaag aaacattcta tataacaacc ccaatatac          49

<210> SEQ ID NO 2
<211> LENGTH: 46
<212> TYPE: DNA
<213> ORGANISM: Artificial Sequence
<220> FEATURE:
<223> OTHER INFORMATION: Synthetic

<400> SEQUENCE: 2
cttgttcgtg ctgtttatta tttaatcact gcaccatttg gaattg             46
```